US012357565B2

(12) United States Patent
Blizzard et al.

(10) Patent No.: US 12,357,565 B2
(45) Date of Patent: Jul. 15, 2025

(54) OCULAR IMPLANT CONTAINING A TYROSINE KINASE INHIBITOR

(71) Applicant: Ocular Therapeutix, Inc., Bedford, MA (US)

(72) Inventors: Charles D. Blizzard, Nashua, NH (US); Arthur Driscoll, Reading, MA (US); Rami El-Hayek, Norwood, MA (US); Michael Goldstein, Cambridge, MA (US); Joseph Iacona, Somerville, MA (US); Peter Jarrett, Burlington, MA (US); Timothy S. Jarrett, Boston, MA (US); Erica Kahn, Cambridge, MA (US); Zachary Lattrell, Newburyport, MA (US)

(73) Assignee: OCULAR THERAPEUTIX, INC., Bedford, MA (US)

( * ) Notice: Subject to any disclaimer, the term of this patent is extended or adjusted under 35 U.S.C. 154(b) by 262 days.

(21) Appl. No.: 17/991,762

(22) Filed: Nov. 21, 2022

(65) Prior Publication Data

US 2023/0118774 A1    Apr. 20, 2023

Related U.S. Application Data

(63) Continuation of application No. 17/744,189, filed on May 13, 2022, now Pat. No. 11,534,396, which is a continuation of application No. 17/210,696, filed on Mar. 24, 2021, now Pat. No. 11,439,592.

(60) Provisional application No. 63/148,463, filed on Feb. 11, 2021, provisional application No. 63/106,276, filed on Oct. 27, 2020, provisional application No. 62/994,391, filed on Mar. 25, 2020.

(51) Int. Cl.
*A61K 9/00* (2006.01)
*A61K 9/06* (2006.01)
(Continued)

(52) U.S. Cl.
CPC .............. *A61K 9/0051* (2013.01); *A61K 9/06* (2013.01); *A61K 31/4427* (2013.01);
(Continued)

(58) Field of Classification Search
CPC .... A61K 9/0051; A61K 9/06; A61K 31/4439; A61K 47/34; A61P 27/02
See application file for complete search history.

(56) References Cited

U.S. PATENT DOCUMENTS 3,949,750 A    4/1976  Freeman
3,993,071 A    11/1976 Higuchi et al.
(Continued)

FOREIGN PATENT DOCUMENTS

CN    104884049 A    9/2015
CN    107205922 A    9/2017
(Continued)

OTHER PUBLICATIONS

International Search Report for PCT/US2021/023806 mailed Jul. 9, 2021, 4 pages.
(Continued)

*Primary Examiner* — Carlos A Azpuru
(74) *Attorney, Agent, or Firm* — Lowenstein, Sandler LLP

(57) ABSTRACT

The invention relates to a sustained release biodegradable ocular implant containing a tyrosine kinase inhibitor dispersed in a hydrogel for the treatment of a retinal disease for an extended period of time.

10 Claims, 31 Drawing Sheets

(51) Int. Cl.
  *A61K 31/4427* (2006.01)
  *A61K 31/4439* (2006.01)
  *A61K 47/34* (2017.01)
  *A61P 27/02* (2006.01)
  *A61K 45/06* (2006.01)

(52) U.S. Cl.
  CPC .......... *A61K 31/4439* (2013.01); *A61K 47/34* (2013.01); *A61P 27/02* (2018.01); *A61K 9/0019* (2013.01); *A61K 45/06* (2013.01)

(56) References Cited

U.S. PATENT DOCUMENTS

| | | | |
|---|---|---|---|
| 4,915,684 A | 4/1990 | MacKeen et al. | |
| 5,469,867 A | 11/1995 | Schmitt | |
| 5,902,598 A | 5/1999 | Chen et al. | |
| 6,027,470 A | 2/2000 | Mendius | |
| 6,196,993 B1 | 3/2001 | Cohan et al. | |
| 6,509,327 B1 | 1/2003 | Cagle et al. | |
| 6,534,524 B1 | 3/2003 | Kania et al. | |
| 6,646,001 B2 | 11/2003 | Hellberg et al. | |
| 6,726,918 B1 | 4/2004 | Wong et al. | |
| 6,899,717 B2 | 5/2005 | Weber et al. | |
| 6,982,090 B2 | 6/2006 | Gillespie | |
| 7,090,681 B2 | 8/2006 | Weber et al. | |
| 7,998,497 B2 | 8/2011 | de Juan, Jr. et al. | |
| 8,034,366 B2 | 10/2011 | Shiah et al. | |
| 8,034,370 B2 | 10/2011 | Shiah et al. | |
| 8,039,470 B2 | 10/2011 | Liang et al. | |
| 8,409,606 B2 | 4/2013 | Sawhney et al. | |
| 8,506,987 B2 | 8/2013 | Shiah et al. | |
| 8,512,738 B2 | 8/2013 | Hughes et al. | |
| 8,512,749 B2 | 8/2013 | Edelman et al. | |
| 8,524,709 B2 | 9/2013 | Liang et al. | |
| 8,535,705 B2 | 9/2013 | Edelman et al. | |
| 8,563,027 B2 | 10/2013 | Sawhney et al. | |
| 8,685,435 B2 | 4/2014 | Nivaggioli et al. | |
| 8,791,140 B2 | 7/2014 | Campeta et al. | |
| 8,956,655 B2 | 2/2015 | Lyons et al. | |
| 8,961,501 B2 | 2/2015 | Jarrett et al. | |
| 9,125,807 B2 | 9/2015 | Sawhney et al. | |
| 9,192,511 B2 | 11/2015 | Shiah et al. | |
| 9,205,150 B2 | 12/2015 | El-Hayek et al. | |
| 9,254,267 B2 | 2/2016 | Sawhney | |
| 9,278,139 B2 | 3/2016 | Rau et al. | |
| 9,320,647 B2 | 4/2016 | Lerner et al. | |
| 9,370,485 B2 | 6/2016 | Sawhney et al. | |
| 9,447,469 B2 | 9/2016 | Lamont | |
| 9,463,114 B2 | 10/2016 | Odrich et al. | |
| 9,504,653 B2 | 11/2016 | Liu et al. | |
| 9,539,259 B2 | 1/2017 | Zack et al. | |
| 9,572,800 B2 | 2/2017 | Zarnitsyn et al. | |
| 9,636,189 B2 | 5/2017 | Ahari et al. | |
| 9,775,906 B2 | 10/2017 | Sawhney et al. | |
| 9,849,082 B2 | 12/2017 | de Juan, Jr. et al. | |
| 9,931,330 B2 | 4/2018 | Zarnitsyn et al. | |
| 9,980,901 B2 | 5/2018 | Ni | |
| 10,010,610 B2 | 7/2018 | Horn | |
| 10,076,526 B2 | 9/2018 | Shiah et al. | |
| 10,111,886 B2 | 10/2018 | Ng et al. | |
| 10,119,202 B2 | 11/2018 | Mao et al. | |
| 10,226,417 B2 | 3/2019 | Jarrett et al. | |
| 10,251,954 B2 | 4/2019 | Sawhney et al. | |
| 10,300,014 B2 | 5/2019 | de Juan, Jr. et al. | |
| 10,420,724 B2 | 9/2019 | Jarrett et al. | |
| 10,570,202 B2 | 2/2020 | Martini et al. | |
| 10,617,563 B2 | 4/2020 | Jarrett et al. | |
| 10,688,092 B2 | 6/2020 | Ni et al. | |
| 10,702,539 B2 | 7/2020 | Shiah et al. | |
| 10,786,462 B2 | 9/2020 | Jarrett et al. | |
| 10,869,924 B2 | 12/2020 | Andrews et al. | |
| 10,874,605 B2 | 12/2020 | Nivaggioli et al. | |
| 10,874,606 B2 | 12/2020 | de Juan, Jr. et al. | |
| 10,905,765 B2 | 2/2021 | Jarrett et al. | |
| 11,053,224 B2 | 7/2021 | Liang et al. | |
| 11,129,690 B2 | 9/2021 | Fisher | |
| 11,439,592 B2 * | 9/2022 | Blizzard | A61K 47/34 |
| 11,534,396 B2 * | 12/2022 | Blizzard | A61K 9/06 |
| 2002/0169409 A1 | 11/2002 | Gillespie | |
| 2003/0065060 A1 | 4/2003 | Qvist et al. | |
| 2003/0108511 A1 | 6/2003 | Sawhney | |
| 2004/0175410 A1 | 9/2004 | Ashton et al. | |
| 2005/0197614 A1 | 9/2005 | Pritchard et al. | |
| 2005/0232972 A1 | 10/2005 | Odrich | |
| 2005/0244475 A1 | 11/2005 | Edelman et al. | |
| 2005/0283109 A1 | 12/2005 | Peyman | |
| 2006/0095108 A1 | 5/2006 | Chowdhury et al. | |
| 2007/0298075 A1 | 12/2007 | Borgia et al. | |
| 2008/0124400 A1 | 5/2008 | Liggins et al. | |
| 2008/0140192 A1 | 6/2008 | Humayun et al. | |
| 2008/0247984 A1 | 10/2008 | Messersmith et al. | |
| 2009/0227981 A1 | 9/2009 | Bennett | |
| 2012/0059338 A1 | 3/2012 | Beeley et al. | |
| 2012/0156259 A1 | 6/2012 | Rau et al. | |
| 2014/0128478 A1 | 5/2014 | Asgharian et al. | |
| 2015/0037422 A1 | 2/2015 | Kaplan et al. | |
| 2016/0296627 A1 | 10/2016 | Garcia et al. | |
| 2016/0331738 A1 * | 11/2016 | Jarrett | A61K 31/517 |
| 2017/0182173 A1 | 6/2017 | Ng et al. | |
| 2018/0085307 A1 | 3/2018 | Sawhney et al. | |
| 2018/0353431 A1 | 12/2018 | Guo et al. | |
| 2019/0070339 A1 | 3/2019 | Gerecht et al. | |
| 2019/0336441 A1 | 11/2019 | Whitcup et al. | |
| 2019/0388522 A1 | 12/2019 | Burian et al. | |
| 2020/0306182 A1 | 10/2020 | Das et al. | |
| 2020/0337989 A1 | 10/2020 | Jarrett et al. | |
| 2021/0007973 A1 | 1/2021 | Patel et al. | |
| 2021/0017266 A1 | 1/2021 | Racine et al. | |
| 2022/0054476 A1 | 2/2022 | Rosen et al. | |
| 2022/0054477 A1 | 2/2022 | Rosen et al. | |
| 2022/0054478 A1 | 2/2022 | Rosen et al. | |
| 2022/0062273 A1 | 3/2022 | Sprogøe et al. | |
| 2022/0080044 A1 | 3/2022 | Chen et al. | |
| 2023/0116809 A1 | 4/2023 | Knappe et al. | |
| 2023/0140691 A1 | 5/2023 | Byrne et al. | |
| 2023/0302156 A1 | 9/2023 | Jiang et al. | |
| 2023/0338286 A1 | 10/2023 | Bassett et al. | |

FOREIGN PATENT DOCUMENTS

| | | | |
|---|---|---|---|
| CN | 109982683 A | | 7/2019 |
| CN | 116419755 A | | 7/2023 |
| WO | 02/43785 A2 | | 6/2002 |
| WO | 2009/008946 | | 1/2009 |
| WO | 2010/093873 | | 8/2010 |
| WO | 2010111449 A1 | | 9/2010 |
| WO | 2013/039706 A1 | | 3/2013 |
| WO | 2013/086015 | | 6/2013 |
| WO | 2013/188273 A1 | | 12/2013 |
| WO | 2016/094646 | | 6/2016 |
| WO | 2016/183296 | | 11/2016 |
| WO | 2017/015591 | | 1/2017 |
| WO | 2017/015616 A1 | | 1/2017 |
| WO | 2017/091749 | | 6/2017 |
| WO | 2018/058048 | | 3/2018 |
| WO | 2019/094652 A1 | | 5/2019 |
| WO | 2020/219890 A1 | | 10/2020 |
| WO | 2020243608 A1 | | 12/2020 |

OTHER PUBLICATIONS

Written Opinion of the International Searching Authority for PCT/US2021/023806 mailed Jul. 9, 2021, 9 pages Narvekar et al., "Axitinib-Loaded Poly(Lactic-Co-Glycolic Acid) Nanoparticles for Age-Related Macular Degeneration: Formulation development and In Vitro Characterization", ASSAY and Drug Development Technologies, May/Jun. 2019, pp. 167-177, vol. 17, No. 4.

Das, et al., "A review of emerging tyrosine kinase inhibitors as durable treatment of neovascular age-related mascular degeneration", Expert Opinion on Emerging Drugs, 2023, 9 pgs.

Mattessich, et al., "Transforming Drug Delivery Leveraging a Novel Technology Platform," Oct. 10, 2020.

(56) References Cited

OTHER PUBLICATIONS

El-Hayek, et al., "Efficacy of a 6 moth Sustained Hydrogel Delivery System for Tyrosine Kinase Inhibitors in a VEGF Induced Retinal Leakage Model," Association for Research in Vision and Ophthalmology 2017 Annual Meeting; Baltimore, MD, May 7-11, 2017.
Jarrett, P., et al., "Tolerability of a 6 month Sustained Hydrogel Delivery System for Tyrosine Kinase Inhibitors in Dutch Belted Rabbits," Association for Research in Vision and Ophthamology 2017 Annual Meeting; Baltimore, MD May 7-11, 2017.
Jarrett, T., et al., "Pharmacokinetics of a 6 month Sustained Hydrogel Delivery System for Tyrosine Kinase Inhibitors in Dutch Belted Rabbits," Association for Research in Vision and Ophthamology 2017 Annual Meeting; Baltimore, MD May 7-11, 2017.
El-Hayek, et al., "Effectiveness of Sustained release TKI Hydrogel Combined with Bevacizumab in a VEGF Induced Retinal Leakage Model Through 12 Months," Association for Research in Vision and Ophthalmology 2018 Annual Meeting; Honolulu, HI, Apr. 29-May 3, 2018.
Jarrett, P, et al., "Efficacy and Tolerability of OTX-TKI, a Sustained Hydrogel Delivery System for a Tyrosine Kinase Inhibitor, in a VEGF-Induced Retinal Leakage Model through 12 Months," presented at the ARVO Annual Meeting May 2018.
Jarrett, P., et al., "Efficacy & Tolerability of OTX-TKI, a Sustained Hydrogel Delivery System for a Tyrosine Kinase Inhibitor, in a VEGF Induced Retinal Leakage Model: 1 Year Results," Association for Research in Vision and Ophthalmology, Canada Apr. 28-May 2, 2019.
Csaky, et al., "Evaluating safety, tolerability and biological activity of OTX-TKI, a hydrogel-based, sustained-release Intravitreal axitinib implant, in subjects with neovascular age-releated mascular degeneraiton (nAMD)—preliminary findings from phase 1 trail," Prize Paper Session 2: New Drug Treatment and Technology Session.
Ocular TTherapeutix™ Reports Second Quarter 2020 Financial Results and Business Update, Newly Published Physician Fee Schedules for 0356T for the Administration of Intracanalicular Inserts to Support Ongoing DEXTENZA® Launch, Firefox, 9 pgs.
Kim et al., "Persistent Remnants of Dexamethasone Intravitreal Implant (Ozurdex)", Retina, The Journal of Retinal and Vitreous Diseases, vol. 00, No. 00, Feb. 13, 2020, pp. 1-6, published by Retina.
Gillies et al., "A Randomized Clinical Trial of Intravitreal Bevacizumab versus Intravitreal Dexamethasone for Diabetic Macular Edema", Opthamology, vol. 121, No. 12, Dec. 2014, pp. 2473-2481, published by American Academy of Opthamology.
Bacharach et al., "Phase 3, Randomized, 20-Month Study of the Efficacy and Safety of Bimatoprost Implant in Patients with Open-Angle Glaucoma and Ocular Hypertension (ARTEMIS 2)", Drugs, vol. 81 No. 17, pp. 2017-2033, published by Adis.
Rahic et al., "Novel Drug Delivery Systems Fighting Glaucoma: Formulation Obstacles and Solutions", Pharmaceutics, vol. 13, No. 28, pp. 1-58, published by MDPI.
Pardo-Lopez et al., "Anterior chamber migration of dexametasona intravitreal implant (Ozurdex)", Graefe's Archive for Clinical and Experimental Opthalmology, Nov. 2011, vol. 250, pp. 1703-1704, Published by Springer.
European Search Report for Application No. 21164737.5 dated Aug. 18, 2021, 4 pgs.
Avery, et al., "Preliminary Findings from a Phase 1 Trial Evaluating the Safety, Tolerability and Biological Activity of OTX-TKI, a Hydrogel-Based, Sustained-Release Intravitreal Axitinib Implant, in Subjects with Neovascular Age-Related Macular Degeneration," Retina Society Annual Scientific Meeting, 2020.
Avery, Robert L., "Safety and Efficacy of OTX-TKI, a Novel Tyrosine Kinase Inhibitor Hydrogel Intravitreal Implant," Annual VIT Buckle Society Meeting, Apr. 2020.
Csaky, et al., "Evaluating Safety, Tolerability and Biological Activity of OTX-TKI, a Hydrogel-Based, Sustained-Relese Intravitreal Axitinib Implant, in Subjects with Neovascular Age-Related Macular Degeneration Preliminary Findings from a Phase 1 Trial," Euretina Congress 2020.
Mattessich, et al., "Transforming Drug Delivery Leveraging a Novel Technology Platform," Sep. 2020.
Bao, Zhi et al., "Preparation of axitnib in biodegradable drug membranes for ocular surface", Chin J. Clin. Pharmacol, vol. 33, No. 17, Sep. 2017, 4 pages.
Kahn, Erica et al., "A Safety and Pharmacokinetic Study of a Novel Hydrogel-based Axitnib Intravitreal Implant (OTX-TKI) in Non-Human Primates", Investigative Ophthalmology & Visual Science, Jun. 2022, vol. 63, 4 pages.
Giddabasappa et al., "Axitinib inhibits retinal and choroidal neovascularization in in vitro and in vivo models", Experimental Eye Research, 2016, pp. 373-379. vol. 145, Elsevier.

* cited by examiner

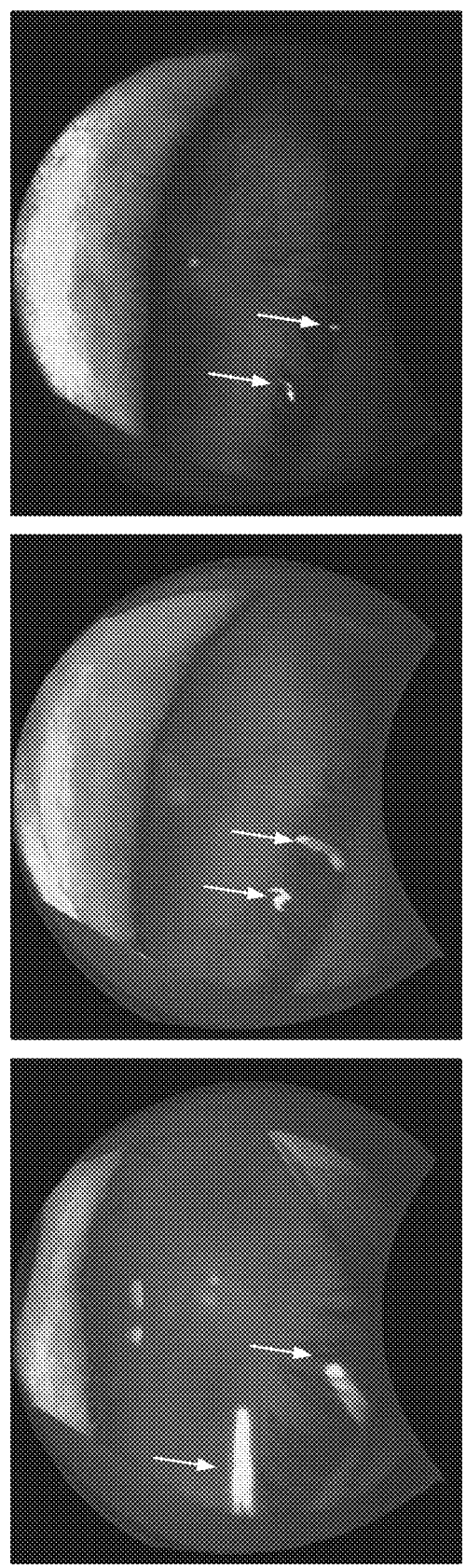

FIG. 25A
FIG. 25B
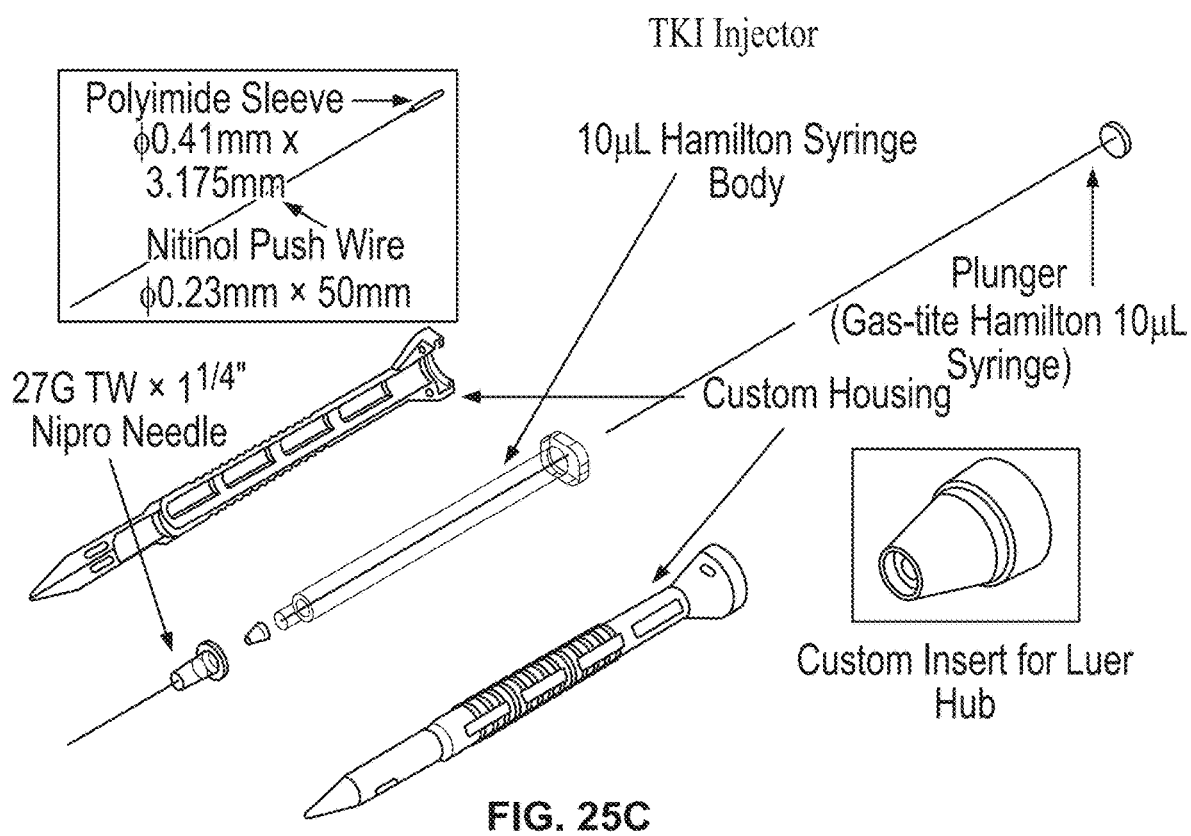
FIG. 25C

OCULAR IMPLANT CONTAINING A TYROSINE KINASE INHIBITOR

CROSS-REFERENCE TO RELATED APPLICATIONS

The present invention claims priority to U.S. Provisional Application Ser. No. 62/994,391 filed Mar. 25, 2020, to International Application PCT/US2020/029827 filed 24 Apr. 2020, to U.S. Provisional Application Ser. No. 63/106,276 filed Oct. 27, 2020, and to U.S. Provisional Application Ser. No. 63/148,463 filed Feb. 11, 2021, which are all hereby incorporated by reference herein.

TECHNICAL FIELD

The present invention relates to the treatment of ocular diseases, for example neovascular age-related macular degeneration (AMD), also referred to as "wet AMD". According to the present invention, ocular diseases are treated by administering an injection (e.g., intravitreally) of an implant that is biodegradable and provides sustained release of a tyrosine kinase inhibitor such as axitinib.

BACKGROUND

Macular diseases, including AMD, are among the leading causes of visual impairment and irreversible blindness in the world for people over the age of 50. Specifically, AMD was one of the most common retinal diseases in the United States (U.S.) in 2019, affecting approximately 16.9 million people, and this is expected to grow to 18.8 million people in 2024 (Market Scope. Ophthalmic Comprehensive Reports. 2019 Retinal Pharmaceuticals Market Report: A Global Analysis for 2018 to 2019, September 2019). AMD can be subdivided into different disease stages. Early AMD is characterized by the presence of a few (<20) medium-size drusen or retinal pigmentary abnormalities. Intermediate AMD is characterized by at least one large druse, numerous medium-size drusen, or geographic atrophy that does not extend to the center of the macula. Advanced or late AMD can be either non-neovascular (dry, atrophic, or non-exudative) or neovascular (wet or exudative). Advanced non-neovascular AMD is characterized by drusen and geographic atrophy extending to the center of the macula. Advanced neovascular AMD is characterized by choroidal neovascularization and its sequelae (Jager et al., Age-related macular degeneration. N Engl J Med. 2008; 358(24):2606-17).

The more advanced form of wet AMD is characterized by an increase in vascular endothelial growth factor (VEGF), which promotes the growth of new vessels (angiogenesis) that grow beneath the retina and leak blood and fluid into and below the macular and subretinal space. Successful interference of this pathway has been achieved with the development of inhibitors of vascular endothelial growth factor subtypes, i.e., VEGF inhibitors, initially used to treat various cancers. Photodynamic therapy in combination with anti-VEGF and steroid administration are currently reserved as a second-line therapy for patients not responding to monotherapy with an anti-VEGF agent (Al-Zamil et al., Recent developments in age-related macular degeneration: a review. Clin Interv Aging. 2017; 12:1313-30).

Other common retinal diseases are diabetic macular edema (DME) and retinal vein occlusion (RVO). DME was one of the most common retinal diseases in the US in 2019, affecting approximately 8 million people, and this is expected to grow to 8.8 million people in 2024 (Market Scope 2019, supra). The condition is categorized by a decrease in retinal tension and an increase in vascular pressure caused by the upregulation of VEGF, retinal vascular autoregulation (Browning et al., Diabetic macular edema: evidence-based management. 2018 Indian journal of ophthalmology, 66(1), p. 1736) and inflammatory cytokines and chemokines (Miller et al., Diabetic macular edema: current understanding, pharmacologic treatment options, and developing therapies. 2018, Asia-Pacific Journal of Ophthalmology, 7(1):28-35). The changes that occur from these inflammatory and vasogenic mediators result in the breakdown of the blood retinal barrier (BRB) in the vascular endothelium (Miller et al, supra). Hard exudates enter into the extracellular space causing blurred and distorted central vision, resulting in a decrease in the patient's visual acuity (Schmidt-Erfurth et al., guidelines for the Management of Diabetic Macular Edema by the European Society of Retina Specialists (EURETINA). 2017, Ophthalmologica. 237(4): 185-222). On average, a patient will experience an 8% decrease in visual acuity after 3 years following the start of the condition.

The basis of all available treatments for DME is to try to control the metabolic functions of hyperglycemia and blood pressure (Browning et al., supra). Anti-VEGF therapy is currently considered a first line therapy in the standard of care treatment of DME as it is proven to be less destructive and damaging than other treatment methods (Schmidt-Erfurth et al., supra). The pharmacological route is beneficial because the drugs are manufactured to specifically target VEGF pathways and inhibit the upregulation that occurs with DME (Miller et al., supra). Other treatment options include intravitreal corticosteroid injections, focal laser photocoagulation, and vitrectomy (Browning et al., supra).

RVO affected approximately 1.3 million people in the US in 2019 and is predicted to affect 1.4 million people in the US in 2024 (Market Scope 2019, supra). RVO is a chronic condition in which the retinal circulation contains a blockage leading to leakage, retinal thickening, and visual impairment (Ip and Hendrick, Retinal Vein Occlusion Review. 2018, Asia-Pacific Journal of Ophthalmology, 7(1):40-45; Pierru et al., Occlusions veineuses rétiniennes retinal vein occlusions. 2017, Journal Français d'Ophtalmologie, 40(8): 696-705). The condition is typically seen in patients 55 and older who have a pre-existing condition such as high blood pressure, diabetes, and glaucoma. RVO does not have a projected course as it can either deteriorate a patient's vision quickly or remain asymptomatic. Prognosis of RVO and associated treatment options depend on the classification of the disease as the different variants have different risk factors despite behaving similarly. Classification of the disease is categorized depending on the location of the impaired retinal circulation: branch retinal vein occlusion (BRVO), hemiretinal vein occlusion (HRVO), and central retinal vein occlusion (CRVO). BRVO is more common affecting 0.4% worldwide and CRVO affecting 0.08% worldwide. Studies show that BRVO is more prevalent in Asian and Hispanic groups compared to Caucasians (Ip and Hendrick, supra).

Treatment of RVO currently includes symptomatic maintenance of the condition to avoid further complications, macular edema, and neovascular glaucoma. Anti-VEGF treatment is currently the standard of care treatment and may temporarily improve vision. Other treatment options include lasers, steroids, and surgery (Pierru et al., supra).

Anti-VEGF agents are currently considered the standard of care treatment for wet AMD, DME, and RVO. The first treatment approved for wet AMD by the FDA in 2004 was MACUGEN® (pegaptanib sodium injection by Bausch &

Lomb). Since then, LUCENTIS® (ranibizumab injection by Genentech, Inc.) and EYLEA® (aflibercept injection by Regeneron Pharmaceuticals, Inc.) have been approved for the treatment of wet AMD in 2006, and 2011 respectively, as well as DME and macular edema following RVO. Additionally, in October 2019, BEOVU® (brolucizumab injection by Novartis Pharmaceuticals Corp) was approved by the FDA for the treatment of wet AMD. Other developments are reported in Amadio et al., Targeting VEGF in eye neovascularization: What's new?: A comprehensive review on current therapies and oligonucleotide-based interventions under development. 2016, Pharmacological Research, However, despite these advancements, there are limitations to anti-VEGF treatment. Most patients currently require multiple injections (such as monthly) essentially for the rest of their lives due to rapid vitreous clearance. Moreover, not all patients respond to anti-VEGF treatment. Additionally, these treatment options further have potential risks associated with administration including infection, macular atrophy, loss of vision over time, retinal detachment and elevated intraocular pressure (IOP). Patient complaints include discomfort, eye pain, decreased vision, and increased photosensitivity. In addition to the burden on the patient and risks associated with frequent injections, there are other limitations that are known to be associated with current anti-VEGF treatments such as the potential risk of immunogenicity, complex manufacturing requirement of biologics, macular atrophy, and retinal vasculitis. Importantly, regardless of the number of medications, patients are currently expected to remain on treatment indefinitely.

Tyrosine kinase inhibitors were developed as chemotherapeutics that inhibit signaling of receptor tyrosine kinases (RTKs), which are a family of tyrosine protein kinases. RTKs span the cell membrane with an intracellular (internal) and extracellular (external) portion. Upon lig and binding to the extracellular portion, receptor tyrosine kinases dimerize and initiate an intracellular signaling cascade driven by autophosphorylation using the coenzyme messenger adenosine triphosphate (ATP). Many of the RTK ligands are growth factors such as VEGF. VEGF relates to a family of proteins binding to VEGF-receptor (VEGFR) types, i.e. VEGFR1-3 (all RTKs), thereby inducing angiogenesis. VEGF-A, which binds to VEGFR2, is the target of the anti-VEGF drugs described above. Besides VEGFR1-3 several other RTKs are known to induce angiogenesis such as platelet-derived growth factor receptor (PDGFR) activated by PDGF or stem cell growth factor receptor/type III receptor tyrosine kinase (c-Kit) activated by stem cell factor.

Some TKIs have been evaluated for the treatment of AMD via different administration routes, including pazopanib (GlaxoSmithKline: NCT00463320), regorafenib (Bayer: NCT02348359), and PAN90806 (PanOptica: NCT02022540) all administered as eye drops, as well as X-82, an oral TKI (Tyrogenex; NCT01674569, NCT02348359). However, topically applied eye drops result in poor penetration into the vitreous and limited distribution to the retina due to low solution concentration of TKIs, which tend to have low water solubility, and short residence time of the TKIs on the ocular surface. Moreover, drug concentration upon topical administration is difficult to control due to wash out or user error. Furthermore, systemic administration of TKIs is not practicable, as high doses are required to achieve effective concentrations of the drug in the eye and particularly at the desired tissue. This leads to unacceptable side effects due to high systemic exposure. In addition, drug concentrations are difficult to control. Alternatively, intravitreal injections of TKI suspensions have been performed. However, this way of administration results in rapid clearance of the drug and therefore injections have to be repeated frequently, such as on a daily or at least a monthly basis. In addition, several TKIs are poorly soluble which leads to the formation of aggregates upon intravitreal injection, which can migrate or settle onto the retina and lead to local contact toxicity and holes, such as macular or retinal holes.

Thus, there is an urgent need for an improved treatment of ocular diseases such as AMD, DME, and RVO with TKIs, which is effective over an extended period of time avoiding the need for frequent (monthly or even daily) injections which are currently required for common anti-VEGF therapies, especially for individuals not responding to anti-VEGF therapies (e.g. up to 33% of subjects with DME).

All references disclosed herein are hereby incorporated by reference in their entireties for all purposes.

OBJECTS AND SUMMARY OF THE INVENTION

It is an object of certain embodiments of the present invention to provide an ocular implant comprising a tyrosine kinase inhibitor (TKI) such as axitinib that is effective for treating ocular diseases such as neovascular age-related macular degeneration (AMD), DME, and RVO in a patient for an extended period of time.

Another object of certain embodiments of the present invention is to provide an ocular implant comprising a tyrosine kinase inhibitor (TKI) such as axitinib that provides for sustained release of the TKI into the eye.

Another object of certain embodiments of the present invention is to provide an ocular implant comprising a TKI such as axitinib that is pre-loaded into a syringe, thereby avoiding contamination of the implant prior to injection as no further preparation steps are needed.

Another object of certain embodiments of the present invention is to provide an ocular implant comprising a TKI such as axitinib that is sufficiently biodegradable, i.e., cleared from the eye within a time coinciding with TKI release, avoiding floaters within the patient's eye (empty implant vehicle residues) and/or avoiding the need for removal of the empty implant from the eye after the treatment period.

Another object of certain embodiments of the present invention is to provide an ocular implant comprising a TKI such as axitinib that is biodegradable, wherein decomposition of the implant into smaller particles that may e.g. impact vision are avoided during implant degradation.

Another object of certain embodiments of the present invention is to provide an ocular implant comprising a TKI such as axitinib, wherein the stability of the ocular implant is less affected by varying environments in the eye such as vitreous humor viscosity, pH of the vitreous humor, composition of the vitreous humor and/or intraocular pressure (IOP) when compared to hydrogels formed in situ after injection.

Another object of certain embodiments of the present invention is to provide an ocular implant comprising a TKI such as axitinib that is biocompatible and non-immunogenic due to the implant being free or substantially free of animal- or human-derived components.

Another object of certain embodiments of the present invention is to provide an ocular implant comprising a TKI such as axitinib that is free of preservatives, such as antimicrobial preservatives.

Another object of certain embodiments of the present invention is to provide an ocular implant comprising a TKI such as axitinib that is easy to inject, in particular intravitreally.

Another object of certain embodiments of the present invention is to provide an ocular implant comprising a TKI such as axitinib that contains a therapeutically effective amount of said TKI but is relatively small in length and/or diameter.

Another object of certain embodiments of the present invention is to provide an ocular implant comprising a TKI such as axitinib that is dimensionally stable when in a dry state but changes its dimensions upon hydration, e.g. after administration to the eye.

Another object of certain embodiments of the present invention is to provide an ocular implant comprising a TKI such as axitinib that has a small diameter when in a dry state to fit into the lumen of a fine-diameter needle (such as a 22- to 30-gauge needle) and increases in diameter but decreases in length upon hydration, e.g. after administration to the eye; thus, providing a minimally invasive method of administration.

Another object of certain embodiments of the present invention is to provide an ocular implant comprising a TKI such as axitinib that is injected in a dry form and hydrates in situ (i.e. in the eye) when injected.

Another object of certain embodiments of the present invention is to provide an ocular implant comprising a TKI such as axitinib that when placed in the eye has low TKI concentration at the implant surface thereby avoiding toxicity of the TKI when the implant gets in contact with ocular cells or tissues such as the retina.

Another object of certain embodiments of the present invention is to provide an ocular implant comprising a TKI such as axitinib that is stable and has a defined shape and surface area both in a dry state prior to as well as in a hydrated state after the injection (i.e. inside the eye).

Another object of certain embodiments of the present invention is to provide an ocular implant comprising a TKI such as axitinib that is easy to handle, in particular that does not spill or fragment easily.

Another object of certain embodiments of the present invention is to provide an ocular implant comprising a TKI such as axitinib that enables administration of an exact dose (within a broad dose range), thereby avoiding the risk of over- and under-dosing.

Another object of certain embodiments of the present invention is to provide an ocular implant comprising a TKI such as axitinib that generally stays in the area of the eye to which it was administered.

Another object of certain embodiments of the present invention is to provide an ocular implant comprising a TKI such as axitinib, wherein the implant causes minimal or no visual impairment after administration.

Another object of certain embodiments of the present invention is to provide an ocular implant comprising a TKI such as axitinib that is safe and well tolerated.

Another object of certain embodiments of the present invention is to provide an ocular implant comprising a TKI such as axitinib that does not induce severe adverse events, such as severe ocular adverse events.

Another object of certain embodiments of the present invention is to provide an ocular implant comprising a TKI such as axitinib that provides for sustained release of a therapeutically effective amount of the TKI such as axitinib over an extended period of time, such as over a period of up to 3 months or longer, such as at least 6, at least 9, at least 11 months, or at least 13 months.

Another object of certain embodiments of the present invention is to provide an ocular implant comprising a TKI such as axitinib that provides for sustained release of a TKI such as axitinib over an extended period of time, such as over a period of up to 3 months or longer, such as at least 6, at least 9, at least 11 months, or at least 13 months, thereby avoiding the need for frequent implant administrations.

Another object of certain embodiments of the present invention is to provide an ocular implant comprising a TKI such as axitinib that provides for sustained release of the TKI such as axitinib over an extended period of time, such as over a period of up to 3 months or longer, such as at least 6, at least 9, at least 11 months, or at least 13 months, thereby inhibiting angiogenesis over this period of time.

Another object of certain embodiments of the present invention is to provide an ocular implant comprising a TKI such as axitinib that provides for sustained release of the TKI over an extended period of time, such as over a period of up to 3 months or longer, such as at least 6, at least 9, at least 11 months, or at least 13 months, wherein the TKI levels in ocular tissues such as the retina and the choroid, as well as the vitreous humor are consistently maintained at a therapeutically efficient level, in particular at a level sufficient for inhibition of angiogenesis, over this period of time.

Another object of certain embodiments of the present invention is to provide an ocular implant comprising a TKI such as axitinib that provides for sustained release of a TKI such as axitinib over an extended period of time, such as over a period of up to 3 months or longer, such as at least 6, at least 9, at least 11 months, or at least 13 months, wherein no toxic concentrations of the TKI are observed in ocular tissues such as the retina and the choroid, as well as the vitreous humor over this period of time.

Another object of certain embodiments of the present invention is to provide an ocular implant comprising a TKI such as axitinib that provides for sustained release of a TKI such as axitinib over an extended period of time, such as over a period of up to 3 months or longer, such as at least 6, at least 9, at least 11 months, or at least 13 months, wherein the TKI is not accumulating in the anterior chamber of the eye.

Another object of certain embodiments of the present invention is to provide an ocular implant comprising a TKI such as axitinib that provides sustained release of a TKI over an extended period of time, such as over a period of up to 3 months or longer, such as at least 6, at least 9, at least 11 months, or at least 13 months, wherein the TKI is not or is not substantially resorbed systemically thereby substantially avoiding systemic toxicity.

Another object of certain embodiments of the present invention is to provide a method of treating ocular diseases such as AMD, DME, and RVO in a patient in need thereof, for a treatment period of up to 3 months or longer, such as at least 6, at least 9, at least 11 months, or at least 13 months.

Another object of certain embodiments of the present invention is to provide a method of treating ocular diseases such as AMD, DME, and RVO in a patient in need thereof, for a treatment period of up to 3 months or longer, such as at least 6, at least 9, at least 11 months, or at least 13 months, without the need for the administration of rescue medication during the treatment period, or wherein rescue medication is required to be administered only rarely, such as 1, 2 or 3 times, during the treatment period.

Another object of certain embodiments of the present invention is to provide a method of treating ocular diseases such as AMD, DME, and RVO in a patient in need thereof, such as a patient who has been treated with anti-VEGF before or a patient who is naïve for anti-VEGF treatment.

Another object of certain embodiments of the present invention is to provide a method of treating ocular diseases such as AMD, DME, and RVO in a patient in need thereof, such as a patient who has been treated with anti-VEGF before and has not responded to the previous anti-VEGF treatment.

Another object of certain embodiments of the present invention is to provide a method of treating ocular diseases such as AMD, DME, and RVO in a patient in need thereof, such as a patient with a diagnosis of primary subfoveal neovascularization (SFNV) secondary to AMD.

Another object of certain embodiments of the present invention is to provide a method of treating ocular diseases such as AMD, DME, and RVO in a patient in need thereof, such as a patient with a diagnosis of previously treated subfoveal neovascularization (SFNV) secondary to neovascular AMD with leakage involving the fovea, who has been previously treated with anti-VEGF.

Another object of certain embodiments of the present invention is to provide a method of manufacturing an ocular implant comprising a TKI such as axitinib.

Another object of certain embodiments of the present invention is to provide a method of protecting an ocular implant from premature hydration during storage and handling, wherein the ocular implant is sensitive to moisture such that it for instance changes its dimensions upon hydration.

Another object of certain embodiments of the present invention is to provide a method of minimizing potential tissue damage during injection of an ocular implant.

Another object of certain embodiments of the present invention is to provide a kit comprising one or more ocular implants comprising a TKI such as axitinib and optionally comprising a means for injecting the ocular implant.

Another object of certain embodiments of the present invention is to provide a method of reducing the central subfield thickness as measured by optical coherence tomography in a patient whose central subfield thickness is elevated due to an ocular disease involving angiogenesis by for instance reducing retinal fluid.

Another object of the present invention is to provide a method of essentially maintaining or preventing a clinically significant increase of the central subfield thickness as measured by optical coherence tomography in a patient whose central subfield thickness is elevated due to an ocular disease involving angiogenesis while not increasing retinal fluid.

Another object of certain embodiments of the present invention is to provide a method of reducing, essentially maintaining or preventing a clinically significant increase of the central subfield thickness as measured by optical coherence tomography in a patient whose central subfield thickness is elevated due to an ocular disease involving angiogenesis while improving or at least not impairing the patient's visual acuity as measured for instance by means of best corrected visual acuity.

Another object of certain embodiments of the present invention is to provide a method of improving the vision of a patient whose vision is impaired due to an ocular disease involving angiogenesis.

Another object of certain embodiments the present invention is to provide a method of improving the vision of a patient whose vision is impaired due to the presence of retinal fluid (caused for instance by an ocular disease involving angiogenesis) by means of reducing retinal fluid in the patient (as for instance evidenced by a reduction the central subfield thickness as measured by optical coherence tomography).

One or more of these objects of the present invention and others are solved by one or more embodiments as disclosed and claimed herein.

The individual aspects of the present invention are disclosed in the specification and claimed in the independent claims, while the dependent claims claim particular embodiments and variations of these aspects of the invention. Details of the various aspects of the present invention are provided in the detailed description below.

Throughout this application various references are cited. The disclosures of these references are hereby incorporated by reference into the present disclosure. In case of conflict, the disclosure in the present application prevails.

BRIEF DESCRIPTION OF THE DRAWINGS

FIG. 4A In vitro axitinib release under non-sink dissolution conditions from different implants, comprising an axitinib dose of 625, 716, 245, and 490 (2×245) μg. FIG. 4B In vitro accelerated axitinib release from a 556 μg implant.

FIG. 5A Infrared reflectance (IR) of 1, 2, and 3 implants in rabbits one month post injection. The overall shape of the implants remained intact independent of the number of implants administered. FIG. 5B Vascular leakage was efficiently suppressed for all three doses (15, 30, and 45 μg) after 1 month, while vascular leakage was high for the control animals without implant. Error bars represent standard deviation (SD; solely upper error bars presented).

FIG. 7A Significant biodegradation of the hydrogel component of the implant in rabbit eye was observed over time. At weeks 4 and 8 after injection the implant was still intact, whereas at week 12 early stages of hydrogel degradation were visible. Implant was further narrowed at week 16 due to loss of hydrogel structure. Finally, hydrogel was absent after 20 and 26 weeks and free (undissolved) axitinib particles (white specs) were visible in proximity to the former implant site. FIG. 7B Histopathological analysis demonstrated no inflammation after 26 weeks in regions of undissolved axitinib. Images are presented at 20× magnification (scale: 1000 µm) and 200× magnification (scale: 100 µm).

FIG. 14A) Axitinib was completely released from the 200 µg implant after 225 days as observed by the in vitro real-time assay. FIG. 14B Axitinib was completely released from the 200 µg implant after 12 days as observed by the in vitro accelerated assay. In vitro data were not indicated for in vivo release observed.

FIG. 15 One embodiment of IR images of subject #1 from cohort 2 (2 implants, 400 µg axitinib in total per eye). Implants are clearly visible and well-shaped on the injection day. After 9 months, implants are fully degraded while undissolved axitinib is remaining at the former implant locations. The undissolved axitinib continues to release drug, while after 11 months almost no undissolved axitinib is left.

FIG. 25A, FIG. 25B and FIG. 25C One embodiment of an injector according to the present invention for injecting an implant into the vitreous humor of a patient. This depicted embodiment of an injector comprises a Hamilton syringe body and a Nitinol push wire to deploy the implant. FIG. 25A shows the Hamilton syringe body inside of an injection molded casing. FIG. 25B shows the injection molded casing without the Haimlton syringe body therein. FIG. 25C shows an exploded view of the components of this embodiment of the injector.

DEFINITIONS

Figure 1:
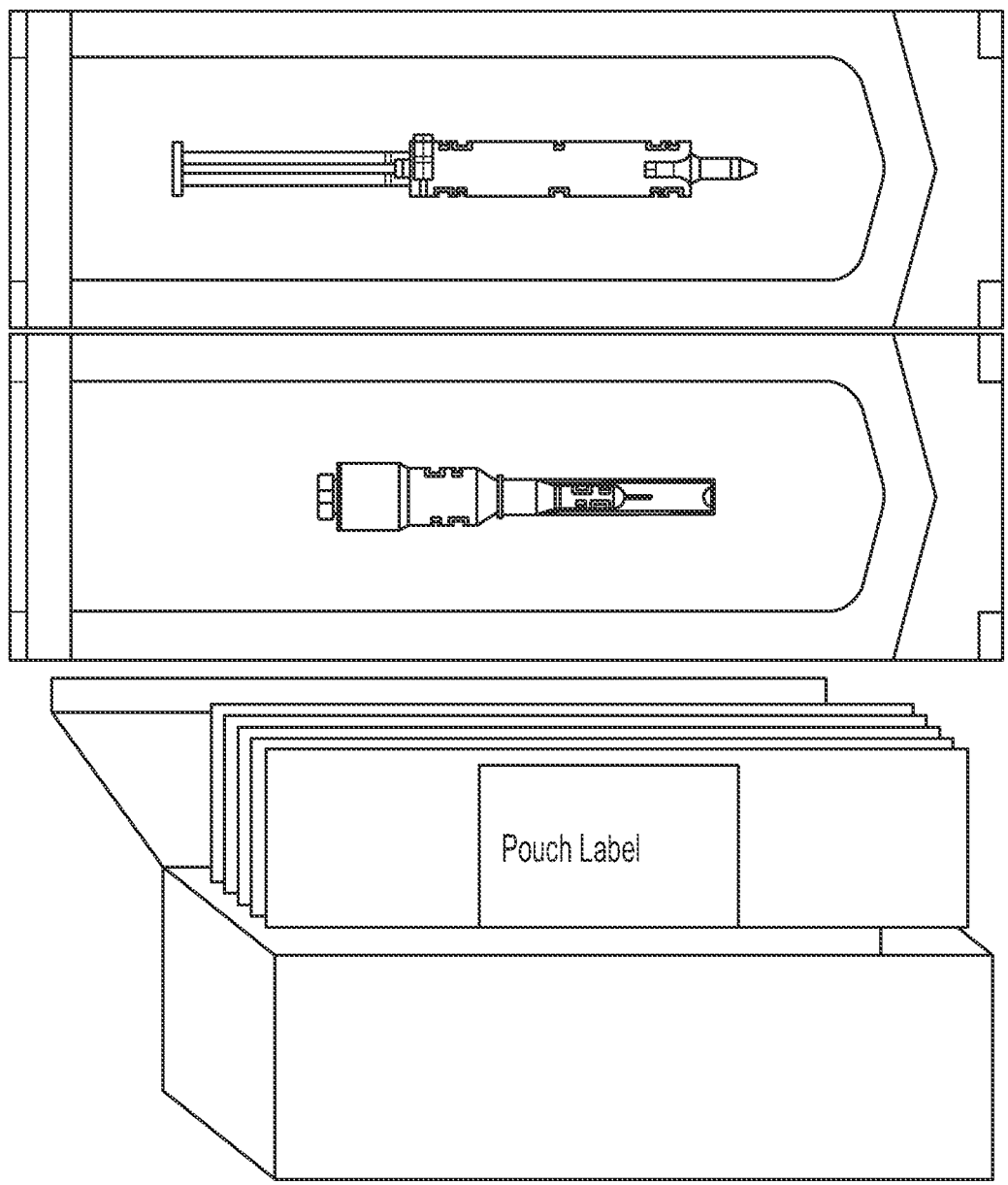
FIG. 1 Schematic representation of one embodiment of the implant packaging. In this embodiment, implants are pre-loaded into thin-walled needles separately packaged from the injection device. An all-in-one device with needles already connected to the injection device is also possible.

The term "implant" as used herein (sometimes also referred to as "depot") refers to an object that contains an active agent, specifically a tyrosine kinase inhibitor (TKI) such as axitinib, as well as other compounds as disclosed herein, and that is administered into the human or animal body, e.g., to the vitreous humor of the eye (also called "vitreous chamber" or "vitreous body") where it remains for a certain period of time while it releases the active agent into the surrounding environment. An implant can have any predetermined shape (such as disclosed herein) before being injected, which shape is maintained to a certain degree upon placing the implant into the desired location, although dimensions of the implant (e.g. length and/or diameter) may change after administration due to hydration as further disclosed herein. In other words, what is injected into the eye is not a solution or suspension, but an already shaped, coherent object. The implant has thus been completely formed as disclosed herein prior to being administered, and in the embodiments of the present invention is not created in situ at the desired location in the eye (as would generally also be possible with suitable formulations). Once administered, over the course of time the implant is biodegraded (as disclosed below) in physiological environment, may thereby change its shape while it decreases in size until it has been completely dissolved/resorbed. Herein, the term "implant" is used to refer both to an implant in a hydrated (also referred to herein as "wet") state when it contains water, e.g. after the implant has been hydrated or re-hydrated once administered to the eye or otherwise immersed into an aqueous environment (such as in vitro), as well as to an implant in its/a dry (dried/dehydrated) state, i.e., after the implant has been produced and dried and just prior to being loaded into a needle, or after having been loaded into a needle as disclosed herein, or wherein the implant has been manufactured in a dry state without the need for dehydration. Thus, in certain embodiments, an implant in its dry/dried state in the context of the present invention may contain no more than about 1% by weight water. The water content of an implant in its dry/dried state may be measured e.g. by means of a Karl Fischer coulometric method. Whenever dimensions of an implant (i.e., length, diameter, or volume) are reported herein in the hydrated state, these dimensions are measured after the implant has been immersed in phosphate-buffered saline at 37° C. for 24 hours. Whenever dimensions of an implant are reported herein in the dry state, these dimensions are measured after the implant has been fully dried (and thus, in certain embodiments, contain no more than about 1% by weight water) and the implant is in a state to be loaded into a needle for subsequent administration. In certain embodiments, the implant is kept in an inert atmosphere glove box containing below 20 ppm of both oxygen and moisture for at least about 7 days. Details of an embodiment of the dimension measurement are reported in Example 6.1.

The term "ocular" as used in the present invention refers to the eye in general, or any part or portion of the eye (as an "ocular implant" according to the invention can in principle be administered to any part or portion of the eye) or any disease of the eye (as in one aspect the present invention generally refers to treating any diseases of the eye ("ocular diseases"), of various origin and nature. The present invention in certain embodiments is directed to intravitreal injection of an ocular implant (in this case the "ocular implant" is thus an "intravitreal implant"), and to the treatment of ocular diseases affecting the posterior segment of the eye, as further disclosed below.

The term "patient" herein includes both human and animal patients. The implants according to the present invention are therefore suitable for human or veterinary medicinal applications. The patients enrolled and treated in the clinical study reported in Example 6 are referred to as "subjects". Generally, a "subject" is a (human or animal) individual to which an implant according to the present invention is administered, such as during a clinical study. A "patient" is a subject in need of treatment due to a particular physiological or pathological condition.

The term "biodegradable" refers to a material or object (such as the ocular implant according to the present invention) which becomes degraded in vivo, i.e., when placed in the human or animal body. In the context of the present invention, as disclosed in detail herein below, the implant comprising the hydrogel within which particles of a TKI such as particles of axitinib, are dispersed, slowly biodegrades over time once deposited within the eye, e.g., within the vitreous humor. In certain embodiments biodegradation takes place at least in part via ester hydrolysis in the aqueous environment of the vitreous. The implant slowly dissolves until it is fully resorbed and is no longer visible in the vitreous.

A "hydrogel" is a three-dimensional network of hydrophilic natural or synthetic polymers (as disclosed herein) that can swell in water and hold an amount of water while maintaining or substantially maintaining its structure, e.g., due to chemical or physical cross-linking of individual polymer chains. Due to their high water content, hydrogels are soft and flexible, which makes them very similar to natural tissue. In the present invention the term "hydrogel" is used to refer both to a hydrogel in the hydrated state when it contains water (e.g. after the hydrogel has been formed in an aqueous solution, or after the hydrogel has been (re-) hydrated once implanted into the eye or other part of the body or otherwise immersed into an aqueous environment) and to a hydrogel in its dry (dried/dehydrated) state when it has been dried to a low water content of e.g. not more than 1% by weight. In the present invention, wherein an active principle is contained (e.g. dispersed) in a hydrogel, the hydrogel may also be referred to as a "matrix".

The term "polymer network" describes a structure formed of polymer chains (of the same or different molecular structure and of the same or different molecular weight) that are crosslinked with each other. The types of polymers suitable for the purposes of the present invention are disclosed herein. The polymer network may also be formed with the aid of a crosslinking agent as also disclosed herein.

The term "amorphous" refers to a polymer or polymer network or other chemical substance or entity which does not exhibit crystalline structures in X-ray or electron scattering experiments.

The term "semi-crystalline" refers to a polymer or polymer network or other chemical substance or entity which possesses some crystalline character, i.e., exhibits some crystalline properties in X-ray or electron scattering experiments.

The term "crystalline" refers to a polymer or polymer network or other chemical substance or entity which has crystalline character as evidenced by X-ray or electron scattering experiments.

The term "precursor" herein refers to those molecules or compounds that are reacted with each other and that are thus connected via crosslinks to form the polymer network and thus the hydrogel matrix. While other materials might be present in the hydrogel, such as active agents or buffers, they are not referred to as "precursors".

The parts of the precursor molecules that are still present in the final polymer network are also called "units" herein. The "units" are thus the building blocks or constituents of the polymer network forming the hydrogel. For example, a polymer network suitable for use in the present invention may contain identical or different polyethylene glycol units as further disclosed herein.

The molecular weight of a polymer precursor as used for the purposes of the present invention and as disclosed herein may be determined by analytical methods known in the art. The molecular weight of polyethylene glycol may for example be determined by any method known in the art, including gel electrophoresis such as SDS-PAGE (sodium dodecyl sulphate-polyacrylamide gel electrophoresis), gel permeation chromatography (GPC), including GPC with dynamic light scattering (DLS), liquid chromatography (LC), as well as mass spectrometry such as matrix-assisted laser desorption/ionization-time of flight (MALDI-TOF) spectrometry or electrospray ionization (ESI) mass spectrometry. The molecular weight of a polymer, including a polyethylene glycol precursor as disclosed herein, is an average molecular weight (based on the polymer's molecular weight distribution), and may therefore be indicated by means of various average values, including the weight average molecular weight (Mw) and the number average molecular weight (Mn). In the case of polyethylene glycol precursors as used in the present invention, the molecular weight indicated herein is the number average molecular weight (Mn).

In certain embodiments of the present invention, the term "fiber" (used interchangeably herein with the term "rod") characterizes an object (i.e., in the present case the implant according to the present invention) that in general has an elongated shape. Specific dimensions of implants of the present invention are disclosed herein. The implant may have a cylindrical or essentially cylindrical shape, or may have a non-cylindrical shape. The cross-sectional area of the fiber or the implant may be either round or essentially round, but may in certain embodiments also be oval or oblong, or may in other embodiments have different geometries, such as cross-shaped, star-shaped or other as disclosed herein.

The term "release" (and accordingly the terms "released", "releasing" etc.) as used herein refers to the provision of agents such as an API from an implant of the present invention to the surrounding environment. The surrounding environment may be an in vitro or in vivo environment as described herein. In certain specific embodiments, the surrounding environment is the vitreous humor and/or ocular tissue, such as the retina and the choroid. Thus, whenever it is herein stated that the implant "releases" or "provides for (sustained) release" of a TKI such as axitinib, this not only refers to the provision of TKI such as axitinib directly from the implant while the hydrogel has not yet (fully) biodegraded, but also refers to the continued provision of TKI such as axitinib to the surrounding environment following full degradation of the hydrogel when remaining TKI is still present in this surrounding environment (e.g. in an agglomerated form as further disclosed herein) for an extended period of time and continues to exert its therapeutic effect. Accordingly, the "treatment period" referred to herein (i.e., the period during which a certain therapeutic effect as described herein is achieved) may extend to a period of time even after the implant/the hydrogel has fully biodegraded as further disclosed herein.

The term "sustained release" is defined for the purposes of the present invention to refer to products (in the case of the present invention the products are implants) which are formulated to make a drug available over an extended period of time, thereby allowing a reduction in dosing frequency compared to an immediate release dosage form (such as e.g. a solution of an active principle that is injected into the eye).

Other terms that may be used herein interchangeably with "sustained release" are "extended release" or "controlled release". "Sustained release" thus characterizes the release of an API, specifically, the TKI, such as axitinib, that is contained in an implant according to the present invention. The term "sustained release" per se is not associated with or limited to a particular rate of (in vitro or in vivo) release, although in certain embodiments of the invention an implant may be characterized by a certain average rate of (in vitro or in vivo) release or a certain release profile as disclosed herein. As an implant of the present invention (whether explicitly referred to herein as a "sustained release" implant or simply as an "implant") provides for sustained release of the API, an implant of the present invention may therefore also be referred to as a "depot".

Whenever it is stated herein that a certain administration or injection is performed "concurrently with" or "simultaneously to" or "at the same time as" an administration or injection of an implant according to the present invention, this means that the respective injection of either two or more implants or the injection of one or more implant(s) together with the injection of a suspension or solution e.g. of an anti-VEGF agent as disclosed herein is normally performed immediately one after the other, i.e., without any significant delay. For example, if a total dose of about 400 μg axitinib is to be administered to one eye and that total dose is comprised in two implants according to the invention, each containing about 200 μg of axitinib, these two implants are normally injected into the vitreous chamber immediately one after the other within the same treatment session, of course by respecting all precautions for a safe and precise injection at the desired site, but without any unnecessary delay. The same applies to the administration of one or more implant(s) according to the present invention concurrently with/simultaneously to/at the same time with the administration of an additional anti-VEGF agent as described herein. In case the additional anti-VEGF agent is administered by an intravitreal injection of a suspension or solution containing the anti-VEGF agent, this injection is also normally intended to take place immediately (as disclosed above) before or after the intravitreal injection of the one or more implant(s) according to the present invention, i.e., ideally during one treatment session.

However, under specific circumstances, e.g. in case complications during the administration of the first implant are experienced and/or the physician carrying out the injection concludes that a second injection during the same session on the same day, or within the following days, may not be advisable, the second implant may also be administered e.g. one or two weeks after the first implant. Since, as will be disclosed in more detail herein, the implants may persist in the vitreous of a human eye for a duration of an extended period of time, such as for about 9 to about 12 months, the administration of two implants e.g. one or two weeks apart is still regarded as "concurrently" in the context of the present invention. Similar considerations apply for the "concurrent" administration of an implant according to the present invention and an anti-VEGF agent. Thus, an anti-VEGF agent can be administered concurrently, i.e., at or around the same time as described herein, with the intravitreal administration of an implant of the present invention.

In certain other embodiments, however, an anti-VEGF agent can also be administered in combination with an intravitreal implant of the present invention such that the anti-VEGF agent is administered later, such as 1 month or 2 months or 3 months after the intravitreal injection of an implant according to the present invention.

The term "rescue medication" generally refers to a medication that may be administered to a patient under predefined conditions (e.g. during a study in case a patient does not sufficiently respond to investigational treatment), or to manage an emergency situation. The conditions for administering rescue medication in the clinical study disclosed in Example 6 herein are indicated under the sub-heading "Rescue medication" in the description of Example 6 (for % rescue medication administration, see in particular Table 27). In certain embodiments of the present invention, "rescue medication" refers to one dose of an anti-VEGF agent as disclosed herein, administered as an intravitreal injection of a solution or suspension of the anti-VEGF agent. In certain specific embodiments, the rescue medication is one dose (2 mg) aflibercept administered by means of intravitreal injection.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that.

The term "average" as used herein refers to a central or typical value in a set of data(points), which is calculated by dividing the sum of the data(points) in the set by their number (i.e., the mean value of a set of data).

As used herein, the singular forms "a," "an", and "the" include plural references unless the context clearly indicates otherwise.

The term "and/or" as used in a phrase such as "A and/or B" herein is intended to include both "A and B" and "A or B".

Open terms such as "include," "including," "contain," "containing" and the like as used herein mean "comprising" and are intended to refer to open-ended lists or enumerations of elements, method steps, or the like and are thus not intended to be limited to the recited elements, method steps or the like but are intended to also include additional, unrecited elements, method steps or the like.

The term "up to" when used herein together with a certain value or number is meant to include the respective value or number.

The terms "from A to B", "of from A to B", and "of A to B" are used interchangeably herein and all refer to a range from A to B, including the upper and lower limits A and B.

The terms "API", "active (pharmaceutical) ingredient", "active (pharmaceutical) agent", "active (pharmaceutical) principle", "(active) therapeutic agent", "active", and "drug" are used interchangeably herein and refer to the substance used in a finished pharmaceutical product (FPP) as well as the substance used in the preparation of such a finished pharmaceutical product, intended to furnish pharmacological activity or to otherwise have direct effect in the diagnosis, cure, mitigation, treatment or prevention of a disease, or to have direct effect in restoring, correcting or modifying physiological functions in a patient.

In certain embodiments, the TKI used according to the present invention is axitinib. Axitinib is the active ingredient in INLYTA® (Pfizer, NY), indicated for the treatment of advanced renal cell carcinoma. It is a small molecule (386.47 Daltons) synthetic tyrosine kinase inhibitor. The primary mechanism of action is inhibition of angiogenesis (the formation of new blood vessels) by inhibition of receptor tyrosine kinases, primarily: VEGFR-1, VEGFR-2, VEGFR-3, PDGFR-β and c-Kit (Keating. Axitinib: a review in advanced renal cell carcinoma. 2015, Drugs, 75(16): 1903-13; Kernt et al., Inhibitory activity of ranibizumab, sorafenib, and pazopanib on light-induced overexpression of platelet-derived growth factor and vascular endothelial growth factor A and the vascular endothelial growth factor receptors 1 and 2 and neuropilin 1 and 2. 2012, Retina, 32(8):1652-63), which are involved in pathologic angiogenesis, tumor growth, and cancer progression. Axitinib is therefore a multi-target inhibitor that inhibits both VEGF and PDGF pathways.

The molecular formula of axitinib is $C_{22}H_{18}N_4OS$, and its IUPAC name is N-methyl-2-[3-((E)-2-pyridin-2-yl-vinyl)-1H-indazol-6-ylsulfanyl]-benzamide. It has the following chemical structure:

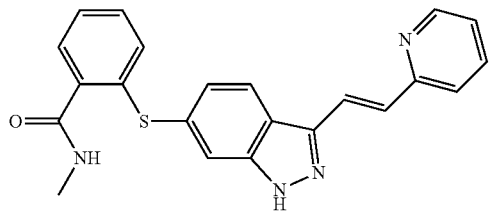 [SMILES: CNC(=O)c1ccccc1Sc1ccc2c(/C=C/c3ccccn3)n[nH]c2c1]

The solubility of axitinib in biorelevant media (PBS, pH 7.2 at 37° C.) has been determined to be low, approximately 0.4 to 0.5 µg/mL. Its partition coefficient (n-octanol/water) is 4.2 (log P; cf. DrugBank entry "axitinib").

For the purposes of the present invention, active agents (including axitinib) in all their possible forms, including any active agent polymorphs or any pharmaceutically acceptable salts, anhydrates, hydrates, other solvates or derivatives of active agents, can be used. Whenever in this description or in the claims an active agent is referred to by name, e.g., "axitinib", even if not explicitly stated, it also refers to any such polymorphs, pharmaceutically acceptable salts, anhydrates, solvates (including hydrates) or derivatives of the active agent.

The term "polymorph" as used herein refers to any crystalline form of an active agent such as axitinib. Frequently, active agents that are solid at room temperature exist in a variety of different crystalline forms, i.e, polymorphs, with one polymorph being the thermodynamically most stable at a given temperature and pressure.

With respect to axitinib, suitable solid forms and polymorphs of axitinib including anhydrous forms and solvates are for example disclosed in A. M. Campeta et al., Journal of Pharmaceutical Sciences, Vol. 99, No. 9, September 2010, 3874-3886. All axitinib polymorphs (whether anhydrous forms or solvates) can be used for preparing implants according to certain embodiments of the present invention, including the most thermodynamically stable polymorph of axitinib referred to as XLI in e.g. US 8,791,140 B2. XLI is an anhydrous crystalline form of axitinib. In certain embodiments of the invention, the axitinib used for preparing the implants according to the present invention is the anhydrous crystalline form XLI. In certain other embodiments, crystalline anhydrous forms of axitinib that are suitable for use in the present invention include (but are not limited to) polymorphs I, IV, VI, and XXV. In addition to the anhydrous forms, there exist numerous solvates of axitinib with various solvents, as also described in the cited art, which also can all be used for preparing implants according to the present invention. All the above-mentioned forms are well-characterized and described in the art, such as in the paper by Campeta et al. cited above, or in the patent literature, including, but not limited to U.S. 8,791,140 B2, U.S. 2006/0094763, and WO 2016/178150 A1. Any of the axitinib polymorphic forms known and disclosed in the art, specifically (but not limited to) the references cited herein, may be used in the present invention.

In certain specific embodiments, the axitinib used for preparing the implants according to the present invention and/or present in the implants according to the present invention is characterized by an XRD pattern comprising at least five characteristic 2θ peaks selected from 8.3, 9.3, 13.7, 15.6, 16.1, 16.5, 17.6, 18.6, 21.0, 22.6, 23.1, 23.4, 24.1, and 26.0, each value ±0.2 2θ°. Particularly, axitinib used for preparing the implants according to the present invention and/or present in the implants according to the present invention is characterized by an XRD pattern comprising at least five characteristic 2θ° peaks selected from 8.3, 9.3, 15.6, 16.5, 17.6, 21.0, 24.1 and 26.0, each value ±0.2 2θ°, and/or $^{13}C$ NMR in DMSO solvent comprising chemical shifts at 26.1, 114.7, 154.8 and 167.8, each shift ±0.2 ppm, and/or $^{13}C$ solid state NMR comprising chemical shifts at 171.1, 153.2, 142.6, 139.5, 131.2, 128.1 and 126.3, each shift ±0.2 ppm, and/or characterized by a DSC isotherm comprising two endothermic peaks ranging between 213° C. to 217° C. (Peak 1) and 219° C. to 224° C. (Peak 2). In one specific embodiment, the non-solvated crystalline form SAB-I of axitinib disclosed in WO 2016/178150 may be used for preparing the implants according to the present invention.

Axitinib inhibits VEGF signaling and it also inhibits PDGF signaling. In addition to inhibiting VEGF/PDGF, it inhibits c-kit, a survival factor for developing blood vessels with a clearance half-life ($t_{1/2}$) of a few hours (Rugo et al., Phase I trial of the oral antiangiogenesis agent AG-013736 in patients with advanced solid tumors. 2005, J clin Oncol., 23(24):5474-83), whereas ranibizumab and aflibercept each have $t_{1/2}$ of several days in the human eye. Longer $t_{1/2}$ of these large molecule antibodies enable them to maintain efficacious tissue concentrations for weeks, whereas small molecules are cleared more quickly. However, due to the low solubility of axitinib and its inclusion in the hydrogel implant of the present invention which remains in the vitreous humor (VH) for an extended period of time, such as for months, therapeutically effective amounts of axitinib are delivered over the period the implant persists in the VH. Therefore, intravitreal sustained delivery of axitinib provides a multi-target inhibitor that can in principle inhibit both VEGF and PDGF pathways without the need of combination therapies and without the need for frequent intravitreal injections.

As used herein, the term "therapeutically effective" refers to the amount of drug or active agent needed to produce a certain desired therapeutic result after administration. For example, in the context of the present invention, one desired therapeutic result would be the reduction of the central subfield thickness (CSFT) as measured by optical coherence tomography in a patient suffering from neovascular AMD as patients suffering from neovascular AMD have elevated CSFT. A "therapeutically effective" amount of an active agent in the context of the present invention may also be a multiple of the $IC_{50}$ this active agent provides against a particular substrate, such as 50 or more times the $IC_{50}$. For example, IC$_{50}$ values of the TKI axitinib against angiogenesis-related RTKs are presented in Table 12.

The abbreviation "PBS" when used herein means phosphate-buffered saline.

The abbreviation "PEG" when used herein means polyethylene glycol.

DETAILED DESCRIPTION

I. The Implant

The Active Principle:

One aspect of the present invention is a sustained release biodegradable ocular implant comprising a hydrogel and at least about 150 µg of a tyrosine kinase inhibitor (TKI), wherein TKI particles are dispersed within the hydrogel. In one embodiment, the present invention provides a sustained release biodegradable ocular implant comprising a hydrogel and at least about 150 µg of a tyrosine kinase inhibitor (TKI), wherein TKI particles are dispersed within the hydrogel, and wherein the implant in its dry state has a length of less than about 17 mm.

The active principle contained in an implant of this aspect of the invention is a TKI. Examples for suitable TKIs are axitinib, sorafenib, sunitinib, nintedanib, pazopanib, regorafenib, cabozantinib, and vandetanib. In particular embodiments, the TKI used in this and other aspects of the present invention is axitinib. Details on axitinib, its chemical structure, polymorphs, solvates, salts etc. and its properties such as solubility are provided above in the definitions section.

All features (individually or any combinations of features) disclosed herein with respect to an implant according to the present invention may be used to characterize the sustained release biodegradable ocular implant comprising a hydrogel and at least about 150 µg of a tyrosine kinase inhibitor (TKI), wherein TKI particles are dispersed within the hydrogel, and wherein the implant in its dry state has a length of less than about 17 mm.

In particular embodiments, the implant of the invention is an intravitreal implant, i.e., is administered to the vitreous humor (also referred to herein as "administered intravitreally").

The TKI, such as axitinib, is contained in the implant of the invention in a range of doses as disclosed herein of at least 150 µg, such as from about 150 µg to about 1800 µg, from about 150 µg to about 1200 µg, or from about 200 µg to about 800 µg. Any TKI, such as axitinib, amount within these ranges may be used, such as about 150 µg, about 200 µg, about 300 µg, about 400 µg, about 500 µg, about 600 µg, about 700 µg, about 800 µg, about 900 µg, about 1000 µg, about 1100 µg or about 1200 µg. In alternative embodiments, the dose of TKI contained in an implant of the invention, such as axitinib, may also be up to about 1800 µg, such as about 1300 µg, about 1400 µg, about 1500 µg, about 1600 µg, about 1700 µg, or about 1800 µg. In further alternative embodiments, the dose of TKI contained in an implant of the invention, such as axitinib, may be even higher than about 1800 µg or higher than about 2000 µg, such as up to about 3000 µg, up to about 6000 µg, or up to about 10000 µg. All mentioned values also include a variance of +25% and −20%, or a variance of +/−10%.

In certain particular embodiments, the doses of axitinib contained in an implant of the invention are:

- a range from about 160 µg to about 250 µg, or from about 180 µg to about 220 µg, or about 200 µg (i.e., including a variance of +25% and −20%, or a variance of +/−10% of 200 µg)
- a range from about 320 µg to about 500 µg, or from about 360 µg to about 440 µg, or about 400 µg (i.e., including a variance of +25% and −20%, or a variance of +/−10% of 400 µg)
- a range from about 375 µg to about 600 µg, or from about 450 µg to about 550 µg, or about 500 µg (i.e., including a variance of +25% and −20%, or a variance of +/−10% of 500 µg)
- a range from about 480 µg to about 750 µg, or from about 540 µg to about 660 µg, or about 600 µg (i.e., including a variance of +25% and −20%, or a variance of +/−10% of 600 µg)
- a range from about 640 µg to about 1000 µg, or from about 720 µg to about 880 µg, or about 800 µg (i.e., including a variance of +25% and −20%, or a variance of +/−10% of 800 µg)
- a range from about 800 µg to about 1250 µg, or from about 900 µg to about 1100 µg, or about 1000 µg (i.e., including a variance of +25% and −20%, or a variance of +/−10% of 1000 µg)
- a range from about 960 µg to about 1500 µg, or from about 1080 µg to about 1320 µg, or about 1200 µg (i.e., including a variance of +25% and −20%, or a variance of +/−10% of 1200 µg)
- a range from about 1440 µg to about 2250 µg, or from about 1620 µg to about 1980 µg, or about 1800 µg (i.e., including a variance of +25% and −20%, or a variance of +/−10% of 1800 µg).

In one preferred embodiment, the dose of axitinib contained in one implant of the invention is from about 480 µg to about 750 µg, or from about 540 µg to about 660 µg, or in particular embodiments is about 600 µg.

The disclosed amounts of TKI, such as axitinib, including the mentioned variances, refer to both the final content of the active principle in the implant, as well as to the amount of active principle used as a starting component per implant when manufacturing the implant.

As will be disclosed in more detail herein below and as will become apparent from the Examples section, in certain embodiments of the invention the total dose of the TKI, such as axitinib, to be administered to a patient, may be contained in two, three or more implants administered concurrently. For example, a dose of about 400 µg of TKI, such as axitinib, may be administered in one implant containing about 400 µg axitinib, or in two implants e.g. each containing about 200 µg axitinib and so on. Of course, one may not only combine two or more identical implants (or implants containing the identical dose), but also two or more different implants (or implants containing different doses) in order to arrive at a desired total dose. In a particular embodiment, a total axitinib dose of from about 480 µg to about 750 µg, or from about 540 µg to about 660 µg, or of about 600 µg, is contained in one implant and only one such implant is administered to a patient in need of such treatment in accordance with the invention. In another embodiment, a total dose of higher than about 600 µg, such as from about 800 µg to about 1250 µg, or from about 900 µg to about 1100 µg, or of about 1000 µg, or a total dose from about 960 µg to about 1500 µg, or from about 1080 µg to about 1320 µg, or of about 1200 µg, or a total dose from about 1440 µg to about 2250 µg, or from about 1620 µg to about 1980 µg, or of about 1800 µg is contained in one implant and only one such implant is administered to a patient in need of such treatment in accordance with the invention. In other embodiments, the total dose administered to a patient in accordance with the present invention may be contained in two or more implants (containing the same or different amounts of API) administered concurrently.

The TKI, such as axitinib, is contained in the implant of the invention and is dispersed or distributed in the hydrogel that is comprised of a polymer network. In certain embodiments, the particles are homogeneously or essentially homogeneously dispersed in the hydrogel. The hydrogel may prevent the particles from agglomerating and may provide a matrix for the particles which holds them in the desired location in the eye while slowly releasing drug.

In certain embodiments of the invention, the TKI particles such as the axitinib particles may be microencapsulated. The term "microcapsule" (also referred to as "microparticle") is sometimes defined as a roughly spherical particle with a size varying between e.g. about 50 nm to about 2 mm. Microcapsules have at least one discrete domain (or core) of active agent encapsulated in a surrounding material, sometimes also referred to as a shell. One suitable agent (without limiting the present disclosure to this) for microencapsulating the TKI, such as the axitinib, for the purposes of the present invention, is poly (lactic-co-glycolic acid).

In other embodiments, the TKI particles such as the axitinib particles are not microencapsulated and are thus dispersed in the hydrogel and thus in the implant of the invention as they are, i.e., without being admixed to or adjoined with or microencapsulated by another material such as (but not limited to) poly (lactic-co-glycolic acid).

Figure 24:
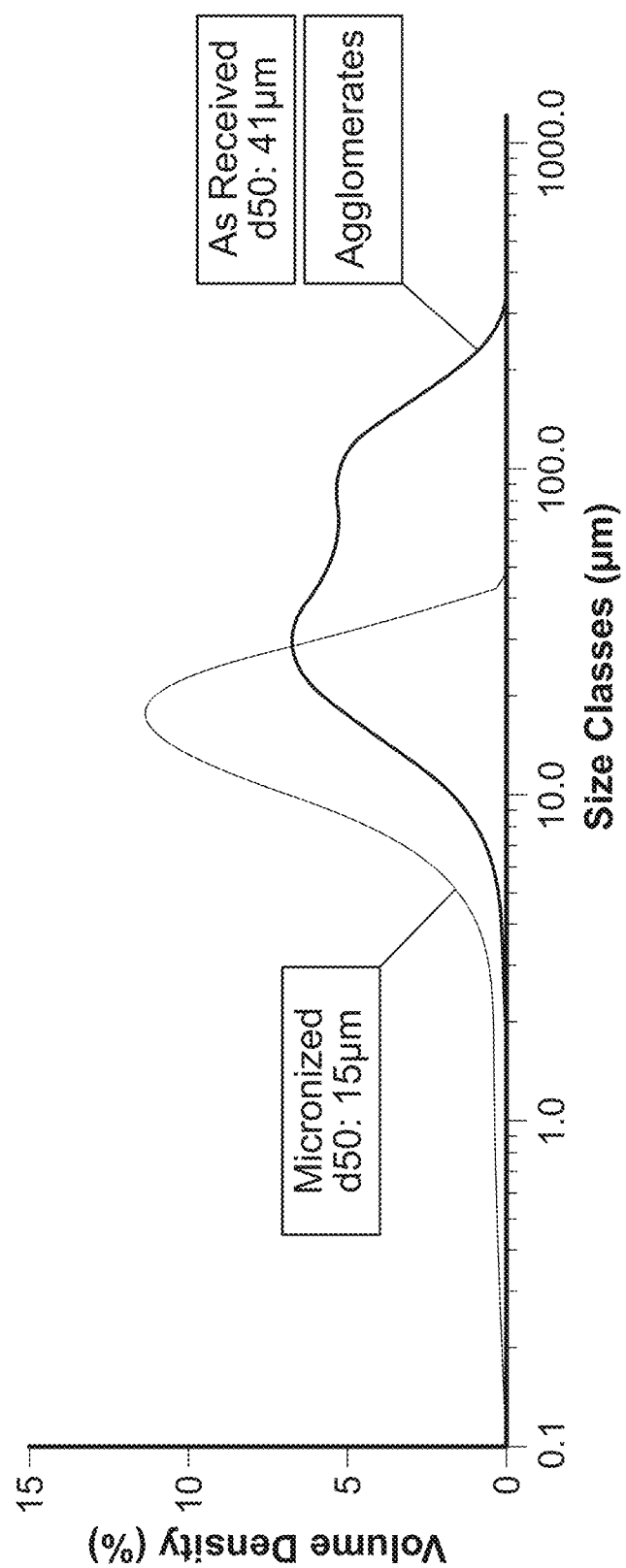
FIG. 24 One embodiment of the agglomeration tendency of axitinib when preparing and casting a hydrogel implant according to an embodiment of the invention using micronized vs. non-micronized axitinib under otherwise identical conditions.

In one embodiment, the TKI particles, such as the axitinib particles, may be micronized particles. In another embodiment, the TKI particles, such as the axitinib particles, may not be micronized. Micronization refers to the process of reducing the average diameter of particles of a solid material. Particles with reduced diameters may have inter alia higher dissolution and erosion rates, which increases the bioavailability of active pharmaceutical ingredients and may have in certain embodiments a positive impact on release kinetics. Furthermore, micronized particles may have a reduced tendency to agglomerate during manufacturing operations (see also FIG. 24). In the composite materials field, particle size is known to affect the mechanical properties when combined with a matrix, with smaller particles providing superior reinforcement for a given mass fraction. Thus, a hydrogel matrix filled with micronized TKI particles may have improved mechanical properties (e.g. brittleness, strain to failure, etc.) compared to a similar mass fraction of larger TKI particles. Such properties are important in manufacturing, during implantation, and during degradation of the implant. Micronization may also promote a more homogeneous distribution of the active ingredient in the chosen dosage form or matrix. The particle size distribution can be measured by methods known in the art, including sieving, laser diffraction or dynamic light scattering. In certain embodiments of the invention the TKI, such as the axitinib, particles used in preparing the implants of the present invention may have a d90 of less than about 100 μm and/or a d50 of less than about 50 μm, or a d90 of less than about 75 μm and/or a d50 or less than about 20 μm as determined by laser diffraction. In specific embodiments, the d90 of the TKI, such as the axitinib, may be less than about 30 μm, less than about 20 μm as determined by laser diffraction. In very particular embodiments, the d90 of the TKI, such as axitinib, is less than about 10 μm as determined by laser diffraction. In these or other embodiments, the d50 of the TKI, such as axitinib, particles used in preparing the implants of the present invention may be less than about 5 μm as determined by laser diffraction. In these or other embodiments, the d10 of the TKI, such as the axitinib, particles used in the present invention may be less than about 3 μm as determined by laser diffraction. In certain embodiments, the d100 of the TKI, such as the axitinib, particles used in the preparation of the implants of the present invention may be less than about 20 μm as determined by laser diffraction. The "d90" (also referred to as "D90" herein) value means that 90 volume-% of all particles within the measured bulk material (which has a certain particle size distribution) have a particle size below the indicated value. For example, a d90 particle size of less than about 10 μm means that 90 volume-% of the particles in the measured bulk material have a particle size below about 10 μm. Corresponding definitions apply to other "d" values, such as the "d10", "d50" or the "d100" values (also referred to herein as the "D10", "D50" and "D100" values, respectively). In certain other embodiments also TKI, such as axitinib, particles with diameters above this specification may be used.

Micronized TKI such as axitinib particles may be purchased per specification from the supplier, or may be prepared e.g. according to the following exemplary procedure for axitinib (disclosed in WO 2016/183296 A1, Example 13): 1800 mL of sterile Water For injection (WFI) is measured into a 2 L beaker and placed on a stir plate stirring at 600 RPM with a stir bar, creating a large WFI vortex in the center of the beaker. One 60 mL BD syringe containing axitinib in ethanol is placed on a syringe pump which is clamped above the WFI beaker. A hypodermic needle (21G, BD) is connected to the syringe and aimed directly into the center of the vortex for dispensation of the axitinib solution. The syringe pump is then run at 7.5 mL/min in order to add the axitinib solution dropwise to the WFI to precipitate micronized axitinib. After micronization, the axitinib is filtered, e.g. through a 0.2 μm vacuum filter and rinsed with WFI. After filtration, the axitinib powder is collected from the filter e.g. by using a spatula and vacuum dried for an extended period of time, such as for about 12 or about 24 hours, in order to remove excess solvent. Another exemplary method of micronizing axitinib is disclosed in Example 9 of WO 2017/091749. The described method of micronization is not limiting, and other methods of micronizing the active agent such as axitinib may equally be used. The disclosed micronization method (or other methods) may also be used for other actives than axitinib.

Another aspect of the present invention is a sustained release biodegradable ocular implant comprising a hydrogel and at least about 150 μg of a tyrosine kinase inhibitor (TKI), wherein TKI particles are dispersed within the hydrogel, and wherein the implant in its dry state has a total weight of about 0.2 mg to about 1.5 mg. In certain embodiments, the TKI is axitinib or another TKI as disclosed herein.

In certain embodiments, the total weight (also referred to herein as "total mass") of an implant according to the present invention in its dry state may be from about 400 μg to about 1.2 mg. In certain specific embodiments, the total weight of an implant according to the invention in its dry state may be from about 0.3 mg to about 0.6 mg, such as from about 0.4 mg to about 0.5 mg, or may be from about 0.8 mg to about 1.1 mg, such as from about 0.9 mg to about 1.0 mg.

All features (individually or any combinations of features) disclosed herein with respect to an implant according to the present invention may be used to characterize the sustained release biodegradable ocular implant comprising a hydrogel and at least about 150 μg of a tyrosine kinase inhibitor (TKI), wherein TKI particles are dispersed within the hydrogel, and wherein the implant in its dry state has a total weight of about 0.2 mg to about 1.5 mg.

The Polymer Network:

In certain embodiments, the hydrogel may be formed from precursors having functional groups that form crosslinks to create a polymer network. These crosslinks between polymer strands or arms may be chemical (i.e., may be covalent bonds) and/or physical (such as ionic bonds, hydrophobic association, hydrogen bridges etc.) in nature.

The polymer network may be prepared from precursors, either from one type of precursor or from two or more types of precursors that are allowed to react. Precursors are chosen in consideration of the properties that are desired for the resultant hydrogel. There are various suitable precursors for use in making the hydrogels. Generally, any pharmaceutically acceptable and crosslinkable polymers forming a hydrogel may be used for the purposes of the present invention. The hydrogel and thus the components incorporated into it, including the polymers used for making the polymer network, should be physiologically safe such that they do not elicit e.g. an immune response or other adverse effects. Hydrogels may be formed from natural, synthetic, or biosynthetic polymers.

Natural polymers may include glycosaminoglycans, polysaccharides (e.g. dextran), polyaminoacids and proteins or mixtures or combinations thereof.

Synthetic polymers may generally be any polymers that are synthetically produced from a variety of feedstocks by different types of polymerization, including free radical polymerization, anionic or cationic polymerization, chain-growth or addition polymerization, condensation polymerization, ring-opening polymerization etc. The polymerization may be initiated by certain initiators, by light and/or heat, and may be mediated by catalysts.

Generally, for the purposes of the present invention one or more synthetic polymers of the group comprising one or more units of polyalkylene glycol, such as polyethylene glycol (PEG), polypropylene glycol, poly(ethylene glycol)-block-poly(propylene glycol) copolymers, or polyethylene oxide, polypropylene oxide, polyvinyl alcohol, poly (vinylpyrrolidinone), polylactic acid, polylactic-co-glycolic acid, random or block copolymers or combinations/mixtures of any of these can be used, while this list is not intended to be limiting.

To form covalently crosslinked polymer networks, the precursors may be covalently crosslinked with each other. In certain embodiments, precursors with at least two reactive centers (for example, in free radical polymerization) can serve as crosslinkers since each reactive group can participate in the formation of a different growing polymer chain.

The precursors may have biologically inert and hydrophilic portions, e.g., a core. In the case of a branched polymer, a core refers to a contiguous portion of a molecule joined to arms that extend from the core, where the arms carry a functional group, which is often at the terminus of the arm or branch. Multi-armed PEG precursors are examples of such precursors and are further disclosed herein below.

Thus a hydrogel for use in the present invention can be made e.g. from one multi-armed precursor with a first (set of) functional group(s) and another multi-armed precursor having a second (set of) functional group(s). By way of example, a multi-armed precursor may have hydrophilic arms, e.g., polyethylene glycol units, terminated with primary amines (nucleophile), or may have activated ester end groups (electrophile). The polymer network according to the present invention may contain identical or different polymer units crosslinked with each other.

Certain functional groups can be made more reactive by using an activating group. Such activating groups include (but are not limited to) carbonyldiimidazole, sulfonyl chloride, aryl halides, sulfosuccinimidyl esters, N-hydroxysuccinimidyl ester, succinimidyl ester, epoxide, aldehyde, maleimides, imidoesters, acrylates and the like. The N-hydroxysuccinimide esters (NHS) are useful groups for crosslinking of nucleophilic polymers, e.g., primary amine-terminated or thiol-terminated polyethylene glycols. An NHS-amine crosslinking reaction may be carried out in aqueous solution and in the presence of buffers, e.g., phosphate buffer (pH 5.0-7.5), triethanolamine buffer (pH 7.5-9.0), borate buffer (pH 9.0-12), or sodium bicarbonate buffer (pH 9.0-10.0).

In certain embodiments, each precursor may comprise only nucleophilic or only electrophilic functional groups, so long as both nucleophilic and electrophilic precursors are used in the crosslinking reaction. Thus, for example, if a crosslinker has only nucleophilic functional groups such as amines, the precursor polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly (allyl amine), or amine-terminated di-or multifunctional poly(ethylene glycol) can be also used to prepare the polymer network of the present invention.

In one embodiment a first reactive precursor has about 2 to about 16 nucleophilic functional groups each (termed functionality), and a second reactive precursor allowed to react with the first reactive precursor to form the polymer network has about 2 to about 16 electrophilic functional groups each. Reactive precursors having a number of reactive (nucleophilic or electrophilic) groups as a multiple of 4, thus for example 4, 8 and 16 reactive groups, are particularly suitable for the present invention. Any number of functional groups, such as including any of 2, 3, 4, 5, 6, 7, 8, 9, 10, 11, 12, 13, 14, 15, or 16 groups, is possible for precursors to be used in accordance with the present invention, while ensuring that the functionality is sufficient to form an adequately crosslinked network.

PEG Hydrogels:

In a certain embodiments of the present invention, the polymer network forming the hydrogel contains polyethylene glycol (PEG) units. PEGs are known in the art to form hydrogels when crosslinked, and these PEG hydrogels are suitable for pharmaceutical applications e.g. as matrix for drugs intended to be administered to all parts of the human or animal body.

The polymer network of the hydrogel implants of the present invention may comprise one or more multi-arm PEG units having from 2 to 10 arms, or 4 to 8 arms, or 4, 5, 6, 7 or 8 arms. The PEG units may have a different or the same number of arms. In certain embodiments, the PEG units used in the hydrogel of the present invention have 4 and/or 8 arms. In certain particular embodiments, a combination of 4- and 8-arm PEG units is utilized.

The number of arms of the PEG used contributes to controlling the flexibility or softness of the resulting hydrogel. For example, hydrogels formed by crosslinking 4-arm PEGs are generally softer and more flexible than those formed from 8-arm PEGs of the same molecular weight. In particular, if stretching the hydrogel prior to or after drying as disclosed herein below in the section relating to the manufacture of the implant is desired, a more flexible hydrogel may be used, such as a 4-arm PEG, optionally in combination with another multi-arm PEG, such as an 8-arm PEG as disclosed above.

In certain embodiments of the present invention, polyethylene glycol units used as precursors have an average molecular weight in the range from about 2,000 to about 100,000 Daltons, or in a range from about 10,000 to about 60,000 Daltons, or in a range from about 15,000 to about 50,000 Daltons. In certain particular embodiments the polyethylene glycol units have an average molecular weight in a range from about 10,000 to about 40,000 Daltons, or of about 20,000 Daltons. PEG precursors of the same average molecular weight may be used, or PEG precursors of different average molecular weight may be combined with each other. The average molecular weight of the PEG precursors used in the present invention is given as the number average molecular weight (Mn), which, in certain embodiments, may be determined by MALDI.

In a 4-arm PEG, each of the arms may have an average arm length (or molecular weight) of the total molecular weight of the PEG divided by 4. A 4a20kPEG precursor, which is one precursor that can be utilized in the present invention thus has 4 arms with an average molecular weight of about 5,000 Daltons each. An 8a20k PEG precursor, which may be used in addition to the 4a20kPEG precursor in the present invention, thus has 8 arms each having an average molecular weight of 2,500 Daltons. Longer arms may provide increased flexibility as compared to shorter arms. PEGs with longer arms may swell more as compared to PEGs with shorter arms. A PEG with a lower number of arms also may swell more and may be more flexible than a PEG with a higher number of arms. In certain particular embodiments, combinations of PEG precursors with different numbers of arms, such as a combination of a 4-arm PEG precursor and an 8-arm precursor, may be utilized in the present invention. In addition, longer PEG arms have higher melting temperatures when dry, which may provide more dimensional stability during storage. For example, an 8-arm PEG with a molecular weight of 15,000 Dalton crosslinked with trilysine may not be able to maintain a stretched configuration at room temperature, whereas a 4-arm 20,000 Dalton PEG crosslinked with an 8-arm 20,000 Dalton PEG may be dimensionally stable in a stretched configuration at room temperature.

When referring to a PEG precursor having a certain average molecular weight, such as a 15kPEG- or a 20kPEG-precursor, the indicated average molecular weight (i.e., a Mn of 15,000 or 20,000, respectively) refers to the PEG part of the precursor, before end groups are added ("20k" here means 20,000 Daltons, and "15k" means 15,000 Daltons—the same abbreviation is used herein for other average molecular weights of PEG precursors). In certain embodiments, the Mn of the PEG part of the precursor is determined by MALDI. The degree of substitution with end groups as disclosed herein may be determined by means of $^1$H-NMR after end group functionalization.

In certain embodiments, electrophilic end groups for use with PEG precursors for preparing the hydrogels of the present invention are N-hydroxysuccinimidyl (NHS) esters, including but not limited to: "SAZ" referring to a succinimidylazelate end group, "SAP" referring to a succinimidyladipate end group, "SG" referring to a succinimidylglutarate end group, and "SS" referring to a succinimidylsuccinate end group.

In certain embodiments, nucleophilic end groups for use with PEG precursors for preparing the hydrogels of the present invention are amine (denoted as "NH$_2$") end groups. Thiol (—SH) end groups or other nucleophilic end groups are also possible.

In certain preferred embodiments, 4-arm PEGs with an average molecular weight of about 20,000 Daltons and an electrophilic end group as disclosed above and 8-arm PEGs also with an average molecular weight of about 20,000 Daltons and with a nucleophilic end group as disclosed above are crosslinked for forming the polymer network and thus the hydrogel according to the present invention.

Reaction of nucleophilic group-containing PEG units and electrophilic group-containing PEG units, such as amine end-group containing PEG units and activated ester-group containing PEG units, results in a plurality of PEG units being crosslinked by a hydrolyzable linker having the formula:

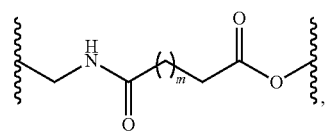

wherein m is an integer from 0 to 10, and specifically is 1, 2, 3, 4, 5, 6, 7, 8, 9, or 10. In one particular embodiment, m is 6, e.g. in the case a SAZ-end group-containing PEG is used. For a SAP-end group, m would be 3, for a SG-end group, m would be 2 and for an SS-end group m would be 1. All crosslinks within the polymer network may be the same, or may be different.

In certain preferred embodiments, the SAZ end group is utilized in the present invention. This end group may provide for increased duration in the eye, and the implant of certain embodiments of the present invention comprising a hydrogel comprising PEG-SAZ units is biodegraded in the eye, such as in the vitreous humor of a human eye, only after an extended period of time, e.g., 9 to 12 months as further disclosed below, and may in certain circumstance persist even longer. The SAZ group is more hydrophobic than e.g. the SAP-, SG- or SS-end groups because of a higher number of carbon atoms in the chain (m being 6, and the total of carbon atoms between the amide group and the ester group being 7).

In certain preferred embodiments, a 4-arm 20,000 Dalton PEG precursor is combined with an 8-arm 20,000 Dalton PEG precursor, such as a 4-arm 20,000 Dalton PEG precursor having a SAZ group (as defined above) combined with an 8-arm 20,000 Dalton PEG precursor having an amine group (as defined above). These precursors are also abbreviated herein as 4a20kPEG-SAZ and 8a20kPEG-NH$_2$, respectively. The chemical structure of 4a20kPEG-SAZ is:

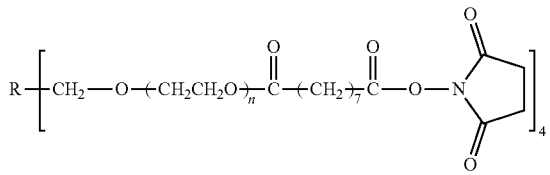

wherein R represents a pentaerythritol core structure. The chemical structure of 8a20kPEG-NH$_2$ (with a hexaglycerol core) is:

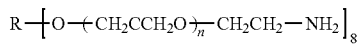

R = hexaglycerol core structure

In the above formulae, n is determined by the molecular weight of the respective PEG-arm.

In certain embodiments, the molar ratio of the nucleophilic and the electrophilic end groups reacting with each other is about 1:1, i.e., one amine group is provided per one SAZ group. In the case of 4a20kPEG-SAZ and 8a20kPEG-NH$_2$ this results in a weight ratio of about 2:1, as the 8-arm PEG contains double the amount of end groups as the 4-arm PEG. However, an excess of either the electrophilic (e.g. the NHS end groups, such as the SAZ) end groups or of the nucleophilic (e.g. the amine) end groups may be used. In particular, an excess of the nucleophilic, such as the amine-end group containing precursor may be used, i.e., the weight ratio of 4a20kPEG-SAZ and 8a20kPEG-NH$_2$ may also be less than 2:1.

Each and any combination of electrophilic- and nucleophilic-group containing PEG precursors disclosed herein may be used for preparing the implant according to the present invention. For example, any 4-arm or 8-arm PEG-NHS precursor (e.g. having a SAZ, SAP, SG or SS end group) may be combined with any 4-arm or 8-arm PEG-NH$_2$ precursor (or any other PEG precursor having a nucleophilic group). Furthermore, the PEG units of the electrophilic- and the nucleophilic group-containing precursors may have the same, or may have a different average molecular weight.

Another nucleophilic group-containing crosslinking agent may be used instead of a PEG-based crosslinking agent. For example, a low-molecular weight amine linker can be used, such as trilysine (or a trilysine salt or derivative, such as trilysine acetate) or other low-molecular weight multi-arm amines.

In certain embodiments, the nucleophilic group-containing crosslinking agent may be bound to or conjugated with a visualization agent. A visualization agent is an agent that contains a fluorophoric or other visualization-enabling group. Fluorophores such as fluorescein, rhodamine, coumarin, and cyanine may for example be used as visualization agents. The visualization agent may be conjugated with the crosslinking agent e.g. through some of the nucleophilic groups of the crosslinking agent. Since a sufficient amount of the nucleophilic groups are necessary for crosslinking, "conjugated" or "conjugation" in general includes partial conjugation, meaning that only a part of the nucleophilic groups are used for conjugation with the visualization agent, such as about 1% to about 20%, or about 5% to about 10%, or about 8% of the nucleophilic groups of the crosslinking agent may be conjugated with a visualization agent. In other embodiments, a visualization agent may also be conjugated with the polymer precursor, e.g. through certain reactive (such as electrophilic) groups of the polymer precursors.

Additional Ingredients:

The implant of the present invention may contain, in addition to the polymer units forming the polymer network as disclosed above and the active principle, other additional ingredients. Such additional ingredients are for example salts originating from buffers used during the preparation of the hydrogel, such as phosphates, borates, bicarbonates, or other buffer agents such as triethanolamine. In certain embodiments of the present invention sodium phosphate buffers (specifically, mono- and dibasic sodium phosphate) are used.

Optionally, preservatives may be used for the implants of the present invention. However, in certain embodiments, the implants of the present invention including the implants containing axitinib as active agent, are free of preservatives, such as anti-microbial preservatives (including, but not limited to benzalkonium chloride (BAK), chlorobutanol, sodium perborate, and stabilized oxychloro complex (SOC)), or are substantially free of such preservatives.

If an in situ gelation is preferred in an embodiment of the invention, possible additional ingredient may be other agents used during manufacture of the hydrogel, such as (without being limited to) viscosity-influencing agents (such as hyaluronic acid etc.), surfactants etc.

In certain embodiments, the inserts of the present invention may contain a visualization agent. Visualization agents that may be used in the context of the invention are all agents that can be conjugated with the components of the hydrogel or can be entrapped within the hydrogel, and that are visible, or may be made visible when exposed e.g. to light of a certain wavelength, or that are constrast agents. Suitable visualization agents for use in the present invention are (but are not limited to) e.g. fluoresceins, rhodamines, coumarins, cyanines, europium chelate complexes, boron dipyromethenes, benzofrazans, dansyls, bimanes, acridines, triazapentalenes, pyrenes and derivatives thereof. A visualization agent may be conjugated with either the nucleophilic- or the electrophilic group-containing precursor of which the polymer network is formed, as disclosed above, or the visualization agent may be a separate (non-conjugated) agent that is added during the manufacture of the implant and that is present in the hydrogel.

Formulation:

In certain embodiments, implants according to the present invention comprise a TKI, a polymer network made from one or more polymer precursors as disclosed herein above in the form of a hydrogel, and optional additional components such as salts etc. remaining in the implant from the production process (such as phosphate salts used as buffers etc.). In certain preferred embodiments, the TKI is axitinib.

In certain embodiments, the implants according to the present invention in their dry state may contain from about 15% to about 80%, such as from about 25% to about 75% by weight TKI and from about 15% to about 80%, such as from about 20% to about 60% by weight polymer units, or in particular embodiments from about 35% to about 65% by weight TKI and from about 25% to about 50% by weight polymer units (dry composition). In specific embodiments, the implants according to the present invention may contain from about 45% to about 55% by weight TKI and from about 37% to about 47% by weight polymer units (dry composition), with the TKI and the polymer units being selected from those disclosed herein above. In other specific embodiments, the implants according to the present invention in their dry state may contain from about 55% to about 75% by weight TKI and from about 20% to about 40% by weight polymer units (dry composition), with the TKI and the polymer units being selected from those disclosed herein above. In other specific embodiments, the implants according to the present invention in their dry state may contain from about 30% to about 45% by weight TKI and from about 47% to about 70% by weight polymer units (dry composition), with the TKI and the polymer units being selected from those disclosed herein above.

In one particular embodiment, the implants according to the present invention in their dry state may contain from about 25% to about 75% by weight axitinib and from about 20% to about 60% by weight PEG units, or from about 35% to about 65% by weight axitinib and from about 25% to about 50% by weight PEG units, or from about 45% to about 55% by weight axitinib and from about 37% to about 47% by weight PEG units, or from about 48% to about 52% by weight axitinib and from about 40% to about 44% by weight PEG units (dry composition). In other particular embodiments, the implants according to the present invention in their dry state may contain from about 55% to about 75% by weight axitinib and from about 20% to about 40% by weight PEG units, or from about 60% to about 75% by weight axitinib and from about 21% to about 31% by weight PEG units (dry composition).

In one further particular embodiment, on a dry weight basis the axitinib to PEG ratio in an implant according to the invention may be approximately 50% by weight or more axitinib to approximately 40% by weight or less PEG, the balance being phosphate salt. Alternatively, on a dry weight basis the axitinib to PEG ratio in an implant according to the invention may be from about 1:1 to about 3:1.

In certain embodiments, the balance of the implant in its dried state (i.e., the remainder of the formulation when TKI, such as axitinib, and polymer hydrogel, such as PEG hydrogel, have already been taken account of) may be salts remaining from buffer solutions as disclosed above. In certain embodiments, such salts are phosphate, borate or (bi) carbonate salts. In one embodiment the buffer salt is sodium phosphate (mono- and/or dibasic).

The amounts of the TKI and the polymer(s) may be varied, and other amounts of the TKI and the polymer hydrogel may be used to prepare implants according to the invention.

In certain embodiments, the maximum amount of drug within the formulation is about two times the amount of the polymer (e.g., PEG) units, but may be higher in certain cases, but it is desired that the mixture comprising, e.g., the precursors, buffers and drug (in the state before the hydrogel has gelled completely) can be uniformly cast into a mold or tubing.

In one embodiment of the invention, the hydrogel after being formed and prior to being dried, i.e., in a wet state, may comprise about 3% to about 20% polyethylene glycol representing the polyethylene glycol weight divided by the fluid weight×100. In one embodiment, the hydrogel in a wet state comprises about 5% to about 15%, such as about 7.5% to about 15%, or about 5% to about 10% polyethylene glycol representing the polyethylene glycol weight divided by the fluid weight×100.

In one embodiment of the invention, the wet hydrogel composition (i.e., after the hydrogel composition has been formed, i.e., all components forming the hydrogel have been admixed) comprises from about 5% to about 50% by weight active principle, such as axitinib, and from about 5% to about 50% or from about 5% to about 30% by weight PEG units.

In certain embodiments, a solids content of about 10% to about 50%, or of about 25% to about 50% (w/v) (wherein "solids" means the combined weight of polymer precursor(s), salts and the drug in solution/suspension) may be utilized in the wet composition when forming the hydrogel for the implants according to the present invention. Thus, in certain embodiments, the total solids content of the wet hydrogel composition to be cast into a mold or tubing in order to shape the hydrogel may be no more than about 60%, or no more than about 50%, or no more than about 40%, such as equal to or lower than about 35% (w/v). The content of TKI, such as axitinib, may be no more than about 40%, or no more than about 30%, such as equal to or lower than about 25% (w/v) of the wet composition. The solids content may influence the viscosity and thus may also influence the castability of the wet hydrogel composition.

In certain embodiments, the water content of the hydrogel implant in its dry (dehydrated/dried) state, e.g. prior to being loaded into a needle, or when loaded in a needle, may be very low, such as not more than 1% by weight of water. The water content may in certain embodiments also be lower than that, possibly not more than 0.25% by weight or even not more than 0.1% by weight. In the present invention the term "implant" is used to refer both to an implant in a hydrated state when it contains water (e.g. after the implant has been (re-)hydrated once administered to the eye or otherwise immersed into an aqueous environment) as well as to an implant in its dry (dried/dehydrated) state, e.g., when it has been dried to a low water content of e.g. not more than about 1% by weight or when the preparation results in such a low water content implant without the necessity of a drying step. In certain embodiments, an implant in its dry state is an implant that after production is kept under inert nitrogen atmosphere (containing less than 20 ppm of both oxygen and moisture) in a glove box for at least about 7 days prior to being loaded into a needle. The water content of an implant may be e.g. measured using a Karl Fischer coulometric method.

In certain embodiments, the total weight (also referred to herein as "total mass") of an implant according to the present invention in its dry state may be from about 200 µg (i.e., 0.2 mg) to about 1.5 mg, or from about 400 µg to about 1.2 mg. In certain specific embodiments, the total weight of an implant according to the invention in its dry state may be from about 0.3 mg to about 0.6 mg, such as from about 0.4 mg to about 0.5 mg, e.g. in case the implant contains axitinib in an amount of from about 160 µg to about 250 µg. In certain other specific embodiments, the total mass of an implant according to the invention in its dry state may be from about 0.75 mg to about 1.25 mg, or from about 0.8 mg to about 1.1 mg, or from about 0.9 mg to about 1.0 mg, e.g. in case the implant contains axitinib in an amount of from about 480 µg to about 750 µg.

In certain embodiments, an implant according to the present invention in its dry state may contain from about 200 µg to about 1000 µg TKI, such as axitinib, per $mm^3$ (i.e., per 1 $mm^3$ volume of the dry implant). In certain specific embodiments, an implant according to the present invention in its dry state may contain from about 200 µg to about 300 µg axitinib per $mm^3$, e.g. in case the implant contains axitinib in an amount of from about 160 µg to about 250 µg. In certain other specific embodiments, an implant according to the present invention in its dry state may contain from about 500 µg to about 800 µg axitinib per $mm^3$, e.g. in case the implant contains axitinib in an amount of from about 480 µg to about 750 µg.

The implants of the present invention may thus have different densities. The densities of the final implants (i.e., in their dry state) may be controlled and determined by various factors, including but not limited to the concentration of the ingredients in the wet composition when forming the hydrogel, and certain conditions during manufacturing of the implant. For example, the density of the final implant in certain embodiments can be increased by means of sonication or degassing, e.g. using vacuum, at certain points during the manufacturing process.

In certain embodiments, implants according to the invention contain a therapeutically effective amount of TKI such as axitinib for release over an extended period of time, but are nevertheless relatively small in length and/or diameter. This is advantageous both in terms of ease of administration (injection) as well as in terms of reducing possible damage to ocular tissue and reducing a possible impact of the patient's vision while the implant is in place. The implants of the present invention combine the benefits of a suitably high dose of the TKI (i.e., a therapeutically effective dose adjusted to a particular patient's need) with a relatively small implant size.

Exemplary implants according to the invention are disclosed in the Examples section, in Tables 1, 6, 21.1, 21.2, and 29 (including prophetic examples of implants according to the invention containing a high amount of TKI which are disclosed in Table 29).

Dimensions of the Implant and Dimensional Change upon Hydration through Stretching:

The dried implant may have different geometries, depending on the method of manufacture, such as the use of mold or tubing into which the mixture comprising the hydrogel precursors including the TKI is cast prior to complete gelling. The implant according to the present invention is also referred as a "fiber" (which term is used interchangeably herein with the term "rod"), wherein the fiber is an object that has in general an elongated shape. The implant (or the fiber) may have different geometries, with specific dimensions as disclosed herein.

In one embodiment, the implant is cylindrical or has an essentially cylindrical shape. In this case, the implant has a round or an essentially round cross-section.

In other embodiments of the invention, the implant is non-cylindrical, wherein the implant is optionally elongated in its dry state, wherein the length of the implant is greater than the width of the implant, wherein the width is the largest cross sectional dimension that is substantially perpendicular to the length. In certain embodiments, the width may be about 0.1 mm to about 0.5 mm. Various geometries of the outer implant shape or its cross-section may be used in the present invention. For example, instead of a round diameter fiber (i.e., a cylindrical implant), a cross-shaped fiber (i.e., wherein the cross-sectional geometry is cross-like) may be used. Other cross-sectional geometries, such as oval or oblong, rectangular, triangular, star-shaped etc. may generally be used. In certain embodiments, the fiber may also be twisted. In embodiments where the implant is administered to the eye by means of a needle, the dimensions of the implant (i.e., its length and diameter) and its cross-sectional geometry must be such as to enable loading the implant into the needle, particularly a fine-diameter needle such as a 25-gauge or 27-gauge needle as further disclosed herein.

The polymer network, such as the PEG network, of the hydrogel implant according to certain embodiments of the present invention may be semi-crystalline in the dry state at or below room temperature, and amorphous in the wet state. Even in the stretched form, the dry implant may be dimensionally stable at or below room temperature, which may be advantageous for loading the implant into the needle and for quality control.

Upon hydration of the implant in the eye (which can be simulated by immersing the implant into PBS, pH 7.2 at 37° C.) the dimensions of the implant according to the invention may change: generally, the diameter of the implant may increase, while its length may decrease or at least may stay essentially the same. An advantage of this dimensional change is that, while the implant in its dry state is sufficiently thin to be loaded into a fine diameter needle (such as a 25-, or 27-, or in some cases even a smaller diameter needle, such as a 30-gauge needle) to be injected into the eye, once it has been placed in eye, e.g., in the vitreous humor, the implant may become shorter to better fit within the limited, small volume of the eye. The needles used for injection of the implants of the present invention as disclosed herein, such as the 25- or 27-gauge needles in certain embodiments, are small in diameter (and e.g. may have an inner diameter of about 0.4 mm). As the implant also may become softer upon hydration, injuries of any ocular tissue can be prevented or minimized even when the implant comes into contact with such tissue. In certain embodiments, the dimensional change is enabled at least in part by the "shape memory" effect introduced into the implant by means of stretching the implant in the longitudinal direction during its manufacture (as also disclosed below in the section "Method of manufacture"). In certain embodiments, the stretching may either be performed in the dry or in the wet state, i.e., after drying the hydrogel implant, or before drying. It is noted that if no stretching is performed, and the hydrogel implant is only dried and cut into a desired length, the implant may increase in both diameter and length upon hydration. If this is not desired, the hydrogel fiber may be dry or wet stretched.

In pre-formed dried hydrogels, a degree of molecular orientation may be imparted by dry-stretching the material then allowing it to solidify, locking in the molecular orientation. This can be accomplished in certain embodiments by drawing the material (optionally while heating the material to a temperature above the melting point of the crystallizable regions of the material), then allowing the crystallizable regions to crystallize. Alternatively, in certain embodiments the glass transition temperature of the dried hydrogel can be used to lock in the molecular orientation for polymers such as PVA that have a suitable glass transition temperature. Still another alternative is to stretch the gel prior to complete drying (also referred to as "wet stretching") and then drying the material while under tension. The molecular orientation provides one mechanism for anisotropic swelling upon introduction into a hydrating medium such as the vitreous. Upon hydration the implant of certain embodiments will swell only in the radial dimension, while the length will either decrease or be essentially maintained. The term "anisotropic swelling" means swelling preferentially in one direction as opposed to another, as in a cylinder that swells predominantly in diameter, but does not appreciably expand (or does even contract) in the longitudinal dimension.

The degree of dimensional change upon hydration may depend inter alia on the stretch factor. As an example, stretching at e.g. a stretch factor of about 1.3 (e.g. by means of wet stretching) may have a less pronounced effect or may not change the length during hydration to a large extent. In contrast, stretching at e.g. a stretch factor of about 1.8 (e.g. by means of wet stretching) may result in a markedly shorter length during hydration. Stretching at e.g. a stretch factor of 4 (e.g. by means of dry stretching) could result in a much shorter length upon hydration (such as, for example, a reduction in length from 15 to 8 mm). One skilled in the art will appreciate that other factors besides stretching can also affect swelling behavior.

Among other factors influencing the possibility to stretch the hydrogel and to elicit dimensional change of the implant upon hydration is the composition of the polymer network. In the case PEG precursors are used, those with a lower number of arms (such as 4-armed PEG precursors) contribute in providing a higher flexibility in the hydrogel than those with a higher number of arms (such as 8-armed PEG precursors). If a hydrogel contains more of the less flexible components (e.g. a higher amount of PEG precursors containing a larger number of arms, such as the 8-armed PEG units), the hydrogel may be firmer and less easy to stretch without fracturing. On the other hand, a hydrogel containing more flexible components (such as PEG precursors containing a lower number of arms, such as 4-armed PEG units) may be easier to stretch and softer, but also swells more upon hydration. Thus, the behavior and properties of the implant once it has been placed into the eye (i.e., once the hydrogel becomes (re-) hydrated) can be tailored by means of varying structural features as well as by modifying the processing of the implant after it has been initially formed.

Exemplary dimensions of implants used in the Examples herein below are provided inter alia in Tables 6, 21.1 and 21.2 of the Examples section. Specific implants containing about 200 µg and about 600 µg axitinib are disclosed in Tables 21.1 and 21.2. Implants containing about 200 µg or about 600 µg axitinib may however also have dimensions (i.e., lengths and/or diameters) differing from the dimensions disclosed in these Tables. The dried implant dimensions inter alia depend on the amount of TKI incorporated as well as the ratio of TKI to polymer units and can also be controlled by the diameter and shape of the mold or tubing in which the hydrogel is allowed to gel. Furthermore, the diameter of the implant is further determined inter alia by (wet or dry) stretching of the hydrogel strand once formed. The dried strand (after stretching) is cut into segments of the desired length to form the implant; the length can thus be chosen as desired.

In the following, embodiments of implants with specific dimensions are disclosed. Whenever the dimensional ranges or values disclosed herein relate to the length and the diameter of an implant, the implant is cylindrical or essentially cylindrical. However, all values and ranges disclosed herein for lengths and diameters of cylindrical implants may equally be used for lengths and widths, respectively, of non-cylindrical implants as also disclosed herein.

In certain embodiments, an implant of the present invention may have in its dry state a length of less than about 17 mm. In specific embodiments, the length of an implant in its dry states may be less than about 15 mm, or less than or equal to about 12 mm, or less than or equal to about 10 mm, or less than or equal to about 8.5 mm. In specific embodiments, an implant of the present invention may have in its dry state a length of about 12 to about 17 mm, or may have in its dry state a length of about 6 mm to about 10 mm or specifically of about 6 mm to about 9 mm.

In certain embodiments, an implant of the present invention may have in its dry state a diameter of about 0.1 mm to about 0.5 mm. In certain other embodiments, an implant in its dry state may have a diameter of about 0.2 mm to about 0.5 mm. In specific embodiments, an implant in its dry state may have a diameter of about 0.2 mm to about 0.4 mm, or of about 0.3 mm to about 0.4 mm. In specific embodiments, an implant of the present invention may have a diameter in the dry state of about 0.2 mm to about 0.3 mm, or of about 0.3 mm to about 0.4 mm.

In particular embodiments, an implant in its dry state may have a legth of about 6 mm to about 10 mm and a diameter of about 0.2 to about 0.4 mm.

In certain embodiments, an implant of the present invention may have in its wet/hydrated state a length of about 6 mm to about 12 mm. In certain other embodiments, an implant of the present invention may have in its wet/hydrated state a length of equal to or less than about 10 mm, or of about 6 mm to about 10 mm. In specific embodiments, an implant of the present invention in its wet/hydrated state may have a length of about 6 mm to about 8 mm.

In certain embodiments, an implant of the present invention may have in its wet/hydrated state a diameter of equal to or less than about 0.8 mm, or of about 0.5 mm to about 0.8 mm, or of about 0.65 mm to about 0.8 mm. In specific embodiments, an implant of the present invention may have a diameter in its wet/hydrated state of about 0.7 mm to about 0.8 mm.

In particular embodiments, an implant in its wet/hydrated state may have a legth of equal to or less than about 10 mm and a diameter of equal to or less than about 0.8 mm.

In embodiments of the present invention, the diameter of an implant in its dry state must be such that the implant can be loaded into a thin-diameter needle as disclosed herein, such as a 25-gauge or 27-gauge needle. Specifically, in one embodiment an implant containing from about 480 µg to about 750 µg axitinib may have a diameter such that it can be loaded into a 25-gauge needle, or that it can be loaded into a 27-gauge needle without afflicting any damage to the implant while loading, and such that the implant remains stably in the needle during further handling (including packaging, sterilization, shipping etc.).

Whenever herein a length or a diameter of an implant of the invention in the wet/hydrated state is disclosed (in mm), this disclosure refers to the implant's length or the diameter, respectively, determined after 24 hours at 37° C. at pH 7.2. It is understood that in this context a pH of 7.2 comprises a pH range of about 7.2 to about 7.4.

The dimensions of an implant may further change (e.g. the length may increase slightly again) over the course of time (i.e., after 24 hours) when the implant remains in these conditions. However, whenever hydrated dimensions of an implant are reported herein, these are measured after 24 hours at a pH of 7.2 at 37° C. in PBS as disclosed above.

In case several measurements of the length or diameter of one implant are conducted, or several datapoints are collected during the measurement, the average (i.e., mean) value is reported as defined herein. The length and diameter of an implant according to the invention may be measured e.g. by means of microscopy, or by means of an (optionally automated) camera system as described in Example 6.1.

In certain embodiments, an implant of the present invention may have a ratio of the diameter in the hydrated state to the diameter in the dry state of less than about 5 mm, or less than about 4 mm, or less than about 3.25 mm, or less than about 2.5 mm, or less than about 2.25 mm, or less than about 2.10 mm.

In certain same or other embodiments, an implant of the present invention may have a ratio of the length in the dry state to the length in the hydrated state of greater than about 0.7, or greater than about 0.8, or greater than about 0.9, or greater than about 1.0. In certain specific embodiments, the ratio of the length of an implant in the dry state to the length of the implant in the hydrated state may be greater than about 1.5, or even greater than about 2.0. This ratio of length in the dry state to length in the hydrated state may apply in addition to, or independently of, the ratio of the diameter in the hydrated state to the diameter in the dry state disclosed above.

A small diameter in the dry state may be advantageous as the implant may fit into a small diameter needle for injection as disclosed herein, such as a 25-gauge or 27-gauge needle. Also, only moderate swelling upon hydration may be advantageous for the implant to not occupy too much space in the vitreous humor. A relatively shorter length of the implant may be advantageous in reducing the potential likelihood for contact with the retina.

In one embodiment, an implant of the present invention contains from about 160 µg to about 250 µg, or from about 180 µg to about 220 µg, or a bout 200 µg axitinib, is in the form of a fiber (or cylinder) and has a length of about 14.5 mm to about 17 mm, or of about 15 mm to about 16.5 mm and a diameter of about 0.20 mm to about 0.30 mm in the dried state. Such an implant may decrease in length and increase in diameter upon hydration in vivo in the eye, such as in the vitreous humor, or in vitro (wherein hydration in vitro is measured in phosphate-buffered saline at a pH of 7.2 at 37° C. after 24 hours) to a length of about 6.5 mm to about 8 mm or of about 7 mm to about 8.5 mm, and a diameter of about 0.65 mm to about 0.8 mm, or of about 0.70 to about 0.80 mm. In one embodiment, this dimensional change may be achieved by dry stretching as disclosed herein at a stretch factor of about 2 to about 5, or a stretch factor of about 3 to about 4.5.

In another embodiment, an implant of the present invention contains from about 480 µg to about 750 µg, or from about 540 µg to about 660 µg, or a bout 600 µg of axitinib, is in the form of a fiber (cylinder) and in its dried state may have a length of in the range of from about 6 mm or about 7 mm to about 12 mm and a diameter of about 0.25 mm to about 0.50 mm, or a length of about 7 mm to about 10 mm, or of about 8 mm to about 11 mm, and a diameter of about 0.3 mm to about 0.4 mm. In specific embodiments, an implant of the present invention that contains from about 480 µg to about 750 µg, or from about 540 µg to about 660 µg, or a bout 600 µg of axitinib, is in the form of a fiber (cylinder) and in its dried state may have a length of from about 7 mm to about 10 mm, such as from about 7 mm to about 9 mm, and a diameter of from about 0.3 mm to about 0.4 mm, such as from about 0.35 mm to about 0.39 mm.

Such an implant may increase in diameter upon hydration in vivo in the eye, such as in the vitreous humor, or in vitro (wherein hydration in vitro is measured in phosphate-buffered saline at a pH of 7.2 at 37° C. after 24 hours) while its length may be essentially maintained or may be reduced, or only slightly increased to a length of e.g. in the range of from about 6 mm or about 9 mm to about 12 mm and a diameter of about 0.5 mm to about 0.8 mm, or a length of about 9.5 mm to about 11.5 mm and a diameter of from about 0.65 mm to about 0.75 mm or about 0.8 mm in its hydrated state. In specific embodiments, an implant of the present invention that contains from about 480 µg to about 750 µg, or from about 540 µg to about 660 µg, or a bout 600 µg of axitinib and is in the form of a fiber (cylinder) in its hydrated state (i.e., at a pH of 7.2 at 37° C. after 24 hours as explained above) may have a length of from about 6 mm to about 10.5 mm, such as from about 6.5 mm to about 8.5 mm, and a diameter from about 0.7 mm to about 0.8 mm.

In one embodiment, the length of an implant of the present invention that contains from about 480 µg to about 750 µg, or from about 540 µg to about 660 µg, or a bout 600 µg of axitinib in the dried state is no longer than 10 mm, and in the hydrated state (as measured in phosphate-buffered saline at a pH of 7.2 at 37° C. after 24 hours) is also no longer or not substantially longer than about 10 mm, or no longer than about 9 mm, or no longer than about 8 mm.

In one or more embodiment(s), the above-described dimensional change can be achieved by wet stretching at a stretch factor of about 0.5 to about 5, or a stretch factor of about 1 to about 4, or a stretch factor of about 1.3 to about 3.5, or a stretch factor of about 1.7 to about 3, or a stretch factor of about 2 to about 2.5. In other embodiments the implant of the present invention containing from about 480 µg to about 750 µg, or from about 540 µg to about 660 µg, or a bout 600 µg of axitinib may be longer than about 12 mm in the dry state, but may end up being shorter than about 10 mm or about 9 mm in the hydrated state.

In certain embodiments, the stretching thus creates a shape memory, meaning that the implant upon hydration when administered into the eye, e.g., into the vitreous cavity, will shrink in length and widen in diameter until it approaches (more or less) its equilibrium dimensions, which are determined by the original molded dimensions and compositional variables. While the narrow dry dimensions facilitate administration of the product through a small gauge needle, the widened diameter and shortened length after administration yield a shorter implant (such as about 9 to 10 mm long, or at least not much longer than that) in the posterior chamber of the eye relative to the eye diameter minimizing potential contact with surrounding eye tissues. Thus, in one aspect the present invention also relates to a method of imparting shape memory to a hydrogel fiber comprising an active agent such as a TKI, e.g. axitinib, dispersed in the hydrogel by stretching the hydrogel fiber in the longitudinal direction. In another aspect the present invention relates to a method of manufacturing an ocular implant comprising a hydrogel comprising an active agent, such as a TKI, e.g. axitinib, dispersed therein, wherein the implant changes its dimensions upon administration to the eye, the method comprising preparing a fiber of the hydrogel and stretching the fiber in the longitudinal direction.

Figure 4A:
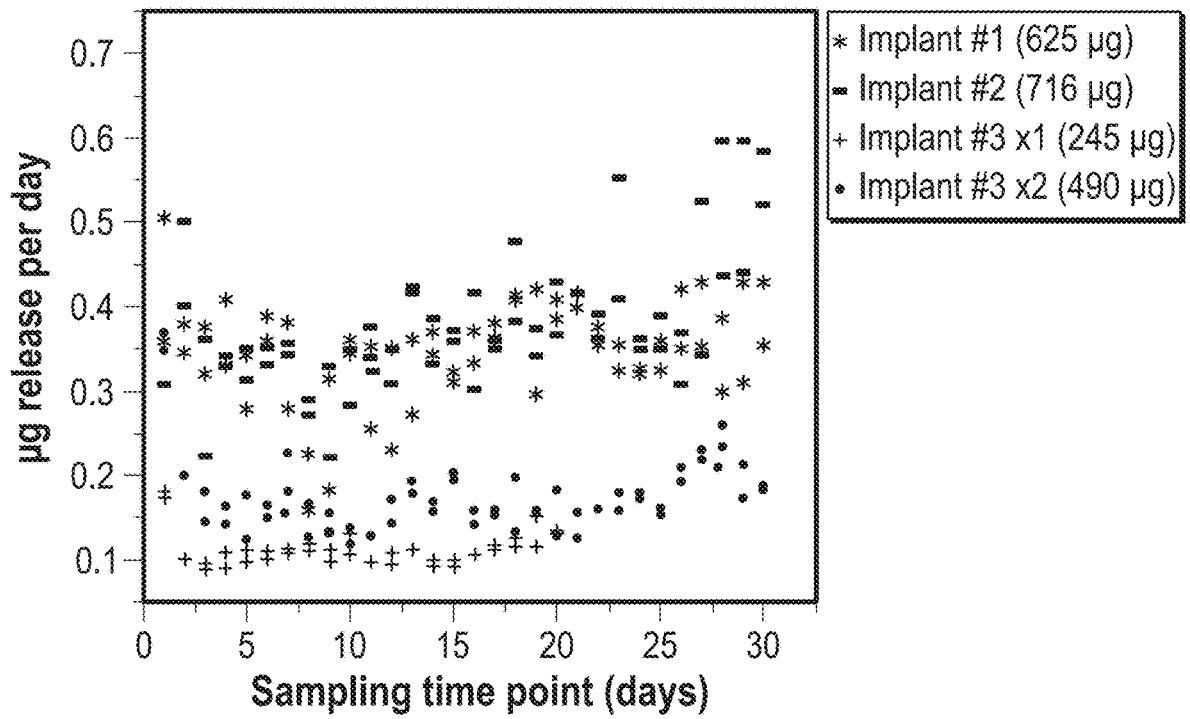
FIG. 4A and FIG. 4B One embodiment of in vitro axitinib release per day for different implants.

In Vitro Release:

The in vitro-release of TKI from the implants of the invention can be determined by various methods disclosed in detail in Example 2:

Briefly, one method to determine the in vitro release of the TKI from the implant is under non-sink simulated physiological conditions in PBS (phosphate-buffered saline, pH 7.2) at 37° C., with daily replacement of PBS in a volume comparable to the vitreous volume in the human eye. Results for exemplary implants are shown in FIG. 4A. In the tested implants comprising axitinib in a PEG hydrogel matrix as described in Example 2 the higher dose strengths resulted in higher axitinib concentrations in the release medium.

Generally, in embodiments of the invention, an implant according the invention may release on average about 0.1 µg to about 3 µg, or a bout 0.25 µg to about 2.5 µg, or a bout 0.1 µg to about 2 µg, or may release about 0.25 µg to about 1.5 µg per day in vitro in PBS at pH 7.2 and 37° C. for a period of 30 days.

In one embodiment, an implant according to the invention containing about 200 µg axitinib, may release on average in vitro about 0.01 µg to about 0.15 µg of axitinib per day in phosphate-buffered saline at pH 7.2 and 37° C. for a period of 30 days.

In one embodiment, an implant according to the invention containing about 600 µg axitinib may release on average in vitro about 0.3 µg to about 0.5 µg of axitinib per day in phosphate-buffered saline at pH 7.2 and 37° C. for a period of 30 days.

Figure 14A:
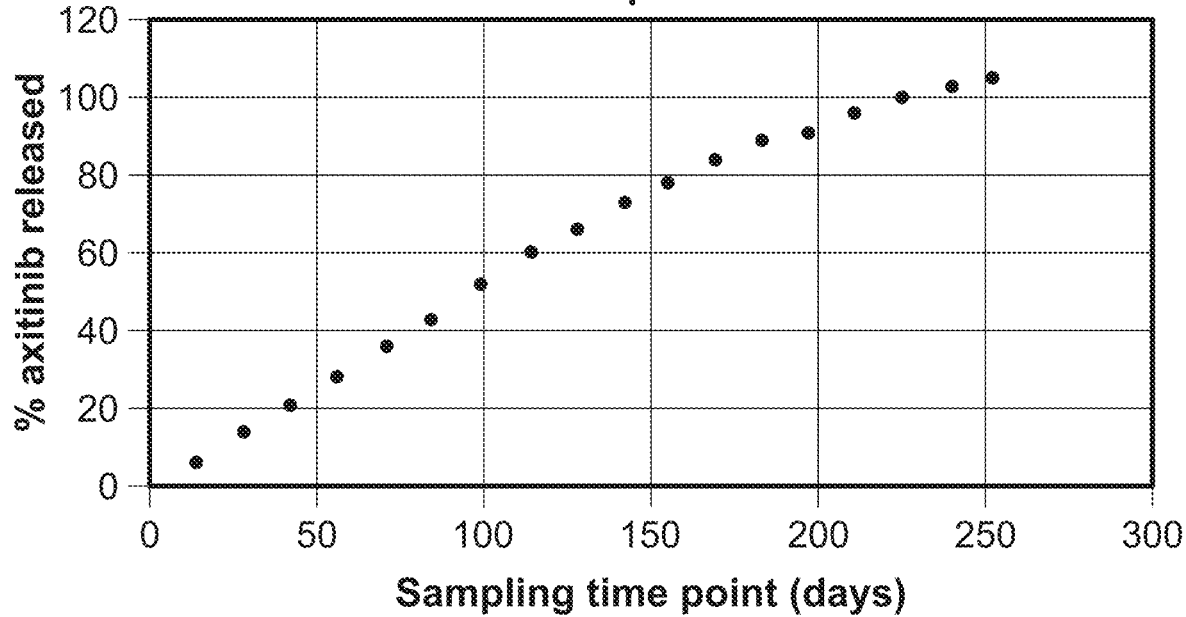
FIG. 14A and FIG. 14B One embodiment of in vitro axitinib release from a 200 µg implant.
Figure 14B:
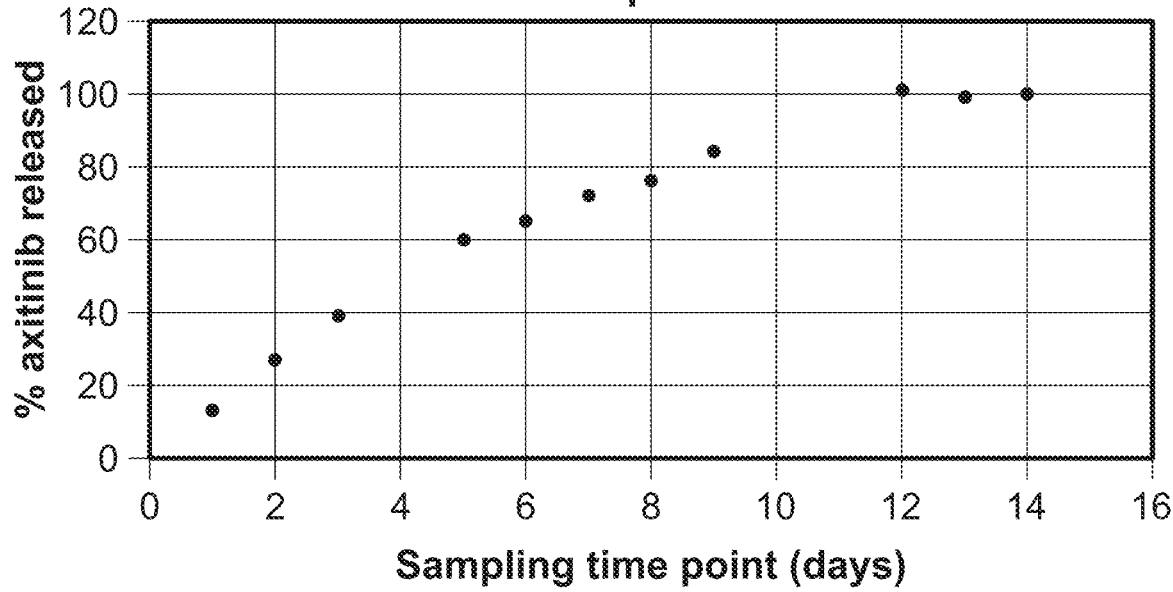

In an accelerated in vitro test, also described in detail in Example 2, the release of the TKI from the implant can be determined in a 25:75 ethanol/water mixture (v/v) at 37° C. This accelerated in vitro test can be completed in about 2 weeks. FIG. 14B shows the accelerated in vitro release data for an implant according to the invention containing about 200 µg axitinib, and FIG. 4B the accelerated in vitro release data for an implant according to the invention containing about 556 µg axitinib.

In one embodiment, an implant according to the invention containing about 200 µg axitinib releases in vitro about 35% to about 45% of the axitinib in 3 days, about 65% to about 75% of the axitinib in 7 days, and about 90% to about 100% of the axitinib in 12 to 13 days in a 25:75 ethanol/water mixture (v/v) at 37° C.

In one embodiment, an implant according to the invention containing about 600 µg axitinib releases in vitro about 40% to about 60% of the axitinib in 2 days, about 65% to about 85% of the axitinib in 4 days, and about 75% to about 90% of the axitinib in 6 days in a 25:75 ethanol/water mixture (v/v) at 37° C. An implant according to the invention containing about 600 µg axitinib may also release in vitro about 45% to about 55% of the axitinib in 2 days, about 70% to about 80% of the axitinib in 4 days, and about 80% to about 90% of the axitinib in 6 days in a 25:75 ethanol/water mixture (v/v) at 37° C.

Finally, the release of TKI from implants of the present invention can also be determined under real-time sink simulated physiological conditions, as also described in detail in Example 2. For this real-time test, release of the TKI is determined in PBS (pH 7.2)/0.01% NaF at 37° C. with an octanol top layer on the PBS. This is one method to qualitatively simulate release of the TKI from the implant into the vitreous humor and from there resorption of the TKI into ocular tissue. An exemplary real-time release profile for an implant according to the present invention containing about 200 µg axitinib is shown in FIG. 14A.

In one embodiment, an implant according to the invention containing about 200 µg axitinib releases in vitro about 25% to about 35% of the axitinib in 2 months, about 47% to about 57% of the axitinib in 3 months, about 70% to about 80% of the axitinib in 5 months, and about 90% to about 100% of the axitinib in 7 months in phosphate buffered saline at a pH of 7.2, at 37° C. and with an octanol top layer.

The in vitro release tests, especially the accelerated in vitro release test described herein, may be used inter alia to compare different implants (e.g. of different production batches, of different composition, and of different dosage strength etc.) with each other, for example for the purpose of quality control or other qualitative assessments.

In Vivo Release and Persistence:

In an embodiment of the present invention, when the dried implant of the present invention is administered to the eye, such as the vitreous humor, it becomes hydrated and changes its dimensions as disclosed above, and is then over time biodegraded until it has been fully resorbed. When the implant is biodegraded, such as through ester hydrolysis, it gradually may swell and soften, then become smaller, softer and more liquid until it is fully dissolved and no longer visible. As recognized by the inventors from the animal studies presented in the Examples section herein below, an implant according to the invention may persist about 2 to about 6 months, or about 5 to about 6 months in rabbit eyes (see FIGS. 7A, 9 and 10). After full degradation of the implant, undissolved axitinib particles may remain at the former site of the implant and have been observed to agglomerate, i.e., merge into a monolithic structure. These remaining undissolved axitinib particles may continue to dissolve slowly at a rate sufficient to provide therapeutically effective axitinib levels. If in certain embodiments two or more implants are administered to achieve a desired total dose, they are equally biodegraded over time, and the remaining axitinib particles also merge into one single monolithic structure (see FIG. 9).

In the human eye, such as in the vitreous humor, the implant of the invention in certain embodiments biodegrades within about 2 to about 15 months after administration, or within about 4 to about 13 months after administration, or within about 9 to about 12 months after administration, specifically within about 9 to about 10.5 months after administration. This has been demonstrated in the clinical trials with one or two implant(s), each comprising about 200 µg axitinib. See the Examples section, in particular Example 6 and FIG. 15.

In one embodiment, the implant after administration to the vitreous humor releases (as defined herein) the TKI, such as a therapeutically effective amount of TKI, such as axitinib, over a period of at least about 3 months, at least about 6 months, at least about 9 months, at least about 10 months, at least about 11 months, or at least about 12 months, or at least about 13 months or longer after administration. In particular embodiments, the implant releases the TKI, such as axitinib, for a period of about 6 to about 9 months.

In one embodiment of the invention, the implant provides for a treatment period of at least about 3 months, at least about 9 months, at least about 10 months, at least about 11 months, at least about 12 months, or at least about 13 months or longer after administration of the (i.e., a single) implant into the vitreous humor of a patient.

In one embodiment of the invention, TKI, such as axitinib is released from the implant at an average rate of about 0.1 µg/day to about 10 µg/day, or about 0.5 µg/day to about 7 µg/day, or about 0.5 µg/day to about 2 µg/day, or about 1 µg/day to about 5 µg/day in the vitreous humor, over a time period of at least 3, or at least 6, or at least 9, or at least 11, or at least 12, or at least 13 months. In particular embodiments the release of TKI, such as axitinib, is maintained for about 6 to about 9 months after administration of the implant.

Pre-clinical studies in animals as well as clinical studies in humans, as presented in the Examples section herein, have shown that the implants of the invention may continuously release therapeutically effective amounts of TKI over an extended period of time, until the implants are fully biodegraded. Any remaining undissolved TKI particles (if present) may essentially remain at the site of the former implant and may agglomerate to form an essentially monolithic structure (see FIGS. 7A, 9 and 10) that may continue to release TKI into the vitreous at levels sufficient to achieve the therapeutic effect. In certain embodiments, however, the entire amount of TKI contained in the implant is released from the implant prior to complete biodegradation of the implant. In this case, no undissolved TKI particles would remain (and/or agglomerate) near the site of the former implant or elsewhere in the eye after complete biodegradation of the implant.

In one embodiment, the persistence of the hydrogel within an aqueous environment and in the human eye depends inter alia on the hydrophobicity of the carbon chain in proximity to the degradable ester group. In the implants used in the Examples herein, this carbon chain comprises 7 carbon atoms as it stems from the SAZ functional group of the 4a20k PEG precursor. This may provide an extended persistence in the human eye of up to about 9 to about 12 months, or from about 9 to about 10.5 months. In other embodiments, different precursors than the 4a20kPEG-SAZ and the 8a20kPEG-NH$_2$ may be used to prepare hydrogel implants that biodegrade in the human eye and have similar or different persistence as the implants exemplified in the Examples.

In certain embodiments, the hydrogel implant softens over time as it degrades, which may depend inter alia on the structure of the linker that crosslinks the PEG units in the hydrogel. An implant as used in the examples of the present application formed from a 4a20kPEG-SAZ and a 8a20kPEG-NH$_2$ softens rather slowly over time.

Mechanism of Release:

Without wishing to be bound by theory, the mechanism of release of the TKI from an implant of the invention may be explained as follows: In embodiments of the invention, release of the TKI into the eye and into the vitreous humor is dictated by diffusion and drug clearance. An exemplary TKI according to the present invention is axitinib. The solubility of axitinib has been determined to be very low in physiological medium (about 0.4 to about 0.5 μg/mL in PBS at pH 7.2). According to the present invention, the TKI, such as axitinib, is confined in a biodegradable hydrogel having a particular geometry and surface. The liquid in the posterior chamber of the eye is viscous, has a slow clearance and a relatively stagnant flow (at least as compared to the anterior chamber of the eye).

In certain embodiments, the implant of the present invention comprises a hydrogel made of a polymer network and a drug dispersed within the hydrogel. The drug gradually gets dissolved and diffuses out of the hydrogel into the eye. This may happen first at the outer region of the hydrogel (i.e., the drug particles that are located in the outermost region of the hydrogel get dissolved and diffuse out first, the innermost last) that is in contact with the liquid environment of the vitreous. Thereby, in certain embodiments, the outer region of the hydrogel becomes devoid of drug particles. This region is therefore also called the "clearance zone", which is limited to dissolved drug only, with a concentration at or below the solubility of the drug. In certain embodiments, this low surface concentration may protect tissue (retinal or other cells) from potential drug toxicity by physically separating drug particles from the tissue should the implant get in contact with such tissue. In other embodiments, upon hydration the "clearance zone" is an outer region that has a concentration of active agent that is less than the active agent in an inner region of the hydrated hydrogel.

In embodiments with clearance zones, because drug has dissolved and has diffused out of the clearance zone, this area of the hydrogel develops voids and becomes softer and weaker. Concurrently with the drug diffusing out of the hydrogel, the hydrogel may also be slowly degraded by means of, e.g., ester hydrolysis in the aqueous environment of the eye. This degradation occurs uniformly throughout the bulk of the hydrogel. At advanced stages of degradation, distortion and erosion of the hydrogel begins to occur. As this happens, the hydrogel becomes softer and more liquid (and thus its shape becomes distorted) until the hydrogel finally dissolves and is resorbed completely. This process is schematically shown on FIG. 3 and demonstrated by means of infrared reflectance (IR) imaging e.g. in FIG. 10.

As axitinib is a relatively low solubility drug, undissolved axitinib particles may remain at the former site of the implant after the implant has already fully degraded in certain embodiments. Since these remaining undissolved axitinib particles are no longer fixated and held apart by the hydrogel, they may agglomerate and form a substantially monolithic structure. This monolithic axitinib structure may still continue to release axitinib, at rates sufficient to achieve the therapeutic effect (specifically, to reduce CSFT).

In one embodiment, however, the entire amount of axitinib is released prior to the complete degradation of the hydrogel. As the hydrogel may hold the axitinib particles in place and prevent them from agglomeration the release of axitinib from the hydrogel can be faster as long as the hydrogel has not yet fully degraded. When the hydrogel has fully degraded, remaining axitinib particles may form a monolithic structure from which axitinib may slowly be dissolved. Therefore, complete release of the axitinib prior to full degradation of the hydrogel is desired in one embodiment of the invention.

This whole process makes it possible in certain embodiments to advantageously maintain the therapeutic effect of the implant of the present invention over an extended period of time, such as at least 3 months, or at least 6 months, or at least 9 months, or at least 11 months, or at least 12 months, or at least 13 months, or at least 14 months, or even longer, such as up to 15 months. It has been demonstrated by the present inventors that this is a great advantage for patients receiving treatment for neovascular age-related macular degeneration, which treatment previously involved very frequent intravitreal injections of an anti-VEGF agent. In contrast, the implants according to the present invention may need to be injected only at much greater intervals of time, which is advantageous for the patient for a number of reasons as already disclosed above in the section "Objects and Summary".

Specific Implant Containing from about 160 μg to about 250 μg such as about 200 μg Axitinib:

In one particular embodiment, the present invention relates to a sustained release biodegradable ocular implant containing axitinib in an amount in the range from about 160 μg to about 250 μg, or from about 180 μg to about 220 μg, and specifically about 200 μg dispersed in a hydrogel, wherein the hydrogel comprises a polymer network comprising polyethylene glycol units, and wherein the implant is in a dried state. In this embodiment the polymer network contains polyethylene glycol units comprising multi-arm polyethylene glycol units, such as 4-arm and/or 8-arm polyethylene glycol units having an average molecular weight in the range of from about 10,000 Daltons to about 60,000 Daltons. In this embodiment, the polymer network of this implant is formed by reacting 4a20kPEG-SAZ with 8a20kPEG-NH$_2$, at a weight ratio of about 2:1. In this embodiment the hydrogel when formed and before being dried (i.e., the wet composition) contains about 6.5% to about 7.5% polyethylene glycol, representing the polyethylene glycol weight divided by the fluid weight×100. Also, in this embodiment the implant in a dried state contains from about 45% to about 55% by weight axitinib and from about 37% to about 47% by weight polyethylene glycol units, or from about 47% to about 52% by weight axitinib and from about 40% to about 45% by weight polyethylene glycol units, such as about 49% to about 50% by weight axitinib and about 42% by weight PEG units, or about 47% by weight axitinib and about 44% by weight PEG units (dry composition), the balance being sodium phosphate. The implant furthermore in its dried state may contain not more than about 1% by weight water, or not more than about 0.25% by weight water.

In this embodiment, the implant containing axitinib in an amount in the range from about 160 μg to about 250 μg, or from about 180 μg to about 220 μg, and specifically about 200 μg releases in vitro about 0.01 μg to about 0.15 μg of axitinib per day in phosphate-buffered saline at 37° C. for a period of 30 days. Furthermore, in this embodiment the implant releases in vitro about 35% to about 45% of the axitinib in 3 days, about 65% to about 75% of the axitinib in 7 days, and about 90% to about 100% of the axitinib in 12 to 13 days in a 25:75 ethanol/water (v/v) mixture at 37° C. In this embodiment the implant may also release in vitro about 25% to about 35% of the axitinib in 2 months, about 47% to about 57% of the axitinib in 3 months, about 70% to about 80 of the axitinib in 5 months, and about 90% to about 100% of the axitinib in 7 months in phosphate buffered saline at a pH of 7.2, at 37° C. and with an octanol top layer.

In this embodiment, the implant containing about 200 µg axitinib may be in the form of a fiber (or cylinder) and may have a length of less than about 20 mm, or less than about 17 mm, or of about 15 mm to about 16.5 mm and a diameter of about 0.20 mm to about 0.30 mm in its dried state and may decrease in length and increases in diameter upon hydration in vivo in the vitreous humor or in vitro (wherein hydration in vitro is measured in phosphate-buffered saline at a pH of 7.2 at 37° C. after 24 hours) to a length of about 6.5 mm to about 8 mm and a diameter of about 0.70 mm to about 0.80 mm in the hydrated state. This dimensional change upon hydration may be achieved by imparting shape memory to the implant by dry stretching the implant in the longitudinal direction as explained in more detail elsewhere herein, by a stretch factor of about 2 to about 5, or a stretch factor of about 3 to about 4.5. In other embodiments, the implant may be non-cyclindrical.

In this embodiment, the implant containing about 200 µg axitinib may have a ratio of the diameter in the hydrated state to the diameter in the dry state of less than about 3.25 mm, and/or a ratio of the length in the dry state to the length in the hydrated state of greater than about 1.5.

The total weight of an implant as disclosed in this embodiment in its dry state may be from about 0.3 mg to about 0.6 mg, such as from about 0.4 mg to about 0.5 mg. Such an implant in the dry state may contain about 10 µg to about 15 µg of axitinib per 1 mm final length, and may contain from about 200 µg to about 300 µg axitinib per mm³.

In this embodiment, prior to administration, the implant containing an axitinib dose of about 200 µg is loaded into a 25-gauge needle or a 27-gauge needle (or an even smaller gauge needle, such as a 30-gauge needle) for injection into the vitreous humor.

To summarize and exemplify, the individual characteristics of an implant of the invention disclosed with respect to the embodiment described in this section containing a dose of about 200 µg (including the implant that is used in the clinical study presented in Example 6) are provided in Table 21.1 in the Examples section, which is also reproduced here:

| | Implant type | Implant #1 |
|---|---|---|
| Formulation (% dry basis w/w) | Axitinib | 49.4% |
| | Dose | (200 µg) |
| | PEG Hydrogel | 42.0% |
| | 4a20K PEG-SAZ | 28% |
| | 8a20K PEG-NH2 | 14% |
| | Sodium phosphate | 8.6% |
| Formulation (% wet basis w/w) | Axitinib | 7.5% |
| | PEG Hydrogel | 6.9% |
| | 4a20K PEG-SAZ | 4.6% |
| | 8a20K PEG-NH2 | 2.3% |
| | Sodium phosphate | 1.5% |
| | WFI | 84.1% |
| | Axitinib per final dry length | 12.1 µg/mm |
| | Approximate Implant Mass (dose µg/API %) | 423 |
| Configuration | Stretching Method (Stretch Factor) | Dry (4.5) |
| | Needle Size | 27G TW 1.25" (0.27 mm ID) |
| | Injector/Syringe | Implant Injector |
| | Packaging | Foil Pouches |
| | Sterilization Type | Gamma |
| | Site Storage | Refrigerated |

| | Implant type | Implant #1 |
|---|---|---|
| Dimensions | Dried | |
| | Diameter | 0.24 ± 0.013 mm |
| | Length | 16.5 ± 0.26 mm |
| | Volume | 0.75 ± 0.08 mm³ |
| | Implant Mass | 0.45 mg |
| | Axitinib per volume (µg/mm³) | 266.7 |
| | Hydrated | |
| | Diameter | 0.75 mm |
| | Length | 7.5 mm |
| | Ratio of diameter (hydrated) to diameter (dry) | 3.13 |
| | Ratio of length (dry) to length (hydrated) | 2.20 |

The sustained release biodegradable ocular implant of claim 1, wherein the implant is an intravitreal implant and comprises from about 180 µg to about 220 µg axitinib, is cylindrical and has in its dry state a length of less than about 17 mm and a diameter of about 0.2 mm to about 0.3 mm, and in its hydrated state (after 24 hours in phosphate-buffered saline at a pH of 7.2 at 37° C.) has a length of from about 6.5 mm to about 8 mm and a diameter of from about 0.7 mm to about 0.8 mm, and wherein the hydrogel comprises crosslinked 4a20k and 8a20k PEG units, wherein the crosslinks between the PEG units include a group represented by the following formula

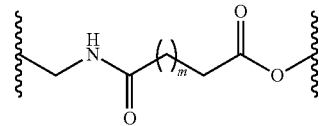

wherein m is 6.

Alternatively, an implant of this particular embodiment may also be non-cyclindrical as disclosed herein.

Specific Implant Containing about 480 µg to about 750 µg such as about 600 µg Axitinib:

In another particular embodiment, the present invention relates to a sustained release biodegradable ocular implant containing axitinib in an amount in the range from about 480 µg to about 750 µg dispersed in a hydrogel, wherein the hydrogel comprises a polymer network that comprises crosslinked polyethylene glycol units. The amount of axitinib in said implant may also be in the range from about 540 µg to about 660 µg, or may specifically be about 600 µg.

In this implant, the polyethylene glycol units comprise multi-arm polyethylene glycol units, such as 4-arm and/or 8-arm polyethylene glycol units having an average molecular weight in the range of from about 10,000 Daltons to about 60,000 Daltons. In this embodiment, the polymer network of the implant comprises 4a20kPEG and 8a20kPEG units and is formed by reacting 4a20kPEG-SAZ with 8a20kPEG-NH$_2$, in a weight ratio of about 2:1.

In this embodiment, the implant in a dried state may contain from about 45% to about 55% by weight axitinib and from about 37% to about 47% by weight polyethylene glycol units, or may contain from about 60% to about 75% by weight axitinib and from about 21% to about 31% polyethylene glycol units, such as from about 63% to about 72% by weight axitinib and from about 23% to about 27% polyethylene glycol units (dry composition), the balance being sodium phosphate. In certain specific embodiments the implant may contain about 68% to about 69% axitinib and about 26% polyethylene glycol units (dry composition), the balance being sodium phosphate. The implant may contain not more than about 1% by weight water, or not more than about 0.25% by weight water.

In this embodiment, this implant containing axitinib in an amount in the range from about 480 μg to about 750 μg, or from about 540 μg to about 660 μg, or specifically about 600 μg releases in vitro about 0.3 μg to about 0.5 μg of axitinib per day in phosphate-buffered saline at 37° C. for a period of 30 days. Furthermore, this implant releases in vitro about 40% to about 60% of the axitinib in 2 days, about 65% to about 85% of the axitinib in 4 days, and about 75% to about 90% of the axitinib in 6 days in a 25:75 (v/v) ethanol/water mixture at 37° C. In this embodiment, this implant may also release in vitro about 45% to about 55% of the axitinib in 2 days, about 70% to about 80% of the axitinib in 4 days, and about 80% to about 90% of the axitinib in 6 days in a 25:75 ethanol/water (v/v) mixture at 37° C.

In this embodiment, the implant containing about 600 μg axitinib may be in the form of a fiber (or cylinder) and may have in its dried state a length of less than about 20 mm, or less than about 17 mm, or less than about 15 mm, or less than or equal to about 12 mm, such as about 7 mm to about 12 mm and a diameter of about 0.25 mm to about 0.50 mm, or a length of from about 7 mm or about 8 mm to about 11 mm and a diameter of about 0.3 mm to about 0.4 mm, and may increase in diameter upon hydration in vivo in the vitreous humor or in vitro (wherein hydration in vitro is measured in phosphate-buffered saline at a pH of 7.2 at 37° C. after 24 hours). In specific embodiments, an implant containing about 600 μg of axitinib in its dried state may have a length of less than or equal to about 10 mm, or less than or equal to about 8.5 mm, or from about 7 mm to about 9 mm, or from about 7 mm to about 8.5 mm and a diameter of from about 0.3 mm to about 0.4 mm, such as from about 0.35 mm to about 0.39 mm.

The dimensions of this implant after hydration in vivo or in vitro (wherein in vitro hydration is measured in phosphate-buffered saline at a pH of 7.2 at 37° C. after 24 hours) may be a length of less than or equal to about 10 mm, such as of from about 6 mm or about 9 mm to about 12 mm and a diameter of about 0.5 mm to about 0.8 mm, or a length of about 9.5 mm to about 11.5 mm, or a length of not more than about 10 mm or not more than about 9 mm, and a diameter of from about 0.65 mm to about 0.75 mm or to about 0.80 mm. In specific embodiments, an implant containing about 600 μg of axitinib in its hydrated state (wherein hydration in vitro is measured in phosphate-buffered saline at a pH of 7.2 at 37° C. after 24 hours) may have a length of from about 6 mm to about 10.5 mm, such as from about 6.5 mm to about 8.5 mm, and a diameter of from about 0.7 mm to about 0.8 mm. In particular embodiments, a length of about 10 mm or less, such as about 9 mm or less when hydrated in the vitreous humor of the eye is an acceptable length given the limited volume of the eye.

This dimensional change upon hydration may be achieved by wet stretching in the longitudinal direction prior to drying as disclosed in more detail below by a stretch factor of about 0.5 to about 5, or a stretch factor of about 1 to about 4, or a stretch factor of about 1.3 to about 3.5, or a stretch factor of about 1.7 to about 3, or a stretch factor of about 2 to about 2.5.

In this embodiment, the implant containing about 600 μg axitinib may have a ratio of the diameter in the hydrated state to the diameter in the dry state of less than about 2.25 mm and/or a ratio of the length in the dry state to the length in the hydrated state of greater than 0.75.

The total weight of an implant as disclosed herein containing about 600 μg axitinib may in the dry state be from about 0.8 mg to about 1.1 mg, such as from about 0.9 mg to about 1.0 mg. Such an implant in the dry state may contain about 70 μg to about 85 μg of axitinib per 1 mm final length, and may contain from about 500 μg to about 800 μg axitinib per mm$^3$.

In this embodiment, the preferred shape of the implant is cylindrical or essentially cylindrical (and may also be referred to as a fiber). In other embodiments, the implant may be non-cylindrical. Prior to administration, this implant containing an axitinib dose of about 600 μg is loaded into a 25-gauge (or a smaller gauge, such as a 27-gauge) needle for injection into the eye, e.g., the vitreous humor.

To summarize, the individual characteristics of implants of the invention disclosed with respect to the embodiment described in this section containing a dose of about 600 μg axitinib are provided in Table 21.2 in the Examples section, which is also reproduced here:

| | Implant type | Implant #2 | Implant #3 | Implant #4 |
|---|---|---|---|---|
| Formulation (% dry basis w/w) | Axitinib | 49.8% | 68.6% | 68.6% |
| | Dose | (600 μg) | (600 μg) | (600 μg) |
| | PEG Hydrogel | 42.0% | 26.0% | 26.0% |
| | 4a20K PEG-SAZ | 28% | 17.4% | 17.4% |
| | 8a20K PEG-NH2 | 14% | 8.7% | 8.7% |
| | Sodium phosphate | 8.2% | 5.4% | 5.4% |
| Formulation (% wet basis w/w) | Axitinib | 12.0% | 16.5% | 16.5% |
| | PEG Hydrogel | 6.3% | 6.3% | 6.3% |
| | 4a20K PEG-SAZ | 4.2% | 4.2% | 4.2% |
| | 8a20K PEG-NH2 | 2.1% | 2.1% | 2.1% |
| | Sodium phosphate | 1.3% | 1.3% | 1.3% |
| | WFI | 80.4% | 75.9% | 75.9% |
| | Axitinib per final dry length | 71.4 μg/mm | 71.4 μg/mm | 81.1 μg/mm |
| | Approximate Implant Mass (dose ug/API %) | 1205 | 875 | 875 |
| Configuration | Stretching Method (Stretch Factor) | Wet (2.1) | Wet (2.1) | Wet (2.1) |
| | Needle Size | 25G UTW 1" (0.4 mm ID) | 25G UTW 1" (0.4 mm ID) | 25G UTW 0.5" (0.4 mm ID) |
| | Injector/Syringe | Implant Injector | Implant Injector | Implant Injector |

-continued

| Implant type | | Implant #2 | Implant #3 | Implant #4 |
|---|---|---|---|---|
| | Packaging | Foil Pouches | Foil Pouches | Foil Pouches |
| | Sterilization Type | Gamma | Gamma | Gamma |
| | Site Storage | Refrigerated | Refrigerated | Refrigerated |
| Dimensions | Dried | | | |
| | Diameter | 0.36 mm | 0.37 ± 0.014 mm | 0.37 ± 0.008 mm |
| | Length | 8.4 mm | 8.4 ± 0.04 mm | 7.4 ± 0.03 mm |
| | Volume | 0.86 mm³ | 0.90 ± 0.07 mm³ | 0.81 ± 0.05 mm³ |
| | Implant Mass | 1.20 mg | 0.95 ± 0.04 mg | 0.95 ± 0.01 mg |
| | Axitinib per volume (µg/mm³) | 697.7 | 666.7 | 740.7 |
| | Hydrated | | | |
| | Diameter | 0.7 mm | 0.68 mm | 0.77 mm |
| | Length | 10 mm | 8.23 mm | 6.8 mm |
| | Ratio of diameter (hydrated) to diameter (dry) | 1.94 | 1.84 | 2.08 |
| | Ratio of length (dry) to length (hydrated) | 0.84 | 1.02 | 1.09 |

In a particular embodiment, the sustained release biodegradable ocular implant of the present invention is an intravitreal implant and comprises from about 540 µg to about 660 µg axitinib, is cylindrical and has in its dry state a length of less than or equal to 10 mm and a diameter of about 0.3 mm to about 0.4 mm, and in its hydrated state (after 24 hours in phosphate-buffered saline at a pH of 7.2 at 37° C.) has a length of from about 6 mm to about 10.5 mm and a diameter of from about 0.6 mm to about 0.8 mm, and wherein the hydrogel comprises crosslinked 4a20k and 8a20k PEG units, wherein the crosslinks between the PEG units include a group represented by the following formula

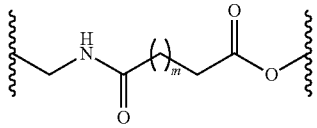

wherein m is 6.

Alternatively, an implant of this particular embodiment may also be non-cyclindrical as disclosed herein.

II. Manufacture of the Implant

Manufacturing Process:

In certain embodiments, the present invention also relates to a method of manufacturing a sustained release biodegradable ocular implant as disclosed herein. Generally, the method comprises the steps of forming a hydrogel comprising a polymer network and TKI particles dispersed within the hydrogel, shaping the hydrogel and drying the hydrogel. In certain embodiments the method comprises the steps of forming a hydrogel comprising a polymer network from reactive group-containing precursors (e.g., comprising PEG units) and TKI particles dispersed in the hydrogel, shaping the hydrogel and drying the hydrogel, more specifically the polymer network is formed by mixing and reacting an electrophilic group-containing multi-arm PEG precursor with a nucleophilic group-containing multi-arm PEG precursor or another nucleophilic group-containing crosslinking agent (precursors and crosslinking agent as disclosed herein in the sections "The polymer network" and "PEG hydrogels") in a buffered solution in the presence of TKI particles and allowing the mixture to gel to form the hydrogel. In embodiments of the invention, the hydrogel is shaped into a hydrogel strand as disclosed herein, by casting the mixture into a tubing prior to complete gelling of the hydrogel. In certain embodiments, the hydrogel strand is stretched in the longitudinal direction prior to or after drying as further disclosed herein.

In certain embodiments, the TKI in the method of manufacturing according to the invention in all its aspects is axitinib. In one embodiment the TKI, such as axitinib, may be used in micronized form for preparing the implant as disclosed herein, and may have a particle diameter as also disclosed herein in the section "The active principle". In certain specific embodiments, the axitinib may have a d90 of less than about 30 µm, or less than about 10 µm. Using micronized TKI, specifically micronized axitinib, may have the effect of reducing the tendency of the TKI, specifically axitinib, particles to agglomerate during casting of the hydrogel strands, as demonstrated in FIG. 24. In another embodiment, the TKI, such as axitinib, may be used in non-micronized form for preparing the implant.

The precursors for forming the hydrogel of certain embodiments have been disclosed in detail above in the section relating to the implant itself. In case PEG precursors are used to prepare a crosslinked PEG network, the method of manufacturing the implant in certain embodiments may comprise mixing and reacting an electrophilic group-containing polymer precursor, such as an electrophilic group-containing multi-arm polyethylene glycol, such as 4a20kPEG-SAZ, with a nucleophilic group-containing polymer precursor or other cross-linking agent, such as a nucleophilic group-containing multi-arm polyethylene glycol, such as 8a20kPEG-NH₂, in a buffered solution in the presence of the tyrosine kinase inhibitor, and allowing the mixture to gel. In certain embodiments, the molar ratio of the electrophilic groups to the nucleophilic groups in the PEG precursors is about 1:1, but the nucleophilic groups (such as the amine groups) may also be used in excess of the electrophilic groups. Other precursors, including other electrophilic group-containing precursors and other nucleophilic group-containing precursors or crosslinking agents may be used as disclosed in the section "The polymer network" and the section "PEG hydrogels" herein.

In certain embodiments, a mixture of the electrophilic group-containing precursor, the nucleophilic group-containing precursor or other crosslinking agent, the TKI and optionally buffer (and optionally additional ingredients as disclosed in the section "Additional ingredients") is prepared. This may happen in a variety of orders, including but not limited to first preparing separate mixtures of the electrophilic and the nucleophilic group-containing precursors each in buffer solution, then combining one of the buffer/precursor mixtures, such as the buffer/nucleophilic group-containing precursor mixture, with the TKI and subsequently combining this TKI-containing buffer/precursor mixture with the other buffer/precursor mixture (in this case the buffer/electrophilic group-containing precursor mixture). After a mixture of all components has been prepared (i.e., after all components have been combined and the wet composition has been formed), the mixture is cast into a suitable mold or tubing prior to complete gelling of the hydrogel in order to provide the desired final shape of the hydrogel. The mixture is then allowed to gel. The resulting hydrogel is then dried.

The viscosity of the wet hydrogel composition to be cast into a mold or tubing may depend inter a/ia on the concentration and the solids content of the hydrogel composition, but may also depend on external conditions such as the temperature. Castability of the wet hydrogel composition especially in case the composition is cast into fine-diameter tubing, may be improved by decreasing the viscosity of the wet composition, including (but not limited to) decreasing the concentration of ingredients in the solvent and/or decreasing the solids content, or other measures such as increasing the temperataure etc. Suitable solids contents are disclosed herein in the section "Formulation".

In case the implant should have the final shape of a fiber (such as a cylinder), the reactive mixture may be cast into a fine diameter tubing (of e.g. an inner diameter of about 1.0 mm to about 1.5 mm), such as a PU or silicone tubing, in order to provide for the extended cylindrical shape. Different geometries and diameters of the tubing may be used, depending on the desired final cross-sectional geometry of the hydrogel fiber, its initial diameter (which may still be decreased by means of stretching), and depending also on the ability of the reactive mixture to uniformly fill the tubing.

Thus, the inside of the tubing may have a round geometry or a non-round geometry, such as a cross-shaped (or other) geometry. By means of a cross-shaped geometry, the surface of the implant may be increased. Also, in certain embodiments, the amount of TKI incorporated in the implant may be increased with such cross-shaped geometry. Overall, by using a cross-shaped geometry, release of the API from the implant may in certain embodiments be increased. Other cross-sectional geometries of the implant may be used as disclosed herein.

In certain embodiments, after the hydrogel has formed and has been left to cure to complete gelling, the hydrogel strand may be longitudinally stretched in the wet or dry state as already disclosed in detail herein e.g. in the section relating to the dimensional change of the implant upon hydration. In certain embodiments, a stretching factor (also referred to herein as "stretch factor") may be in a range of about 1 to about 4.5, or about 1.3 to about 3.5, or about 2 to about 2.5, or within other ranges also as disclosed herein (e.g. in, but not limited to, the section "Dimensions of the implant and dimensional change upon hydration through stretching". The stretch factor indicates the ratio of the length of a certain hydrogel strand after stretching to the length of the hydrogel strand prior to stretching. For example, a stretch factor of 2 for dry stretching means that the length of the dry hydrogel strand after (dry) stretching is twice the length of the dry hydrogel strand before the stretching. The same applies to wet stretching. When dry stretching is performed in certain embodiments, the hydrogel is first dried and then stretched. When wet stretching is performed in certain embodiments, the hydrogel is stretched in the wet (undried) state and then left to dry under tension. Optionally, heat may be applied upon stretching. Further optionally, the hydrogel fiber may additionally be twisted. In certain embodiments, the stretching and/or drying may be performed when the hydrogel is still in the tubing. Alternatively, the hydrogel may be removed from the tubing prior to being stretched. In certain embodiments, the implant maintains its dimensions even after stretching as long as it is kept in the dry state at or below room temperature.

After stretching and drying the hydrogel strand is removed from the tubing (if still located inside the tubing) and cut into segments of a length desired for the final implant in its dry state, such as disclosed herein (if cut within the tubing, the cut segments are removed from the tubing after cutting). A particularly desired length of the implant in the dry state for the purposes of the present invention is for example a length of equal to or less than about 12 mm, or equal to or less than about 10 mm, as disclosed herein.

In certain embodiments, the final prepared implant is then loaded into a fine diameter needle. In certain embodiments, the needle has a gauge size of from 22 to 30, such as gauge 22, gauge 23, gauge 24, gauge 25, gauge 26, gauge 27, gauge 28, gauge 29 or gauge 30. In specific embodiments, the needle is a 25- or 27-gauge needle, or an even smaller gauge needle, such as a 30-gauge needle, depending on the diameter of the dried (and optionally stretched) implant.

In certain embodiments, the needles containing implant are then separately packaged and sterilized e.g. by means of gamma irradiation.

In certain embodiments, an injection device, such as a syringe or another injection device, may be separately packaged and sterilized e.g. by means of gamma irradiation as disclosed below for the kit (which is another aspect of the present invention, see the section "Injection device and kit").

A particular embodiment of a manufacturing process according to the invention is disclosed in detail in Example 1.

(PEG) Tipping the Needle:

In one embodiment, after the implant has been loaded into the needle the tip of the needle is dipped into a melted low-molecular weight PEG. Alternatively, molten PEG may be injected or placed/dripped into the needle tip lumen. This low-molecular PEG is liquid (molten) at body temperature, but solid at room temperature. After applying the molten PEG to the needle tip, either by dipping or dripping, upon cooling the needle a hardened small drop or section (also referred to herein as "tip") of PEG remains at and in the top of the needle which occludes the needle lumen. The location of this tip/plug is shown in FIG. 25B.

The low-molecular weight PEG used in this embodiment may be a linear PEG and may have an average molecular weight of up to about 1500, or up to about 1000, or may have an average molecular weight of about 400, about 600, about 800 or about 1000. Also mixtures of PEGs of different average molecular weights as disclosed may be used. In specific embodiments the average molecular weight of the PEG used for this purpose of tipping the needle is about 1000. This 1 k (1000) molecular weight PEG has a melting point between about 33° C. and about 40° C. and melts at body temperature when the needle is injected into the eye.

Alternatively to the PEG materials, any other material for tipping the injection needle may be used that is water soluble and biocompatible (i.e., that may be used in contact with the human or animal body and does not elicit topical or systemic adverse effects, e.g. that is not irritating) and that is solid or hardened at room temperature but liquid or substantially liquid or at least soft at body temperature. Alternatively to PEG, also the following materials may e.g. be used (without being limited to these): poloxamers or poloxamer blends that melt/are liquid at body temperature; crystallized sugars or salts (such as trehalose or sodium chloride), agarose, cellulose, polyvinyl alcohol, poly(lactic-co-glycolic acid), a UV-curing polymer, chitosan or combinations of mixtures thereof.

The plug or tip aids in keeping the implant in place within the needle during packaging, storage and shipping and also further protects the implant from prematurely hydrating during handling as it occludes the needle lumen. It also prevents premature rehydration of the implant within the needle due to moisture ingress during the administration procedure, i.e., during the time the physician prepares the needle and injector for administration, and also at the time when the implant is about to be injected and the needle punctures into the eye (as the positive pressure in the eye could cause at least some premature hydration of the implant just before it is actually injected). The tip or plug additionally provides lubricity when warmed to body temperature and exposed to moisture and thereby allows successful deployment of the implant. Moreover, by occluding the needle lumen, the needle tipping minimizes the potential for tissue injury, i.e., tissue coring, a process by which pieces of tissue are removed by a needle as it passes through the tissue.

In order to apply the PEG (or other material) tip/plug to the needle lumen, in one embodiment the needle containing the implant may be manually or by means of an automated apparatus dipped into a container of molten PEG (or the respective other material). The needle may be held dipped in the molten material for a few seconds to enable the molten material to flow upward into the needle through capillary action. The dwell time, the dip depth and the temperature of the molten material determine the final size or length of the tip/plug. In certain embodiments, the length of the PEG (or other) tip/plug at the top end of the needle may be from about 1 to about 5 mm, such as from about 2 to about 4 mm. In certain embodiments, in case a 1 k PEG is used the weight of the tip/plug may be from about 0.1 mg to about 0.6 mg, such as from about 0.15 mg to about 0.55 mg. It was demonstrated that implants according to the present invention can be successfully deployed in vivo and in vitro from an injector carrying a needle with a 1 k PEG tip as disclosed herein.

The tipping of an injection needle as disclosed herein may also be used for the injection of other implants or other medicaments or vaccines to be injected into the human or animal body (including other locations within the eye, or other areas or tissue of the body) by means of a needle, where the effect of protection of the implant (or medicament or vaccine) from moisture and the protective effect on tissue into which the implant (or medicament or vaccine) is injected is desirable and advantagoues.

Stretching:

The shape memory effect of the stretching has already been disclosed in detail above with respect to the properties of the implant. In certain embodiments, the degree of shrinking upon hydration depends inter alia on the stretch factor as already disclosed above.

In certain embodiments, the present invention thus also relates to a method of imparting shape memory to a hydrogel strand comprising an active agent dispersed in the hydrogel by stretching the hydrogel strand in the longitudinal direction.

Likewise, in certain embodiments, the present invention thus also relates to a method of manufacturing an ocular implant comprising a hydrogel comprising an active agent dispersed therein, wherein the implant changes its dimensions upon administration to the eye, the method comprising preparing a strand of the hydrogel and stretching it in the longitudinal direction.

Stretch factors for use in these methods of the invention may be utilized as already disclosed above. The described method of manufacture including the stretching methods are not limited to implants comprising TKI inhibitors or axitinib, but may also be used for hydrogels comprising other active pharmaceutical agents, or for implants comprising hydrogels that are not formed from PEG units, but from other polymer units as disclosed herein above that are capable of forming a hydrogel.

In embodiments where the implant contains axitinib in an amount in a range from about 160 µg to about 250 µg, or in an amount of about 200 µg, the stretching may be performed after drying the hydrogel by a stretch factor of about 2 to about 5, or a stretch factor of about 3 to about 4.5 (dry stretching).

In certain embodiments where the implant contains axitinib in an amount in a range from about 480 µg to about 750 µg, or in an amount of about 600 µg, the stretching may be performed in a wet state prior to drying the hydrogel by a stretch factor of about 0.5 to about 5, or a stretch factor of about 1 to about 4, or a stretch factor of about 1.3 to about 3.5, or a stretch factor of about 1.7 to about 3, or a stretch factor of about 2.0 to 2.5 (wet stretching).

III. Injection Device and Kit

In certain embodiments, the present invention is further directed to a kit (which may also be referred to as a "system") comprising one or more sustained release biodegradable ocular implant(s) as disclosed above or manufactured in accordance with the methods as disclosed above and one or more needle(s) for injection, wherein the one or more needle(s) is/are each pre-loaded with one sustained release biodegradable ocular implant in a dried state. In certain embodiments the needle(s) has a gauge size of from 22 to 30, such as 22, 23, 24, 25, 26, 27, 28, 29, or 30 gauge. In specific embodiments, the neeles may be 25- or 27-gauge needle(s) or may be smaller gauge, such as 30-gauge needle(s). The diameter of the needle is chosen based on the final diameter of the implant in the dried (and optionally stretched) state. The active contained in the implant is generally a TKI, such as axitinib.

In one embodiment the kit comprises one or more, such as two or three 22- to 30-gauge, such as 25- or 27-gauge needle(s) each loaded with an implant containing axitinib in an amount in the range from about 180 µg to about 220 µg, or in an amount of about 200 µg.

In yet another embodiment the kit comprises one 25-gauge needle loaded with an implant containing axitinib in an amount in the range from about 540 µg to about 660 µg, or in an amount of about 600 µg. In another embodiment, the kit comprises one 27-gauge needle loaded with an implant containing axitinib in an amount in the range from about 540 µg to about 660 µg, or in an amount of about 600 µg.

If two or more implants are contained in the kit, these implants may be identical or different, and may contain identical or different doses of TKI.

In certain embodiments, the lumen of the needle containing the implant may be occluded by a material that is solid at room temperature but soft or liquid at body temperature, such as a 1 k PEG material, as disclosed herein in detail in the section "Manufacture of the Implant" and specifically the subsection "(PEG) Tipping the needle" thereof.

The kit may further contain an injection device for injecting the implant(s) into the eye of a patient, such as into the vitreous humor of the patient. In certain embodiments the injection device is provided and/or packaged separately from the one or more needle(s) loaded with implant. In such embodiments the injection device must be connected to the one or more needle(s) loaded with implant prior to injection.

In certain embodiments the number of injection devices provided separately in the kit equals the number of needles loaded with the implant provided in the kit. In these embodiments the injection devices are only used once for injection of one implant.

In other embodiments the kit contains one or more injection device(s) for injecting the implant into the eye of a patient, such as into the vitreous humor of the patient, wherein each injection device is or is not pre-connected to a needle loaded with implant. The present invention thus in one aspect also relates to a pharmaceutical product comprising a sustained release biodegradable ocular implant loaded in a needle and an injection device, wherein the needle is pre-connected to the injection device. In case the needle is not yet pre-connected to the injection device, the physician administering the implant needs to remove both the needle containing the implant and the injection device from the packaging, and connect the needle to the injection device to be able to inject the implant into the patient's eye.

In some embodiments the injection device contains a push wire to deploy the implant from the needle into the vitreous humor. The push wire may be a Nitinol push wire or may be a stainless steel/Teflon push wire. The push wire allows deploying the implant from the needle more easily.

In other embodiments the injection device and/or the injection needle may contain a stop feature that controls the injection depth.

In some embodiments the injection device is or comprises a modified Hamilton glass syringe that may be placed into a plastic syringe housing, such as inside an injection molded housing. A push wire, such as a Nitinol wire, is inserted into the syringe and advances with the plunger of the syringe during deployment of the implant. To facilitate entry of the nitinol push wire into the needle, a hub insert may be added into the needle hub. FIGS. 25A and 25B show one embodiment of an injector according to the present invention for injecting an implant into the vitreous humor of a patient. This depicted embodiment of an injector comprises a Hamilton syringe body and a Nitinol push wire to deploy the implant. FIG. 25A shows the Hamilton syringe body inside of an injection molded casing. FIG. 25B shows a schematic view of the components of this embodiment of the injector. In certain embodiments, the injector comprising the Hamilton syringe body and the plastic housing parts are pre-assembled in a kit according to the invention and the injector is ready for use (without or without mounted needle containing the implant). In other embodiments, the injector must be assembled by the physician prior to mounting the needle containing the implant.

In other embodiments, the injection device is an injection molded injector. A schematic exploded view of an embodiment of such injection molded injector is shown in FIG. 26. In this case the number of assembly steps by the physician just prior to administering the implant to a patient is reduced.

The kit may further comprise one or more doses, in particular one dose, of an anti-VEGF agent ready for injection. The anti-VEGF agent may be selected from the group consisting of aflibercept, bevacizumab, pegaptanib, ranibizumab, and brolucizumab. In certain embodiments the anti-VEGF agent is bevacizumab. In other embodiments the anti-VEGF agent is aflibercept. The anti-VEGF agent may be provided in a separate injection device connected to a needle, or may be provided as a solution or suspension in a sealed vial, from which the solution or suspension may be aspirated through a needle into a syringe or other injection device prior to administration.

The kit may further comprise an operation manual for the physician who is injecting the ocular implant(s). The kit may further comprise a package insert with product-related information.

In addition to the kit, the present invention in one aspect is also directed to an injection device per se that is suitable for injecting a sustained release biodegradable ocular implant according to the invention into the eye. The injection device may contain means for connecting the injection device to a needle, wherein the needle is pre-loaded with the implant. The injection device may further contain a push wire to deploy the implant from the needle into the eye when the injection device has been connected to the needle, which push wire may be made of Nitinol or stainless steel/Teflon or another suitable material. The injection device may further be obtainable by affixing the wire to the plunger and encasing it between two snap fit injector body parts and securing the plunger with a clip. An injection device and a needle pre-loaded with implant in accordance with certain embodiments of the present invention is depicted in FIG. 1.

Figure 26A:
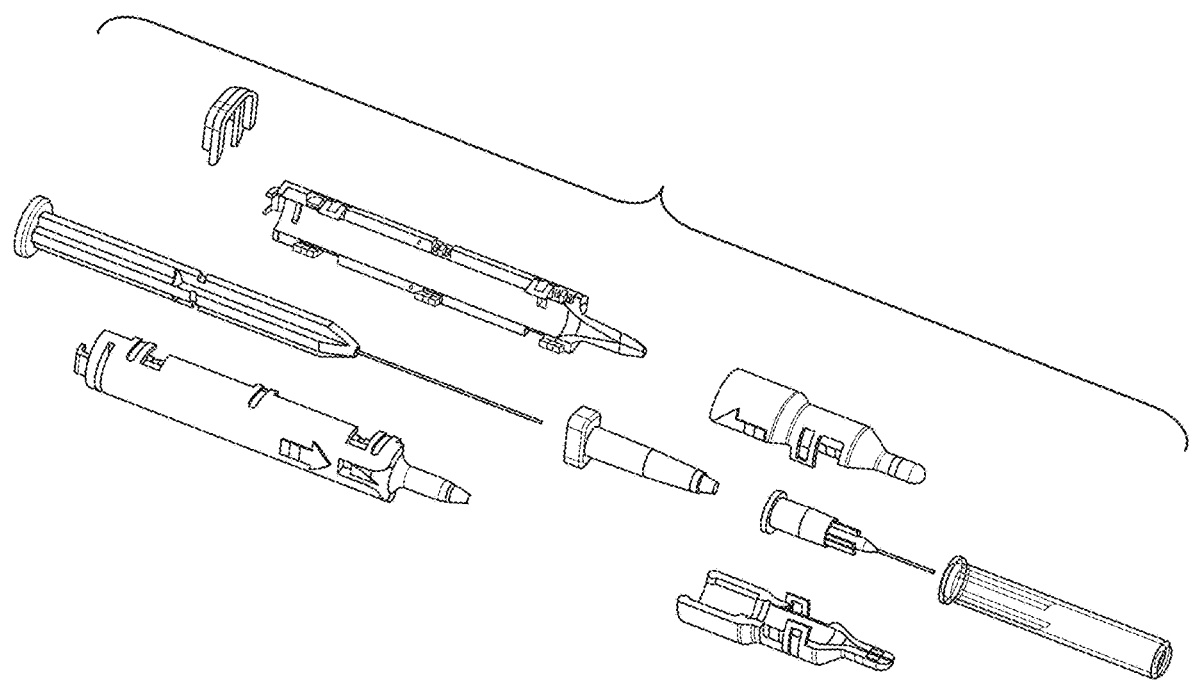
FIG. 26A Exploded view diagram of one embodiment of an injector according to the present invention that is made of an injection molded body.
Figure 26B:
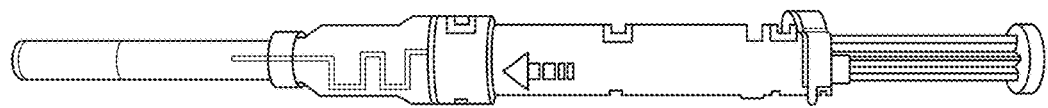
FIG. 26B shows a photograph of the fully assembled injector.
Figure 26C:
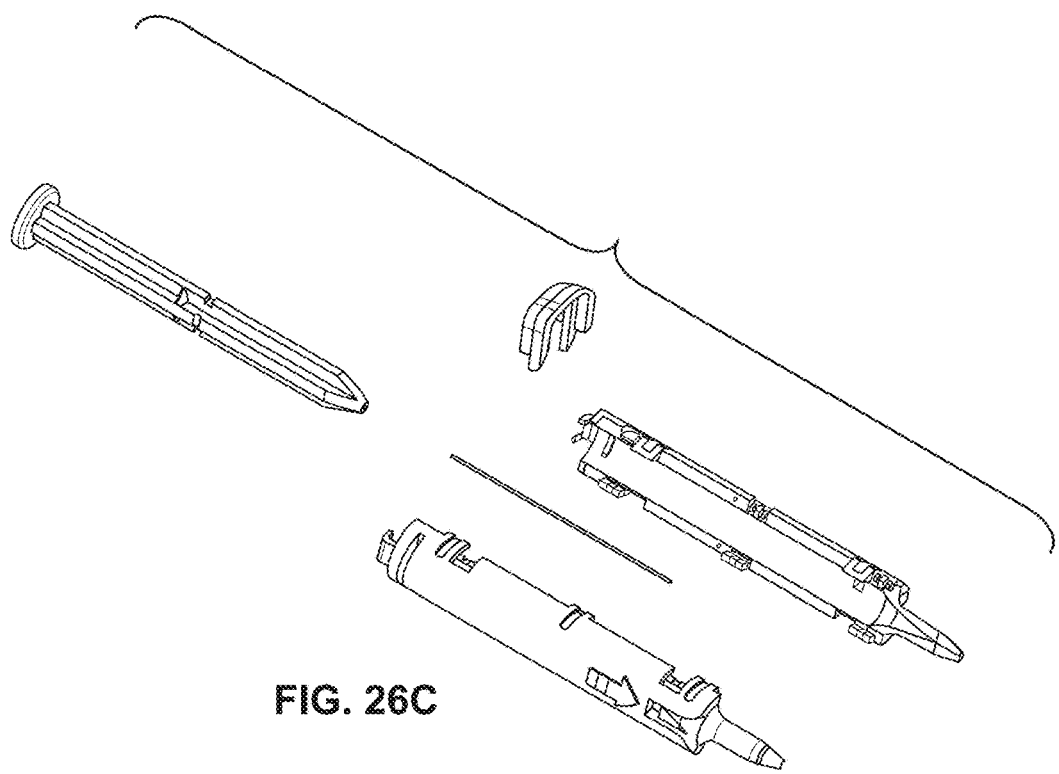
FIG. 26C shows an exploded view of a first assembly of an injector according to the present invention.

As illustrated in FIG. 1, in some embodiments, the injection device (e.g., implant injector device) may include a first assembly and a second assembly that are packaged separately (e.g., in separate enclosures). FIG. 26C is an exploded view of the first assembly and FIG. 26D is an exploded view of the second assembly.

Referring to FIG. 26C, the first assembly includes a body forming a first interior volume, a plunger including a first distal end disposed within the first interior volume, a wire including a first distal end secured to the first distal end of the plunger, and a plunger clip. The plunger clip is configured to interface with the plunger and the body to prevent actuation of the plunger. The body may include a first body half and a second body half configured to interconnect with each other. The body may include a living hinge that interfaces with a protrusion of the plunger resposnive to actuation of the plunger. The living hinge may allow actuation of the plunger responsive to application of a threshold force.

Figure 26D:
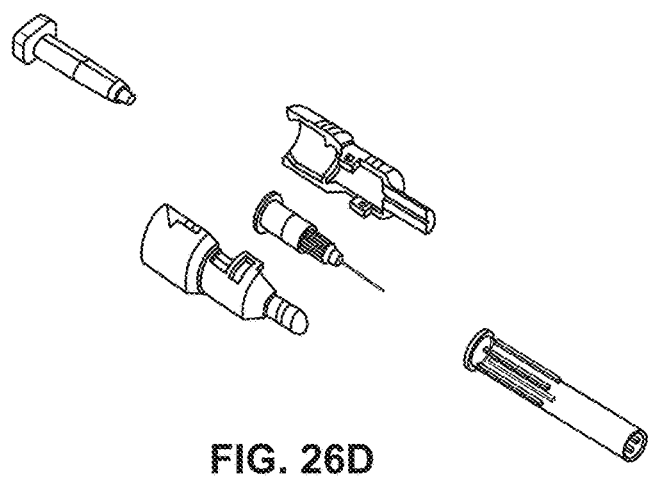
FIG. 26D shows an exploded view of a second assembly of an injector according to the present invention.

Referring the FIG. 26D, the second assembly includes a cowl forming a second interior volume, a needle including a base and a lumen, a cowl cap disposed within the base, and a needle shiled configured to secure to the cowl and to be disposed around a portion of the lumen. An implant is configured to be disposed within the lumen of the needle. The cowl may include a first cowl half and a second cowl half configured to interconnect with each other. The second assembly may further include a polymer tip (e.g., PEG tip) disposed on a second distal end of the lumen. The implant is secured in the lumen between the cowl cap and the polymer tip. The polymer tip is configured to liquefy (e.g., dissolve) within a user to allow the implant to be injected into the user.

In some embodiments, the second assembly is made from materials that include less moisture and/or undergoes conditioning (e.g., nitrogen conditioning) prior to being sealed in an enclosure to prevent the implant from absorbing moisture. In some embodiments, the first assembly is made from materials that include more moisture and/or does not undergo conditioning prior to being sealed in an enclosure since the implant is not included in the enclosure with the first assembly.

Figure 26E:
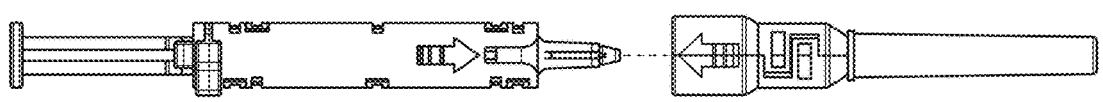
FIG. 26E shows that the first and the second assembly can be aligned.
Figure 26F:
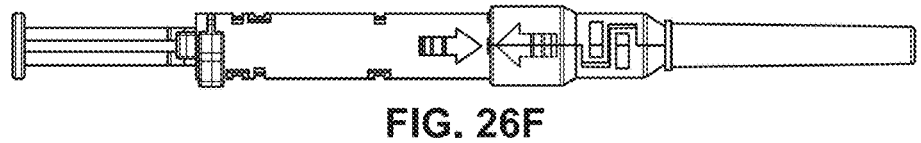
FIG. 26F shows the cowl of the second assembly being secured to the body of the first assembly.
Figure 26G:
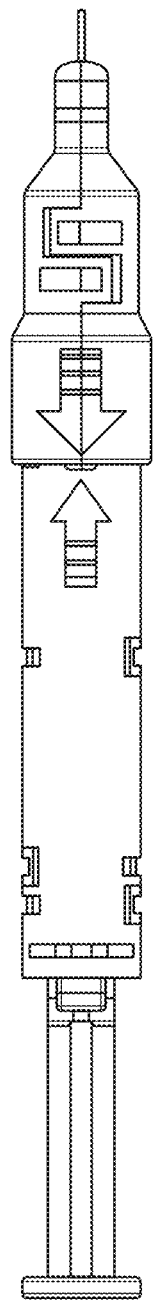
FIG. 26G shows the needle shield being removed from the cowl of the second assembly and the plunger clip being removed from the body and plunger of the first assembly.
Figure 26H:
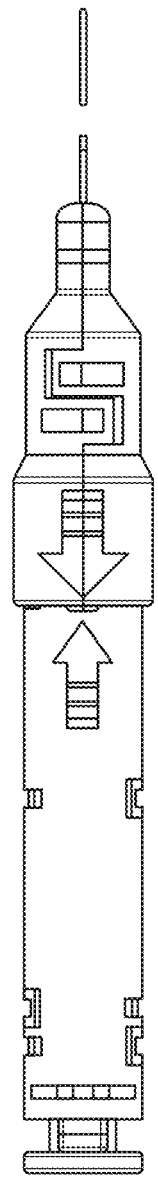
FIG. 26H shows the plunger of the first assembly being actuated to deploy the implant from the lumen of the needle of the second assembly.
Figure 27:
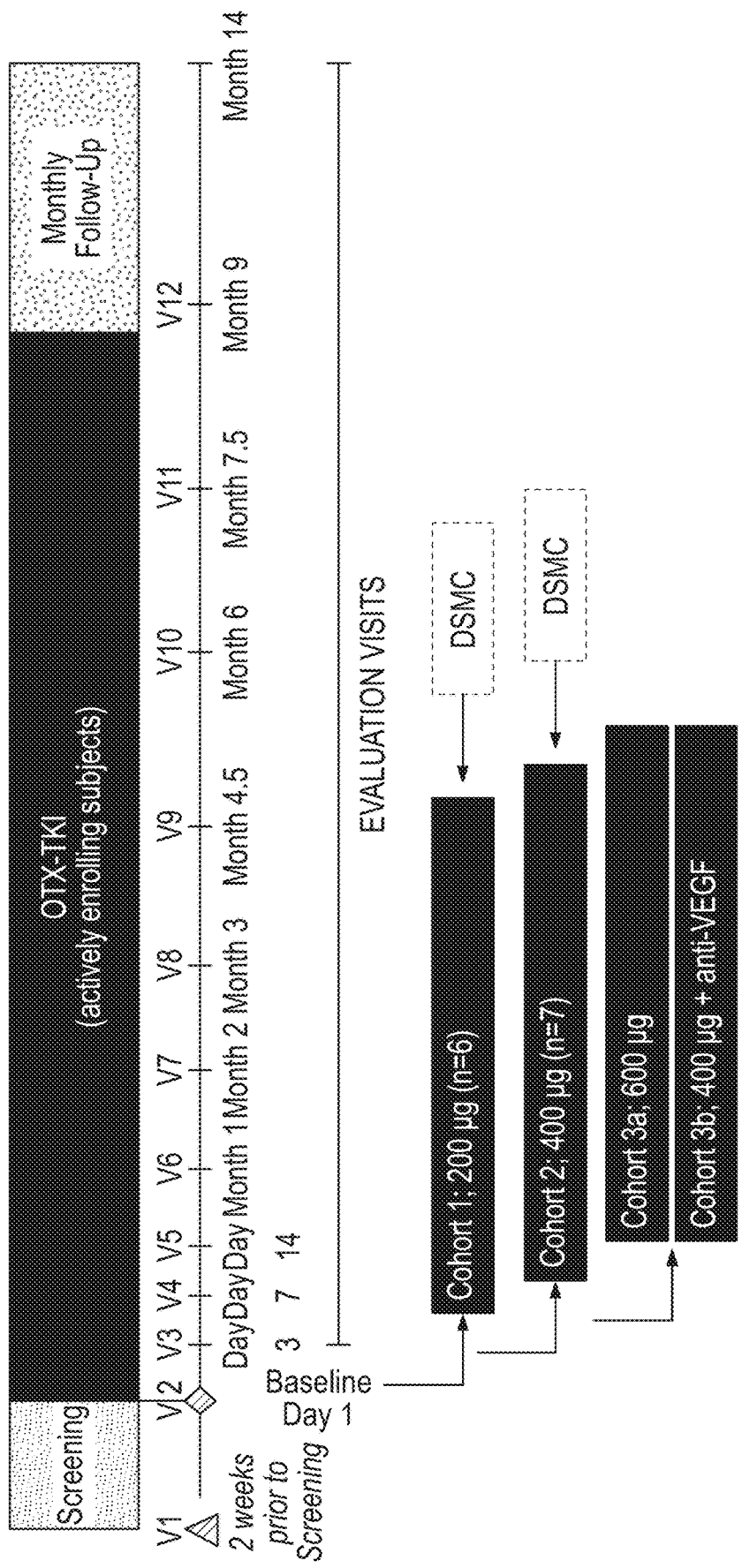
FIG. 27 Phase 1 study design with implants containing 200 μg axitinib according to one embodiment of the invention.

The first assembly may be removed from a first enclosure of FIG. 1 and a second assembly may be removed from a second enclosure of FIG. 1. Referring to FIG. 26E, the first assembly and the second assembly may be aligned. One or more exterior recesses of the first assembly may align with one or more interior protrusions of the second assembly. The first assembly and second assembly may include markings (e.g., arrows) to indicate how to align the first assembly and the second assembly. Referring to FIG. 26F, the cowl of the second assembly is secured to the body of the first assembly (e.g., via the interior protrusions of the cowl entering the exterior recesses of the body). Referring to FIG. 26G, the needle shield is removed from the cowl of the second assembly and the plunger clip is removed from the body and plunger of the first assembly. Referring to FIG. 26H, the plunger of the first assembly is actuated (e.g., pushed into the body of the first assembly) to deploy the implant from the lumen of the needle of the second assembly. In some embodiments, the body has a living hinge that allows actuation of the plunger responsive to a threshold force being applied to the plunger. In some embodiments, the lumen of the needle has a polymer tip (e.g., a polymer, such as PEG, disposed at least in the distal end of the lumen) blocking the implant from being deployed from the lumen. Insertion of the lumen with a polymer tip into a user may prevent coring of tissue of the user (e.g., cutting a piece of tissue the diameter of the inside of the lumen to later be deployed into the user). The lumen may be inserted in a user for a threshold amount of time (e.g., 1 to 5 seconds) to liquefy (e.g., dissolve) the polymer tip. After the polymer tip is liquefied, the implant may be deployed from the lumen via actuation of the plunger.

IV. Therapy

In certain embodiments, the present invention is further directed to a method of treating an ocular disease in a patient in need thereof, the method comprising administering to the patient the sustained release biodegradable ocular implant comprising the hydrogel and the tyrosine kinase inhibitor as disclosed above.

In specific embodiments, the present invention is directed to a method of treating an ocular disease in a patient in need thereof, the method comprising administering to the patient a sustained release biodegradable ocular implant comprising a hydrogel and at least about 150 µg of a tyrosine kinase inhibitor (TKI), wherein TKI particles are dispersed within the hydrogel.

In this treatment, the dose per eye administered once for a treatment period of at least 3 months is at least about 150 µg, such as from about 150 µg to about 1800 µg, or from about 150 µg to about 1200 µg of the tyrosine kinase inhibitor. In certain preferred embodiments the tyrosine kinase inhibitor is axitinib.

In certain embodiments the dose of the TKI, and specifically of axitinib, administered per eye once for (i.e., during) the treatment period is in the range of about 200 µg to about 800 µg. In certain embodiments the dose is in the range from about 160 µg to about 250 µg, or from about 180 µg to about 220 µg, or of about 200 µg.

In yet other specific embodiments this dose is in the range from about 320 µg to about 500 µg, or from about 360 µg to about 440 µg, or of about 400 µg. In yet other embodiments this dose is in the range from about 480 µg to about 750 µg, or from about 540 µg to about 660 µg, or of about 600 µg. In yet other embodiments this dose is in the range from about 640 µg to about 1000 µg, or from about 720 µg to about 880 µg, or of about 800 µg. In yet other embodiments this dose is in the range from about 800 µg to about 1250 µg, or from about 900 µg to about 1100 µg, or of about 1000 µg. In yet other embodiments this dose is in range from about 960 µg to about 1500 µg, or from about 1080 µg to about 1320 µg, or of about 1200 µg. In particular embodiments, the dose administered per eye once for the treatment period is about 600 µg axitinib. In particular embodiments, this dose of 600 µg is contained in one single implant.

In certain embodiments, the treatment period for the treatment of an ocular disease as disclosed herein with an implant of the present invention is least 3 months, at least 4.5 months, at least 6 months, at least 9 months, at least 11 months, at least 12 months, at least 13 months, at least 14 months or even longer, and may for example be about 6 to about 9 months.

In certain embodiments the ocular disease involves angiogenesis.

In other embodiments the ocular disease may be mediated by one or more receptor tyrosine kinases (RTKs), such as VEGFR-1, VEGFR-2, VEGFR-3, PDGFR-α/β, and/or by c-Kit.

In some embodiments the ocular disease is a retinal disease including Choroidal Neovascularization, Diabetic Retinopathy, Diabetic Macula Edema, Retinal Vein Occlusion, Acute Macular Neuroretinopathy, Central Serous Chorioretinopathy, and Cystoid Macular Edema; wherein the ocular disease is Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpignous Choroiditis, Subretinal Fibrosis, Uveitis Syndrome, or Vogt-Koyanagi-Harada Syndrome; wherein the ocular disease is a vascular disease or exudative diseases, including Coat's Disease, Parafoveal Telangiectasis, Papillophlebitis, Frosted Branch Angitis, Sickle Cell Retinopathy and other Hemoglobinopathies, Angioid Streaks, and Familial Exudative Vitreoretinopathy; or wherein the ocular disease results from trauma or surgery, including Sympathetic Ophthalmia, Uveitic Retinal Disease, Retinal Detachment, Trauma, Photodynamic Laser Treatment, Photocoagulation, Hypoperfusion During Surgery, Radiation Retinopathy, or Bone Marrow Transplant Retinopathy.

In alternative embodiments the sustained release biodegradable ocular implant comprising the hydrogel and the tyrosine kinase inhibitor of the present invention can be applied in treating ocular conditions associated with tumors. Such conditions include e.g., Retinal Disease Associated with Tumors, Solid Tumors, Tumor Metastasis, Benign Tumors, for example, hemangiomas, neurofibromas, trachomas, and pyogenic granulomas, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, or intraocular Lymphoid Tumors.

In general, the ocular implants of the present invention can also be applied for treatment of any ocular disease involving vascular leakage.

In certain embodiments the ocular disease is one selected from the list consisting of neovascular age-related macular degeneration (AMD), diabetic macula edema (DME), and retinal vein occlusion (RVO). In particular embodiments the ocular disease is neovascular age-related macular degeneration.

In some embodiments the treatment is effective in reducing the central subfield thickness (CSFT) as measured by optical coherence tomography in a patient whose central subfield thickness is elevated. Elevated within that context means that the CSFT is higher in the patient when compared to other individuals not suffering from the specific ocular disease. The elevated CSFT may be caused by retinal fluid such as sub- or intraretinal fluid. The reduction of CSFT in a patient may be determined with respect to a baseline CSFT measured in that patient prior to the start of the treatment, i.e., prior to the administration of the implant of the present invention. The capacity of the implants of the present invention to reduce CSFT and to maintain or to substantially maintain a reduced CSFT over an extended period of time in a cohort of patients is demonstrated in Example 6.3 and 6.4. In other embodiments, by means of the treatment according to the present invention involving the administration of an implant according to the present invention the CSFT of a patient whose CSFT is elevated due to an ocular disease involving angiogenesis is essentially maintained at a certain given level, or a clinically significant increase of the CSFT is prevented in the patient while sub- or intraretinal fluid is not substantially increased, i.e., is also essentially maintained.

In a particular embodiment, the CSFT is reduced in a patient and maintained at a reduced level over a period of at least 3 months, at least 4.5 months, at least 6 months, at least 9 months, at least 11 months, at least 12 months, at least 13 months, at least 14 months or even longer after administration of the implant of the invention. In a very particular embodiment, the CSFT is reduced for at least 6 months or at least 9 months or at least 12 months after administration of the implant with respect to the baseline CSFT of that patient prior to administration of the implant. In other particular embodiments, a reduced amount of retinal fluid and/or a reduced CSFT is maintained in a patient over a treatment period of at least 3 months, at least 4.5 months, at least 6 months, at least 9 months, at least 11 months, at least 12 months, at least 13 months, at least 14 months or even longer after administration of the implant of the invention without the need for administration of rescue medication (such as an injection of an anti-VEGF agent), or wherein rescue medication is administered only rarely, such as 1, 2, or 3 times during the treatment period. Thus, in this embodiment, during the treatment period with an implant according to the present invention the patient receiving the treatment may not need any rescue medication, or the administration of rescue medication is only required rarely, such as 1, 2 or 3 times during the treatment period.

In certain embodiments, the rescue medication is an anti-VEGF agent, such as aflibercept or bevacizumab, that is administered in the form of a suspension or solution by means of intravitreal injection. In certain specific embodiments, the rescue medication is one dose (2 mg) of aflibercept, administered by means of intravitreal injection. In line with the definitions herein, concurrent (i.e., planned) administration of an anti-VEGF agent together with an implant according to another embodiment of the present invention disclosed herein does not constitute a "rescue medication". In more particular embodiments, the treatment period wherein the level of fluid and/or the CSFT (as reduced by means of the administration of an implant according to the invention) is maintained or essentially maintained without the administration of rescue medication (or with rescue medication administered only rarely) is from about 6 to about 9 months after administration of the implant. In certain embodiments, the patients treated with an implant according to the invention do not require the concomitant administration of steroids (e.g., dexamethasone or prednisolone drops) during the treatment period.

In another embodiment, by means of the treatment according to the present invention involving the administration of an implant according to the present invention the CSFT of a patient whose CSFT is elevated due to angiogenesis is reduced, essentially maintained, or a clinically significant increase of the CSFT is prevented while the patient's vision (e.g. expressed by means of the best corrected visual acuity, also referred to herein as "BCVA") is not impaired, or is not significantly impaired. In certain embodiments, by means of the treatment according to the present invention involving the administration of an implant according to the present invention a patient's vision (where the patient's vision is impaired due to an ocular disease involving angiogenesis) as e.g. expressed by the BCVA may improve during the treatment period of at least 3 months, at least 6 months, at least 9 months, at least 11 months, at least 12 months, at least 13 months or at least 14 months.

Thus, in certain embodiments the present invention provides a method of improving the vision of a patient whose vision is impaired e.g. due to retinal fluid caused by an ocular disease involving angiogenesis, wherein the method comprises administering an implant according to the invention to the patient, such as by means of intravitreal injection. The improvement of the vision of a patient may be assessed for instance by means of the BCVA. An improvement of vision may manifest itself by an increase of the patient's BCVA e.g. by at least 10, or at least 15, or at least 20 ETDRS letters.

In certain embodiments, the total dose of TKI, such as axitinib, per eye administered once for the treatment period may be contained in one or more implants. In certain embodiments the dose per eye administered once for the treatment period is contained in one implant as for instance in one implant comprising a dose of about 600 μg or of about 200 μg axitinib. In other embodiments the total dose per eye administered once for the treatment period is contained in e.g. two implants, wherein each implant comprises a dose of e.g. about 200 μg axitinib (resulting in a total dose of about 400 μg in that case). In yet other embodiments the dose per eye administered once for the treatment period is contained in e.g. three implants, wherein each implant comprises a dose of e.g. about 200 μg axitinib (resulting in a total dose of about 600 μg in that case). In particular embodiments of the methods of treatment of the present invention, the dose of axitinib administered to one eye is about 600 μg and is contained in one implant.

For the injection of implants according to the present invention into the eye, such as into the vitreous humor, of a patient in the course of a treatment of an ocular disease, such as a retinal disease, including AMD, it is generally desirable to use implants having a therapeutically effective dose of TKI (i.e., one that is appropriate in view of particular patient's type and severity of condition) in a relatively small implant in order to facilitate administration (injection) as well as to reduce possible damage to ocular tissue as well as a possible impact of the patient's vision while the implant is in place. The implants of the present invention advantageously combine the benefits of a suitably high dose of the TKI (i.e., a therapeutically effective dose adjusted to a particular patient's need) with a relatively small implant size.

In certain embodiments, the implant may be administered by means of an injection device according to the present invention connected to a needle pre-loaded with implant as disclosed herein, or may be administered by means of another injection device suitable to be connected to a needle pre-loaded with an implant as disclosed herein, such as a (modified) Hamilton syringe. In other embodiments, a hollow microneedle may be used for suprachoroidal administration as disclosed in U.S. Pat. No. 8,808,225 which is incorporated by reference herein.

In embodiments wherein two or more implants are administered, the implants are generally administered concurrently as disclosed herein above. The implants administered concurrently can be the same or different. In cases where an administration during the same session is not possible e.g. due to administration complications or patient-related reasons a successive administration during two or more different sessions may alternatively be applied, such as for instance administration of two implants 7 days apart. This may still be considered as a "concurrent" administration in the context of the present invention.

In certain embodiments the dry implants are loaded in a needle, such as a needle with a gauge siz of from 22 to 23, such as a 25-gauge or a 27-gauge needle, or a smaller gauge needle, for injection and are administered to the eye, e.g. to the vitreous humor, through this needle. In one embodiment, the injector used for injecting the implant into the eye is an injection device according to another aspect of the present invention as disclosed above. Implants containing 200 μg and 600 μg, respectively, that are suitable for the therapeutic applications according to the present application are exemplarily presented in Tables 21.1 and 21.2.

The implant can generally be administered by means of intravitreal, subconjunctival, subtenon, suprachoroidal, or intracameral injection. In certain embodiments the implant is administered to the vitreous humor, e.g. the implant is administered intravitreally into the posterior section of the vitreous humor. In other embodiments, the implant is administered by means of a hollow microneedle, such as into the sclera of the eye at an insertion site into the suprachoroidal space of the eye as disclosed in U.S. Pat. No. 8,808,225, which is incorporated herein by reference.

In certain embodiments, the treatment period is at least 3 months, but may be at least 4.5 months, at least 6 months, at least 9 months, at least 11 months or at least 12 months. In particular embodiments, the treatment period is at least 6 months, at least 9 months, at least 11 months, at least 12 months, at least 13 months, or at least 14 months. In certain embodiments, the treatment period may also be longer, such as up to about 15 months. "Treatment period" according to one embodiment of the invention means that a certain therapeutic effect of an implant of the present invention once administered is maintained, essentially maintained or partially maintained over that period of time. In other words, only one injection (of the implant of the present invention) is required in certain embodiments for maintaining a therapeutic effect of reducing or essentially maintaining or of preventing a clinically significant increase of the CSFT during the extended period of time referred to herein as "treatment period". This is a considerable advantage over currently used anti-VEGF treatments for AMD which require more frequent administration, and thus improves the patient's quality of life. Another advantage is that the necessity and/or frequency of the administration of rescue medication during the treatment period is very low. In certain embodiments, no rescue medication is necessary during the treatment period, such as a treatment period of from about 6 to about 9 months after administration of the implant. In certain other embodiments, rescue medication only has to be administered rarely, such as 1, 2 or 3 times during the treatment period. The vision of a patient may be improved as evidenced e.g. by an increase in the BCVA (such as by at least 10, at least 15 or at least 20 ETDRS letters) following administration of an implant of the invention.

In one particular embodiment the invention is directed to a method of treating neovascular age-related macular degeneration in a patient in need thereof, the method comprising administering to the patient a sustained release biodegradable ocular implant comprising a hydrogel that comprises a polymer network and about 200 μg of a tyrosine kinase inhibitor, wherein one implant per eye is administered once for a treatment period of at least 9 months, and wherein the patient has a history of an anti-VEGF treatment. In this embodiment the treatment results in a reduction in central subfield thickness (CSFT), or at least maintenance of CSFT, as measured by optical coherence tomography during the treatment period. In this embodiment the TKI may further be axitinib, which is dispersed in the hydrogel which comprises a polymer network formed by reacting 4a20kPEG-SAZ with 8a20kPEG-NH$_2$, and wherein the implant is in a dried state prior to administration. In this embodiment the hydrogel when formed and before being dried contains about 7.5% polyethylene glycol, representing the polyethylene glycol weight divided by the fluid weight×100. Alternatively, the patient treated may also have no history of an anti-VEGF treatment (AMD treatment naïve).

In another particular embodiment the invention is directed to a method of treating neovascular age-related macular degeneration in a patient in need thereof, the method comprising administering to the patient a sustained release biodegradable ocular implant comprising a hydrogel that comprises a polymer network and about 200 μg of a tyrosine kinase inhibitor, wherein two implants per eye forming a total dose of about 400 μg are administered once for a treatment period of at least 3 months, or for at least 9 months, and wherein the patient has a history of an anti-VEGF treatment or has no history of an anti-VEGF treatment (AMD treatment naïve). In this embodiment the treatment results in a reduction (or at least maintenance of) central subfield thickness (CSFT) as measured by optical coherence tomography during the treatment period. In this embodiment the TKI may further be axitinib which is dispersed in the hydrogel which comprises a polymer network formed by reacting 4a20kPEG-SAZ with 8a20kPEG-NH$_2$, and wherein the implant is in a dried state prior to administration. In this embodiment the hydrogel when formed and before being dried contains about 7.5% polyethylene glycol, representing the polyethylene glycol weight divided by the fluid weight×100.

In yet another particular embodiment the invention is directed to a method of treating neovascular age-related macular degeneration in a patient in need thereof, the method comprising administering to the patient a sustained release biodegradable ocular implant comprising a hydrogel that comprises a polymer network and about 200 µg of a tyrosine kinase inhibitor, wherein three implants per eye forming a total dose of about 600 µg are administered once for a treatment period of at least 3 months, or for at least 9 months, and wherein the patient has a history of an anti-VEGF treatment or has no history of an anti-VEGF treatment (AMD treatment naïve). In this embodiment the treatment results in a reduction (or at least maintenance of) central subfield thickness (CSFT) as measured by optical coherence tomography during the treatment period. In this embodiments the TKI may further be axitinib which is dispersed in the hydrogel which comprises a polymer network formed by reacting 4a20kPEG-SAZ with 8a20kPEG-NH$_2$, and wherein the implant is in a dried state prior to administration. In this embodiment the hydrogel when formed and before being dried contains about 7.5% polyethylene glycol, representing the polyethylene glycol weight divided by the fluid weight×100.

In yet other embodiments the invention is directed to a method of treating neovascular age-related macular degeneration in a patient in need thereof, the method comprising administering to the patient a sustained release biodegradable ocular implant comprising axitinib in an amount in the range from about 480 µg to about 750 µg dispersed in a hydrogel comprising a polymer network, wherein the implant is administered once for a treatment period of at least 3 months. In certain of these embodiments the axitinib is contained in the implant in an amount of from about 560 µg to about 660 µg, or of about 600 µg. For specific properties of the implant reference is made to the sections above directed to an implant according to the present invention containing axitinib in an amount in the range from about 480 µg to about 750 µg, or in an amount from about 560 µg to about 660 µg, or of about 600 µg.

The implant may be administered into the vitreous humor, e.g. by means of a fine diameter, such as a 25-gauge, needle. The treatment period as defined above may be at least 4.5 months, or at least 6 months, or at least 9 months, or at least 11 months, or at least 12 months, or at least 13 months, or at least 14 months or even longer, such as up to about 15 months. In particular embodiments, the treatment period is at least 6 months, or at least 9 months, or at least 12 months, or from about 6 to about 9 months.

In some embodiments concurrently with the treatment with the sustained release biodegradable ocular implant(s) containing a TKI, or a treatment with the sustained release biodegradable ocular implant(s) containing axitinib according to the invention, an anti-VEGF agent is administered to the patient. The anti-VEGF agent may be selected from the group consisting of aflibercept, bevacizumab, pegaptanib, ranibizumab, and brolucizumab. In certain embodiments the anti-VEGF agent is bevacizumab. In particular embodiments the anti-VEGF agent is aflibercept. In certain embodiments the anti-VEGF agent is administered by means of an intravitreal injection concurrently (as defined above) with the administration of the sustained release biodegradable ocular implant, optionally at the same time, i.e., in one session as already disclosed above in detail. In cases where an administration of the anti-VEGF agent and the implant of the present invention may not be possible in the same session, e.g. due to administration complications or patient-related reasons a successive administration during two or more different sessions may alternatively be applied, such as for instance administration of two implants 7 days apart. This may still be considered as a "concurrent" administration in the context of the present invention.

In other embodiments, an anti-VEGF agent may be administered in combination with an implant of the present invention, but not at the same time (i.e., not concurrently), but at an earlier or a later point during the treatment period of the implant of the present invention. In certain embodiments, an anti-VEGF agent may be administered within about 1, about 2, or about 3, or more months of the administration of the implant, i.e., may be pre- or post-administered as compared to the implant. This combined (and planned) co-administration of an anti-VEGF agent differs from a rescue medication as defined herein.

In certain embodiments of the present invention the patient has a diagnosis of primary subfoveal (such as active sub- or juxtafoveal CNV with leakage involving the fovea) neovascularization (SFNV) secondary to AMD.

In certain embodiments of the present invention the patient has a diagnosis of previously treated subfoveal neovascularization (SFNV) secondary to neovascular AMD with leakage involving the fovea. In such patient, the previous treatment was with an anti-VEGF agent.

In some embodiments the patient is at least 50 or at least 60 years old. The patient may be male or female. The patient may have retinal fluid such as intra-retinal fluid or sub-retinal fluid.

In some embodiments the patient receiving the implant has a history of an anti-VEGF treatment e.g. such as treatment with LUCENTIS® and/or EYLEA®. In certain embodiments the patient receiving the implant has a history of anti-VEGF treatment but has not responded to this anti-VEGF treatment, i.e. the disease state of the patient was not improved by the anti-VEGF treatment. In embodiments where the patient has a history of an anti-VEGF treatment before starting the treatment with the implant according to the present invention, administration of the implant of the present invention may prolong the effect of the prior anti-VEGF treatment over an extended period of time, such as over the treatment period defined above. In other embodiments the patient receiving the implant has no history of an anti-VEGF treatment (anti-VEGF naïve, AMD treatment naïve).

In certain embodiments the systemic plasma concentration of the TKI such as axitinib is below 1 ng/mL, or below 0.5 ng/ml, or below 0.3 ng/mL, or below 0.1 ng/mL (or below the limit of quantification). As systemic concentrations of TKI are kept at a minimum, the risk of drug-to-drug interactions or systemic toxicity is also kept at a minimum. Therefore, in one embodiment additional medication(s) taken by the patients do not provide a significant risk. This is especially beneficial in older patients who are frequently suffering from ocular diseases and are additionally taking other medications.

Once injected the implants of certain embodiments of the invention (comprising the hydrogel and the drug) biodegrade within an extended period of time as disclosed above, e.g., about 9 to 12 months. In certain embodiments it may be that once the hydrogel is fully degraded undissolved axitinib particles remain localized at the site where the implant was located. These undissolved particles may further maintain a rate of TKI delivery sufficient for therapeutic effect (i.e. inhibition of vascular leakage) when the hydrogel is degraded. FIG. 15 exemplarily presents the resorption of the hydrogel and remaining axitinib particles at the former implant location in one patient until 11 months after administration. In certain embodiments, however, the entire amount of TKI is dissolved prior to complete degradation of the hydrogel.

In certain embodiments only mild or moderate adverse events such as ocular adverse events are observed over the treatment period. In certain embodiments no serious ocular adverse events are observed, and no treatment-related serious ocular adverse events are observed. Tables 23 and 25 show the occurrence of adverse events in the cohort 1 and 2, as well as the cohort 3a and 3b subjects, respectively, of the clinical study the results of which (as far as available) are presented in Example 6.4.

The invention in certain embodiments is further directed to a method of reducing, essentially maintaining or preventing a clinically significant increase of the central subfield thickness as measured by optical coherence tomography in a patient whose central subfield thickness is elevated due to an ocular disease involving angiogenesis, the method comprising administering to the patient the sustained release biodegradable ocular implant containing a tyrosine kinase inhibitor of the present invention as disclosed herein. In certain embodiments the ocular disease involving angiogenesis is neovascular age-related macular degeneration. In other embodiments the central subfield thickness is reduced, essentially maintained or a clinically significant increase of the central subfield thickness is prevented during a period of at least 3 months, at least 4.5 months, at least 6 months, at least 9 months, at least 11 months, at least 12 months, at least 13 months, or at least 14 months or even longer, such as at least 15 months after administration to the patient whose central subfield thickness is elevated due to an ocular disease involving angiogenesis, such as neovascular age-related macular degeneration. In certain embodiments, the patient's vision expressed e.g. by the BCVA is not substantially impaired during the treatment. In certain other embodiments, the patient's vision expressed e.g. by the BCVA may even be improved. Accordingly, the invention in certain embodiments is also directed to a method of improving the vision of a patient whose vision is impaired e.g. due to retinal fluid caused by an ocular disease involving angiogenesis, wherein the method comprises administering an implant according to the invention to the patient, such as by means of intravitreal injection.

ADDITIONAL DISCLOSURE

In addition to the disclosure above, the present invention also discloses the following items and lists of items:

First List of Items

1. A sustained release biodegradable ocular implant comprising a hydrogel and about 150 µg to about 1200 µg of a tyrosine kinase inhibitor.
2. The sustained release biodegradable ocular implant of item 1, wherein the tyrosine kinase inhibitor is axitinib.
3. The sustained release biodegradable ocular implant of claim 1 or 2, comprising the tyrosine kinase inhibitor in an amount in the range from about 200 µg to about 800 µg.
4. The sustained release biodegradable ocular implant of item 1 or 2, comprising the tyrosine kinase inhibitor in an amount in the range from about 160 µg to about 250 µg.
5. The sustained release biodegradable ocular implant of claim 4, comprising the tyrosine kinase inhibitor in an amount in the range from about 180 µg to about 220 µg.
6. The sustained release biodegradable ocular implant of item 5, comprising the tyrosine kinase inhibitor in an amount of about 200 µg.
7. The sustained release biodegradable ocular implant of claim 1 or 2, comprising the tyrosine kinase inhibitor in an amount in the range from about 320 µg to about 500 µg.
8. The sustained release biodegradable ocular implant of item 7, comprising the tyrosine kinase inhibitor in an amount in the range from about 360 µg to about 440 µg.
9. The sustained release biodegradable ocular implant of claim 8, comprising the tyrosine kinase inhibitor in an amount of about 400 µg.
10. The sustained release biodegradable ocular implant of item 1 or 2, comprising the tyrosine kinase inhibitor in an amount in the range from about 480 µg to about 750 µg.
11. The sustained release biodegradable ocular implant of claim 10, comprising the tyrosine kinase inhibitor in an amount from about 540 µg to about 660 µg.
12. The sustained release biodegradable ocular implant of item 11, comprising the tyrosine kinase inhibitor in an amount of about 600 µg.
13. The sustained release biodegradable ocular implant of item 1 or 2, comprising the tyrosine kinase inhibitor in an amount in the range from about 640 µg to about 1000 µg.
14. The sustained release biodegradable ocular implant of item 13, comprising the tyrosine kinase inhibitor in an amount from about 720 µg to about 880 µg.
15. The sustained release biodegradable ocular implant of item 14, comprising the tyrosine kinase inhibitor in an amount of about 800 µg.
16. The sustained release biodegradable ocular implant of any of the preceding items, wherein the implant is for administration into the posterior section of the eye.
17. The sustained release biodegradable ocular implant of item 16, wherein the administration is into the vitreous humor.
18. The sustained release biodegradable ocular implant of any of the preceding items, wherein the tyrosine kinase inhibitor particles are dispersed within the hydrogel.
19. The sustained release biodegradable ocular implant of item 18, wherein the tyrosine kinase inhibitor particles are micronized particles.
20. The sustained release biodegradable ocular implant of any of the preceding items, wherein the implant is in a dried state prior to administration and becomes hydrated once administered into the eye.
21. The sustained release biodegradable ocular implant of any of the preceding items, wherein the hydrogel comprises a polymer network comprising one or more units of polyethylene glycol, polyethylene oxide, polypropylene oxide, polyvinyl alcohol, poly (vinylpyrrolidinone), polylactic acid, polylactic-co-glycolic acid, random or block copolymers or combinations or mixtures of any of these, or one or more units of polyaminoacids, glycosaminoglycans, polysaccharides, or proteins.
22. The sustained release biodegradable ocular implant of item 21, wherein the hydrogel comprises a polymer network that comprises crosslinked polymer units that are identical or different.
23. The sustained release biodegradable ocular implant of item 22, wherein crosslinked polymer units are one or more crosslinked polyethylene glycol units.

24. The sustained release biodegradable ocular implant of any of items 21 to 23, wherein the polymer network comprises polyethylene glycol units having an average molecular weight in the range from about 2,000 to about 100,000 Daltons.
25. The sustained release biodegradable ocular implant of item 24, wherein the polyethylene glycol units have an average molecular weight in the range from about 10,000 to about 60,000 Daltons.
26. The sustained release biodegradable ocular implant of item 25, wherein the polyethylene glycol units have an average molecular weight in the range from about 20,000 to about 40,000 Daltons.
27. The sustained release biodegradable ocular implant of item 26, wherein the polyethylene glycol units have an average molecular weight of about 20,000 Daltons.
28. The sustained release biodegradable ocular implant of any of items 21 to 27, wherein the polymer network comprises one or more crosslinked multi-arm polymer units.
29. The sustained release biodegradable ocular implant of item 28, wherein the multi-arm polymer units comprise one or more 2- to 10-arm polyethylene glycol units.
30. The sustained release biodegradable ocular implant of item 29, wherein the multi-arm polymer units comprise one or more 4- to 8-arm polyethylene glycol units.
31. The sustained release biodegradable ocular implant of item 30, wherein the multi-arm polymer units comprise one or more 4-arm polyethylene glycol units.
32. The sustained release biodegradable ocular implant of any of items 21 to 31, wherein the polymer network comprises both 4-arm and 8-arm polyethylene glycol units.
33. The sustained release biodegradable ocular implant of any of items 21 to 32, wherein the polymer network is formed by reacting an electrophilic group-containing multi-arm-polymer precursor with a nucleophilic group-containing multi-arm polymer precursor.
34. The sustained release biodegradable ocular implant of any of items 21 to 33, wherein the nucleophilic group is an amine group.
35. The sustained release biodegradable ocular implant of any of items 21 to 34, wherein the electrophilic group is an activated ester group.
36. The sustained release biodegradable ocular implant of item 35, wherein the electrophilic group is an N-hydroxysuccinimidyl (NHS) group.
37. The sustained release biodegradable ocular implant of item 36, wherein the electrophilic group is a succinimidylazelate (SAZ) group.
38. The sustained release biodegradable ocular implant of any of items 32 to 37, wherein the 4-arm polyethylene glycol units are 4a20kPEG units and the 8-arm polyethylene glycol units are 8a20kPEG units.
39. The sustained release biodegradable ocular implant of item 38, wherein the polymer network is obtained by reacting 4a20kPEG-SAZ with 8a20kPEG-NH$_2$ in a weight ratio of about 2:1 or less.
40. The sustained release biodegradable ocular implant of any of items 1 to 39, wherein the implant in a dried state contains from about 25% to about 75% by weight of the tyrosine kinase inhibitor and from about 20% to about 60% by weight polymer units.
41. The sustained release biodegradable ocular implant of item 40, wherein the implant in a dried state contains from about 35% to about 65% by weight of the tyrosine kinase inhibitor and from about 25% to about 50% by weight polymer units.
42. The sustained release biodegradable ocular implant of item 41, wherein the implant in a dried state contains from about 45% to about 55% by weight of the tyrosine kinase inhibitor and from about 37% to about 47% by weight polymer units.
43. The sustained release biodegradable ocular implant of any of the preceding items, wherein the implant contains one or more phosphate, borate or carbonate salt(s).
44. The sustained release biodegradable ocular implant of item 43, wherein the implant contains phosphate salt originating from phosphate buffer used during the preparation of the hydrogel.
45. The sustained release biodegradable ocular implant of any of the preceding items, wherein the hydrogel in a wet state contains about 3% to about 20% polyethylene glycol representing the polyethylene glycol weight divided by the fluid weight×100.
46. The sustained release biodegradable ocular implant of item 45, wherein the hydrogel contains about 7.5% to about 15% polyethylene glycol representing the polyethylene glycol weight divided by the fluid weight x 100.
47. The sustained release biodegradable ocular implant of any of the preceding items, wherein the implant in a dried state contains not more than about 1% by weight water.
48. The sustained release biodegradable ocular implant of any of the preceding items, wherein the implant has an essentially cylindrical shape or another shape such as a cross shape.
49. The sustained release biodegradable ocular implant of any of the preceding items, wherein the implant is in the form of a fiber.
50. The sustained release biodegradable ocular implant of any of the preceding items, wherein the implant is administered to the eye through a needle.
51. The sustained release biodegradable ocular implant of item 50, wherein the needle is a 25- or 27-gauge needle.
52. The sustained release biodegradable ocular implant of any of the preceding items, wherein upon hydration in vivo in the eye or in vitro the diameter of the implant is increased, or the length of the implant is decreased while its diameter is increased.
53. The sustained release biodegradable ocular implant of item 52, wherein hydration is measured in vitro in phosphate-buffered saline at a pH of 7.2 at 37° C. after 24 hours.
54. The sustained release biodegradable ocular implant of any of items 17 to 53, wherein the implant biodegrades in the vitreous humor within about 2 to about 15 months after administration.
55. The sustained release biodegradable ocular implant of item 54, wherein the implant biodegrades in the vitreous humor within about 4 to about 13 months after administration.
56. The sustained release biodegradable ocular implant of item 55, wherein the implant biodegrades in the vitreous humor within about 9 to about 12 months after administration.
57. The sustained release biodegradable ocular implant of any of items 2 to 56, wherein the implant after administration to the vitreous humor releases a therapeutically effective amount of axitinib over a period of at least about 3 months, at least about 6 months, at least about 9 months, at least about 10 months, at least about 11 months, at least about 12 months, at least about 13 months, or at least about 14 months after administration.

58. The sustained release biodegradable ocular implant of item 57, wherein the implant after administration to the vitreous humor releases a therapeutically effective amount of axitinib over a period of at least about 6 months.

59. The sustained release biodegradable ocular implant of item 57, wherein the implant after administration to the vitreous humor releases a therapeutically effective amount of axitinib over a period of at least about 9 months.

60. The sustained release biodegradable ocular implant of any of items 17 to 59, wherein axitinib is released from the implant after administration at an average rate of about 0.1 μg/day to about 10 μg/day.

61. The sustained release biodegradable ocular implant of item 60, wherein axitinib is released from the implant at an average rate of about 0.5 μg/day to about 7 μg/day.

62. The sustained release biodegradable ocular implant of item 61, wherein axitinib is released from the implant at an average rate about 1 μg/day to about 5 μg/day.

63. The sustained release biodegradable ocular implant of any of items 17 to 62, wherein the implant biodegrades in the vitreous humor prior to complete solubilization of the tyrosine kinase inhibitor particles contained in the implant.

64. The sustained release biodegradable ocular implant of any of items 17 to 63, wherein the entire amount of the tyrosine kinase inhibitor contained in the implant is released prior to the complete degradation of the implant in the vitreous humor.

65. The sustained release biodegradable ocular implant of any of the preceding items, wherein the implant is obtainable by preparing a mixture containing hydrogel precursors and a tyrosine kinase inhibitor, filling the mixture into a tubing, allowing the hydrogel to gel in the tubing to provide a hydrogel shaped as a fiber, and stretching the hydrogel fiber.

66. The sustained release biodegradable ocular implant of item 65, wherein the fiber has been stretched and/or twisted prior to or after drying.

67. The sustained release biodegradable ocular implant of item 66, wherein the fiber has been stretched by a stretch factor in the longitudinal direction of from about 1.0 to about 4.5.

68. A sustained release biodegradable ocular implant containing axitinib in an amount of 160 μg to about 250 μg, or from about 180 μg to about 220 μg, or a bout 200 μg dispersed in a hydrogel, wherein the hydrogel comprises a polymer network comprising polyethylene glycol units, and wherein the implant is in a dried state prior to administration.

69. The sustained release biodegradable ocular implant of item 68, wherein the polymer network is formed by reacting 4a20kPEG-SAZ with 8a20kPEG-NH$_2$.

70. The sustained release biodegradable ocular implant of item 69, wherein the hydrogel when formed and before being dried contains 7.5% polyethylene glycol, representing the polyethylene glycol weight divided by the fluid weight×100.

71. The sustained release biodegradable ocular implant of any of items 68 to 70, wherein the implant in a dried state contains from about 45% to about 55% by weight axitinib and from about 37% to about 47% by weight polyethylene glycol units.

72. The sustained release biodegradable ocular implant of any of items 68 to 71, wherein the implant in a dried state contains not more than about 1% by weight water.

73. The sustained release biodegradable ocular implant of any of items 68 to 72, wherein the polymer network is formed by reacting 4a20kPEG-SAZ with 8a20kPEG-NH$_2$ in a weight ratio of about 2:1 or less.

74. The sustained release biodegradable ocular implant of any of items 68 to 73, wherein the implant releases in vitro about 0.01 μg to about 0.15 μg of axitinib per day in phosphate-buffered saline at 37° C. for a period of 30 days.

75. The sustained release biodegradable ocular implant of any of items 68 to 74, wherein the implant releases in vitro about 35% to about 45% of the axitinib in 3 days, about 65% to about 75% of the axitinib in 7 days, and about 90% to about 100% of the axitinib in 12 to 13 days in a 25:75 ethanol/water mixture (v/v) at 37° C.

76. The sustained release biodegradable ocular implant of any of items 68 to 75, wherein the implant releases in vitro about 25% to about 35% of the axitinib in 2 months, about 47% to about 57% of the axitinib in 3 months, about 70% to about 80% of the axitinib in 5 months, and about 90% to about 100% of the axitinib in 7 months in phosphate buffered saline at a pH of 7.2, at 37° C. and with an octanol top layer.

77. The sustained release biodegradable ocular implant of any of items 68 to 76, wherein the implant is in the form of a fiber that has an average length of about 15 mm to about 16.5 mm and an average diameter of about 0.20 mm to about 0.30 mm in its dried state.

78. The sustained release biodegradable ocular implant of item 77, which decreases in length and increases in diameter upon hydration in vivo in the eye or in vitro, wherein hydration in vitro is measured in phosphate-buffered saline at a pH of 7.2 at 37° C. after 24 hours.

79. The sustained release biodegradable ocular implant of item 77 or 78, wherein the implant in its hydrated state has an average length of about 6.5 to about 8 mm and an average diameter of about 0.70 to about 0.80 mm.

80. The sustained release biodegradable ocular implant of any of items 68 to 79, wherein the implant is obtainable by preparing a mixture containing hydrogel precursors and axitinib, filling the mixture into a tubing, allowing the hydrogel to gel in the tubing to provide a hydrogel shaped as a fiber, and stretching the hydrogel fiber.

81. The sustained release biodegradable ocular implant of item 80, wherein the fiber is stretched after drying by a factor of about 2 to about 5.

82. The sustained release biodegradable ocular implant of item 81, wherein the fiber is stretched after drying by a factor of about 3 to about 4.5.

83. The sustained release biodegradable ocular implant of any of items 68 to 82, wherein the implant in a dried state is loaded in a needle, such as a 25-gauge needle or a 27-gauge needle, for injection into the vitreous humor.

84. A sustained release biodegradable ocular implant containing axitinib in an amount in the range from about 480 μg to about 750 μg dispersed in a hydrogel, wherein the hydrogel comprises a polymer network.

85. The sustained release biodegradable ocular implant of item 84, wherein the polymer network comprises cross-linked polyethylene glycol units.

86. The sustained release biodegradable ocular implant of item 85, wherein the axitinib is contained in an amount in the range from about 540 μg to about 660 μg.
87. The sustained release biodegradable ocular implant of item 86, wherein the axitinib is contained in an amount of about 600 μg.
88. The sustained release biodegradable ocular implant of any of items 84 to 87, wherein the polyethylene glycol units comprise 4-arm and/or 8-arm polyethylene glycol units having an average molecular weight in the range from about 10,000 Daltons to about 60,000 Daltons.
89. The sustained release biodegradable ocular implant of item 88, wherein the polyethylene glycol units comprise 4a20kPEG units.
90. The sustained release biodegradable ocular implant of item 89, wherein the polymer network is formed by reacting 4a20kPEG-SAZ with 8a20kPEG-NH$_2$.
91. The sustained release biodegradable ocular implant of item 90, wherein the weight ratio of 4a20kPEG-SAZ to 8a20kPEG-NH$_2$ is about 2:1 or less.
92. The sustained release biodegradable ocular implant of any of items 84 to 91, wherein the implant in a dried state contains from about 45% to about 55% by weight axitinib and from about 37% to about 47% by weight polyethylene glycol units.
93. The sustained release biodegradable ocular implant of any of items 84 to 92, wherein the implant in a dried state contains not more than about 1% by weight water.
94. The sustained release biodegradable ocular implant of any of items 84 to 93, wherein the implant is in the form of a fiber that in its dried state has an average length of about 7 mm to about 12 mm and an average diameter of about 0.25 mm to about 0.50 mm.
95. The sustained release biodegradable ocular implant of item 94, wherein the implant is in the form of a fiber that in its dried state has an average length of about 8 mm to about 11 mm and an average diameter of about 0.3 mm to about 0.4 mm.
96. The sustained release biodegradable ocular implant of any of items 84 to 95, wherein the implant is for administration to the vitreous humor.
97. The sustained release biodegradable ocular implant of item 94 to 96, which increases in diameter upon hydration in vivo in the eye or in vitro, wherein hydration in vitro is measured in phosphate-buffered saline at a pH of 7.2 at 37° C. after 24 hours.
98. The sustained release biodegradable ocular implant of item 97, wherein the implant in its hydrated state has an average length of about 9 mm to about 12 mm and an average diameter of about 0.5 mm to about 0.8 mm.
99. The sustained release biodegradable ocular implant of item 98, wherein the implant in its hydrated state has an average length of about 9.5 mm to about 11.5 mm and an average diameter of about 0.65 mm to about 0.75 mm, or has an average length in its hydrated state of not more than about 10 mm or not more than about 9 mm.
100. The sustained release biodegradable ocular implant of any of items 84 to 99, wherein the implant contains about 600 μg axitinib and releases in vitro about 0.3 μg to about 0.5 μg of axitinib per day in phosphate-buffered saline at 37° C. for a period of 30 days.
101. The sustained release biodegradable ocular implant of any one of items 84 to 100, wherein the implant releases in vitro about 40% to about 60% of the axitinib in 2 days, about 65% to about 85% of the axitinib in 4 days, and about 75% to about 90% of the axitinib in 6 days in a 25:75 ethanol/water mixture (v/v) at 37° C.
102. The sustained release biodegradable ocular implant of item 101, wherein the implant releases in vitro about 45% to about 55% of the axitinib in 2 days, about 70% to about 80% of the axitinib in 4 days, and about 80% to about 90% of the axitinib in 6 days in a 25:75 ethanol/water mixture (v/v) at 37° C.
103. The sustained release biodegradable ocular implant of any of items 84 to 102, wherein the implant is obtainable by preparing a mixture containing hydrogel precursors and axitinib, filling the mixture into a tubing, allowing the hydrogel to gel in the tubing to provide a hydrogel shaped as a fiber, and stretching the hydrogel fiber.
104. The sustained release biodegradable ocular implant of item 103, wherein the fiber is wet-stretched prior to drying by a factor of about 0.5 to about 5.
105. The sustained release biodegradable ocular implant of item 104, wherein the fiber is wet-stretched prior to drying by a factor of about 1 to about 4.
106. The sustained release biodegradable ocular implant of item 105, wherein the fiber is wet-stretched prior to drying by a factor of about 1.5 to about 3.5.
107. The sustained release biodegradable ocular implant of item 106, wherein the fiber is wet-stretched prior to drying by a factor of about 1.7 to about 3.
108. The sustained release biodegradable ocular implant of any of items 84 to 107, wherein the implant in a dried state is loaded in a needle for injection into the vitreous humor.
109. The sustained release biodegradable ocular implant of item 108, wherein the implant in a dried state is loaded in a 25-gauge or a 27-gauge needle.
110. The sustained release biodegradable ocular implant of any of items 1 to 109, wherein the hydrogel comprises a polymer network which is semi-crystalline in the dry state at or below room temperature, and amorphous in the wet state.
111. The sustained release biodegradable ocular implant of any of items 1 to 110, wherein the implant has undergone wet or dry stretching during manufacture, and wherein the implant in the stretched form is dimensionally stable when in the dry state at or below room temperature.
112. A method of treating an ocular disease in a patient in need thereof, the method comprising administering to the patient a sustained release biodegradable ocular implant comprising a hydrogel and a tyrosine kinase inhibitor according to any of the preceding items, wherein the dose per eye administered once for a treatment period of at least 3 months is from about 150 μg to about 1200 μg of the tyrosine kinase inhibitor.
113. The method of item 112, wherein the tyrosine kinase inhibitor is axitinib.
114. The method of item 112 or 113, wherein the dose administered per eye once for the treatment period is in the range from about 200 μg to about 800 μg.
115. The method of item 112 or 113, wherein the dose is in the range from about 160 μg to about 250 μg, or from about 180 μg to about 220 μg.
116. The method of item 115, wherein the dose is about 200 μg.
117. The method of item 112 or 113, wherein the dose is in the range from about 320 μg to about 500 μg, or from about 360 μg to about 440 μg.
118. The method of item 117, wherein the dose is about 400 μg.

119. The method of item 112 or 113, wherein the dose is in the range from about 480 µg to about 750 µg, or from about 540 µg to about 660 µg.
120. The method of item 119, wherein the dose is about 600 µg.
121. The method of item 112 or 113, wherein the dose is in the range from about 640 µg to about 1000 µg, or from about 720 µg to about 880 µg.
122. The method of item 121, wherein the dose is about 800 µg.
123. The method of any of items 112 to 122, wherein the ocular disease involves angiogenesis.
124. The method of any of items 112 to 123, wherein the ocular disease is mediated by one or more receptor tyrosine kinases (RTKs), specifically VEGFR-1, VEGFR-2, VEGFR-3, PDGFR-α/β, and/or c-Kit.
125. The method of any of items 112 to 124, wherein the ocular disease is a retinal disease including Choroidal Neovascularization, Diabetic Retinopathy, Diabetic Macular Edema, Retinal Vein Occlusion, Acute Macular Neuroretinopathy, Central Serous Chorioretinopathy, and Cystoid Macular Edema; wherein the ocular disease is Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpignous Choroiditis, Subretinal Fibrosis, Uveitis Syndrome, or Vogt-Koyanagi-Harada Syndrome; wherein the ocular disease is a vascular disease or exudative diseases, including Coat's Disease, Parafoveal Telangiectasis, Papillophlebitis, Frosted Branch Angitis, Sickle Cell Retinopathy and other Hemoglobinopathies, Angioid Streaks, and Familial Exudative Vitreoretinopathy; or wherein the ocular disease results from trauma or surgery, including Sympathetic Ophthalmia, Uveitic Retinal Disease, Retinal Detachment, Trauma, Photodynamic Laser Treatment, Photocoagulation, Hypoperfusion During Surgery, Radiation Retinopathy, or Bone Marrow Transplant Retinopathy.
126. The method of any of items 112 to 124, wherein the ocular disease is neovascular age-related macular degeneration, diabetic macular edema or retinal vein occlusion.
127. The method of item 126, wherein the disease is neovascular age-related macular degeneration.
128. The method of any of items 112 to 127, wherein the treatment is effective in reducing, essentially maintaining or preventing a clinically significant increase of the central subfield thickness as measured by optical coherence tomography in a patient whose central subfield thickness is elevated.
129. The method of any of items 112 to 128, wherein the dose per eye administered once for the treatment period is contained in one implant or in two, three or more implants administered concurrently.
130. The method of any of items 112 to 129, wherein the implant is administered by injection into the vitreous humor.
131. The method of any of items 112 to 130, wherein the treatment period is at least 3 about months, at least about 4.5 months, at least about 6 months, at least about 9 months, at least about 11 months, at least about 12 months, at least about 13 months, or at least about 14 months.
132. The method of item 131, wherein the treatment period is at least 6 months, at least about 9 months, or at least about 12 months.
133. The method of any of items 112 to 132, wherein concurrently with the treatment with the sustained release ocular implant an anti-VEGF agent is administered to the patient, or wherein an anti-VEGF agent is administered within about 1, about 2 or about 3 months from the administration of the implant.
134. The method of item 133, wherein the anti-VEGF agent is selected from the group consisting of aflibercept, bevacizumab, pegaptanib, ranibizumab, and brolucizumab.
135. The method of item 134, wherein the anti-VEGF agent is bevacizumab.
136. The method of any of items 133 to 135, wherein the anti-VEGF agent is administered by means of intravitreal injection.
137. The method of any of items 112 to 136, wherein the patient receiving the implant has a history of an anti-VEGF treatment.
138. The method of any of items 112 to 136, wherein the patient receiving the implant has no history of an anti-VEGF treatment (anti-VEGF naïve).
139. A method of treating neovascular age-related macular degeneration in a patient in need thereof, the method comprising administering to the patient a sustained release biodegradable ocular implant comprising a hydrogel that comprises a polymer network and about 200 µg of a tyrosine kinase inhibitor, wherein one implant per eye is administered once for a treatment period of at least 9 months, and wherein the patient has a history of an anti-VEGF treatment.
140. A method of treating neovascular age-related macular degeneration in a patient in need thereof, the method comprising administering to the patient a sustained release biodegradable ocular implant comprising a hydrogel that comprises a polymer network and about 200 µg of a tyrosine kinase inhibitor, wherein two implants per eye forming a total dose of about 400 µg are administered once for a treatment period of at least 3 months, and wherein the patient has a history or has no history of an anti-VEGF treatment.
141. The method of item 139 or 140, wherein the treatment results in a reduction in central subfield thickness (CSFT) as measured by optical coherence tomography during the treatment period.
142. The method of any of items 139 to 141, wherein the tyrosine kinase inhibitor is axitinib and is dispersed in the hydrogel which comprises a polymer network formed by reacting 4a20kPEG-SAZ with 8a20kPEG-NH$_2$, and wherein the implant is in a dried state prior to administration.
143. The method of item 142, wherein the hydrogel when formed and before being dried contains about 7.5% polyethylene glycol, representing the polyethylene glycol weight divided by the fluid weight x 100.
144. The method of any of items 140 to 143 wherein the treatment period is at least 9 months.
145. A method of treating neovascular age-related macular degeneration in a patient in need thereof, the method comprising administering to the patient a sustained release biodegradable ocular implant comprising axitinib in an amount in the range from about 480 µg to about 750 µg dispersed in a hydrogel comprising a polymer network, wherein the implant is administered once for a treatment period of at least 3 months.
146. The method of item 145, wherein the axitinib is contained in the implant in an amount from about 560 µg to about 660 µg.
147. The method of item 146, wherein the axitinib is contained in the implant in an amount of about 600 µg.

148. The method of any of items 145 to 147, wherein the implant is as defined in items 84 to 111.
149. The method of any of items 145 to 148, wherein the implant is administered into the vitreous humor.
150. The method of any of items 145 to 149, wherein the treatment period is at least about 3 months, at least about 6 months, at least about 9 months, at least about 11 months, at least about 12 months, at least about 13 months, or at least about 14 months.
151. The method any of items 145 to 150, wherein the implant is administered by injection into the vitreous humor by means of a 25- or a 27-gauge needle.
152. The method of any of items 145 to 151, wherein the patient receiving the implant has a history of an anti-VEGF treatment, or has no history of an anti-VEGF treatment (anti-VEGF naïve).
153. The method of any of items 145 to 152, wherein an anti-VEGF agent is administered to the patient concurrently with the implant.
154. The method of item 153, wherein the anti-VEGF agent is selected from the group consisting of aflibercept, bevacizumab, pegaptanib, ranibizumab, and brolucizumab.
155. The method of item 154, wherein the anti-VEGF agent is bevacizumab.
156. The method of any of items 153 to 155, wherein the anti-VEGF agent is administered by means of intravitreal injection.
157. The method of any of items 112 to 156, wherein the number of adverse events during the administration of the sustained release biodegradable ocular implant is low.
158. The method of item 157, wherein the number of treatment-related ocular adverse events during the administration of the sustained release biodegradable ocular implant is low.
159. A method of manufacturing a sustained release biodegradable ocular implant comprising a hydrogel and about 150 µg to about 1200 µg of a tyrosine kinase inhibitor according to any of items 1 to 111, the method comprising the steps of forming a hydrogel comprising a polymer network and tyrosine kinase inhibitor particles dispersed in the hydrogel, shaping the hydrogel and drying the hydrogel.
160. The method of item 159, wherein the tyrosine kinase inhibitor is axitinib.
161. The method of item 159 or 160, wherein the tyrosine kinase inhibitor particles are micronized and/or homogeneously dispersed within the hydrogel.
162. The method of any of items 159 to 161, wherein the polymer network is formed by crosslinking multi-arm polyethylene glycol units in a buffered solution.
163. The method of any of items 159 to 162, wherein the hydrogel comprises a polymer network that is formed by mixing and reacting an electrophilic group-containing multi-arm polyethylene glycol with a nucleophilic group-containing multi-arm polyethylene glycol in a buffered solution in the presence of the tyrosine kinase inhibitor, and allowing the mixture to gel.
164. The method of item 163, comprising reacting 4a20kPEG-SAZ with 8a20kPEG-NH$_2$ in a weight ratio of about 2:1.
165. The method of item 163 or 164, wherein the method comprises the steps of filling the mixture into a mold or tubing prior to complete gelling in order to provide the desired final shape of the hydrogel, allowing the mixture to gel, and drying the hydrogel.
166. The method of item 165, wherein the mixture is filled into a fine diameter tubing in order to prepare a hydrogel fiber.
167. The method of item 166, wherein the inside of the tubing has a round geometry.
168. The method of item 166, wherein the inside of the tubing has a non-round geometry.
169. The method of item 168, wherein the inside of the tubing has a cross-shaped geometry.
170. The method of any of items 166 to 169, wherein the method further comprises stretching the fiber and/or twisting the fiber.
171. The method of item 170, wherein the stretching is performed prior to or after drying the hydrogel.
172. The method of item 171, wherein the fiber is stretched by a stretch factor of about 1 to about 4.5.
173. The method of item 171, wherein the implant contains axitinib in an amount of about 200 µg and the stretching is performed after drying the hydrogel by a stretch factor of about 2 to about 5 or a stretch factor of about 3 to about 4.5.
174. The method of item 171, wherein the implant contains axitinib in an amount of about 600 µg and the stretching is performed in a wet state prior to drying the hydrogel at a stretch factor of about 0.5 to about 5, or a stretch factor of about 1 to about 4, or a stretch factor of about 1.3 to about 3.5, or a stretch factor of about 1.7 to about 3.
175. The method of any of items 159 to 174, wherein the method further comprises loading the implant in a dried state into a needle.
176. The method of item 175, wherein the needle is a 25- or 27-gauge needle.
177. A method of imparting shape memory to a hydrogel fiber comprising an active agent dispersed in the hydrogel by stretching the hydrogel fiber in the longitudinal direction.
178. A method of manufacturing an ocular implant comprising a hydrogel comprising an active agent dispersed therein, wherein the implant changes its dimensions upon administration to the eye, the method comprising preparing a fiber of the hydrogel and stretching the fiber in the longitudinal direction.
179. The method of item 177 or 178, wherein the method comprises the step of drying the hydrogel, wherein the fiber is stretched in the longitudinal direction prior to or after said drying (wet or dry stretching).
180. The method of any of items 177 to 179, wherein the fiber is stretched by a factor of about 0.5 to about 5, or a factor of about 1 to about 4.5, or a factor of about 3 to about 4.5 or a factor of about 1 to about 2.
181. The method of any of items 177 to 180, wherein the active agent is a tyrosine kinase inhibitor, such as axitinib.
182. The method of any of items 177 to 181, wherein the hydrogel comprises a polymer network comprising crosslinked polyethylene glycol units.
183. The method of any of items 177 to 182, wherein the fiber upon hydration fully or partly returns to approximately its original length and/or original diameter that it had prior to the stretching.
184. The method of any of items 177 to 183, wherein the change in dimensions is an increase in diameter, or an increase in diameter together with a decrease in length.
185. A kit comprising one or more sustained release biodegradable ocular implant(s) according to any of items 1 to 111 or manufactured in accordance with the method of any of items 159 to 176 and one or more needle(s), wherein the one or more needle(s) is/are each pre-loaded with one sustained release biodegradable ocular implant in a dried state.
186. The kit of item 185, wherein the needle(s) is/are 25- or 27-gauge needle(s).
187. The kit of item 185 or 186, wherein the kit comprises one or more 25- or 27-gauge needle(s) each loaded with an implant containing axitinib in an amount in the range from about 180 µg to about 220 µg.
188. The kit of item 187, wherein the implant contains axitinib in an amount of about 200 µg.
189. The kit of item 185 or 186, wherein the kit comprises one 25-gauge or 27-gauge needle loaded with an implant containing axitinib in an amount in the range from about 540 µg to about 660 µg.
190. The kit of item 189, wherein the implant contains axitinib in an amount of about 600 µg.
191. The kit of any of items 185 to 190, further containing an injection device for injecting the implant into the eye of a patient.
192. The kit of item 191, wherein the injection device is provided in the kit separately from the one or more needle(s) loaded with implant.
193. The kit of item 191, wherein the injection device is pre-connected to a needle loaded with implant.
194. The kit of item 191 or 192, wherein the injection device contains a push wire to deploy the implant from the needle into the eye.
195. The kit of any of items 185 to 194, further comprising one dose of an anti-VEGF agent ready for injection.
196. An injection device suitable for injecting a sustained release biodegradable ocular implant according to any of items 1 to 111 into the eye.
197. The injection device of item 196 containing means for connecting the injection device to a needle,
198. The injection device of item 196 or 197, wherein the needle is pre-loaded with the implant.
199. The injection device of any of items 196 to 198 containing a push wire to deploy the implant from the needle into the eye when the injection device has been connected to the needle.
200. The injection device of item 199, wherein the push wire is made of Nitinol or stainless steel/Teflon.
201. The injection device of item 199 or 200, obtainable by affixing the wire to the plunger and encasing it between two snap fit injector body parts and securing the plunger with a clip.
202. A pharmaceutical product comprising the sustained release biodegradable ocular implant of any of items 1 to 111 loaded in a needle and an injection device according to any of items 196 to 201, wherein the needle is pre-connected to the injection device.
203. A sustained release biodegradable ocular implant containing a tyrosine kinase inhibitor according to any of items 1 to 111 for use in treating an ocular disease in a patient in need thereof according to any of items 112 to 138 or in treating neovascular age-related macular degeneration in a patient in need thereof according to any of items 139 to 158, 210 or 211.
204. Use of a sustained release biodegradable ocular implant containing a tyrosine kinase inhibitor according to any of items 1 to 111 in the preparation of a medicament for the treatment of an ocular disease in a patient in need thereof according to any of items 112 to 138 or for the treatment of neovascular age-related macular degeneration in a patient in need thereof according to any of items 139 to 158, 210 or 211.
205. A method of reducing, essentially maintaining or preventing a clinically significant increase of the central subfield thickness as measured by optical coherence tomography in a patient whose central subfield thickness is elevated due to an ocular disease involving angiogenesis, the method comprising administering to the patient the sustained release biodegradable ocular implant containing a tyrosine kinase inhibitor according to any of items 1 to 111.
206. The method of item 205, wherein the ocular disease is neovascular age-related macular degeneration.
207. The method of item 205 or 206, wherein the central subfield thickness is reduced, essentially maintained or a clinically significant increase of the central subfield thickness is prevented in the patient during a period of at least about 3 months, at least about 6 months, at least about 9 months, at least about 11 months, at least about 12 months, at least about 13 months, or at least about 14 months after administration of the implant with respect to a baseline central subfield thickness measured in that patient prior to the administration of the implant.
208. A sustained release biodegradable ocular implant containing a tyrosine kinase inhibitor according to any of items 1 to 111 for use in reducing, essentially maintaining or preventing a clinically significant increase of the central subfield thickness as measured by optical coherence tomography in a patient whose central subfield thickness is elevated due to an ocular disease involving angiogenesis according to any of items 205 to 207, 210 or 211.
209. Use of a sustained release biodegradable ocular implant containing a tyrosine kinase inhibitor according to any of items 1 to 111 in the preparation of a medicament for reducing, essentially maintaining or preventing a clinically significant increase in the central subfield thickness as measured by optical coherence tomography in a patient whose central subfield thickness is elevated due to an ocular disease involving angiogenesis according to any of items 205 to 207, 210 or 211.
210. The method of any of items 128 to 158 or any of items 205 to 207, wherein the patient's vision expressed by means of the best corrected visual acuity is not impaired, or is improved.
211. The method of any of items 128 to 158, any of items 205 to 207 or item 210, wherein rescue medication is not required to be administered during the treatment period, or wherein rescue medication is only required to be administered rarely, such as 1, 2 or 3 times, during the treatment period.
212. The method of item 211, wherein the duration of the treatment period is from about 6 to about 9 months after administration of the sustained release biodegradable ocular implant.
213. A method of improving the vision of a patient whose vision is impaired due to an ocular disease involving angiogenesis, the method comprising administering to the patient the sustained release biodegradable ocular implant containing a tyrosine kinase inhibitor according to any of items 1 to 111.
214. The method of item 213, wherein the ocular disease is neovascular age-related macular degeneration, diabetic macular edema or retinal vein occlusion.
215. The method of item 213 or item 214, wherein the patient's vision is impaired due to the presence of retinal fluid.
216. The method of any of items 213 to 215, wherein the improvement of vision is manifested by means of an increase in best corrected visual acuity.
217. The method of item 216, wherein the best corrected visual acuity is increased by at least 10, at least 15, or at least 20 ETDRS letters.
218. A sustained release biodegradable ocular implant containing a tyrosine kinase inhibitor according to any of items 1 to 111 for use in improving the vision of a patient whose vision is impaired due to an ocular disease involving angiogenesis according to the method of any of items 213 to 217.
219. Use of a sustained release biodegradable ocular implant containing a tyrosine kinase inhibitor according to any of items 1 to 111 in the preparation of a medicament for improving the vision of a patient whose vision is impaired due to an ocular disease involving angiogenesis according to the method of any of items 213 to 217.

Second List of Items

1. A sustained-release biodegradable ocular hydrogel implant comprising a tyrosine kinase inhibitor, a polymer network, and a clearance zone, wherein the clearance zone is devoid of the TKI prior to release of the TKI.

2. The ocular hydrogel of item 1, wherein the TKI is not in contact with retinal cells when the TKI is comprised inside the hydrogel implant.

3. The ocular hydrogel of item 1 or 2, wherein the TKI is present in the hydrogel implant at or near its saturation level.

4. The ocular hydrogel implant of any one of items 1 to 3, wherein the size of the clearance zone increases as a function of the amount of TKI release.

5. The ocular hydrogel implant of any one of items 1 to 4, wherein the ocular hydrogel implant is fully degraded following release of the TKI or following release of at least 90% of the TKI.

6. The ocular hydrogel implant of any one of items 1 to 5, wherein the ocular hydrogel implant is fully degraded after about 30 days or after about 3 months following complete release of the TKI.

7. The ocular hydrogel implant of any one of items 1 to 4, wherein degradation of the ocular hydrogel occurs prior to release of the TKI.

8. The ocular hydrogel implant of any one of items 1 to 7, wherein the polymer network comprises a plurality of polyethylene glycol (PEG) units.

9. The ocular hydrogel implant of any one of items 1 to 8, wherein the polymer network comprises a plurality of multi-arm PEG units.

10. The ocular hydrogel implant of any one of items 1 to 9, wherein the polymer network comprises a plurality of 4- or 8-arm PEG units.

11. The ocular hydrogel implant of any one of items 1 to 9, wherein the polymer network comprises a plurality of PEG units having the formula:

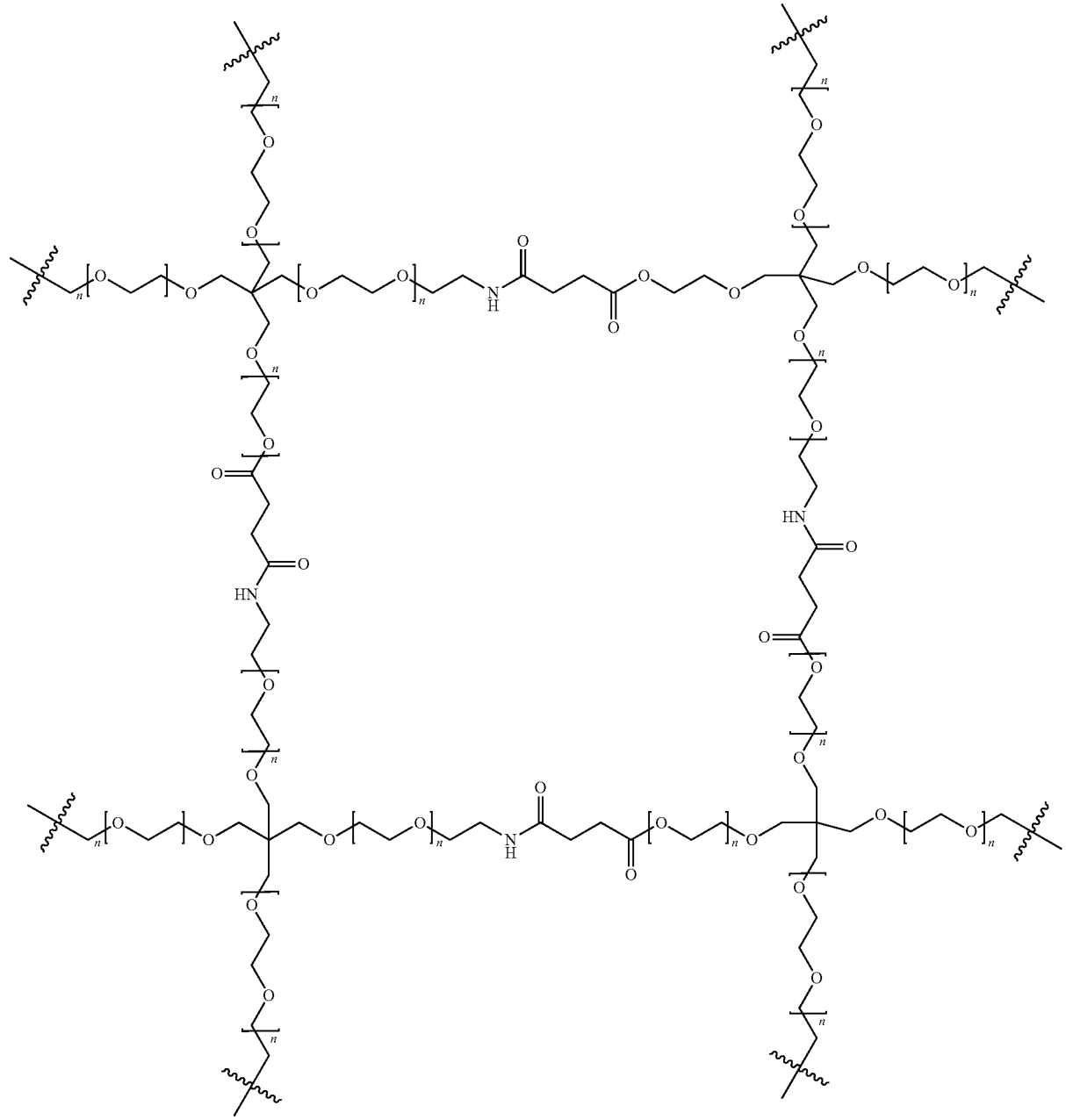

wherein n represents an ethylene oxide repeating unit and the wavy lines represent the points of repeating units of the polymer network.

12. The ocular hydrogel implant of any one of items 1 to 11, wherein the polymer network is fomed by reacting a plurality of polyethylene glycol (PEG) units selected from 4a20k PEG-SAZ, 4a20k PEG-SAP, 4a20k PEG-SG, 4a20k PEG-SS, 8a20k PEG-SAZ, 8a20k PEG-SAP, 8a20k PEG-SG, and 8a20k PEG-SS with one or more PEG or lysine based-amine groups selected from 4a20k PEG-NH$_2$, 8a20k PEG-NH$_2$, and trilysine, or a salt thereof.

13. The ocular hydrogel implant of any one of items 1 to 12, wherein the polymer network is fomed by reacting 4a20k PEG-SAZ with 8a20k PEG-NH$_2$.

14. The ocular hydrogel implant of any one of items 1 to 13, wherein the polymer network is amorphous (under aqueous conditions).

15. The ocular hydrogel implant of any one of items 1 to 14, wherein the polymer network is semi-crystalline in the absence of water.

16. The ocular hydrogel implant of any one of items 1 to 15, wherein the tyrosine kinase inhibitor is homogenously dispersed within the polymer network.

17. The ocular hydrogel implant of any one of items 1 to 16, wherein the tyrosine kinase inhibitor is released over a period of at least 15 days.

18. The ocular hydrogel implant of any one of items 1 to 17, wherein the tyrosine kinase inhibitor is released over a period of at least 30 days.

19. The ocular hydrogel implant of any one of items 1 to 18, wherein the tyrosine kinase inhibitor is released over a period of at least 60 days.

20. The ocular hydrogel implant of any one of items 1 to 19, wherein the tyrosine kinase inhibitor is released over a period of at least 90 days.

21. The ocular hydrogel implant of any one of items 1 to 20, wherein the tyrosine kinase inhibitor is released over a period of at least 180 days.

22. The ocular hydrogel implant of any one of items 1 to 21, wherein the tyrosine kinase inhibitor is released over a period of at least 365 days.

23. The ocular hydrogel implant of any one of items 1 to 22, wherein the tyrosine kinase inhibitor is in the form of an encapsulated microparticle.

24. The ocular hydrogel implant of any one of items 1 to 23, wherein the tyrosine kinase inhibitor is in the form of an encapsulated microparticle comprising poly(lactic-co-glycolic acid).

25. The ocular hydrogel implant of any one of items 1 to 24, wherein the tyrosine kinase inhibitor is selected from abemaciclib, acalabrutinib, afatinib, alectinib, axitinib, baricitinib, binimetinib, brigatinib, cabozantinib, ceritinib, coblmetinib, crizotinib, dabrafenib, dacomitinib, dasatinib, encorafenib, erlotinib, everolimus, fostamatinib, gefitinib, gilteritinib, ibrutinib, imatinib, larotrectinib, lenvatinib, lorlatinib, axitinib, idelalisib, lenvatinib, midostaurin, neratinib, netarsudil, nilotinib, nintedanib, osimertinib, palbociclib, pazopanib, ponatinib, regorafenib, ribociclib, ruxolitinib, sirolimus, sorafenib, sunitinib, temsirolimus, tofacitinib, trametinib, vandetanib, and vemurafenib.

26. The ocular hydrogel implant of item 1 or 25, wherein the tyrosine kinase inhibitor is axitinib.

27. The ocular hydrogel implant of any one of items 1 to 26, wherein the ocular hydrogel implant is injected into the vitreous humor, injected into the anterior chamber, or is affixed to the upper or lower punctum of the eye.

28. A method of treating an ocular condition in a subject in need thereof, comprising injecting or affixing the ocular hydrogel implant of any one of items 1 to 27 to the subject.

29. The method of item 28, wherein the ocular condition is selected from maculopathies, retinal degeneration, uveitis, retinitis, choroiditis, vascular diseases, exudative diseases, traumas, proliferative diseases, infectious disorders, genetic disorders, retinal tears, holes, and tumors.

30. The method of item 28 or 29, wherein the ocular condition is selected from age-related macular degeneration, choroidal neovascularization, diabetic retinopathy, acute macular neuroretinopathy, central serous chorioretinopathy, cystoid macular edema, diabetic macular edema, acute multifocal placoid pigment epitheliopathy, Behcet's disease, birdshot retinochoroidopathy, intermediate uveitis, multifocal choroiditis, multiple evanescent white dot syndrome (MEWDS), ocular sarcoidosis, posterior scleritis, serpiginous choroiditis, subretinal fibrosis and uveitis syndrome, Vogt-Koyanagi-Harada syndrome, Coats disease, parafoveal telangiectasis, papillophlebitis, frosted branch angiitis, sickle cell retinopathy, angioid streaks, familial exudative vitreoretinopathy, sympathetic ophthalmia, uveitic retinal disease, retinal detachment, proliferative diabetic retinopathy, ocular histoplasmosis, ocular toxocariasis, viral retinitis, acute retinal necrosis, ocular syphilis, ocular tuberculosis, congenital stationary night blindness, cone dystrophies, retinal detachment, macular hole, giant retinal tear, solid tumors, posterior uveal melanoma, choroidal hemangioma, choroidal osteoma, choroidal metastasis, retinoblastoma, vasoproliferative tumors of the ocular fundus, retinal astrocytoma, and intraocular lymphoid tumors.

31. The method of item 29 or 30, wherein the condition is age-related macular degeneration.

32. The method of any one of items 29 to 31, wherein the subject was previously treated with an anti-VEGF therapy.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

Example 1: Preparation of Axitinib Implants

The axitinib implants of the present application are (essentially) cylindrical (and are also referred to herein as "fibers"), with axitinib homogeneously dispersed and entrapped within a PEG-based hydrogel matrix to provide sustained release of axitinib based on its low aqueous solubility in the vitreous humor of the eye.

The polymer network of the implants was formed by reacting 2 parts 4a20K PEG-SAZ (a 20 kDa PEG with 4 arms with a N-hydroxysuccinimidyl reactive end group, sometimes also referred to as "NHS" end group) with 1 part 8a20K PEG NH2 (a 20 kDa PEG with 8 arms with an amine end group). Therefore, a polyurethane tubing was cut into appropriate length pieces. After that, an 8a20K PEG NH2 sodium phosphate dibasic solution was prepared and sterile filtered to remove endotoxins as well as other particles over 0.2 μm (pore size of the filter). The desired volume of the PEG amine solution was then weighed into a syringe. Next, corresponding amounts of solid axitinib depending on the desired final axitinib dose in the implant were weighed into another syringe. The powdered axitinib syringe and the PEG amine syringe were mixed carefully to suspend and disperse the particles. The syringe comprising the suspension mixture was then sonicated to break up any powdered agglomerates. After that, a 4a20K PEG SAZ sodium phosphate monobasic solution was prepared and sterile filtered as described for the PEG amine solution. The desired volume of PEG SAZ solution was then weighed into another syringe. In the next step, the ingredients of both syringes (4a20K PEG SAZ sodium phosphate monobasic solution and axitinib-8a20K PEG NH2 mixture) were mixed to initiate the reaction leading to gelation. The liquid suspension was cast through the prepared polyurethane tubing before the material crosslinks and solidifies. Gelling time was confirmed by performing a gel tap test. The gel-comprising tubing was then placed into a high humidity curing chamber for 2 hours in order to prevent premature drying of the hydrogel prior to hydrogel gelation. In the chamber, the hydrogel axitinib suspension in the tubing was allowed to cross-link to completion creating a highly reacted and uniform gel, thus forming a hydrogel strand.

After curing, different implant stretching methods were performed as disclosed herein. Implants were either dry stretched or wet stretched as outlined below. For dry stretching, strands were cut into shorter segments after curing and the strands were dried for 48 to 96 hours. After drying, dried strand segments were removed from the tubing and placed on clamps of a custom stretcher. The strands were then slowly dry stretched at a controlled rate to achieve the desired diameter that fits into a small gauge needle (stretch factor of about 2 to about 5, or about 3 to about 4.5). The stretching step was performed in an oxygen and moisture free environment to protect the product. For wet stretching, strands were placed on clamps of a custom stretcher. The strands were then slowly wet stretched at a controlled rate to achieve the desired diameter that fits into a small gauge needle (stretch factor of about 1 to about 3, or about 1.3 to about 2.6). After stretching, the strands were dried under tension under the conditions as described for the dry stretching process.

The stretching creates a shape memory, meaning that the implant upon hydration when administered into the vitreous cavity of the eye will rapidly shrink in length and widen in diameter until it approaches its original wet casted dimension. While the narrow dry dimensions facilitate administration of the product through a smaller gauge needle, the widened diameter and shortened length after administration yield a shorter implant (in certain embodiments not much longer than about 10 mm) in the posterior chamber relative to the eye diameter minimizing potential contact with surrounding eye tissues. In general, the degree of shrinking upon hydration depends inter alia on the stretch factor. For instance, stretching at e.g. a stretch factor of about 1.3 (wet stretching) will have a less pronounced effect or will not change the length during hydration to a large extent. In contrast, stretching at e.g. a stretch factor of about 1.8 (wet stretching) will result in a markedly shorter length during hydration. Stretching at e.g. a stretch factor of about 4 (dry stretching) could result in a much shorter length upon hydration (such as, for example, a reduction in length from about 15 to about 8 mm).

Stretched hydrogel strands were removed from the stretcher and then cut to the desired final length. The implant fibers were then placed on the inspection station. If the implants passed the quality control, they were loaded into a 25 or 27 gauge needle (e.g. an FDA-approved 25G UTW ½" having an inner diameter of about 0.4 mm, or a 25G UTW 1" or a 27G TW 1.25" needle) using a customized vacuum device and capped safely to avoid any needle tip damage.

The loaded needles were placed into a glove box for 6 to 9 days to remove any moisture (the remaining water content in the implant is intended to not exceed 1% water). All steps from then on were performed in the glove box. The loaded needle was dipped into a melted low-molecular weight 1 k PEG to tip the needle. Upon cooling a hardened small drop of PEG remains, which provides lubricity, keeps the implant in place within the needle, allows successful deployment and prevents premature rehydration of the implant within the needle during administration. Moreover, PEG tipping is minimizing tissue injury i.e. tissue coring, a process by which pieces of tissue are removed by a needle as it passes through the tissue. The PEG-tipped needles were then again inspected, needles which did not meet the quality requirements were discarded. Passed needles were again capped to ensure the needles were not suffering any additional damage. Needles were then individually pouched and sealed to prevent them from moisture and keep them sterile. The injection device, for instance a modified Hamilton glass syringe, had a push wire (e.g. a Nitinol push wire) that allows deploying the implant from the needle more easily. The injection needle may contain a stop feature that controls the injection depth. The injection device can be separately packaged and sealed under nitrogen in foil pouches in the same way as described for the needle (FIG. 1), or could be pre-assembled with the implant-loaded needle or within a preloaded injector. The packaged needles and injection devices were removed from the glove box and stored refrigerated (2-8° C.) prior to sterilization using gamma irradiation. After sterilization the packages were stored refrigerated (2-8° C.) or frozen protected from light prior to use and were equilibrated 30 min to room temperature prior to injection.

Figure 2:
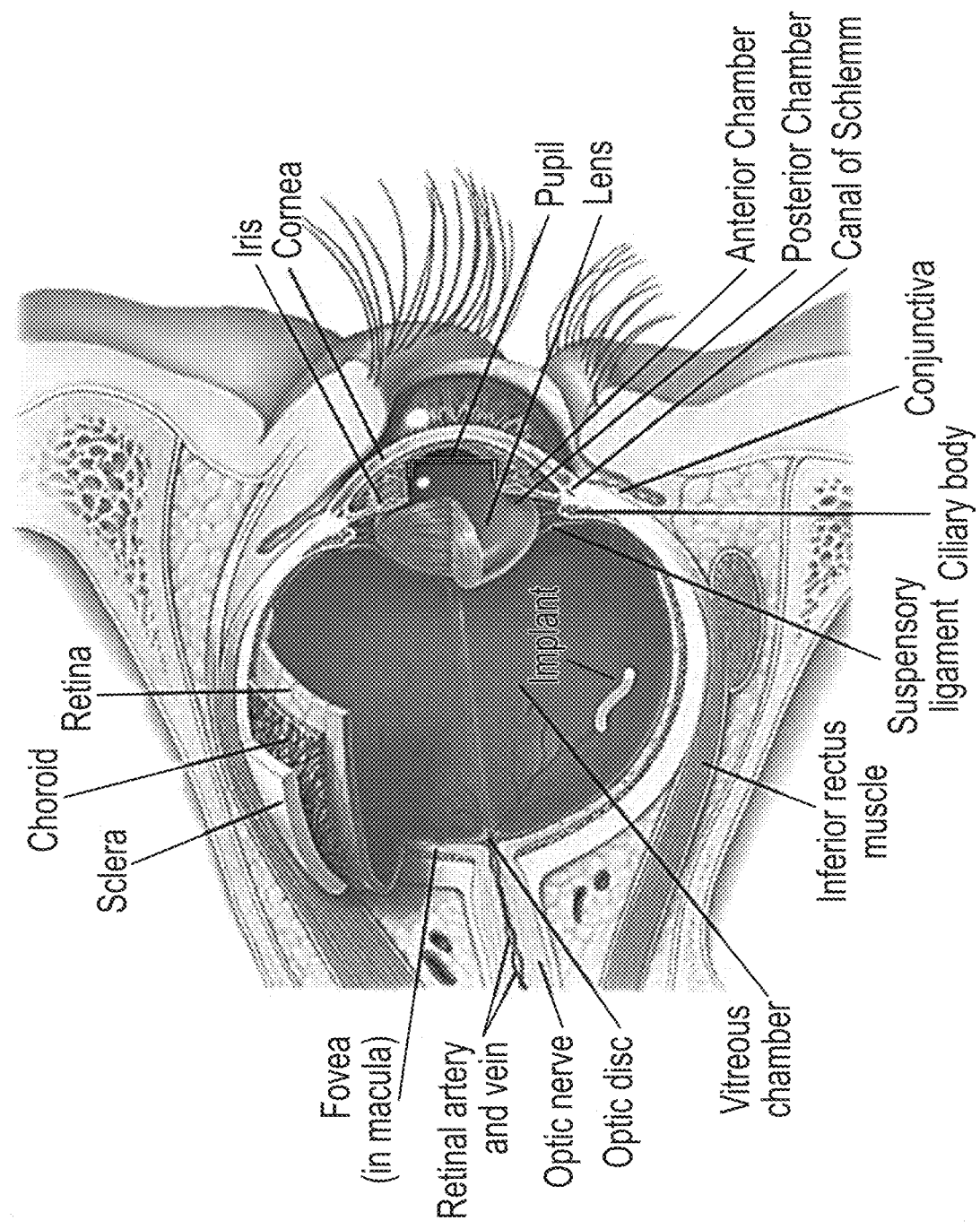
FIG. 2 Schematic representation of one embodiment of implant localization. After injection the implant hydrates in situ while maintaining a cylindrical shape. The implant is localized in the posterior part of the eye.
Figure 3:
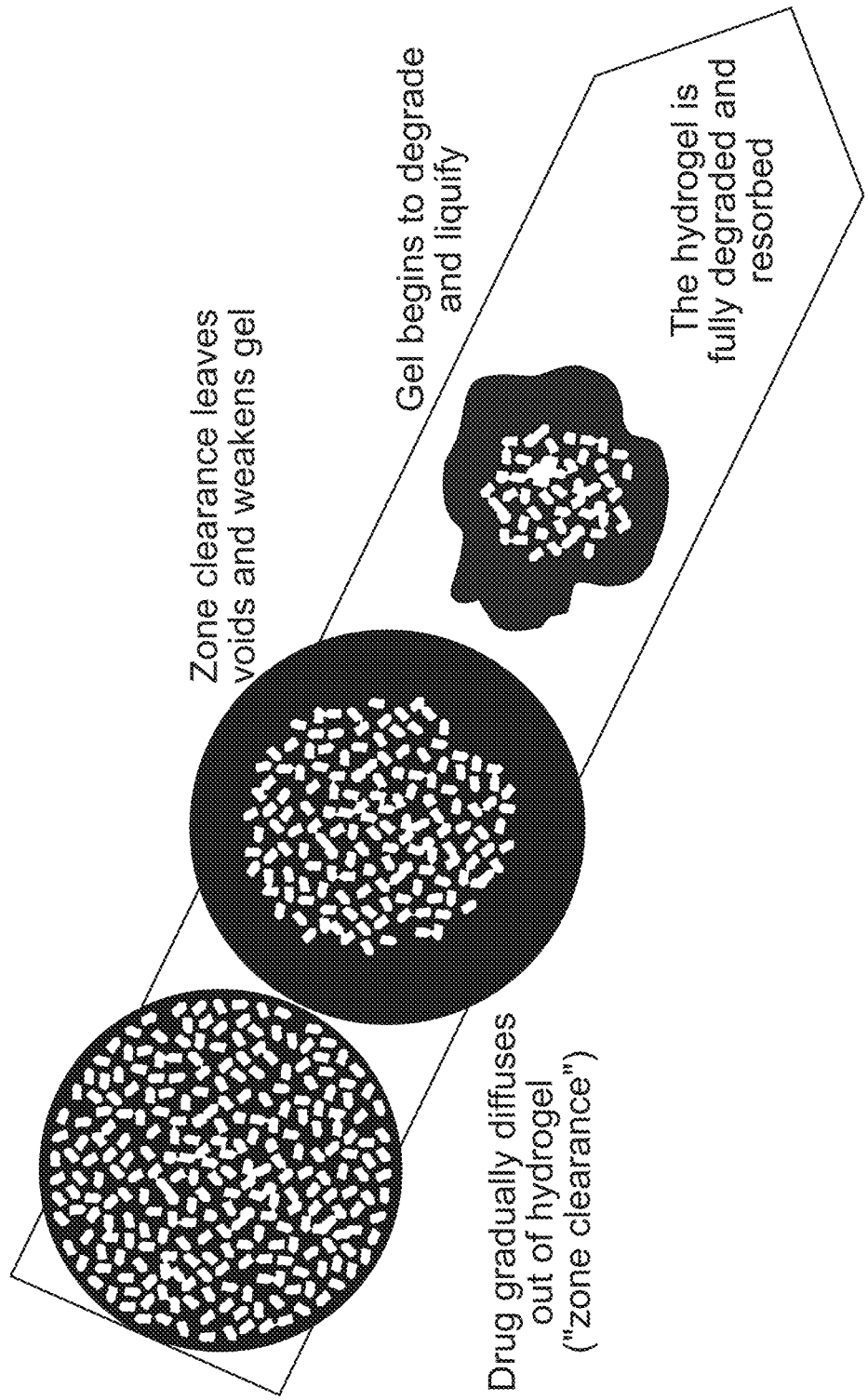
FIG. 3 Schematic representation of hydrogel biodegradation over time. As the drug is released, a clearance zone is formed (black) as low solubility drug particles (white) gradually dissolve and drug diffuses from hydrogel to the aqueous surrounding (as for instance the vitreous humor). Over time, the gel degrades and is resorbed, while drug diffuses out. During the degradation process, the gel gradually swells until degradation is advanced to the point of shrinkage and distortion.

Administration of the implants occurs via intravitreal injection, wherein the implant localizes in the posterior segment of the eye (FIG. 2). After injection, the implants hydrate in situ. Upon hydration upon contact with the vitreous, the implant softens and increases in diameter and may also shrink in length. By trapping axitinib into the hydrogel a defined and limited localization of axitinib in the eye can be provided. The hydrogel matrix of the implant is formulated to biodegrade via ester hydrolysis in the aqueous environment of the vitreous. Axitinib releases for a sustained period from the hydrogel by diffusion into the vitreous and then into the surrounding ocular tissues based on the drug's low solubility under physiological conditions (FIG. 3). The drug release rate from the implants is inter alia influenced by diffusion, drug clearance, vitreous viscosity, concentration gradients within and proximate to the implant, implant dose, implant surface area and geometry, as well as the number of implants and their localization within the vitreous.

Example 2: In Vitro axitinib Release

In a next step, the release rate of axitinib from implants in different formulations was determined by in vitro testing. The in vitro assays can be additionally used for quality control of the implants.

In Vitro Axitinib Release Under Non-Sink Simulated Physiological Conditions

In one in vitro assay set-up, axitinib release was evaluated under non-sink simulated physiological conditions at a daily replacement volume comparable to the volume of vitreous humor in a human eye.

Three exemplarily selected implant formulations were examined (Table 1). Implant variants #1 and 2 were examined using one implant, implant variant #3 using one and two implants (four conditions in total). All conditions were conducted in duplicate.

TABLE 1

Formulation, configuration, and dry-dimensions of three exemplarily selected axitinib implants. Formulation percentages represent weight by weight (w/w).

| Implant variant | | Implant #1 | Implant #2 | Implant #3 |
|---|---|---|---|---|
| Formulation | Axitinib | 61.3% | 61.3% | 49.4% |
| | (amount per implant) | (625 µg) | (716 µg) | (245 µg) |
| | 4a20k PEG-SAZ | 21.1% | 21.1% | 27.7% |
| | 8a20k PEG-NH2 | 10.6% | 10.6% | 13.8% |
| | Sodium Phosphate Monobasic | 1.9% | 1.9% | 2.5% |
| | Sodium Phosphate Dibasic | 5.0% | 5.0% | 6.6% |
| Configuration | No. of Implants | 1 | 1 | 1 or 2 |
| | Packaging | Implant sealed in foil pouches and sealed under nitrogen. Glass vial w/5 mL PBS. | Implant sealed in foil pouches and sealed under nitrogen. Glass vial w/5 mL PBS. | Implant sealed in foil pouches and sealed under nitrogen. Glass vial w/5 mL PBS. |
| | Storage | Frozen | Frozen | Frozen |
| Dimensions | Dried Diameter (mm) | 0.325 | 0.499 | 0.259 |
| | Dried Length (mm) | 9.37 | 7.65 | 16.47 |

Prior to the performance of the in vitro release assay the starting drug content of the implants was examined by liquid chromatography coupled to fragmentation-based mass spectrometry (LC-MS/MS) using ethanol as extraction solvent (Table 2; for details on implant dissolution and LC-MS/MS reference is made to Example 3.5). The determined axitinib amounts matched well with the formulated amounts.

TABLE 2

Starting axitinib content in the implants as determined by LC-MS/MS.

| Condition | Axitinib (µg) |
|---|---|
| Implant #1 | 609 ± 48.1 |
| Implant #2 | 720 ± 35.4 |
| Implant #3 ×2 | 458 ± 38.9 |
| Implant #3 ×1 | 258 ± 33.9 |

In vitro released and non-released axitinib was determined for each group without (control) and with daily release media sampling.

For control implant release, samples were placed in tubes. Five mL of PBS (pH 7.2) were added to each tube on day 0 and the tubes were covered with a lid. Samples were then placed in a 37° C. incubator and gently rocked for 20 (1× implant #3) or 30 days (implant #1 and #2, 2× implant #3). At the end of the test period, the PBS was removed (1 mL PBS was saved for testing). One mL of ethanol was added to the residual sample. Both PBS samples and residual samples were tested for axitinib amount released.

For daily implant release, samples were placed in tubes. Five mL of PBS were added to each tube on day 0 and the tubes were covered with a lid. Samples were then placed in a 37° C. incubator and rocked gently. After 24 hours, 4 mL of PBS were removed from each sample from which 1 mL was used for testing and the remaining 3 mL were disposed. Four mL of fresh PBS were added back into each tube. This process was repeated for 20 (1× implant #3) or 30 days (implant #1 and #2, 2× implant #3). On the final day of the study, 1 mL of PBS was used for testing each sample and the remaining 4 mL were disposed. One mL of ethanol was added to the remaining residual implants and was tested for total remaining axitinib.

The axitinib concentration in PBS from control implant release measurements after 20 or 30 days, respectively, represented a maximal solubility determination of axitinib after prolonged incubation in the release media (Table 3). The higher dose strengths resulted in higher axitinib concentrations in the release media. The apparent maximal axitinib solubility ranged from 0.24 to 0.40 µg/mL, which was consistent with results reported in the literature for INLYTA® [NDA 202324].

TABLE 3

Control release data. Axitinib amounts and concentrations are presented as mean and standard deviation (SD).

| Condition | Axitinib Remaining (µg) | Total Axitinib Released (µg) | Axitinib concentration in media (µg/mL) |
|---|---|---|---|
| Implant #1 | 595 ± 42.4 | 2.01 ± 0.004 | 0.40 ± 0.707 |
| Implant #2 | 679 ± 48.8 | 1.90 ± 0.007 | 0.38 ± 1.41 |
| Implant #3 ×2 | 458 ± 50.9 | 1.21 ± 0.032 | 0.24 ± 6.36 |
| Implant #3 ×1 | 251 ± 35.4 | 1.35 ± 0.449 | 0.27 ± 89.8 |

Test results demonstrated that the two high dose samples (implants #1 and 2) released more axitinib per day than the lower dose groups (Table 4). The amount of axitinib released per day over the study duration is presented in FIG. 4A. The amount of total axitinib released was higher in the groups that removed and replaced PBS daily compared to the no PBS exchange (control). Implants #1 and #2 released more axitinib per day than two implants of implant #3. The mean value of total axitinib released was slightly different in both high dose groups, but the median amounts released daily were comparable, indicating no apparent difference between the two higher dose groups.

TABLE 4

Daily sampling data. Axitinib amounts are presented as mean and standard deviation (SD).

| Condition | Axitinib Remaining (μg) | Total Axitinib Released (μg) | Axitinib Daily Released (μg) |
|---|---|---|---|
| Implant #1 | 566 ± 43.8 | 10.44 ± 0.35 | 0.36 ± 0.049 |
| Implant #2 | 622 ± 43.8 | 11.48 ± 0.38 | 0.36 ± 0.073 |
| Implant #3 ×2 | 456 ± 16.3 | 5.26 ± 0.18 | 0.16 ± 0.044 |
| Implant #3 ×1 | 231 ± 6.36 | 2.26 ± 0.11 | 0.11 ± 0.019 |

The study results demonstrate that a single administration of an implant containing approximately 0.6 to 0.7 mg of axitinib releases more axitinib per day into solution in simulated physiological conditions under non-sink conditions at a volume representative of the vitreous humor eye volume compared to the one or two lower dosage total strengths. Two implants containing approximately 0.2 mg each didn't release as much axitinib as a single higher dose implant under these conditions. These in vitro results indicate that a single implant at a higher dose may release more axitinib per day in the eye in the non-sink conditions of the eye than two implants of a lower total dose.

In Vitro Axitinib Release Under Real-Time Sink Simulated Physiological Conditions In another in vitro set-up, axitinib release was evaluated under real-time sink simulated physiological conditions.

Therefore, implants were placed in 5 mL of a physiologically relevant media, i.e. PBS, pH 7.2 with 0.01% NaF with a layer of 1-octanol on top of the solution to provide a sink phase allowing transference of the axitinib into the octanol layer. Implants were incubated under mild agitation at 37° C. in an air chamber. Axitinib was measured at pre-determined sampling time points in the octanol layer by taking the UV absorbance at 333 nm. The amount of axitinib released at each time point is determined relative to a standard curve prepared from an axitinib reference. The accelerated in vitro release profile is determined as the percent of cumulative release of axitinib. The duration to complete drug release was several months.

For an exemplarily release profile under real-time sink conditions reference is made to FIG. 14A.

In Vitro Axitinib Release Under Accelerated Conditions

In a further in vitro set-up, axitinib release was evaluated under accelerated conditions.

Therefore, the implants were placed into an ethanol and water mixture (25:75 ratio, v/v) to increase axitinib solubility at 37° C. in an air chamber with mild agitation. The solubility of axitinib in pure ethanol is 1.4 mg/mL and is approximately 19 μg/mL in a 25% ethanol/75% water mix (v/v; physiologically non relevant media). At pre-determined sampling time points, an aliquot is removed and analyzed for axitinib by taking the UV at 332 nm. The amount of axitinib released at each time point is determined relative to a standard curve prepared from an axitinib reference. The accelerated in vitro release profile is determined as the percent of cumulative release of axitinib. The duration of release under accelerated conditions is approximately two weeks.

Figure 4B:
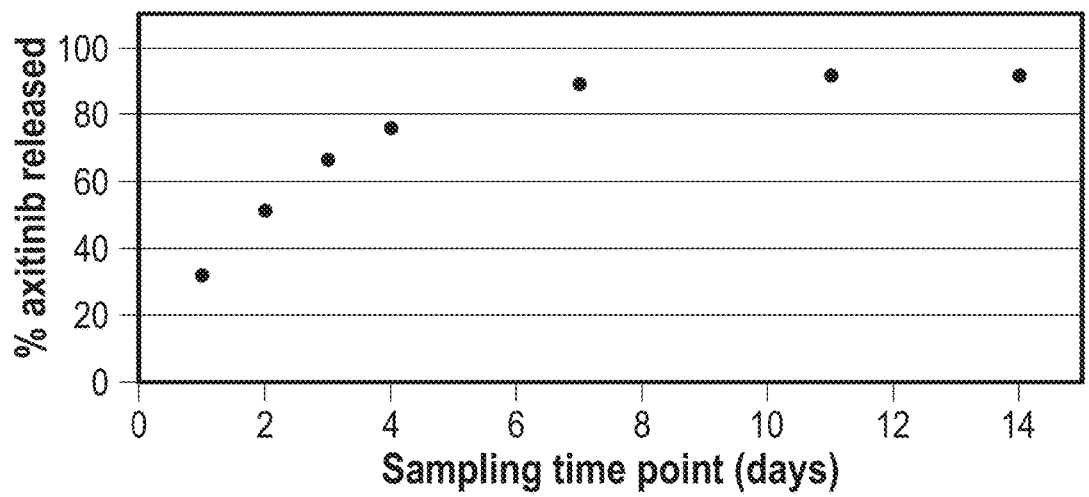

For an exemplarily release profile under accelerated conditions reference is made to FIG. 14B (200 μg implant) and FIG. 4B (556 μg implant).

Example 3: Evaluation of Axitinib Implants in Rabbits

In order to evaluate safety, tolerability, drug release, as well as efficacy of axitinib implants, several pre-clinical studies in Dutch belted rabbits were performed. A broad range of doses were examined either delivered by one or more implants. An overview of the different rabbit studies performed is presented in Table 5. Further studies were performed in beagle dogs and African green monkeys.

TABLE 5

Overview of pre-clinical studies with axitinib implants in rabbits.

| Drug dose and number of implants per eye (bilaterally) | Study purpose | Example No. |
|---|---|---|
| Primary low-dose screen | | |
| 15 μg axitinib in one implant; administration of one, two, or three implants | Safety, tolerability, and efficacy at low dose | 3.1 |
| Administration of one implant | | |
| 227 μg axitinib in one implant; administration of one implant | Tolerability, safety and efficacy | 3.2 |
| Administration of two implants | | |
| 128 μg axitinib per implant, total dose of 256 μg; administration of two implants | Tolerability and safety | 3.3 |
| Administration of two implants either with or without co-administration of Avastin ® | | |
| 145 μg axitinib per implant, total dose of 290 μg; administration of two implants | Tolerability, safety and efficacy with and without co-administration of anti-VEGF drug | 3.4 |
| Drug release from axitinib implants | | |
| 109 μg axitinib in one implant; administration of one implant 227 μg axitinib in one implant; administration of one implant 145 μg axitinib per implant, total dose of 290 μg; administration of two implants 145 μg axitinib per implant, total dose of 290 μg with Avastin ®; administration of two implants | Monitoring drug release from the implants in different eye tissues; Evaluation of systemic axitinib concentration | 3.5 |
| Acute exposure to axitinib | | |
| 600 μg axitinib suspension injected intravitreal | Evaluation of safety of an axitinib bolus dose | 3.6 |

Table 6 gives an exemplarily overview of formulations, configurations, and dimensions of implants used in animal studies (cf. Examples 3.2 to 6). The dimensions of hydrated implants were examined after 24 hours in biorelevant media (PBS, pH 7.2 at 37° C.). Although implant #5 showed a slight increase in length, the hydrated length was still below 10 mm.

TABLE 6

Formulation, configuration, and dimensions of different implants (#1 to #5) as used in animal studies. For instance, implant #4 was used for African green monkey studies (cf. Example 5). Formulation percentages represent weight by weight (w/w).

| Implant type | | Implant #1 | Implant #2 | Implant #3 | Implant #4 | Implant #5 |
|---|---|---|---|---|---|---|
| Formulation | Axitinib | 54.6% | 54.7% | 58.1% | 54.8% | 38.0% |
| | (amount per implant) | (128 µg) | (145 µg) | (227 µg) | (138 µg) | (109 µg) |
| | PEG Hydrogel | 37.2% total | 37.1% total | 29.1% total | 37.0% total | 50.9% total |
| | 4a20K PEG-SAZ | 24.8% | 24.7% | 19.4% | 24.7% | 33.9% |
| | 8a20K PEG-NH2 | 12.4% | 12.4% | 9.7% | 12.3% | 17.0% |
| | Sodium phosphate | 8.2% | 8.2% | 12.8% | 8.1% | 11.1% |
| Configuration | Stretching Method | Dry | Dry | Dry | Dry | Wet |
| | Needle Size | 27G TW 1.25" | 27GTW 1.25" | 25G UTW 1" | 25G UTW 1" | 27G TW 1.25" |
| | Injector/Syringe | 10 µL Modified Hamilton | 10 µL Modified Hamilton | 50 µL Modified Hamilton | 50 µL Modified Hamilton | Implant Injector |
| | Packaging | Foil Pouches | Foil Pouches | Foil Pouches | Foil Pouches | Foil Pouches |
| | Push Wire | Nitinol Wire | Nitinol Wire | Teflon Stainless Steel Wire | Teflon Stainless Steel Wire | Nitinol Wire |
| | Sterilization Type | Gamma | Gamma | Gamma | Gamma | Gamma |
| | Site Storage | Refrigerated | Frozen | Refrigerated | Refrigerated | Refrigerated |
| Dimensions | Dried Diameter | 0.20 mm | 0.24 mm | 0.24 mm | 0.24 mm | 0.2 mm |
| | Length | 12.4 mm | 12.3 mm | 12.5 mm | 12.6 mm | 7.0 mm |
| | Hydrated Diameter | 0.63 mm | 0.64 mm | 0.65 mm | 0.67 mm | 0.5 mm |
| | Length | 5.1 mm | 5.2 mm | 5.5 mm | 4.9 mm | 9.2 mm |

Prior to implant administration, animals were anesthetized with an intramuscular injection of ketamine hydrochloride (20 mg/kg) and xylazine (5 mg/kg). Eyes and the surrounding area were cleaned with a 5% Betadine solution and rinsed with balanced salt solution. One to two drops of topical proparacaine hydrochloride anesthetic (0.5%) was applied. The eye was draped, and a sterile wire speculum was placed to retract the eyelids. The injection needle was placed approximately 3 to 5 mm away from the limbus and deployed in a single stroke.

In summary, the axitinib implants showed a good safety profile, were well tolerable and highly effective independent of the dose or way of delivery (by one or more implants). Moreover, the drug was efficiently released in target tissues, while systemic concentrations in blood remained very low or undetectable.

Example 3.1: Primary Low-Dose Screen of Axitinib Implants

For primary safety, tolerability, and efficacy investigation of the axitinib-containing implants, a low dose of 15 µg axitinib per implant was administered as either one (group 1, n=5), two (group 2, n±5) or three implants (group 3, n=5) per eye bilaterally via intravitreal injection using a 30G 0.5" needle in rabbits including control animals receiving saline. The implants used in this study had a diameter of 0.15±0.13 mm and a length of 6.9±0.1 mm in a dried state. After hydration for 24 hours in biorelevant media (PBS, pH 7.2 at 37° C.) the diameter was 0.42±0.02 mm and the length was 10.6±0.4 mm.

Over a time of 1 month, general health, body weights, and intraocular pressure (IOP) were recorded. Clinical ophthalmic exams were scored at baseline and at 1 month according to the modified McDonald-Shadduck scoring system (McDonald, T. O., and Shadduck, J. A. "Eye irritation". Advances in Modern Toxicology, IV: Dermatotoxicology and Pharmacology, 1977). Infrared reflectance (IR) imaging was collected at 1 month for representative images of the one, two and three implants in the vitreous. Ocular distribution of axitinib was examined using LC-MS/MS essentially as described under Example 3.5. In order to evaluate efficacy of the implants, the rabbits with and without implants were challenged by recurring intravitreal injection of VEGF to induce retinal vascular leakage essentially as described under Example 3.2.

No notable effects on body weight were observed in none of the groups. Moreover, IOP values were normal and comparable between all groups. Ocular health was not or only mildly affected indicating overall safety and tolerability. Clinical ophthalmic examinations at one-month demonstrated no ocular findings for any animals administered a single implant. Mild corneal opacity was observed in one eye of animals administered two or three implants. Mild and moderate conjunctival discharge was observed in two eyes of animals administered three implants.

Figure 5A:
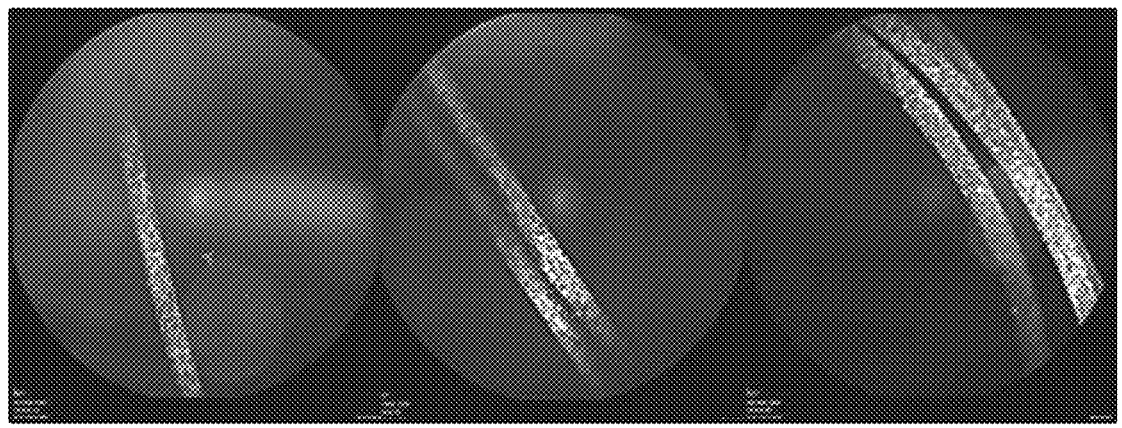
FIG. 5A and FIG. 5B One embodiment of low dose study in rabbits.

IR imaging revealed that the overall shape of the implants, independently of the number administered, remained intact (FIG. 5A).

Pharmacokinetic results of axitinib concentrations in the ocular tissues at 1 month for each group are presented in Table 7. Two eyes were excluded from analysis because one eye in the retina tissue samples in group 2 and one eye in the choroid/RPE (retinal pigment epithelium) samples in group 3 likely included a portion of the implant creating erroneously high concentrations in those two tissue samples due to preferential dissolution in the extraction organic solvent system employed prior to LC-MS/MS analysis (cf. Example 3.5). The solubility of axitinib in PBS, pH 7.2 at 37° C. was determined to be approximately 0.5 µg/mL and any tissue values markedly higher than this potentially indicates either tissue accumulation or sample contamination. Axitinib concentrations were either low or absence in the AH compared to the other ocular tissues indicating little migration of axitinib from the posterior chamber to the anterior chamber. The ocular distribution results demonstrated that a single implant dose (group 1) appeared to be almost fully depleted at 1 month with only 0.3 µg remaining in the VH. 25.5 µg were released from the 30 µg starting dose (two implants, group 2) over the first month for a daily release rate of approximately 0.8 μg/day. 33.8 μg were released from the 45 μg starting dose (three implants, group 3) over the first month for a daily release rate of approximately 1.1 μg/day. Median axitinib levels in the retina were 31 ng/g for group 1, 65 ng/g for group 2 and 148 ng/g for group 3 demonstrating a dose dependent release into the retina tissue. Saturation was not achieved in this study.

TABLE 7

Ocular tissue distribution of axitinib released from 1, 2, and 3 implants with an axitinib dose of 15 μg per implant (groups 1, 2, and 3, respectively). Axitinib concentrations in AH, retina, and choroid/RPE, as well as remaining axitinib in the implant (recovered from the VH) are presented after 1 month as average (mean) including standard deviation, coefficient of variation (CV) as well as the confidence interval (CI) of the mean. In addition, minimum, median, and maximum values for each data point are presented.

| Tissue | Group | N Eyes | Average | Min. | Median | Max. | SD | CV | 95% CI |
|---|---|---|---|---|---|---|---|---|---|
| AH | 1 | 10 | 0.1 | 0.0 | 0.0 | 0.3 | 0.1 | 213% | 0.1 |
| (ng/mL) | 2 | 9 | 0.1 | 0.0 | 0.0 | 0.3 | 0.1 | 203% | 0.1 |
|  | 3 | 9 | 0.1 | 0.0 | 0.0 | 0.2 | 0.1 | 198% | 0.1 |
| Retina | 1 | 10 | 43 | 18 | 31 | 108 | 30 | 69% | 18 |
| (ng/g) | 2 | 9 | 86 | 39 | 65 | 230 | 59 | 69% | 39 |
|  | 3 | 9 | 200 | 64 | 148 | 455 | 123 | 61% | 80 |
| Choroid/RPE | 1 | 10 | 95 | 0 | 32 | 464 | 151 | 159% | 94 |
| (ng/g) | 2 | 9 | 154 | 0 | 104 | 332 | 115 | 75% | 75 |
|  | 3 | 9 | 175 | 49 | 110 | 526 | 156 | 89% | 102 |
| VH + Implant | 1 | 10 | 0.4 | 0.0 | 0.3 | 1.1 | 0.4 | 97% | 0.2 |
| (μg) | 2 | 9 | 4.4 | 1.2 | 4.5 | 7.3 | 2.2 | 50% | 1.5 |
|  | 3 | 9 | 11.2 | 6.3 | 11.2 | 16.9 | 3.4 | 30% | 2.2 |

Figure 5B:
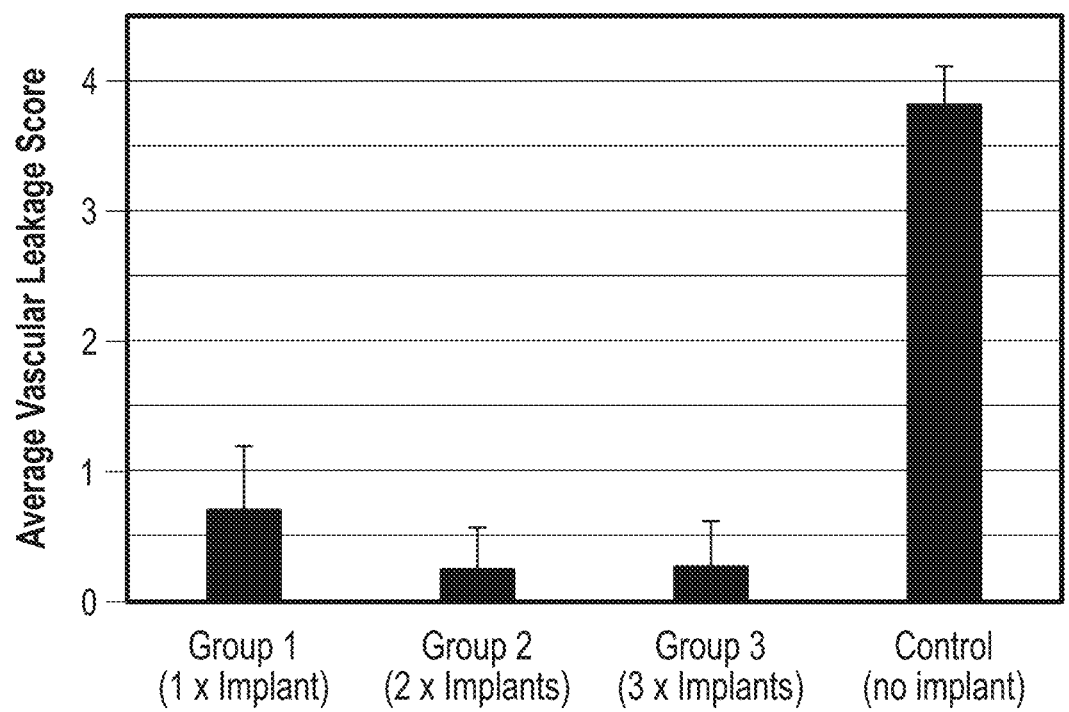

Of note, all three doses demonstrated inhibition of vascular leakage after the VEGF challenge at one month compared to control animals (n=3) not having an implant indicating that even the lowest dose (15 μg) exhibited good efficacy even after short times of 1 month (FIG. 5B).

In summary, the TKI implants administered either as one, two, or three implants per eye were successfully validated for safety, tolerability, as well as axitinib release and efficacy in the primary low dose study.

Example 3.2: Tolerability, Safety and Efficacy Studies with One Axitinib Implant In order to study the tolerability, safety and efficacy of one implant per eye with a higher axitinib dose, rabbits were administered bilaterally via intravitreal injection with a 25G ultra-thin wall needle one implant per eye with an axitinib dose of 227 μg. For implant dimension reference is made to Table 6 (implant type #3).

Tolerability and Safety

For tolerability and safety studies, 9 animals were monitored over 6 months for general health (daily), body weight (0, 1, 3, 6 months) and IOP and ophthalmic exams (each in 0.5 months intervals). Clinical ophthalmic exams were scored according to the modified McDonald-Shadduck scoring system. Electroretinography (ERG) and fluorescein angiography (FA) were performed at 1, 3, and 6 months to assess retinal function and to evaluate the vasculature of the eye, respectively. Optical coherence tomography (OCT) was performed monthly to obtain cross-sectional images of the retina. IR imaging was performed monthly to monitor bio-degradation of implants over the time and persistence of axitinib in the vitreous.

Upon sacrifice (3 animals at 1, 3, and 6 months), whole eyes were prepared for histopathological analysis. Therefore, a suture was placed at the 12 o'clock position for orientation and harvest. Typically, eyes were trimmed in half in the plane from 12 o'clock to 6 o'clock through the lens and optic nerve along the midline. This captures as many optic structures in one plane as possible. The trimmed eyes were examined grossly and abnormalities noted. Hematoxylin and eosin (H&E)-stained slides were prepared that were separated by 1 mm. Each slide contained 2 serial sections.

Histopathology assessments at each time point included vitreous, retinal, scleral, or episcleral inflammation, retinal disruption and fibrosis around the injected area. Scoring was performed on a semi-quantitative scale from 0-5 for any abnormalities, where 0 denotes no change (normal), 1 denotes rare foci of change (minimal), 2 denotes mild diffuse change or more pronounced focal change, 3 denotes moderate diffuse change, 4 denotes marked diffuse change and 5 denotes severe diffuse change.

Figure 6:
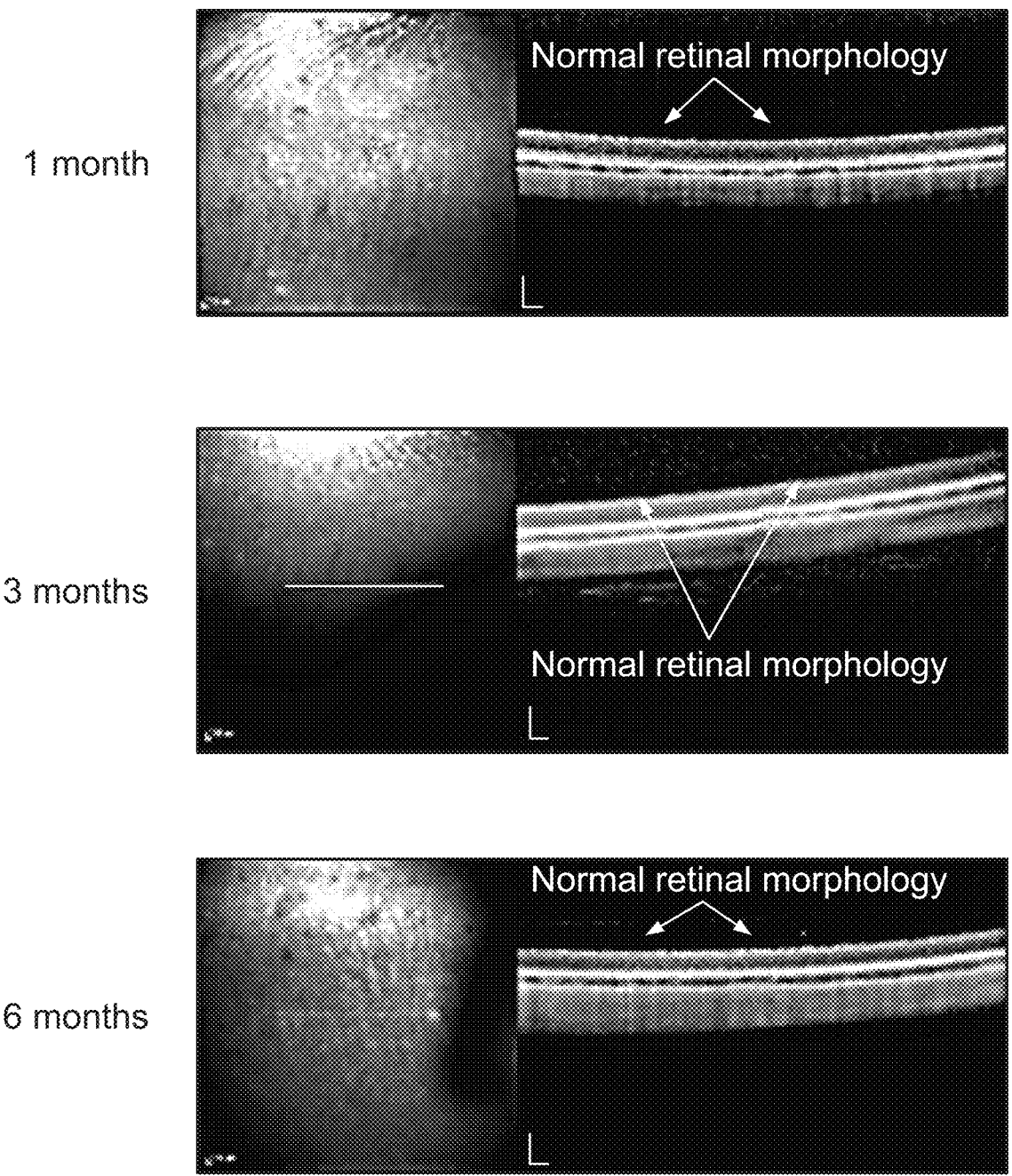
FIG. 6 One embodiment of infrared reflectance (IR) and optical coherence tomography (OCT) imaging of rabbit eyes. IR/OCT images of retinal morphology after 1, 3, and 6 months after implant injection, respectively. Retinal morphology was normal.
Figure 7A:
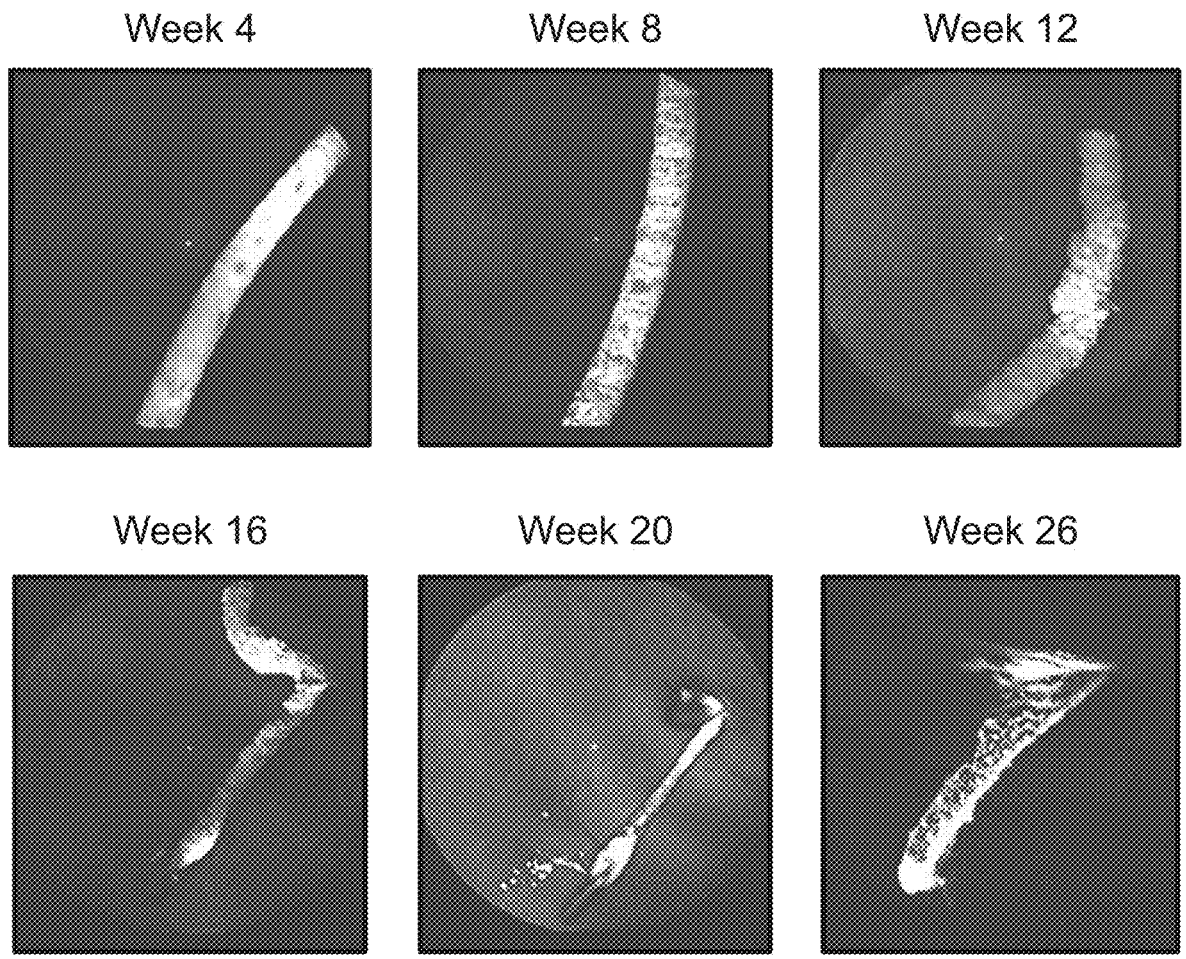
FIG. 7A and FIG. 7B One embodiment of biodegradation of implant and inflammation.
Figure 7B:
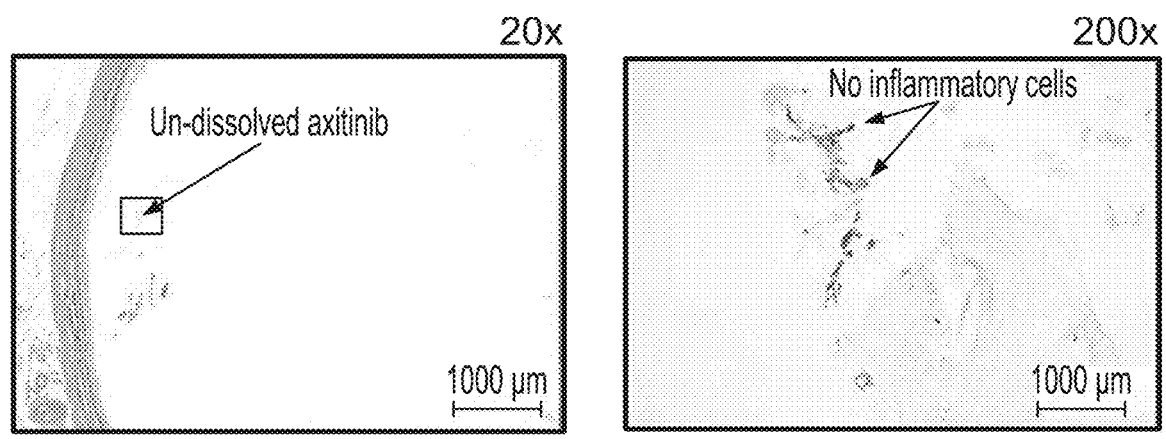

No notable effects on daily health or body weights were observed. IOP was normal for the complete duration of the study. No notable effects from the implants were found based on electroretinography (ERG) measurements. Fluorescein angiography (FA) and OCT imaging revealed no pathologies over the study. For instance, normal retinal morphology was preserved over 6 months (FIG. 6). In addition, ophthalmic exam findings were normal or mild. IR imaging at weeks 4 and 8 revealed an intact implant, whereas images at week 12 demonstrated early stages of hydrogel degradation (FIG. 7A). Images at week 16 showed implant narrowing due to loss of hydrogel structure. Finally, images at weeks 20 and 26 showed the absence of hydrogel, while non-dissolved axitinib particles remained in proximity to the former implant site and formed a single monolithic structure. However, any undissolved axitinib remaining at the implant site was shown to continue to release axitinib at levels sufficient for inhibition of vascular leakage (as demonstrated for instance through 21 months in a VEGF-challenge study, see Example 3.4). In addition, no inflammation was observed in the region of undissolved axitinib particles (FIG. 7B).

The amount of axitinib decreased in the histopathology sections over time indicating bio-resorption of the injected material. There were no observations of gross lesions in the sections noted over the study duration. Mean histopathology results with standard deviations are presented in Table 8. Mean inflammation scores showed that retinal, scleral, or episcleral, vitreous chamber and chronic subcorneal (lymphocytes and phagocytes at cornea edges) inflammation scores were normal to minimal over the study duration. Mean fibrosis scores around the injected test article were normal to minimal over the study duration. Mean retinal disruption scores were minimal over the study duration. Mean retinal vacuolization scores were minimal over the study duration. Retinal detachments were not observed clinically, but were noted in 1 of 68, 5 of 71, and 1 of 72 histologic sections for months 1, 3 and 6, respectively. The position of the detachments was often associated with retinal disruption sites and are consistent with the needle penetration site position, indicating that they were likely procedure related.

biodegradation rates and the potential of the implant to inhibit neovascularization in vivo.

Example 3.3: Tolerability and Safety Studies with Two Axitinib Implants

In a next step, tolerability and safety of two implants with higher axitinib dose (128 µg per implant, total dose of 256 µg per eye) were investigated. Therefore, rabbits (n=9) received two implants (implant type #1 in Table 6) bilaterally with a total axitinib dose of 256 µg (128 µg per implant) via intravitreal injection with a 27G ultra-thin wall needle.

TABLE 8

Histopathological analysis results for rabbits with one implant (227 µg axitinib per implant). Results were scored on a scale of 0-5, where 0 denotes no change (normal), 1 denotes rare foci of change (minimal), 2 denotes mild diffuse change or more pronounced focal change, 3 denotes moderate diffuse change, 4 denotes marked diffuse change and 5 denotes severe diffuse change. Results are presented as mean and standard deviation (SD).

| Month | Retinal Disruption | Retinal Vacuolization | Vitreous Chamber Inflammation | Retinal, Scleral, or Episcleral Inflammation | Fibrosis Around the Implant | Chronic Subcorneal Inflammation |
|---|---|---|---|---|---|---|
| 1 | 0.03 (0.06) | 0.40 (0.24) | 0.07 (0.16) | 0.02 (0.04) | 0.02 (0.04) | 0.02 (0.04) |
| 3 | 0.05 (0.06) | 0.57 (0.21) | 0.07 (0.05) | 0.18 (0.05) | 0.00 (0.00) | 0.10 (0.20) |
| 6 | 0.03 (0.05) | 0.82 (0.25) | 0.30 (0.28) | 0.05 (0.08) | 0.03 (0.05) | 0.40 (0.20) |

Efficacy

For efficacy studies, 12 animals (with and without the implant) received an intravenously VEGF challenge (1 µg) 48 hours prior to selected time points (1, 2, 3, and 6 months after implant injection; 3 animals euthanized at each time point) to induce vascular proliferation and leakage. Rabbits were followed for 6 months from the administration of the implant. Eyes were imaged 48 hours post VEGF challenge using fluorescein angiography (FA) after intravenous injection of fluorescein and were graded on a scale from 0 to 4 (Table 9). Each eye was scored on the left and right side to account for non-uniformity in inflammatory response. FA scores were then averaged for each eye.

TABLE 9

Description of scoring method for imaging by fluorescein angiography (FA).

| Score | Description |
|---|---|
| 0 | Normal eye, vessels appear straight and simple, no haziness or leakage |
| 1 | Some minor tortuosity, but generally vessels appear straight, no haziness or leakage |
| 2 | Some more advanced tortuosity, vessels appear choked and a lot of branching is visible, but still no haziness or leakage |
| 3 | Extreme tortuosity, vessels appear choked and a lot of branching is visible, some slight haziness pointing to leakage of the vessels |
| 4 | Extreme tortuosity and extreme leakage, eye appears as a haze and vessels are difficult to visualize |

Figure 8:
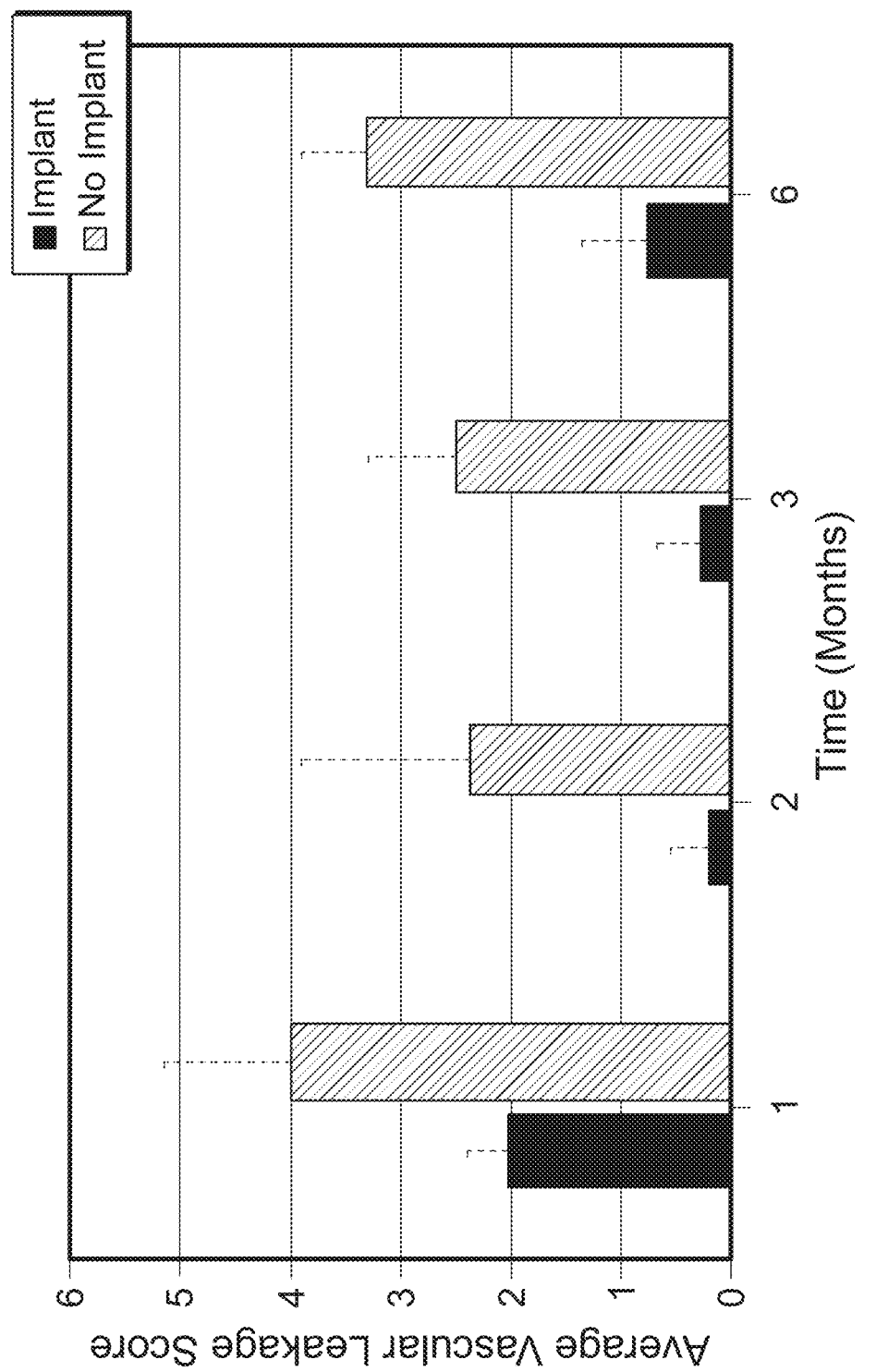
FIG. 8 One embodiment of suppression of vascular leakage in rabbits challenged with VEGF following administration of an axitinib implant with a dose of 227 µg. Vascular leakage scores (0 (normal) to 4 (severe leakage)) are presented in dependency of the time (months) after VEGF challenge for animals with and without the implant. Effective suppression of vascular leakage was observed for animals having the implant for a duration of 6 months. Error bars represent standard deviation (SD; solely upper error bars presented).

Vascular leakage was effectively reduced in animals with the implant when compared to control animals that received saline instead of the implant over a period of 6 months (FIG. 8). Blank control eyes showed high tortuosity and leakage at all time-points.

Taken together, the data demonstrate good tolerability and safety of one higher dose implant, as well as suitable Over a study period of 6.5 months, rabbits were daily monitored for health, IOP, and body weight. Clinical ophthalmic exams (daily) were scored according to the modified McDonalds-Shadduck scoring system. Optical coherence tomography (OCT) was performed to obtain cross-sectional images of the retina (monthly). Infrared (IR) imaging was performed to monitor the persistence and degradation of implants and axitinib in the vitreous (monthly). Electroretinography (ERG) was performed to assess retinal function and fluorescein angiography (FA) was performed to evaluate the vasculature of the eye at months 1, 3, and 6.5. At months 1, 3, and 6.5, each 3 rabbits were sacrificed. After sacrifice, whole eyes were prepared for histopathological analysis (cf. Example 3.2).

No abnormal general health observations were observed. All rabbits either gained or maintained weight over the study duration. Ocular health findings were limited to irritation, swelling, and/or discharge that were sporadic, generally mild and transient. Clinical ophthalmic examinations demonstrated no ocular abnormalities over the course of the study, except of mild conjunctival discharge for half of the animals at day 14, likely procedure related, which resolved by day 27, a single instance of mild retina hemorrhage immediately post-administration which resolved by day 27, mild conjunctival congestion seven weeks post administration, and lens opacity due to attachment of the implant to the lens in one eye at day 195. IOP was normal for the duration of the study. OCT imaging revealed no retinal abnormalities over the study duration. ERG was normal for all study eyes, indicating normal retinal function. FA found normal vascularization and no evidence of dilation or leakage.

Figure 9:
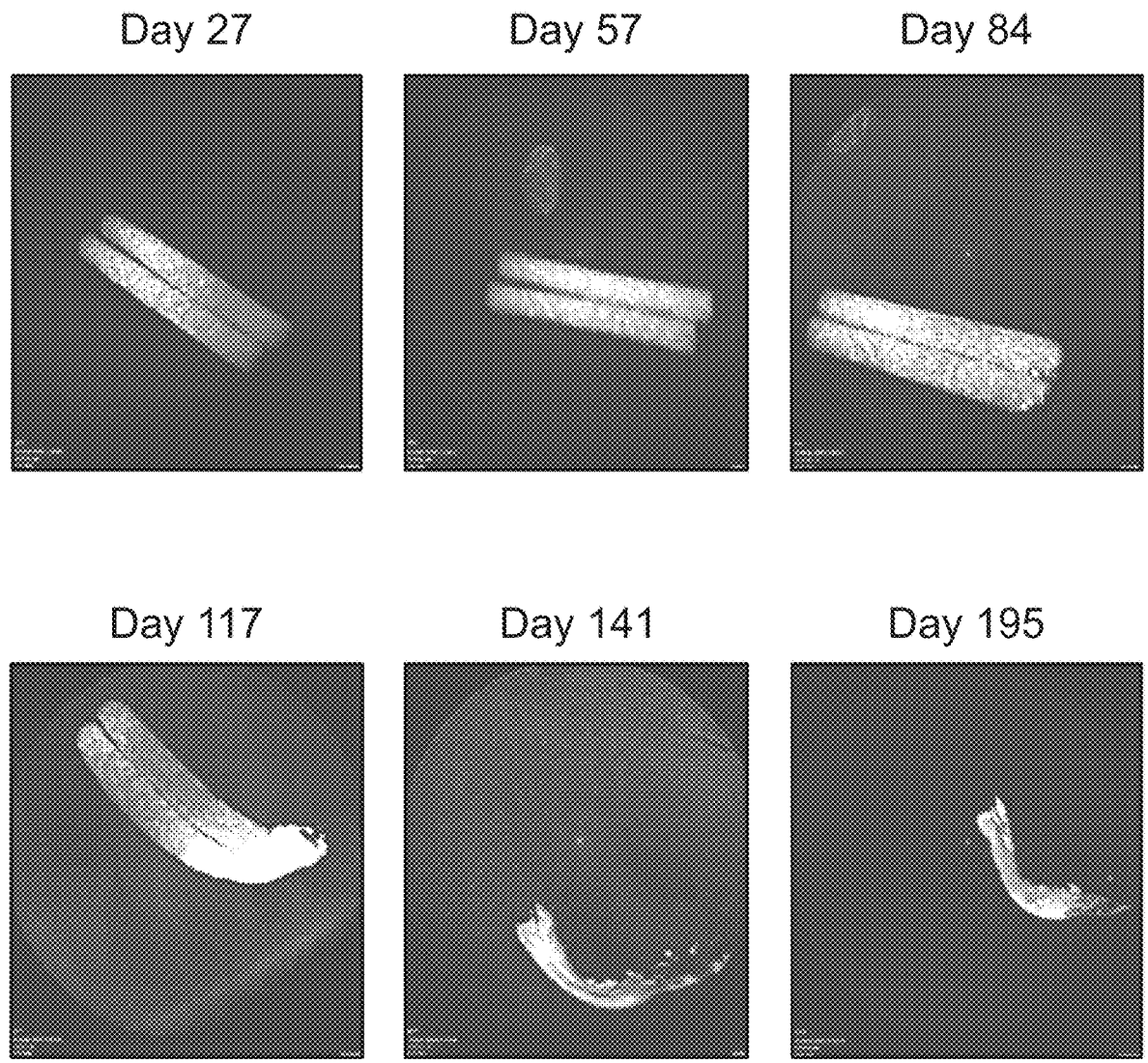
FIG. 9 One embodiment of infrared reflectance (IR) imaging of two implants in rabbit eyes. Implants show degradation over time. Implants were intact at days 27 to 117, while implant narrowing was observed due to hydrogel degradation observed on days 141 and 195. Remaining axitinib particles merged into a single monolithic structure on days 141 and 195. Free axitinib particles (white specs) were noted in proximity to the former implant site post hydrogel degradation.

IR imaging demonstrated hydrogel degradation of the two implants over time and a more monolithic morphology was formed as the axitinib particles were released from the confines of the hydrogel, as seen post day 117 (FIG. 9). These observations were similar to the implant behavior in Example 3.2 (FIG. 7A).

Histopathology noted that the amount of the test article declined in the sections over time, indicating bioresorption of the injected material. Histopathological findings assessing inflammation and fibrosis were absent or minimal over the study duration. Mean histopathology results with standard deviations are presented in Table 10. Mean histopathological inflammation scores showed that retinal, scleral, or episcleral, vitreous chamber and chronic subcorneal (lymphocytes and phagocytes at cornea edges) inflammation scores were normal to minimal over the study duration. Mean fibrosis scores around the injected test article were normal to minimal over the study duration. Mean retinal disruption scores were normal to minimal over the study duration. Mean retinal vacuolization scores were minimal over the study duration. Retinal detachments were not observed clinically, but were noted in 2 of 192 histologic sections for months 1, 3, and 6, respectively. The position of the detachments was often associated with retinal disruption sites and are consistent with the needle penetration through the retina at the injection location indicating that they were likely procedure related.

ings were generally mild in nature for vitreous flare, choroidal/retinal inflammation, and conjunctival discharge. All findings were comparable between implants applied with or without co-administration of Avastin® demonstrating the suitability of the implants to be combined with other therapeutics such as anti-VEGF medicals.

Figure 10:
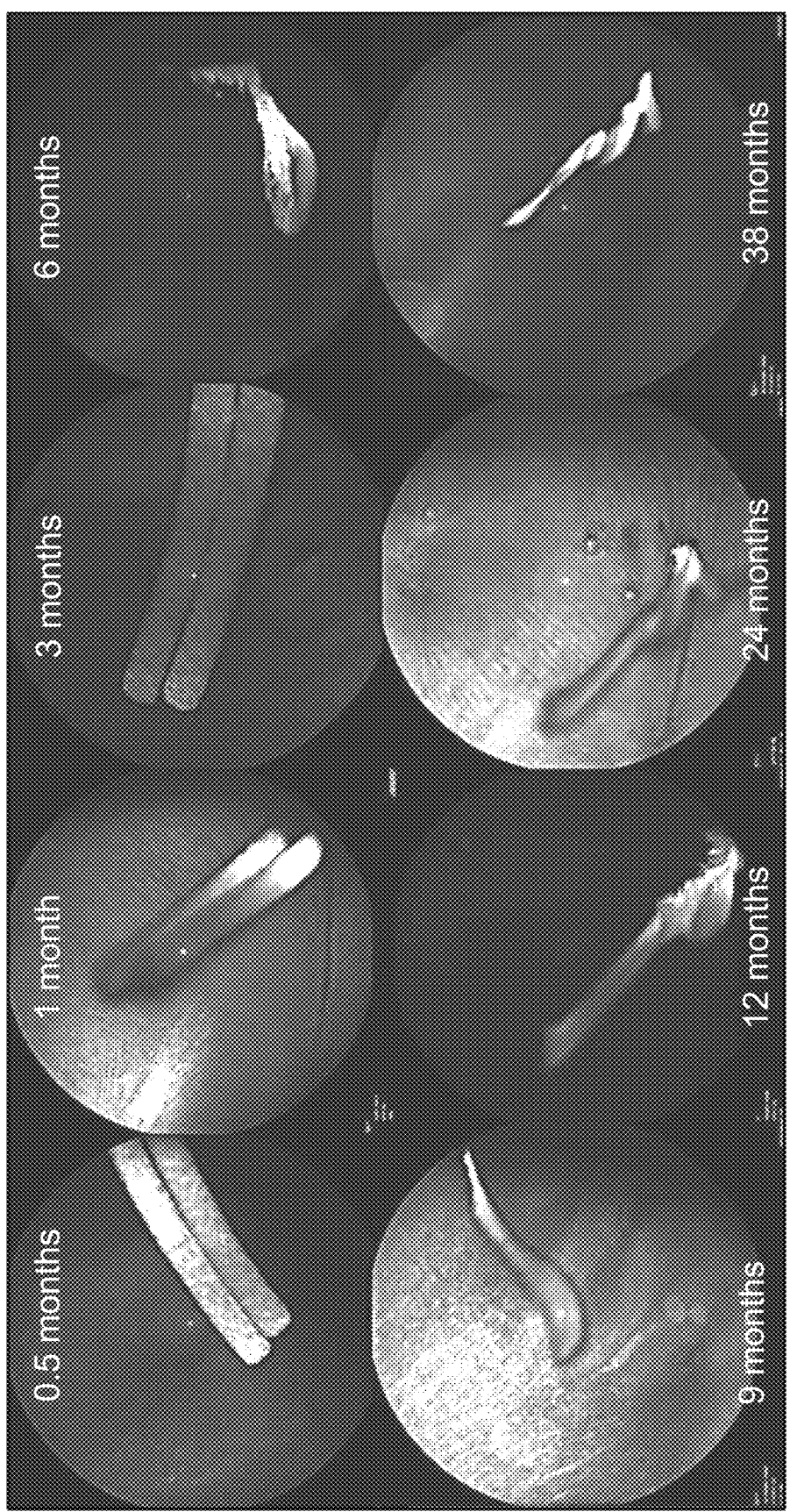
FIG. 10 One embodiment of infrared reflectance (IR) imaging of two implants in rabbit eyes. The implant was intact during 0.5 to 3 months after injection. After 6 months, the implant narrowed due to hydrogel degradation and remaining axitinib particles merged into a single monolithic structure. Free axitinib particles (white specs) were noted in proximity to the former implant site post hydrogel degradation at 24 months up to 38 months.

IR imaging confirmed that the implants dissociated over the study duration and demonstrate hydrogel degradation of the two implants over time and a more monolithic morphology was observed as the axitinib particles merge into a single monolithic structure between 6 and 9 months, wherein the structure demonstrated a reduction in size through study completion (FIG. 10). These observations were also in line with images from Examples 3.2 and 3.3 (FIGS. 7A and 9).

Efficacy

For efficacy studies, 52 rabbits were divided in 4 groups, wherein group 1 received the two implants but did not

TABLE 10

Histopathological analysis results for rabbits with two implants (total dose of 256 µg axitinib per eye). Results were scored on a scale of 0-5, where 0 denotes no change (normal), 1 denotes rare foci of change (minimal), 2 denotes mild diffuse change or more pronounced focal change, 3 denotes moderate diffuse change, 4 denotes marked diffuse change and 5 denotes severe diffuse change. Results are presented as mean and standard deviation (SD).

| Month | Retinal Disruption | Retinal Vacuolization | Vitreous Chamber Inflammation | Retinal, Scleral, or Episcleral Inflammation | Fibrosis Around the Implant | Chronic Subcorneal Inflammation |
|---|---|---|---|---|---|---|
| 1 | 0.03 (0.06) | 0.50 (0.31) | 0.15 (0.23) | 0.02 (0.04) | 0.00 (0.00) | 0.58 (0.31) |
| 3 | 0.00 (0.00) | 0.36 (0.39) | 0.06 (0.09) | 0.00 (0.00) | 0.00 (0.00) | 0.58 (0.48) |
| 6.5 | 0.02 (0.04) | 0.28 (0.41) | 0.02 (0.04) | 0.04 (0.05) | 0.02 (0.04) | 0.42 (0.38) |

Example 3.4: Tolerability, Safety and Efficacy Studies with Two Axitinib Implants with or without Co-Administration of Avastin®

In a next step, the tolerability, safety and efficacy of two axitinib implants (145 µg axitinib resulting in a dose of 290 µg per eye) bilaterally administered via intravitreal injection with a 27G ultra-thin wall needle was assessed with and without co-administration of 1.25 mg Avastin® (bevacizumab). For the animals receiving Avastin®, the anti-VEGF therapeutic was administered intravitreally followed by administration of the two implants. For formulation and dimensions of the implants applied in this study, reference is made to Table 6 (implant type #2).

Tolerability and Safety

For tolerability and safety studies, 30 rabbits (n=15 per group, wherein group 1 did not receive Avastin® and group 2 received 1.25 mg Avastin®) were monitored for a study time of up to 38 months. General health was checked on a daily basis until 31 months and body weight was checked on a daily basis until 21 months. In addition, IR imaging was performed to monitor persistence and degradation of the implants and axitinib in the vitreous over 38 months. Ophthalmic exams and IOP were monitored for 21 months. Ophthalmic exams were scored according to the modified McDonald-Shadduck scoring system.

In summary, no effects on body weight were observed. Daily general health observations solely revealed limited to mild ocular findings which self-resolved. IOP and ocular exams were normal throughout the study. Ophthalmic findreceive Avastin® (n=15), group 2 received the two implants and received Avastin® (n=15), group 3 solely received Avastin® (n=9), and group 4 were control rabbits without implant receiving saline (n=13). Animals from each group were intravenously challenged with VEGF (1 µg) 48 hours prior to selected time points (0.5, 1, 3, 6, 9, 12, 14, 16, 19, 20, and 21 months) to induce vascular proliferation and leakage. Eyes were imaged 48 hours post VEGF challenge time-points using fluorescein angiography (FA) and were graded on a scale from 0 (normal) to 4 (severe leakage) as described under Example 3.2.

Figure 11:
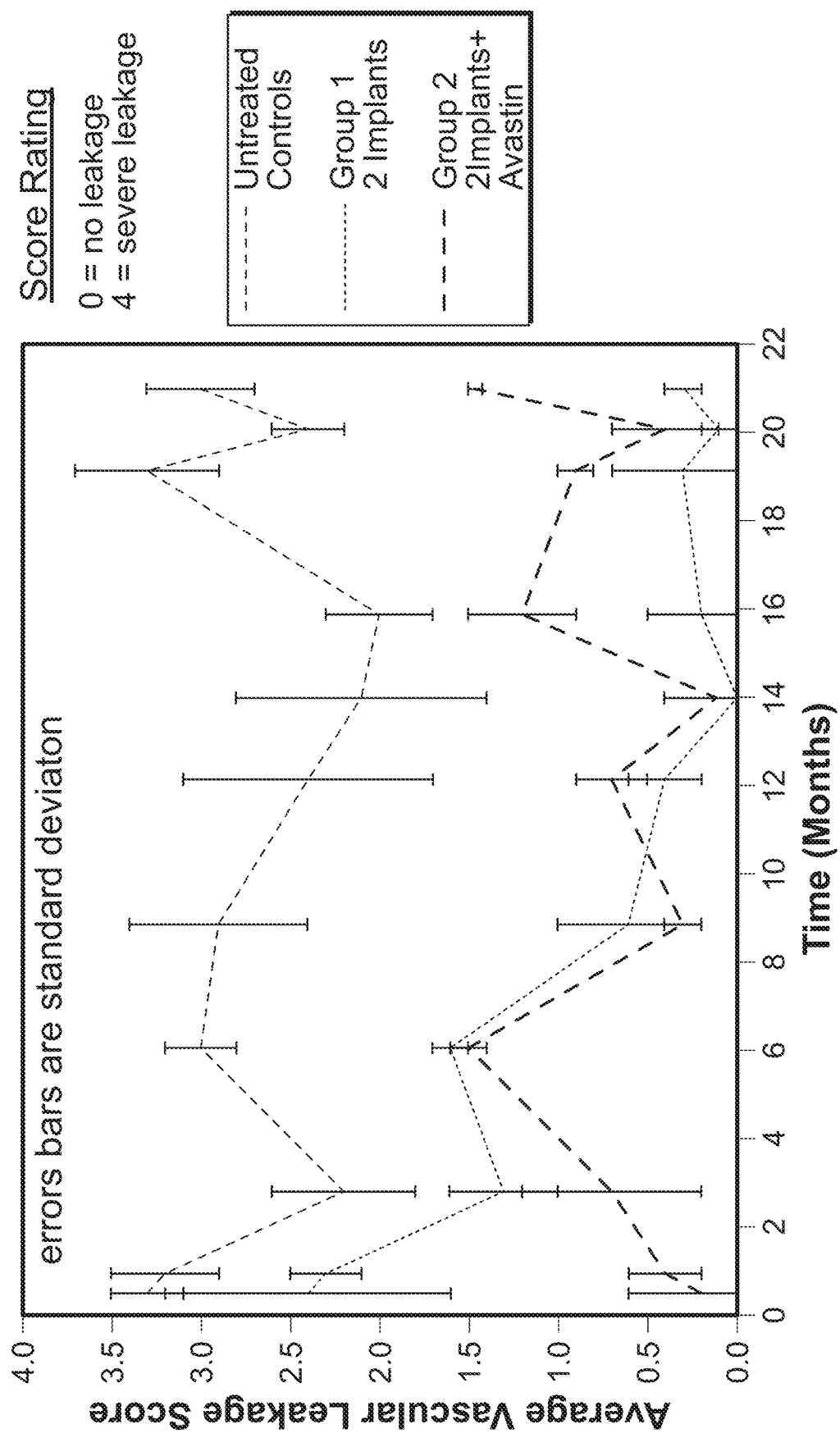
FIG. 11 One embodiment of suppression of vascular leakage in rabbits challenged with VEGF following administration of two axitinib implants with a total dose of 290 µg without (group 1) and with (group 2) co-administration of Avastin®). Vascular leakage scores (0 (normal) to 4 (severe leakage)) are presented in dependency of the time (months) after VEGF challenge for animals from group 1 and 2 and for animals without an implant. Significant suppression of vascular leakage was observed for all groups of animals having the implants. Error bars represent standard deviation.
Figure 12:
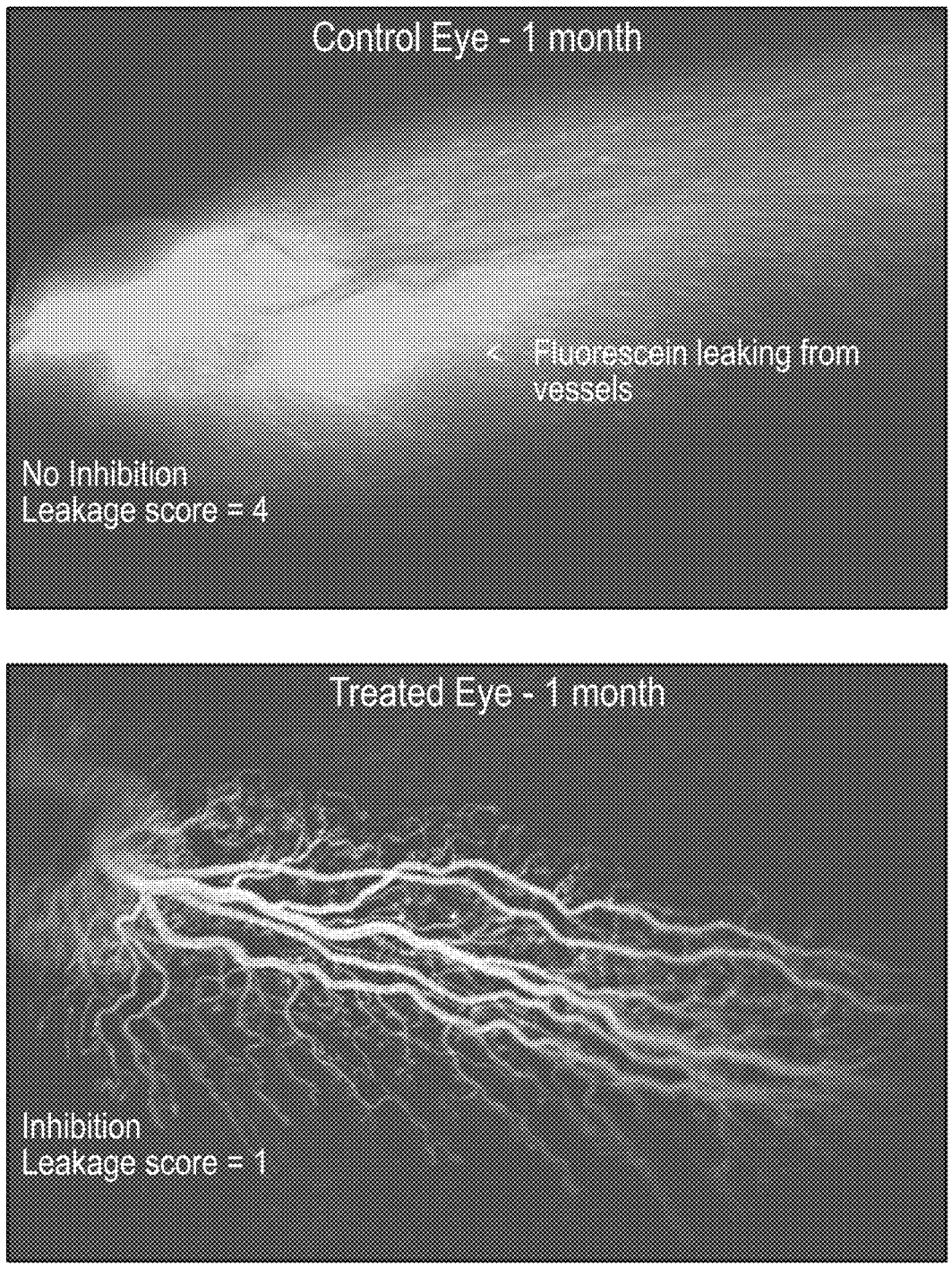
FIG. 12 One embodiment of fluorescein angiography (FA) images revealed significant leakage, with fluorescein seen actively leaking from vasculature immediately following injection of fluorescein 48 hours after the VEGF challenge in the control animals (upper panel) and complete inhibition of leakage from vessels of rabbit eyes comprising the implants (lower panel). Images were collected after VEGF challenge 1 month after the implant injection.
Figure 13:
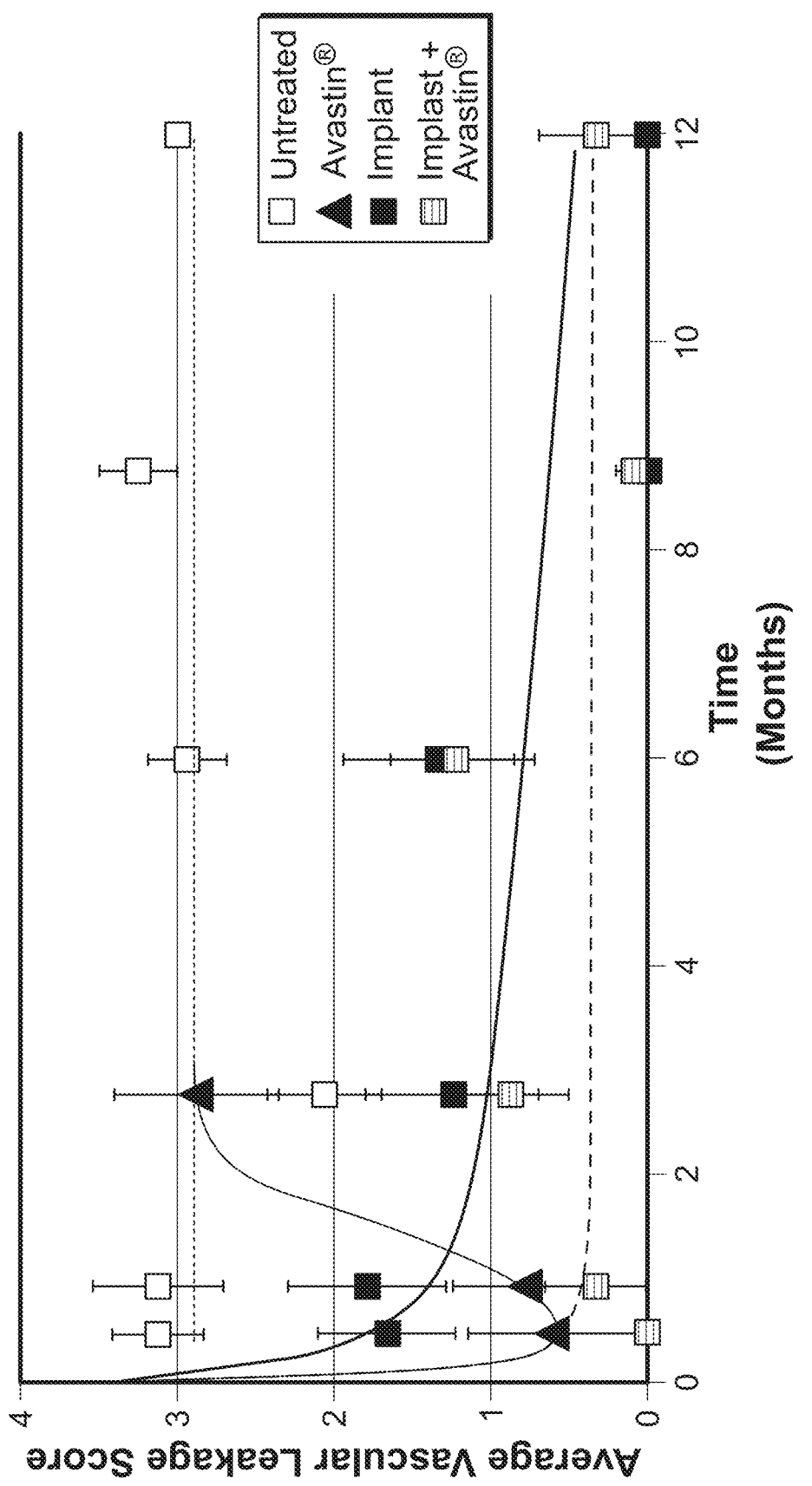
FIG. 13 One embodiment of average vascular leakage score for rabbits which were not treated with implant or anti-VEGF therapeutic (white squares and dashed line), rabbits which were treated with Avastin® only (black triangles, curve fit until 3 months), rabbits with implants (black squares, solid line until 12 months), and rabbits with implants and Avastin® (striped squares and dashed line until 12 months). Vascular leakage was efficiently inhibited for 12 months for all animals that received the implants. Animals solely treated with anti-VEGF therapeutic showed rapid onset of leakage inhibition in the first 2 to 4 weeks, but leakage re-occurred after 3 months. Values represent mean and standard error of the mean (SEM).

It was demonstrated that vascular leakage was prevented with and without the co-administration of Avastin® for up to 21 months with repeated VEGF challenges (FIG. 11). Representative FA images at 1 month post implant injection clearly show effective leakage inhibition 1 month after implant injection for animals of group 2 (FIG. 12). Of note, animals solely receiving Avastin® (group 3) showed rapid leakage inhibition within the first 2 and 4 weeks, however, after 3 months vascular leakage re-occurred to a similar degree than observed in the control animals (group 4; FIG. 13). Blank control eyes showed high tortuosity and leakage at all time-points (Score 3-4).

Taken together, the VEGF challenging data demonstrated the potential of the implants to inhibit neovascularization in vivo in line with the good efficacy resulting from one implant (cf. Example 3.2). Compared to animals solely receiving Avastin®, the beneficial effect of the implants was demonstrated. In contrast to the anti-VEGF therapeutic where effects only lasted until 3 months post injection, the implants enabled a long-term inhibition of neovascularization of up to 21 months.

Example 3.5: Axitinib Release from Implants and Axitinib Distribution in Rabbits Finally, pharmacokinetic studies have been performed in order to evaluate drug-release from the implants and axitinib distribution to the ocular tissues, specifically the retina, choroid/retinal pigment epithelium (RPE), vitreous humor (VH) and aqueous humor (AH) over time following sustained release from the implants. In addition, systemic axitinib concentrations were monitored. Therefore, rabbits were divided into 4 groups. 2 groups received bilaterally one implant comprising either 109 µg axitinib (group 1, n=14) or 227 µg axitinib (cf. Example 3.2, group 2, n=24). Group 3 (cf. Example 3.4; n=15) received bilaterally two implants, each comprising 145 µg, i.e., a total dose of 290 µg axitinib. Group 4 (cf. Example 3.4; n=15) received bilaterally two implants comprising, as for group 3, a total dose of 290 µg axitinib (2×145 µg) and in addition 1.25 mg Avastin® (bevacizumab) intravitreal. Formulations, configurations, and dimensions of implants with corresponding axitinib doses are presented in Table 6.

For investigation of drug release, two rabbits were euthanized per time-point for group 1 (day 1 and 1.5, 3, 4.5, 6, 7.5 and 9 months), six rabbits were euthanized per time-point for group 2 (1, 3, 6, and 7 months), and 3 (0.5, 1, 3, and 6 months) and 1 (9 and 38 months) rabbits were euthanized per time-point for groups 3 and 4. In addition, blood samples were taken from the rabbits prior to euthanasia at time points indicated in Table 11.

Methods Determination of Axitinib in Plasma

For determination of axitinib in plasma, two equivalent quantification methods were carried out. Axitinib was extracted from plasma by supported liquid extraction (SLE) and was dried under nitrogen. The short-term matrix (plasma) stability was up to 4 hours and the extract stability was up to 116 hours.

After reconstitution in methanol/water (50:50 v/v; method 1) or alternatively in methanol/water/formic acid (75:25:0.01 v/v/v; method 2), the samples were analyzed by liquid chromatography-tandem mass spectrometry (LC-MS/MS; API 4000, Applied Biosystems) using a water/formic acid/methanol gradient. Axitinib and the internal standard (IS; axitinib-D3 for method 1 and pazopanib for method 2) were separated on an YMC-Pack Pro C4 column (50×3.0 mm I.D.; method 1) or a Phenomenex Luna C18 column (method 2) and quantitated using electrospray ionization (ESI) selective reaction monitor in g mode with a total run time of approximately 6 min. For quantification, the peak area of axitinib (m/z 387.2 to 356.0) and the IS (m/z 390.2 to 356.0 for axitinib-D3 and m/z 438.2 to 357.1 for pazopanib) were determined and compared to a standard curve, which showed linear behavior in the desired concentration range and a correlation coefficient ($r^2$) of >0.99. The lower limit of quantitation (LLOQ) ranged from about 0.01 ng/mL to about 0.36 ng/mL depending on the study group and sampling time-points (Table 11).

TABLE 11

Sampling time points and corresponding LLOQ (by isomer) for axitinib in plasma or serum. For group 1, plasma samples were analyzed on day 1 and 1.5, 3, 4.5, 6, 7.5 and 9 months. For group 2, plasma samples were analyzed after 3, 6, and 7 months. For groups 3 and 4, serum samples were analyzed after 6 months.

| Study Group | Sampling time points (LLOQ depending on isomer) |
|---|---|
| Group 1 | Day 1 and 1.5, 3, 4.5, 6, 7.5 and 9 months (0.0500 ng/mL; both isomers) |
| Group 2 | 3 months (0.355 ng/mL (trans), 0.146 ng/mL (cis)) 6 months (0.0717 ng/mL (trans), 0.0283 ng/mL (cis) 7 months (0.0158 ng/mL (trans), 0.0106 ng/mL (cis)) |
| Groups 3 and 4 | 6 months (0.0452 ng/mL (trans), 0.00970 ng/mL (cis)) |

Methods Determination of Axitinib in Ocular Tissues

For determination of axitinib concentrations in ocular tissues, eyes were enucleated and frozen in liquid nitrogen at the selected time points (Table 13). The eyes were stored frozen prior to frozen dissection and subsequent bioanalysis. For determination of axitinib in ocular tissues, two equivalent quantification methods were carried out. Equivalency of both methods to determine the axitinib concentrations in AH, VH, retina and choroid homogenate was demonstrated during qualification.

Ocular tissue samples of retina and choroid were homogenized in a methanol/water diluent (50:50, v/v; method 1) or in phosphate buffered saline (PBS; method 2) in tubes containing ceramic beads. Soluble axitinib in VH and AH was diluted directly from the samples with methanol/water diluent (50:50, v/v) and vitreous humor samples containing the implant (undissolved axitinib) were extracted with ethanol (method 1). In method 2, homogenized tissues, soluble axitinib in VH and AH were diluted with methanol/water/formic acid (75:25:0.01 v/v/v). Analyte was extracted from the matrix by protein precipitation (method 1) or SLE (method 2), respectively. The short-term matrix stability was up to 5 hours (AH), up to 5.5 hours (VH), up to 6.6 hours (retina) and up to 4.5 hours (choroid). The extract was stable up to 171 hours (AH), up to 153 hours (VH), up to 115 hours (retina) and up to 114 hours (choroid).

Samples were dried under nitrogen and reconstituted with methanol/water (50:50 v/v) and are analyzed via LC-MS/MS (API 4000, Applied Biosystems) with a water/formic acid/acetonitrile gradient (method 1) or a water/formic acid/methanol gradient (method 2). Axitinib and the internal standard (IS; axitinib-D3 for method 1 and pazopanib for method 2) were separated on an YMC-Pack Pro C4 column (50×3.0 mm I.D.; method 1) or a Phenomenex Luna C18 column (method 2) and quantitated using ESI selective reaction monitor in g mode with a total run time of approximately 6 min. For quantification, the peak area of axitinib (m/z 387.2 to 356.0) and the IS (m/z 390.2 to 356.0 for axitinib-D3 and m/z 438.2 to 357.1 for pazopanib) were determined and compared to a standard curve, which showed linear behavior in the desired concentration range and a correlation coefficient ($r^2$) of >0.99. The LLOQ was 0.100 ng/mL.

Results: Determination of Axitinib in Plasma

The axitinib concentration in plasma and serum was determined at indicated time-points in the different groups (Table 11). Determined concentrations were below the lower limit of quantitation (LLOQ) during the duration of the studies for all groups independent of the axitinib dose (ranging from 109 to 290 µg per eye), demonstrating that the systemic exposure to axitinib was near absent even for a total dose as high as 580 µg axitinib (290 µg axitinib per eye adding up to a total of 580 µg per rabbit). This further underlines safety of the implants even for higher doses.

Results: Determination of Axitinib in Ocular Tissues

After hydrogel degradation, undissolved axitinib was observed to form a localized structure continuing to release axitinib (cf. Examples 3.2 to 3.4). These undissolved axitinib particles may create erroneously high concentrations in tissue samples due to preferential dissolution in the organic solvent used for extraction prior to LC-MS/MS analysis. Therefore, it might have been possible that tissue concentrations of axitinib after hydrogel degradation were elevated due the presence of undissolved axitinib particles contaminating the tissue samples due to either migration near tissues or contamination during tissue dissection. The solubility of axitinib in biorelevant media (PBS, pH 7.2 at 37° C.; Lorget et al., 2016; Characterization of the pH and temperature in the rabbit, pig, and monkey eye: key parameters for the development of long-acting delivery ocular strategies. Molecular pharmaceutics, 13(9), pp. 2891-2896) was determined to be approximately 0.5 µg/mL and any tissue values markedly higher than this potentially indicated either tissue accumulation and/or dissolution of axitinib particles in the organic solvent during extraction. However, in general, measured ocular tissue levels of axitinib correlated well with the visual presence or absence based on IR imaging (FIGS. 7A, 9, and 10).

The aim of the study was to demonstrate axitinib concentrations in the desired target tissues (choroid/RPE, retina, and vitreous humor) well above the IC50 for the targeted tyrosine kinase receptors (Gross-Goupil et al., Clinical Medicine Insights: Oncology, 2013, 7:269-277) and above the half maximal effective concentration (EC50) of free axitinib for inhibition of ocular angiogenesis in a neonatal rat model as investigated in support of INLYTA® (INLYTA® AusPAR 2013, NDA 202324; Table 12) for all doses administered in order to validate efficient drug release.

TABLE 12

$IC_{50}$ values of axitinib for binding to vascular endothelial growth factor receptor 2 (VEGFR2), platelet-derived growth factor receptor β (PDGFR-β), and stem cell growth factor receptor/type III receptor tyrosine kinase (c-Kit), as well as $EC_{50}$ value of axitinib for inhibition of ocular angiogenesis in a rat model.

| | $IC_{50}$ | | $EC_{50}$ Rat Ocular |
|---|---|---|---|
| VEGFR2 | PDGFR-β | c-Kit | Angiogenesis Model |
| 0.08 ng/mL (0.2 nM) | 0.62 ng/mL (1.6 nM) | 0.66 ng/mL (1.7 nM) | 0.19 ng/mL |

Ocular Tissue Distribution in Group 1 (1 Implant, 109 µg Axitinib)

Ocular tissue concentrations for indicated time points are presented in Table 13.

TABLE 13

Ocular tissue distribution of axitinib released from 1 implant with an axitinib dose of 109 µg axitinib. Axitinib concentrations in AH, VH (soluble part), retina, and choroid/RPE are presented in dependence of the analysis time-points as average (mean) including standard deviation, coefficient of variation (CV) as well as the confidence interval (CI) of the mean. In addition, minimum, median, and maximum values for each data point are presented.

| Tissue | Time Months | N Eyes | Average | Min | Median | Max | Std Dev | CV | 95% CI |
|---|---|---|---|---|---|---|---|---|---|
| AH (ng/mL) | 1 day | 4 | 0.5 | 0.0 | 0.5 | 0.9 | 0.4 | 75% | 0.4 |
| | 1.5 | 3 | 2.7 | 0.8 | 1.5 | 5.9 | 2.8 | 102% | 3.1 |
| | 3 | 3 | 1.0 | 0.4 | 0.5 | 2.0 | 0.9 | 89% | 1.0 |
| | 4.5 | 4 | 0.7 | 0.6 | 0.7 | 1.0 | 0.2 | 23% | 0.2 |
| | 6 | 4 | 0.2 | 0.0 | 0.2 | 0.6 | 0.3 | 112% | 0.2 |
| | 7.5 | 3 | 0.0 | 0.0 | 0.0 | 0.0 | 0.0 | n.a. | n.a. |
| | 9 | 3 | 0.0 | 0.0 | 0.0 | 0.1 | 0.1 | 173% | 0.1 |
| VH (ng/mL) | 1 day | 4 | 93.2 | 25.6 | 32.6 | 282.0 | 125.9 | 135% | 123.4 |
| | 1.5 | 3 | 23.1 | 12.9 | 15.1 | 41.3 | 15.8 | 68% | 17.9 |
| | 3 | 3 | 52.1 | 20.3 | 26.0 | 110.0 | 50.2 | 96% | 56.8 |
| | 4.5 | 4 | 115.8 | 58.4 | 89.8 | 225.0 | 77.6 | 67% | 76.0 |
| | 6 | 4 | 296.0 | 85.0 | 264.0 | 571.0 | 209.8 | 71% | 205.6 |
| | 7.5 | 3 | 184.9 | 2.9 | 21.7 | 530.0 | 299.0 | 162% | 338.4 |
| | 9 | 3 | 30.0 | 2.9 | 30.8 | 56.2 | 26.7 | 89% | 30.2 |
| Retina (ng/g) | 1 day | 4 | 184.7 | 116.0 | 147.4 | 328.1 | 97.7 | 53% | 95.7 |
| | 1.5 | 3 | 165.5 | 69.0 | 169.9 | 257.6 | 94.4 | 57% | 106.8 |
| | 3 | 3 | 176.8 | 120.2 | 203.3 | 207.0 | 49.1 | 28% | 55.5 |
| | 4.5 | 4 | 271.8 | 153.0 | 206.0 | 522.1 | 170.3 | 63% | 166.9 |
| | 6 | 4 | 150.0 | 18.8 | 147.1 | 287.0 | 120.7 | 80% | 118.2 |
| | 7.5 | 3 | 15.3 | 13.6 | 14.6 | 17.7 | 2.1 | 14% | 2.4 |
| | 9 | 3 | 13.6 | 9.6 | 10.3 | 20.8 | 6.3 | 46% | 7.1 |
| Choroid/RPE (ng/g) | 1 day | 4 | 124.3 | 78.5 | 119.6 | 179.6 | 48.4 | 39% | 47.5 |
| | 1.5 | 3 | 256.6 | 128.1 | 278.7 | 363.0 | 119.0 | 46% | 134.7 |
| | 3 | 3 | 328.2 | 96.6 | 306.5 | 581.6 | 243.2 | 74% | 275.2 |
| | 4.5 | 4 | 283.3 | 188.8 | 232.4 | 479.5 | 133.1 | 47% | 130.5 |
| | 6 | 4 | 95.0 | 52.0 | 98.4 | 131.0 | 32.6 | 34% | 31.9 |
| | 7.5 | 3 | 35.0 | 18.7 | 33.3 | 52.9 | 17.2 | 49% | 19.4 |
| | 9 | 3 | 34.8 | 15.2 | 22.8 | 66.3 | 27.6 | 79% | 31.2 |

Concentrations of axitinib in AH samples over the study duration were considered low relative to the concentrations observed in the VH, retina and choroid indicating a low level of axitinib migration towards the anterior chamber from the posterior chamber.

Median axitinib concentrations of soluble axitinib in VH samples over the study duration were maximal (264.0 ng/mL) at 6 months. Individual samples ranged from a minimum of 2.9 ng/mL (7.5 and 9 months) to a maximum of 571.0 ng/mL (6 months). Maximum values were similar to the solubility limit of axitinib in biorelevant media, verifying that no undissolved axitinib disturbed the measurements.

Median axitinib concentrations in the retina were similar from day 1 (147.4 ng/g) through 6 months (147.1 ng/g) prior to a noted decrease down to 14.6 ng/g at 7.5 months. This indicates rapid and sustained transport of axitinib to the targeted retina tissues from the implant within 1 day of administration through approximately 6 months. Axitinib concentrations decreased approximately 10-fold from 6 to 7.5 months in the retinal tissue samples (147.1 to 14.6 ng/g). The average median axitinib concentration through 6 months was 175 ng/g in the retina which was well above the IC50 values for VEGFR2, PDGFR-β and c-Kit (2184, 282 and 265-fold, respectively) and therefore at concentrations expected to inhibit neovascularization.

Median axitinib concentrations in the choroid/RPE were similar from day 1 (119.6 ng/g) through 6 months (98.4 ng/g). This indicates rapid and sustained transport of axitinib to the tissues in the back of the eye by the implant within 1 day of administration through approximately 6 months. Axitinib concentrations decreased approximately 3-fold from 6 to 7.5 months in the choroid/RPE tissue samples (98.4 to 33.3 ng/g). The average median axitinib concentration through 6 months was 207 ng/g in the choroid/RPE which was well above the IC50 values for VEGFR2, PDGFR-β and c-Kit (2589, 334 and 314-fold, respectively) and therefore at concentrations expected to inhibit neovascularization.

Ocular Tissue Distribution in Group 2 (1 Implant, 227 µg Axitinib)

Ocular tissue concentrations for indicated time points are presented in Table 14.

TABLE 14

Ocular tissue distribution of axitinib released from 1 implant with an axitinib dose of 227 µg axitinib. Axitinib concentrations in AH, VH (soluble part), retina, and choroid/RPE are presented in dependence of the analysis time-points as average (mean) including standard deviation, coefficient of variation (CV) as well as the confidence interval (CI) of the mean. In addition, minimum, median, and maximum values for each data point are presented.

| Tissue | Months | N Eyes | Average | Min | Median | Max | Std Dev | CV % | 95% CI |
|---|---|---|---|---|---|---|---|---|---|
| AH | 1 | 12 | 8.2 | 0.0 | 0.0 | 69.9 | 20.4 | 247 | 11.5 |
| (ng/mL) | 3 | 18 | 0.0 | 0.0 | 0.0 | 0.4 | 0.1 | 424 | 0.0 |
|  | 6 | 12 | 0.0 | 0.0 | 0.0 | 0.1 | 0.0 | 123 | 0.0 |
|  | 7 | 6 | 0.0 | 0.0 | 0.0 | 0.1 | 0.0 | 93 | 0.0 |
| VH | 1 | 12 | 4829 | 33 | 327 | 36400 | 11113 | 230 | 6288 |
| (ng/mL) | 3 | 18 | 36430 | 48 | 614 | 610984 | 143547 | 394 | 66314 |
|  | 6 | 12 | 9765 | 55 | 5255 | 34355 | 10256 | 105 | 5803 |
|  | 7 | 6 | 8667 | 61 | 2105 | 41000 | 15971 | 184 | 12779 |
| Retina | 1 | 12 | 852 | 124 | 315 | 5080 | 1415 | 166 | 801 |
| (ng/g) | 3 | 18 | 1466 | 124 | 378 | 13990 | 3259 | 222 | 1505 |
|  | 6 | 12 | 21152 | 228 | 4957 | 154000 | 43428 | 205 | 24571 |
|  | 7 | 6 | 54121 | 131 | 13520 | 264000 | 103849 | 192 | 83095 |
| Choroid/RPE | 1 | 12 | 753 | 131 | 332 | 4920 | 1352 | 179 | 765 |
| (ng/g) | 3 | 16 | 7214 | 0 | 240 | 60800 | 17708 | 245 | 8677 |
|  | 6 | 12 | 1918 | 23 | 232 | 10100 | 3201 | 167 | 1811 |
|  | 7 | 6 | 3497 | 0 | 1772 | 10400 | 4265 | 122 | 3413 |

Axitinib concentrations were low in the AH with median values of 0.0 ng/mL through study completion (7 months) indicating little migration of axitinib from the posterior chamber to the anterior chamber.

The axitinib concentration in the VH represents the soluble axitinib that was dissolved in the VH. The median values at 1 and 3 months, prior to hydrogel degradation, were similar to the determined solubility limit of axitinib in in PBS, pH 7.2 at 37° C. (0.4 to 0.5 µg/mL). The high median values at 6 and 7 months likely reflected contamination of VH samples with undissolved axitinib particles that were solubilized during extraction.

The median axitinib concentrations at 1 and 3 months in the retina were similar to the solubility limit of axitinib. The average median axitinib concentration over the first three months was 341 ng/g in the retina which was well above the IC50 values for VEGFR2, PDGFR-β and c-Kit (4264, 569 and 487-fold, respectively) and therefore at concentrations expected to inhibit neovascularization. Similarly to the VH values, the median values at 6 and 7 months likely reflected contamination of retina samples with undissolved axitinib particles that were solubilized during extraction.

The median axitinib concentrations at 1, 3 and 6 months in the choroid/RPE tissue were similar to the solubility of axitinib. The average median axitinib concentration over the first six months was 274 ng/g in the choroid/RPE which was well above the IC50 values for VEGFR2, PDGFR-β and c-Kit (3426, 457 and 391-fold, respectively) and therefore at concentrations expected to inhibit neovascularization. Similarly to VH and retina values, the median values at 7 months likely reflected contamination of choroid samples with undissolved axitinib particles that were solubilized during extraction.

Although the axitinib concentrations at 6 and/or 7 months likely reflected contamination with undissolved axitinib, it was clearly demonstrated that the implant site provided a sustained release of axitinib over the duration of the study.

Ocular Tissue Distribution in Groups 3 and 4 (2 Implants, Total Dose of 290 µg Axitinib with or without Avastin®)

Ocular tissue concentrations for indicated time points are presented in Table 15.

earliest time-point of 0.5 months demonstrated no obvious difference in ocular tissue concentrations between groups 3 and 4 indicating similar drug release when Avastin® concentration would be expected to be highest in the VH in the rabbit model.

Axitinib concentrations in both groups were low in the AH with median values of 0.2 ng/mL or less through study completion indicating little migration of axitinib from the posterior chamber to the anterior chamber. With the exception of one value at 38 months, the others were <1 ng/mL for the study duration.

TABLE 15

Ocular tissue distribution of axitinib released from 2 implants with a total axitinib dose of 290 µg axitinib either without (group 3) or with (group 4) Avastin ®. Axitinib concentrations in AH, VH (soluble part), retina, and choroid/RPE are presented in dependence of the analysis time-points as average (mean) including standard deviation, coefficient of variation (CV) as well as the confidence interval (CI) of the mean. In addition, minimum, median, and maximum values for each data point are presented.
(G = group; Av. = Average)

| Tissue | G | Time Months | N Eyes | Av. | Min | Median | Max | SD | CV % | 95% CI |
|---|---|---|---|---|---|---|---|---|---|---|
| AH (ng/mL) | 3 | 0.5 | 6 | 0.2 | 0.0 | 0.1 | 0.6 | 0.2 | 96 | 0.2 |
| | | 1 | 6 | 0.1 | 0.0 | 0.0 | 0.1 | 0.1 | 110 | 0.0 |
| | | 3 | 6 | 0.1 | 0.0 | 0.0 | 0.2 | 0.1 | 118 | 0.1 |
| | | 6 | 6 | 0.0 | 0.0 | 0.0 | 0.2 | 0.1 | 150 | 0.1 |
| | | 9 | 2 | 0.1 | 0.1 | 0.1 | 0.2 | 0.1 | 40 | 0.1 |
| | | 38 | 2 | 2.4 | 0.0 | 2.4 | 4.8 | 3.4 | 141 | 4.7 |
| | 4 | 0.5 | 6 | 0.8 | 0.3 | 0.6 | 2.1 | 0.7 | 88 | 0.5 |
| | | 1 | 6 | 0.1 | 0.0 | 0.1 | 0.4 | 0.2 | 110 | 0.1 |
| | | 3 | 6 | 0.1 | 0.0 | 0.0 | 0.2 | 0.1 | 127 | 0.1 |
| | | 6 | 6 | 0.2 | 0.0 | 0.2 | 0.3 | 0.1 | 86 | 0.1 |
| | | 9 | 2 | 0.2 | 0.2 | 0.2 | 0.2 | 0.0 | 2 | 0.0 |
| | | 38 | 2 | 0.2 | 0.0 | 0.2 | 0.4 | 0.3 | 141 | 0.4 |
| VH (ng/mL) | 3 | 0.5 | 6 | 642 | 149 | 553 | 1390 | 412 | 64 | 330 |
| | | 1 | 6 | 95 | 22 | 71 | 242 | 86 | 90 | 68 |
| | | 3 | 6 | 1869 | 50 | 277 | 6310 | 2720 | 146 | 2176 |
| | | 6 | 6 | 41 | 26 | 40 | 56 | 13 | 32 | 10 |
| | | 9 | 2 | 76 | 125 | 198 | 271 | 103 | 136 | 143 |
| | | 38 | 2 | 2 | 0 | 2 | 3 | 2 | 141 | 3 |
| | 4 | 0.5 | 6 | 361 | 51 | 328 | 710 | 287 | 80 | 230 |
| | | 1 | 6 | 232 | 61 | 170 | 705 | 240 | 103 | 192 |
| | | 3 | 6 | 1959 | 33 | 672 | 5370 | 2517 | 128 | 2014 |
| | | 6 | 6 | 79 | 32 | 48 | 173 | 62 | 79 | 50 |
| | | 9 | 2 | 53 | 20 | 78 | 135 | 81 | 152 | 112 |
| | | 38 | 2 | 29 | 4 | 29 | 54 | 35 | 124 | 49 |
| Retina (ng/g) | 3 | 0.5 | 6 | 185 | 5 | 94 | 688 | 257 | 139 | 205 |
| | | 1 | 6 | 240 | 40 | 99 | 622 | 261 | 109 | 209 |
| | | 3 | 6 | 9288 | 175 | 369 | 51000 | 20479 | 220 | 16386 |
| | | 6 | 6 | 1126 | 73 | 623 | 4190 | 1567 | 139 | 1254 |
| | | 9 | 2 | 80 | 52 | 183 | 313 | 184 | 232 | 256 |
| | | 38 | 2 | 28 | 0 | 28 | 55 | 39 | 141 | 54 |
| | 4 | 0.5 | 5 | 118 | 39 | 91 | 302 | 106 | 90 | 93 |
| | | 1 | 6 | 205 | 70 | 144 | 448 | 153 | 75 | 123 |
| | | 3 | 6 | 6186 | 189 | 688 | 33700 | 13492 | 218 | 10796 |
| | | 6 | 6 | 4762 | 954 | 4255 | 10500 | 3299 | 69 | 2639 |
| | | 9 | 2 | 2068 | 136 | 4108 | 8080 | 5617 | 272 | 7785 |
| | | 38 | 2 | 28 | 21 | 28 | 36 | 11 | 38 | 15 |
| Choroid/RPE (ng/g) | 3 | 0.5 | 6 | 237 | 90 | 192 | 434 | 153 | 65 | 122 |
| | | 1 | 6 | 1103 | 48 | 114 | 5700 | 2260 | 205 | 1808 |
| | | 3 | 6 | 4631 | 76 | 656 | 16600 | 6926 | 150 | 5542 |
| | | 6 | 6 | 17582 | 139 | 5940 | 81500 | 31603 | 180 | 25287 |
| | | 9 | 2 | 27748 | 335 | 83168 | 166000 | 117143 | 422 | 162349 |
| | | 38 | 2 | 19 | 0 | 19 | 39 | 27 | 141 | 38 |
| | 4 | 0.5 | 6 | 1004 | 37 | 210 | 4940 | 1937 | 193 | 1550 |
| | | 1 | 6 | 2081 | 87 | 1608 | 5360 | 2112 | 101 | 1690 |
| | | 3 | 6 | 8399 | 363 | 6010 | 20300 | 8523 | 101 | 6820 |
| | | 6 | 6 | 17673 | 6740 | 11800 | 49000 | 15651 | 89 | 12523 |
| | | 9 | 2 | 7224 | 5080 | 14390 | 23700 | 13166 | 182 | 18247 |
| | | 38 | 2 | 57 | 17 | 57 | 98 | 58 | 100 | 80 |

An Avastin® dose of 1.25 mg has a half-life of 6.6 days in rabbits (Sinapis et al., 2011; Pharmacokinetics of intravitreal bevacizumab (Avastin®) in rabbits. Clinical ophthalmology (Auckland, NZ), 5, p. 697) and by 1 month the mass remaining approximates 0.05 mg. In line with that, the The axitinib concentration in the VH is the soluble axitinib that is dissolved in the VH. Median maximal concentrations in the VH were 553 ng/mL in group 3 and 672 ng/mL in group 4. These values were similar to the determined solubility limit of axitinib in biorelevant media.

Median concentrations through 9 months demonstrated sustained release of axitinib from the implants in both groups. Axitinib was detected in the VH even at 38 months.

In group 3, the axitinib median concentrations in the retina tissue were maximal at 6 months (623 ng/g) and ranged from 94 to 623 ng/g between 0.5 to 9 months. Concentrations were less (28 ng/g) at 38 months, but still at a biologically effective concentration. The average median axitinib concentration over the first three months was 184 ng/g in the retina which was well above the IC50 values for VEGFR2, PDGFR-β and c-Kit (2300, 307 and 263-fold, respectively) and therefore at concentrations expected to inhibit neovascularization. In group 4, the values were comparable to group 3 through 3 months, but levels were higher at 6 and 9 months and likely reflected contamination with undissolved axitinib particles that were solubilized during extraction. The retina tissue axitinib concentrations at 38 months were comparable between groups 2 and 3.

In group 3, the average median axitinib concentration over the first three months was 231 ng/g in the choroid/RPE tissue which was well above the IC50 values for VEGFR2, PDGFR-β and c-Kit (2888, 386 and 330-fold, respectively) and therefore at concentrations expected to inhibit neovascularization. The median values at 6 and 9 months likely reflected contamination with undissolved axitinib particles that were solubilized during extraction. Concentrations of axitinib in the choroid/RPE were less (19 ng/g) at 38 months, but still at biologically effective concentration. In group 4, axitinib concentrations in the choroid/RPE were similar compared to group 3 at 0.5 months but were much higher at the later time-points. Considering the broad range seen between the minimum and maximum sample concentrations within each time-point, the higher values likely reflected contamination with undissolved axitinib particles that were solubilized during extraction.

Summary of the Ocular Distribution Data

Table 16 gives an overview of median axitinib concentrations observed in the different tissues in all four groups in Dutch Belted rabbits.

TABLE 16

Axitinib concentration measured in samples from aqueous humor (AH), vitreous humor (VH), retina, and choroid/RPE dependent on the axitinib dose (median value). Axitinib concentration (ng/mL or ng/g, respectively) was measured at indicated time points for the different groups using LC-MS/MS.

| Tissue | Group 1<br>1 Implant<br>(109 μg axitinib) | | Group 2<br>1 Implant<br>(227 μg axitinib) | | Group 3<br>2 Implants<br>(290 μg axitinib) | | Group 4<br>2 Implants + Avastin<br>(290 μg axitinib) | |
|---|---|---|---|---|---|---|---|---|
| | Time (months) | Median | Time (months) | Median | Time (months) | Median | Time (months) | Median |
| AH (ng/mL) | 1 day | 0.5 | 1 | 0.0 | 0.5 | 0.1 | 0.5 | 0.6 |
| | 1.5 | 1.5 | 3 | 0.0 | 1 | 0.0 | 1 | 0.1 |
| | 3 | 0.5 | 6 | 0.0 | 3 | 0.0 | 3 | 0.0 |
| | 4.5 | 0.7 | 7 | 0.0 | 6 | 0.0 | 6 | 0.2 |
| | 6 | 0.2 | — | — | 9 | 0.1 | 9 | 0.2 |
| | 7.5 | 0.0 | — | — | 38 | 2.4 | 38 | 0.2 |
| | 9 | 0.0 | — | — | — | — | — | — |
| VH (ng/mL) | 1 day | 33 | 1 | 327 | 0.5 | 553 | 0.5 | 328 |
| | 1.5 | 15 | 3 | 614 | 1 | 71 | 1 | 170 |
| | 3 | 26 | 6 | 5255 | 3 | 277 | 3 | 672 |
| | 4.5 | 90 | 7 | 2105 | 6 | 40 | 6 | 48 |
| | 6 | 264 | — | — | 9 | 198 | 9 | 78 |
| | 7.5 | 22 | — | — | 38 | 2 | 38 | 29 |
| | 9 | 31 | — | — | — | — | — | — |
| Retina (ng/g) | 1 day | 147 | 1 | 315 | 0.5 | 94 | 0.5 | 91 |
| | 1.5 | 170 | 3 | 378 | 1 | 99 | 1 | 144 |
| | 3 | 203 | 6 | 4957 | 3 | 369 | 3 | 688 |
| | 4.5 | 206 | 7 | 13520 | 6 | 623 | 6 | 4255 |
| | 6 | 147 | — | — | 9 | 183 | 9 | 4108 |
| | 7.5 | 15 | — | — | 38 | 28 | 38 | 28 |
| | 9 | 10 | — | — | — | — | — | — |
| Choroid/RPE (ng/g) | 1 day | 120 | 1 | 332 | 0.5 | 192 | 0.5 | 210 |
| | 1.5 | 279 | 3 | 240 | 1 | 114 | 1 | 1608 |
| | 3 | 307 | 6 | 232 | 3 | 656 | 3 | 6010 |
| | 4.5 | 232 | 7 | 1772 | 6 | 5940 | 6 | 11800 |
| | 6 | 98 | — | — | 9 | 83168 | 9 | 14390 |
| | 7.5 | 33 | — | — | 38 | 19 | 38 | 57 |
| | 9 | 23 | — | — | — | — | — | — |

There was a dose-related increase in axitinib concentrations in the vitreous humor tissues for the mid (227 μg) and high dose (290 μg) compared to the low dose (109 μg). There was no dose-related difference in the targeted tissues of the retina and choroid prior to hydrogel degradation. In addition, co-administration of Avastin® in group 4 did not change drug release when compared to group 3. Even after 38 months, axitinib was present at doses above the IC50 and EC50 in the VH, retina, and choroid/RPE demonstrating sustained persistence. Axitinib was either not detected in the aqueous humor or was present only at low concentrations for all dose strengths through the duration of the studies indicating a low level of axitinib migration towards the anterior chamber from the posterior chamber were the implants are localized.

Results: Axitinib Release Rate

In addition, also non-soluble axitinib in VH containing the implant was assessed by LC-MS/MS analysis to determine the remaining amount of axitinib at sacrifice time points. The axitinib dose at the time of administration was determined by averaging values from ten implants spiked into ten bovine VH samples.

In the low dose group (group 1, 109 µg axitinib) and intermediate dose group (group 2, 227 µg axitinib), non-soluble axitinib in VH containing the implant was assessed by LC-MS/MS analysis to determine the remaining amount of axitinib at sacrifice time points. The remaining amount was then compared to the initial dose and the in vivo release rate over time was calculated. The mean amount of axitinib released from the implant over 6 months in rabbits was estimated to be 0.52 µg/day. Following hydrogel degradation, the rate of release appears to slow down as the axitinib forms a localized structure. However, released axitinib levels were still sufficient to inhibit vascular leakage (cf. Example 3.4).

Example 3.6: Acute Exposure to Axitinib Bolus Dose

In order to test acute exposure to axitinib particles, an intravitreal, bilateral bolus dose of a 600 µg (1.2%) suspension of axitinib in ProVisc® (Alcon; 1% 2000 kDa sodium hyaluronate) was administered via a 50 µL injection using a 27G thin wall needle syringe to Dutch belt rabbits (n=3 animals, 6 eyes).

At 1 month, rabbits were sacrificed and whole eyes were prepared for histopathological analysis. The eyes were fixed, sectioned vertically in 12 equal parts, stained with hematoxylin and eosin (H&E) and examined by a board certified veterinary pathologist. Histopathology assessments at each time point included vitreous, retinal, scleral, or episcleral inflammation, retinal disruption and fibrosis around the injected area. Tissues were scored on a semi-quantitative scale from 0-5 for any abnormalities, where 0 denotes no change (normal), 1 denotes rare foci of change (minimal), 2 denotes mild diffuse change or more pronounced focal change, 3 denotes moderate diffuse change, 4 denotes marked diffuse change and 5 denotes severe diffuse change.

IOPs determined weekly remained within the normal range. Intravitreal bolus dosing of 600 µg of axitinib was generally tolerable (Table 17). No gross lesions were noted in any eyes. Minimal histiocytic and multinucleated giant cell inflammation was observed around the axitinib injection site. Mild focal retinal disruptions were observed in two eyes in proximity to the puncture location and considered procedure related. Minimal retinal disruption with a few macrophages in the photoreceptor layer was observed in 1 of 6 eyes. Minimal retinal vacuolization was observed in numerous sections from 4 of 6 eyes. Minimal to mild chronic subcorneal inflammation was observed in 4 of 6 eyes.

In summary, the bolus injection was well-tolerated and safe. The injected dose led to a higher acute localized axitinib dose per compartmental volume in rabbit eyes (1.3 mL/eye) as it would have led to in a human eye (4.5 mL/eye).

Example 4: Evaluation of Axitinib Implants in Beagle Dogs

In order to study the axitinib release from the implants in beagle dogs, 12 dogs received each one implant per eye (bilaterally) with 109 µg axitinib via intravitreal injection using a 27G ultra-thin wall needle to administer the implant. Formulation and dimensions of the implants injected are presented in Table 6 (implant type #5).

Prior to implant administration, animals were anesthetized with an intramuscular injection of ketamine hydrochloride (20 mg/kg) and xylazine (5 mg/kg). Eyes and the surrounding area were cleaned with a 5% Betadine solution and rinsed with balanced salt solution (BSS). One to two drops of topical proparacaine hydrochloride anesthetic (0.5%) was applied. The eye was draped, and a sterile wire speculum was placed to retract the eyelids. The injection needle was placed approximately 3 to 5 mm away from the limbus and deployed in a single stroke.

At predetermined sacrifice time points (3 animals each at 1.5, 3, 4.5, and 6 months post implant administration, respectively) the eyes were collected, flash frozen, and then dissected and weighed for the target tissues of the choroid, retina, vitreous humor and aqueous humor. Plasma was additionally collected at the selected time points. Axitinib concentrations were assessed in AH, VH (soluble axitinib), choroid/RPE, and retina, as well as in plasma. In addition, also non-soluble axitinib in VH containing the implant was assessed by LC-MS/MS analysis to determine the remaining amount of axitinib at sacrifice time points (methods described under Example 3.5).

All values in plasma were reported as below the LLOQ (0.05 ng/mL for both isomers) indicating near absent systemic exposure to axitinib in beagle dogs following implant administration (total administered dose of 218 µg).

Pharmacokinetic data of axitinib concentrations in the target tissues over the study duration are presented in Table 18. Concentrations of axitinib in beagle AH samples over 4.5 months were considered low relative to the concentrations observed in the VH, retina and choroid indicating a low level of axitinib migration towards the anterior chamber from the posterior chamber prior to hydrogel degradation. Axitinib was present at higher concentrations in the AH at 6 months (after hydrogel degradation). This may have been due to migration of undissolved axitinib particles released from the degraded hydrogel towards the anterior chamber from the posterior chamber or due to sample contamination

TABLE 17

Axitinib bolus histopathological study results. Results were scored on a scale of 0-5, where 0 denotes no change (normal), 1 denotes rare foci of change (minimal), 2 denotes mild diffuse change or more pronounced focal change, 3 denotes moderate diffuse change, 4 denotes marked diffuse change and 5 denotes severe diffuse change. Results are presented as mean and standard deviation (SD).

| Result | Retinal Disruption | Retinal Vacuolization | Vitreous Chamber Inflammation | Retinal, Scleral, or Episcleral Inflammation | Fibrosis Around the Article | Chronic Subcorneal Inflammation |
|---|---|---|---|---|---|---|
| Mean (SD) | 0.10 (0.11) | 0.50 (0.46) | 0.23 (0.21) | 0.03 (0.05) | 0.00 (0.00) | 0.28 (0.38) | of the AH by VH during tissue dissection. High axitinib concentrations in the AH were never observed in any of the rabbit studies.

Median axitinib concentrations in the VH were similar over the study duration (range from 11.9 to 27.1 ng/mL). These values were similar to that observed in the monkey study at a similar dose (138 µg; cf. Example 5).

Median axitinib concentrations in the retina were similar over the study duration (range from 15.4 to 31.0 ng/mL) indicating continuous sustained delivery of axitinib from the implant to retina tissues. The average median axitinib concentration over six months was 23 ng/g in the retina which was well above the IC50 values for VEGFR2, PDGFR-β and c-Kit (288, 37 and 35-fold, respectively) and therefore at concentrations expected to inhibit neovascularization. In addition, this concentration was 121-fold higher than the EC50 determined for free axitinib in the ocular angiogenesis neonatal rat model.

Median axitinib concentrations in the choroid/RPE were similar over the study duration (range from 16.2 to 39.8 ng/g) indicating sustained delivery of axitinib from the implant to the choroid tissues through study completion. The average median axitinib concentration over six months was 31 ng/g in the choroid/RPE which was well above the IC50 values for VEGFR2, PDGFR-β and c-Kit (388, 50 and 47-fold, respectively) and therefore at concentrations expected to inhibit neovascularization. In addition, this concentration was 163-fold higher than the EC50 determined for free axitinib in the ocular angiogenesis neonatal rat model.

TABLE 18

Pharmacokinetic study results in beagle dogs. Axitinib concentrations in AH, VH (soluble part), retina, and choroid/RPE are presented in dependence of the analysis time-points as average (mean) including standard deviation, coefficient of variation (CV) as well as the confidence interval (CI) of the mean. In addition, minimum, median, and maximum values for each data point are presented.

| Tissue | Time Months | N Eyes | Average | Min | Median | Max | Std Dev | CV | 95% CI |
|---|---|---|---|---|---|---|---|---|---|
| AH (ng/mL) | 1.5 | 4 | 2.8 | 0.4 | 3.1 | 4.6 | 2.1 | 76 | 2.0 |
|  | 3 | 6 | 1.2 | 0.1 | 0.9 | 3.2 | 1.1 | 87 | 0.8 |
|  | 4.5 | 5 | 0.6 | 0.5 | 0.6 | 0.9 | 0.1 | 22 | 0.1 |
|  | 6 | 6 | 66.4 | 0.5 | 14.5 | 228.0 | 94.9 | 143 | 76.0 |
| VH (ng/mL) | 1.5 | 4 | 26.8 | 20.7 | 27.1 | 32.5 | 5.5 | 20 | 5.4 |
|  | 3 | 6 | 19.4 | 16.5 | 18.4 | 23.3 | 2.5 | 13 | 2.0 |
|  | 4.5 | 5 | 10.1 | 1.8 | 11.9 | 18.1 | 6.5 | 64 | 5.7 |
|  | 6 | 6 | 33.6 | 0.9 | 17.2 | 84.3 | 36.3 | 108 | 29.1 |
| Retina (ng/g) | 1.5 | 4 | 27.6 | 22.2 | 23.9 | 40.6 | 8.7 | 32% | 8.5 |
|  | 3 | 6 | 30.8 | 18.7 | 31.0 | 39.2 | 7.8 | 25% | 6.2 |
|  | 4.5 | 5 | 52.3 | 8.6 | 20.4 | 134.0 | 56.5 | 108% | 49.5 |
|  | 6 | 6 | 16.2 | 1.9 | 15.4 | 35.2 | 11.4 | 70% | 9.1 |
| Choroid/RPE (ng/g) | 1.5 | 4 | 35.7 | 13.5 | 29.3 | 70.8 | 24.6 | 69% | 24.1 |
|  | 3 | 6 | 29.5 | 8.3 | 16.2 | 87.8 | 29.9 | 101% | 24.0 |
|  | 4.5 | 5 | 62.1 | 9.5 | 39.8 | 126.0 | 48.0 | 77% | 42.1 |
|  | 6 | 6 | 72.9 | 5.9 | 38.2 | 250.0 | 90.6 | 124% | 72.5 |

The mean amount of axitinib released from the implant over 6 months in beagle dogs was estimated to be approximately 0.52 µg/day (Table 19), similar to the release rates seen in rabbits with the same dose (cf. Example 3.5). The axitinib dose at the time of administration was determined by averaging values from ten implants spiked into ten bovine VH samples.

TABLE 19

Non-soluble axitinib in VH containing the implant. Baseline values refer to the axitinib amount in the implants prior to administration.

| Time Months | N | Average (ng) | Min (ng) | Median (ng) | Max. (ng) | Std Dev (ng) | CV | 95% CI |
|---|---|---|---|---|---|---|---|---|
| Baseline | 10 | 109 | 95 | 110 | 119 | 7 | 6% | 4 |
| 1.5 | 4 | 75 | 72 | 76 | 77 | 2 | 3% | 2 |
| 3 | 6 | 50 | 28 | 54 | 59 | 11 | 23% | 9 |
| 4.5 | 5 | 42 | 0 | 49 | 67 | 26 | 62% | 23 |
| 6 | 6 | 15 | 0 | 13 | 39 | 16 | 104% | 13 |

Example 5: Evaluation of Axitinib Implants in Non-Human Primates

In order to study safety and drug release in African green monkeys, animals received one implant in either the right or left eye (for drug release studies) or bilaterally (for safety and tolerability studies) via intravitreal injection using a 27G ultra-thin wall needle, the implant comprising an axitinib dose of 138 µg. Formulation and dimensions of the implants injected are presented in Table 6 (implant type #4).

Prior to implant administration, animals were anesthetized with an intramuscular injection of ketamine hydrochloride (20 mg/kg) and xylazine (5 mg/kg). Eyes and the surrounding area were cleaned with a 5% Betadine solution and rinsed with balanced salt solution (BSS). One to two drops of topical proparacaine hydrochloride anesthetic (0.5%) was applied. The eye was draped, and a sterile wire speculum was placed to retract the eyelids. The injection needle was placed approximately 3 to 5 mm away from the limbus and deployed in a single stroke.

Drug Release

To evaluate drug release, 6 monkeys were sacrificed 3 months after implant administration and the eyes were collected, flash frozen, and then dissected and weighed for target tissues of the choroid, retina, vitreous humor and aqueous humor. Serum was additionally collected at the selected time point. Subsequent analysis following axitinib extraction from tissues (where necessary) and dilution was performed, followed by LC-MS/MS for the determination of axitinib concentrations in the samples (methods described under Example 3.5).

Pharmacokinetic data of median axitinib concentrations in the target tissues is presented in Table 20. As observed for rabbits and beagle dogs, axitinib concentrations in the AH were low indicating little movement of axitinib from the posterior to the anterior chamber in the monkey eye. Soluble axitinib concentrations in the VH were low (12 ng/mL) compared to those observed in rabbits, but they were similar to concentrations observed in beagle dogs.

The average median axitinib concentration over the three months was 39 ng/g in the retina which was well above the IC50 values for VEGFR2, PDGFR-β and c-Kit (488, 63 and 59-fold, respectively) and therefore at concentrations expected to inhibit neovascularization. In addition, this concentration was 205-fold higher than the half-maximal effective concentration (EC50=0.19 ng/mL) determined for free axitinib in the ocular angiogenesis neonatal rat model.

The average median axitinib concentration over the three months was 940 ng/g in the choroid/RPE tissue which was well above the IC50 values for VEGFR2, PDGFR-β and c-Kit (11750, 1516 and 1424-fold, respectively) and therefore at concentrations expected to inhibit neovascularization. In addition, this concentration was 4947-fold higher than the EC50 determined for free axitinib in the ocular angiogenesis neonatal rat model.

The choroid/RPE axitinib concentration at 3 months was significantly higher in monkeys (940 ng/g) compared to rabbits (240, 656, and 307 ng/g, respectively) and beagle dogs (16 ng/g). As axitinib was found to bind to melanin in the uveal tract of the eye in mice (INLYTA® support, NDA202324), this might be due to an increased ocular melanin content in the central and peripheral choroid/RPE compared to rabbits and beagles (Durairaj et al., 2012, Intraocular distribution of melanin in human, monkey, rabbit, minipig, and dog eyes. Experimental eye research, 98, pp. 23-27). In addition, also varying vitreous volumes may have contributed to differences observed in tissue concentrations (Dutch belted rabbit=1.3 mL, beagle dog=2.2 mL, and African green monkey=2.4 mL; Glogowski et al., 2012, Journal of ocular pharmacology and therapeutics, 28 (3), pp. 290-298; Struble et al., 2014, Acta Ophthalmologica, 92).

Moreover, the systemic exposure to axitinib in serum from the implant was below the LLOQ (0.088 ng/mL for trans-axitinib and 0.012 ng/mL for cis-axitinib).

Safety and Tolerability

To evaluate safety and tolerability, the 6 monkeys were monitored for 3 months post implant administration. Ocular examination was performed via ophthalmic slit-lamp examination and graded according to the modified Hackett-McDonald scoring system. Ocular examination revealed no notable findings, including no intraocular inflammation or retinal changes over the study duration. No changes in IOP or pupil diameter occurred over the study duration.

Conclusions From Pre-Clinical Animal Studies

In summary, pharmacokinetic results demonstrate levels of axitinib in the relevant ocular tissues (VH, Retina, Choroid/RPE) delivered from the implants significantly above the IC50 for tyrosine kinases and the EC50 for inhibition of angiogenesis in a rat model (Table 12) in all animals examined (dog, beagle, monkey) over a duration of up to 38 months. In general, measured ocular tissue levels of axitinib correlated with the visual presence or absence of the implants and the drug in the posterior chamber based on IR imaging. In contrast, axitinib concentrations in the AH were either absent or very low compared to VH, retina, and choroid/RPE verifying that only a low level of axitinib migration towards the anterior chamber from the posterior chamber were the implants are localized occurred in all three animal species. However, the drug release in humans may differ from non-clinical studies due to comparative differences between animals and humans with respect to vitreous volumes, vitreous viscosities, and drug clearance rates that directly relate to the surface area of the retinal pigment epithelium (RPE) for small molecules.

All animal studies demonstrated that levels in plasma/serum were below the LLOQ indicating near absent systemic exposure to axitinib. Therefore, the plasma/serum levels resulting from implants of the present application were much lower than serum levels reported in the literature for INLYTA®. Because axitinib has no subsequent distribution outside of the intraocular compartment, any drug-drug interaction risk can be considered minimal.

Imaging analysis by IR demonstrated visual biodegradation of the hydrogel in the posterior chamber over time leading to complete degradation after approximately 6 months. Axitinib drug particles remaining at the former implant locations formed a monolithic structure continuing to release axitinib at levels sufficient for sustained inhibition of vascular leakage. Efficacy in suppression of vascular

TABLE 20

Pharmacokinetic study results in African green monkeys. Axitinib concentrations in AH, VH (soluble part), retina, and choroid/RPE are presented in dependence of the analysis time-points as average (mean) including standard deviation, coefficient of variation (CV) as well as the confidence interval (CI) of the mean. In addition, minimum, median, and maximum values for each data point are presented.

| Tissue | Time Months | N Eyes | Average | Min | Median | Max | Std Dev | CV | 95% CI |
|---|---|---|---|---|---|---|---|---|---|
| AH (ng/mL) | 3 | 6 | 0.47 | 0.00 | 0.48 | 0.76 | 0.28 | 59% | 0.22 |
| VH (ng/mL) | 3 | 6 | 16 | 4 | 12 | 37 | 12 | 73% | 9 |
| Retina (ng/g) | 3 | 6 | 52 | 28 | 39 | 89 | 28 | 54% | 22 |
| Choroid/RPE (ng/g) | 3 | 6 | 1107 | 568 | 940 | 1980 | 417 | 38% | 193 | leakage was demonstrated out to 6 and 21 months in rabbit VEGF challenge studies. Co-administration of bevacizumab resulted in an even more rapid inhibition of vascular leakage in the first 3 months when compared to administration of the axitinib implants alone.

Taken together, the data demonstrate that the axitinib implants of the present invention are safe and well-tolerated as well as show sufficient drug-release and good efficacy in rabbits, dogs, and African green monkeys.

Example 6: Human Clinical Trials with Axitinib Implants

The axitinib implants of the present application were examined in humans in a next step. The axitinib implants are applied in order to reduce choroidal/retinal neovascularization and exudation, decrease vascular permeability, decrease (or essentially maintain or prevent a clinically significant increase of) central subfield thickness, while in certain embodiments not impairing or even improving visual acuity. As the implants provide sustained release of axitinib and thus a prolonged provision of axitinib to the vitreous humor and the surrounding tissue, treatment with the implants of the present application reduces the burden on patients and caregivers, as well as the risk of adverse effects associated with frequent injections of anti-VEGF therapeutics.

Subjects with neovascular age-related macular degeneration (wet AMD) who had retinal fluid were enrolled in an open-label, dose-escalation study to evaluate safety, tolerability and efficacy of the axitinib implants of the present invention in human subjects. Patients were naïve or non-naïve to treat

Example 6.1: Formulations

Tables 21.1 and 21.2 give an overview of formulations and dimensions of implants containing about 200 µg and about 600 µg axitinib, some of which are applied in human clinical trials (or are planned or suitable to be applied in future human clinical trials). The dimension of the implants in the dry state were measured after the implants had been produced and had been dried and just before they were loaded into the needles. The implants remained in an inert glove box kept below 20 ppm of both oxygen and moisture for at least about 7 days prior to packaging. The dimensions of hydrated implants indicated in these tables were measured after 24 hours in biorelevant media (PBS, pH 7.2 at 37° C.).

Measurement of the implant dimensions (both in the dry and in the wet state) were performed by a custom 3-camera Keyence Inspection System. 2 Cameras were used to measure the diameter with a tolerance of ±0.002 mm (of all datapoints acquired, the average (=mean) value is recorded), and 1 camera was used to measure the length with a tolerance of ±0.04 mm (of several datapoints, the longest measured length is recorded).

TABLE 21.1

Formulation, configuration and dimensions of an implant with an axitinib dose of about 200 µg that was used in the clinical studies reported in Example 6.3 and 6.4..

| Implant type | | Implant #1 |
|---|---|---|
| Formulation (% dry basis w/w) | Axitinib | 49.4% |
| | Dose | (200 µg) |
| | PEG Hydrogel | 42.0% |
| | 4a20K PEG-SAZ | 28% |
| | 8a20K PEG-NH2 | 14% |
| | Sodium phosphate | 8.6% |
| Formulation (% wet basis w/w) | Axitinib | 7.5% |
| | PEG Hydrogel | 6.9% |
| | 4a20K PEG-SAZ | 4.6% |
| | 8a20K PEG-NH2 | 2.3% |
| | Sodium phosphate | 1.5% |
| | WFI | 84.1% |
| | Axitinib per final dry length | 12.1 µg/mm |
| | Approximate Implant Mass (dose µg/API %) | 423 |
| Configuration | Stretching Method (Stretch Factor) | Dry (4.5) |
| | Needle Size | 27G TW 1.25" (0.27 mm ID) |
| | Injector/Syringe | Implant Injector |
| | Packaging | Foil Pouches |
| | Sterilization Type | Gamma |
| | Site Storage | Refrigerated |
| Dimensions | Dried Diameter | 0.24 ± 0.013 mm |
| | Length | 16.5 ± 0.26 mm |
| | Volume | 0.75 ± 0.08 mm$^3$ |
| | Implant Mass | 0.45 mg |
| | Axitinib per volume (µg/mm$^3$) | 266.7 |
| | Hydrated Diameter | 0.75 mm |
| | Length | 7.5 mm |
| | Ratio of diameter (hydrated) to diameter (dry) | 3.13 |
| | Ratio of length (dry) to length (hydrated) | 2.20 |

TABLE 21.2

Formulations, configurations and dimensions of implants with axitinib doses of about 600 µg.

| Implant type | | Implant #2 | Implant #3 | Implant #4 |
|---|---|---|---|---|
| Formulation (% dry basis w/w) | Axitinib | 49.8% | 68.6% | 68.6% |
| | Dose | (600 µg) | (600 µg) | (600 µg) |
| | PEG Hydrogel | 42.0% | 26.0% | 26.0% |
| | 4a20K PEG-SAZ | 28% | 17.4% | 17.4% |
| | 8a20K PEG-NH2 | 14% | 8.7% | 8.7% |
| | Sodium phosphate | 8.2% | 5.4% | 5.4% |

TABLE 21.2-continued

Formulations, configurations and dimensions of implants with axitinib doses of about 600 μg.

| Implant type | | Implant #2 | Implant #3 | Implant #4 |
|---|---|---|---|---|
| Formulation (% wet basis w/w) | Axitinib | 12.0% | 16.5% | 16.5% |
| | PEG Hydrogel | 6.3% | 6.3% | 6.3% |
| | 4a20K PEG-SAZ | 4.2% | 4.2% | 4.2% |
| | 8a20K PEG-NH2 | 2.1% | 2.1% | 2.1% |
| | Sodium phosphate | 1.3% | 1.3% | 1.3% |
| | WFI | 80.4% | 75.9% | 75.9% |
| | Axitinib per final dry length | 71.4 μg/mm | 71.4 μg/mm | 81.1 μg/mm |
| | Approximate Implant Mass (dose ug/API %) | 1205 | 875 | 875 |
| Configuration | Stretching Method (Stretch Factor) | Wet (2.1) | Wet (2.1) | Wet (2.1) |
| | Needle Size | 25G UTW 1" (0.4 mm ID) | 25G UTW 1" (0.4 mm ID) | 25G UTW 0.5" (0.4 mm ID) |
| | Injector/Syringe | Implant Injector | Implant Injector | Implant Injector |
| | Packaging | Foil Pouches | Foil Pouches | Foil Pouches |
| | Sterilization Type | Gamma | Gamma | Gamma |
| | Site Storage | Refrigerated | Refrigerated | Refrigerated |
| Dimensions | Dried | | | |
| | Diameter | 0.36 mm | 0.37 ± 0.014 mm | 0.37 ± 0.008 mm |
| | Length | 8.4 mm | 8.4 ± 0.04 mm | 7.4 ± 0.03 mm |
| | Volume | 0.86 mm$^3$ | 0.90 ± 0.07 mm$^3$ | 0.81 ± 0.05 mm$^3$ |
| | Implant Mass | 1.20 mg | 0.95 ± 0.04 mg | 0.95 ± 0.01 mg |
| | Axitinib per volume (μg/mm$^3$) | 697.7 | 666.7 | 740.7 |
| | Hydrated | | | |
| | Diameter | 0.7 mm | 0.68 mm | 0.77 mm |
| | Length | 10 mm | 8.23 mm | 6.8 mm |
| | Ratio of diameter (hydrated) to diameter (dry) | 1.94 | 1.84 | 2.08 |
| | Ratio of length (dry) to length (hydrated) | 0.84 | 1.02 | 1.09 |

The 200 μg implant of Table 21.1 and used in the clinical study further described below was also investigated for axitinib release in the in vitro real time and accelerated assays (assays as described in Example 2). The in vitro real-time data suggest complete axitinib release after 225 days, while accelerated release is complete after around 2 weeks (FIG. 14).

Example 6 2 Details of Clinical Study

The clinical study using the 200 μg implant (Implant #1 of Table 21.1 above) was conducted in accordance with the study protocol, which is reproduced in the following (although the study has already begun and parts of it have already been performed, and the results are reported in Example 6.3 and 6.4 herein, as is common for study protocols, the study protocol is nevertheless written in the present and future tense). The implant referred to in the study protocol as "OTX-TKI" is Implant #1 of Table 21.1, above. Depending on the dose, one (dose of 200 μg), two (dose of 400 μg) or three (dose of 600 μg) implants are administered concurrently as described herein. Any abbreviations used in the following study protocol as well as Appendices A to G mentioned herein are provided at the end of the study protocol (i.e., at the end of Example 6.2).

Study Objective

The primary study objective is to evaluate the safety, tolerability and efficacy of OTX-TKI (axitinib implant) for intravitreal use, in subjects who have neovascular age-related macular degeneration (nvAMD).

Study Design

This is a multi-center, open label, dose escalation, Phase 1 safety study. This safety study will enroll approximately 26 subjects at approximately 5 sites in Australia. Three cohorts will be evaluated during this study: 200 μg(Cohort 1) and 400 μg (Cohort 2) dose groups followed by a third cohort (Cohort 3) consisting of two different treatment groups designed to test monotherapy (6 subjects receiving 600 μg OTX-TKI) and combination therapy with anti-VEGF (6 subjects treated with 400 μg OTX-TKI along with a single anti-VEGF injection). Safety data from subjects treated in Cohorts 1 and 2 will be evaluated by the DSMC prior to the initiation of the next cohort. The study will last approximately 9 months; there will be a screening/baseline visit followed by the injection day visit, with approximately 10 additional visits (See Appendix A).

The screening visit (Visit 1) may take place up to 14 days prior to the Injection Visit (Visit 2; Day 1). At Visit 2, subjects will have the OTX-TKI implant(s) injected (for Cohort 3, injections of the OTX-TKI implants and anti-VEGF may be spaced out over 1-4 weeks at the Investigator's discretion). Subjects will return for follow-up visit 2-3 days later for post-operative evaluation at Visit 3. Subjects will then return in approximately one week (Visit 4) and then again at approximately two weeks (Visit 5) for safety evaluations. Following that, subjects will return for safety evaluations on: Visit 6 (Month 1), Visit 7 (Month 2), Visit 8 (Month 3), Visit 9 (Month 4.5), Visit 10 (Month 6), Visit 11 (Month 7.5) and Visit 12 (Month 9) for final safety evaluations, and to be discharged from the study. At the Investigator's discretion, subjects who still have evidence of biological activity at Month 9 should be followed monthly until the CNV leakage has returned to baseline levels or until the Investigator believes the subject is clinically stable.

Cohort 1 is planned to comprise 6 subjects. They will each receive one 200 μg implant per eye which is estimated to provide an approximate drug delivery of about 7 μg per week.

Cohort 2 is planned to comprise 6 to 8 subjects. They will each receive two 200 μg implants per eye which together are estimated to provide an approximate drug delivery of about 14 μg per week.

Cohort 3a (monotherapy) is planned to comprise 6 subjects. They will each receive three 200 μg implants per eye which together are estimated to provide an approximate drug delivery of about 21 μg per week.

Cohort 3b (combination treatment therapy) is planned to comprise 6 subjects. They will each receive two 200 μg implants per eye which together are estimated to provide an approximate drug delivery of about 14 μg per week plus a single dose of an anti-VEGF agent.

Cohort 1 will be fully enrolled and all safety and tolerability data of OTX-TKI for each subject (minimum follow up data for two weeks) will be assessed prior to any subject entering the next cohort. The same process will be repeated for Cohort 2. Dose escalation to the next cohort will be based on the recommendation of the DSMC and confirmed by the MM.

If one DLT is identified in Cohorts 1, 2, or 3a, enrollment will continue until the cohort has been fully enrolled. If a second DLT is seen in Cohorts 1, 2, or 3a, enrollment will stop. If a second DLT is seen in Cohort 3a, enrollment in that cohort will stop and the previous lower dose will be declared the MTD.

In addition to safety and tolerability evaluations, this first clinical study will also determine if there is any evidence of biological activity by assessing changes in central subfield thickness (CSFT), FA and BCVA over time compared with baseline evaluations.

Subjects can have only 1 eye treated with OTX-TKI. The contralateral eye, if needed, will be treated at the Investigator's discretion. This should be standard of care and in no case should another investigational drug be used for the contralateral eye.

If both eyes are eligible, the eye with the worst BCVA will be selected as the study eye. If both eyes are eligible and both have the same BCVA then the Investigator will determine which eye will be selected as the study eye.

Safety Outcome Measures

Safety will be assessed immediately following injection of the implant. During the immediate post-injection time subjects will be monitored for visual acuity and elevated IOP.

The safety outcome measures will include an assessment of:
Incidence of treatment emergent ocular adverse events
Incidence of treatment emergent systemic adverse events
Vital signs
Ocular comfort score (to be assessed by subjects)
BCVA
Change in ocular examination compared to baseline assessment (e.g., slit lamp biomicroscopy, fundus examination)
Anterior chamber cell and flare score
Vitreous cell and haze score
Clinically significant increases in IOP
Potential injection related complications (e.g., endophthalmitis, retinal detachment, etc.)
Growth or development of geography atrophy
Clinically significant change in safety laboratory values
Plasma sample for pharmacokinetic analysis will be taken at Screening/Baseline Visit (Visit 1), Day 1 (Visit 2), Day 3 (Visit 3), and Month 3 (Visit 8).

Efficacy Outcome Measures

Efficacy measures will be observed throughout the conduct of the study. The efficacy outcome measures will include an assessment of:
Mean change in central subfield thickness (CSFT) from baseline over time measured by SD-OCT at 6 months and all visits
Change in BCVA from baseline over time at 6 months and all visits
Clinically significant change in leakage determined by FA and OCT-A
A decrease in CSFT of ≥50 μm at each study visit compared to baseline through Month 9
Absence of any SRF and IRF, both individually and together at each study visit
Need for rescue therapy Subject Selection—Study Population The subjects enrolled in this study will have a diagnosis of primary subfoveal (active sub- or juxtafoveal CNV with leakage involving the fovea) neovascularization (SFNV) secondary to AMD. Subjects with predominantly classic, minimally classic or occult lesions will all be included.

If both eyes qualify (i.e., all inclusion and exclusion criteria are met) then the eye with the worse BCVA will be the study eye. If both eyes qualify AND both eyes have the same BCVA, then the Investigator will determine which eye will be selected as the study eye.

Subject Selection—Inclusion Criteria

Individuals of either gender will be eligible for study participation if they:
1. Are at least 50 years of age
2. Are eligible for standard therapy
3. Have active primary CNVM secondary to AMD, either newly diagnosed or previously treated with documented response to anti-VEGF therapy in the study eye [primary subfoveal CNV secondary to AMD including juxtafoveal lesions that affect the fovea] documented by FA and SD-OCT
4. Have a lesion area<30.5 mm$^2$ (12 disc areas) (measured according to the protocol of the Macular Photocoagulation Study) in the study eye
5. Have a total area of CNV that is ≥50% of total lesion by Fluorescein angiography (FA) and fundus photography in the study eye
6. Have presence of foveal intraretinal or subretinal fluid with CSFT >300 μm on SD-OCT in the study eye
7. Have adequate ocular media and adequate pupillary dilation in the study eye to permit good quality fundus imaging
8. Have had an electrocardiogram within 12 weeks prior to Day 1 (day of injection) that shows no clinically significant abnormalities
9. Are female who is postmenopausal for at least 12 months prior to screening or surgically sterile; or male or female of childbearing potential willing to use two forms of adequate contraception from screening until they exit the study
10. Are able and willing to comply with all study requirements and visits
11. Have provided written informed consent.

Subject Selection—Exclusion Criteria

Individuals are not eligible for study participation if they:
1. Have monocular vision
2. Have a scar, fibrosis or atrophy involving the center of the fovea that is severe (mild fibrosis or atrophy is not exclusionary) in the study eye
3. Have evidence of a scar or fibrosis of >50% of the total lesion in the study eye
4. Have previous laser photocoagulation to the center of the fovea in the study eye
5. Have history of intraocular surgery including cataract surgery or keratorefractive surgery (LASIK, PRK, etc.) or another treatment in the study eye within 3 months of screening
6. Aphakia in the study eye
7. Have expectation of penetrating keratoplasty, vitrectomy, cataract surgery, or LASIK or any other intraocular surgery during the study period in the study eye
8. Have a history of vitreoretinal surgery (including vitrectomy) or other ocular surgeries including scleral buckle or glaucoma filtering/shunt surgery in the study eye. Prior laser treatment, other than for treatment of CNV is allowed
9. Have a presence of a disease other than NV (wet) AMD in the study eye that could affect vision or safety assessments
10. Have a history of significant ocular infection (bacterial, viral, or fungal) within the previous 3 months, or history of herpetic ocular diseases (including herpes simplex virus, varicella zoster or cytomegalovirus retinitis) or toxoplasmosis gondii or chronic/recurrent inflammatory eye disease (i.e., scleritis, uveitis, corneal edema) in either eye
11. Have evidence of a rhegmatogenous retinal detachment or visually significant epiretinal membrane (severe ERM), or macular hole, or tear of the retinal pigment epithelium (RPE) in the macula in the study eye
12. Have proliferative diabetic retinopathy, branch retinal vein occlusion or central retinal vein occlusion in the study eye
13. Have a history of diabetic macular edema (DME) in the study eye
14. Have a history of or presence of vitreous hemorrhage in the study eye. Subject is still eligible if history of past hemorrhagic PVD has resolved
15. Have advanced glaucoma (uncontrolled IOP 25 mmHg despite treatment) or glaucoma filtration surgery in the study eye
16. Have pathologic myopia in the study eye
17. Have a spherical equivalent of the refractive error in the study eye of >10 diopters of myopia
18. Have any prior treatment with tyrosine kinase inhibitors
19. Have an ocular malignancy including choroidal melanoma in either eye
20. Are receiving concurrent treatment with medications known to be toxic to the retina, lens or optic nerve (e.g., chlorpromazine, phenothiazines, tamoxifen, etc.)
21. Have a need for chronic therapy with systemic or topical ocular corticosteroids (a short course of <7 days, if needed during the study is permissible) or have known allergy to fluorescein (e.g., bronchospasm, rash, etc.), or to any component of the study products
22. Have symptomatic or unstable coronary artery disease, angina, congestive heart failure, or an arrhythmia requiring active medical management within the last 30 days of the injection of the implant
23. Have uncontrolled hypertension (defined as >160/100 mm Hg, despite medical treatment)
24. Have a history of or presence of uncontrolled systemic disease or a debilitating disease (e.g., uncontrolled diabetes).
25. Have had a myocardial infarction or other cardiovascular event (e.g., stroke) within the previous 6 months
26. Have participated in any study involving an investigational drug either in the U.S. or outside the U.S. within the past 30 days
27. Are an employee of the site that is directly involved in the management, administration, or support of the study, or be an immediate family member of the same.

Study Data Collection—Study Schematic

The study Time and Event Schedule is presented in Appendix A. Procedures for study Assessments can be found in Appendix B-G herein at the end of the study protocol (i.e., at the end of Example 6.2).

Study Observations and Procedures—Subject Screening and Informed Consent

Potential eligibility will be determined prior to study enrollment. The Investigator and study staff will determine the subject's willingness and ability to meet the follow-up requirements. If the subject desires to participate in the study, written informed consent will be obtained prior to performance of any study-specific examinations. Following completion of all the screening and baseline evaluations a determination will be made by the Investigator and study staff as to whether or not the subject has met all the eligibility criteria. If the subject meets the eligibility criteria and agrees to participate the subject will be enrolled.

Once a subject qualifies for the study and has received the OTX-TKI they must be followed to the end of the study period.

If the injection of the OTX-TKI implant is unsuccessful, record the reason for injection failure on the CRF as an injection failure and not as an AE.

Once the implant is placed in the vitreous the Investigator should verify placement by indirect ophthalmoscopy. At the discretion of the Investigator, images of the implant may be obtained throughout the duration of the study.

If the injection of the OTX-TKI implant is unsuccessful, an additional subject will be assigned to the study according to the same cohort.

Study Observations and Procedures—Screen Failures

Subjects who have signed the Informed Consent Form, but are determined to be ineligible during the screening assessments or at the baseline visit but prior to assignment to a cohort will be considered screen failures, will be withdrawn from the study, and will not require additional study follow-up visits. The reason(s) for the screen failure will be recorded in the CRF.

If subjects who fail eligibility criteria experience an AE during Screening/Baseline, they will be followed until the AE is resolved or stabilized.

Study Observations and Procedures—Subject Withdrawal

All subjects treated in the study will be required to adhere to the follow-up schedule as described in this protocol.

Subjects may withdraw from the clinical study at any time for any reason without jeopardy or prejudice and without compromising their clinical care by the Investigator. The Investigator also has the right to withdraw subjects from the trial in the event of an intercurrent illness, AE, protocol violation and/or administrative reason.

For any subject who withdraws their consent following injection of OTX-TKI, to the extent possible, the reason(s) for withdrawal will be documented on the End of Study CRF.

If the withdrawal from the study is a result of an AE, or death, an AE Form will also be completed. If a subject is withdrawn from the study as a result of an AE, every attempt should be made by the Investigator to follow the subject until the AE has resolved or stabilized.

Every attempt will be made to contact subjects who are non-compliant or lost to follow-up and such attempts will be documented in the subject's study record.

Subjects who withdraw from the study after receiving the OTX-TKI (axitinib implant) for intravitreal use will not be replaced.

Study Observations and Procedures—Product Malfunctions

Following injection, the Investigator will evaluate (i.e. grade) the ease of injection including whether or not there were technical problems such as a failure of the injection device to inject the implant. All malfunctions of the OTX-TKI (axitinib implant) for intravitreal use will be documented on the appropriate CRF and reported to Ocular Therapeutix within 24 hours. Ocular Therapeutix will advise whether the injection device will be returned for analysis. The incidence of malfunctions will be included in the final analysis.

Study Observations and Procedures—Cohort Group Assignment

This is an open-label, dose escalation Phase 1 study. The Principal Investigator will make the determination of eligibility for each subject based on the Inclusion and Exclusion criteria.

For Cohort 1, the first subject will receive the OTX-TKI implant in the study eye before any additional subjects are treated. Once the first subject in Cohort 1 has been evaluated for two weeks, and the MM supports continuation, an additional five subjects will be treated in Cohort 1.

Once Cohort 1 has been fully enrolled and all safety and tolerability data of OTX-TKI for each subject (minimum follow up data for two weeks) has been collected, the DSMC and MM will conduct a review of all available clinical data. Subjects in Cohort 2 will be treated only after:
1. All subjects in Cohort 1 have received the OTX-TKI implant and have been followed for at least 2 weeks
2. Confirmation that no more than 1 out of the 6 subjects has experienced a DLT
3. The DSMC completes a safety review of all available clinical data and recommends dose escalation.

Once Cohorts 1 and 2 have been fully enrolled and all safety and tolerability data of OTX-TKI for each subject (minimum follow up data for two weeks) has been collected, the DSMC and MM will conduct a safety review of all clinical data and will provide their recommendations for dose escalation and continuation.

Cohort 3 will consist of approximately 12 subjects. Six subjects will receive 600 µg OTX-TKI (Cohort 3a: Monotherapy Treatment Group), and 6 will receive 400 µg OTX-TKI along with a single anti-VEGF injection (Cohort 3b: Combination Treatment Group). Cohort 3a (Monotherapy Treatment Group: 600 µg OTX-TKI) will be enrolled prior to Cohort 3b Combination Treatment Group (400 µg OTX-TKI along with a single anti-VEGF injection).

Study Observations and Procedures—Masking

This is an open-label unmasked safety study.

Study Observations and Procedures—Rescue Therapy

If needed, any subject in any treatment arm may receive rescue therapy (i.e., anti-VEGF) at the Investigator's discretion. Eligibility to receive rescue therapy will be at the Investigator's discretion and should be communicated to the medical monitor within 3 days of treatment if not sooner. Subjects receiving rescue therapy should return for an unscheduled visit plus SD-OCT imaging 7-10 days following treatment if no per-protocol study visit is scheduled during that timeframe. Subjects receiving rescue therapy will be followed to the last study visit. The following criteria will be used to identify subjects who will likely require rescue therapy:
  i. loss of ≥15 letters from best previous BCVA due to ARMD, with current BCVA not better than baseline; or
  ii. Loss of ≥10 letters on 2 consecutive visits from best previous BCVA due to AMD, with current BCVA score not better than baseline.
  iii. Evidence of worsening disease activity manifest by greater than 75 microns CSFT from previous best value Study Observations and Procedures—Prohibited Medications The concomitant use of prohibited drugs with OTX-TKI must be avoided beginning 14 days prior to the injection of the implant and continuing for 9 months after the injection.

Co-administration of OTX-TKI and strong CYP3A4/5 inhibitors must be avoided as the plasma bioavailability of axitinib following intravitreal administration is not known. It has been shown that axitinib exposure (i.e., $C_{max}$) increased following co-administration with oral ketoconazole. The following are not permitted at any time beginning with the first screening visit: Ketoconazole, itraconazole, clarithromycin, atazanavir, indinavir, nefazodone, nelfinavir, ritonavir, saquinavir, telithromycin, voriconazole.

Co-administration of OTX-TKI and strong CYP3A4/5 inducers must be avoided as it has been shown that axitinib exposure (i.e., $C_{max}$) decreased following co-administration with rifamycin. The following are not permitted: Rifamycin, rifabutin, rifapentine, phenytoin, carbamazepine, phenobaribital, hypercium (St. John's wort). Intermittent use of topical and oral steroids is permitted.

Study Observations and Procedures—Fundus Imaging, Fluorescein Angiography, Optical Coherence Topography Photographers must be certified by the Central Reading Center before imaging of any study subjects. Imaging will follow a standard protocol.

OCT technicians must also be certified by the Central Reading Center. Spectral domain (SD) OCT images will be made using the Cirrus OCT following a standard protocol.

Instructions for these procedures will be provided in a separate imaging manual.

Study Observations and Procedures—Assessment of Pharmacokinetic Analysis

Plasma levels of axitinib will also be determined; samples will be taken at Screening, Baseline, Day 3 (Visit 3) and Month 3 (Visit 8). For subjects in Cohort 3 who receive three separate OTX-TKI injections (600 μg group) that may be spaced out over 1-4 weeks at Investigator's discretion, the Day 3 (Visit 3) sample for pharmacokinetic analysis may be obtained at the same study visit during which the third and final implant is injected. Instructions are provided in the Lab Manual.

Study Observations and Procedures—Medical History and Concurrent Medications The entirety of the subject's medication treatment history for AMD is to be recorded on the subject's source document form and corresponding CRFs. Additionally, any other concurrent ophthalmic medications and systemic medications, from up to 3 years prior to the Screening Visit, are to be recorded on the subject's source document forms and corresponding CRFs along with the reason the medication was taken, starting at the Screening Visit through the end of the study.

All ophthalmic and cardiac medical history for the subject should also be recorded on the subject's source document form and corresponding CRFs. Additional significant medical history from up to 5 years prior to the Screening visit should be recorded on the subject's source document form and corresponding CRFs.

Study Assessments

Screening Evaluations: Days −14 to Day 0

At the screening visit, the Principal Investigator will make the initial determination of the subject's eligibility for study participation by checking all inclusion and exclusion criteria. If a subject does not meet all of the inclusion criteria and/or meets any of the exclusion criteria the subject will be a screen failure and no further assessments will be done. Details of the procedures for these assessments can be found in Appendices B-G to this section.

The following procedures and assessments may be initiated within 14 days prior to the planned day of injection and must be completed prior to Injection Day (Visit 2/Day 1) in the following recommended order:
Obtain written informed consent
Demographic information to include age, gender, race, ethnicity
Medical and ophthalmic history including treatment and procedures
Inclusion and exclusion criteria
Prior and concomitant medications
Vital signs (pulse rate, blood pressure, and temperature)
Electrocardiogram—evidence of an electrocardiogram within 12 weeks prior to injection Day 1 that shows no clinically significant abnormalities (see Appendix G) must be recorded in the CRF
BCVA (ETDRS)
Slit lamp biomicroscopy and external eye exam
IOP measurement by applanation (Goldmann) tonometry
Dilated fundus exam including fundus imaging
SD-OCT
OCT-A
Fluorescein angiography
Plasma sample for PK analysis
Safety Laboratory testing
Adverse event assessment
Urine pregnancy test: if female of childbearing potential, subject must utilize two forms of adequate contraception from screening through the end of the study following injection of the implant, and have a negative urine pregnancy test
NOTE: All examinations need to be performed on both eyes.

For screen failures due to reasons that are expected to be temporary one re-screening visit can be conducted. The re-screening visit should be scheduled at least 14 days after the $1^{st}$ screening visit. Subjects who are re-screened will be given a new subject number and need to have all screening procedures repeated (including signing of a new Informed Consent). It should be noted on the CRF that this subject is a re-screen.

For eligible subjects, all information must be recorded in the subject's CRF. For subjects who do not meet the eligibility criteria, the minimum information to be recorded in the CRF will be the following: date of screening, subject number and reason for screen failure.

Injection Day, Visit 2 (Day 1)

Prior to Injection
Prior to injection of the OTX-TKI implant the Principal Investigator and study staff must confirm eligibility of the subject and the study eye.

The following procedures and assessments will be performed prior to injection of the OTX-TKI:
Inclusion and exclusion criteria confirmation
Adverse events (prior to injection)
Concomitant medications
Vital signs (pulse rate, blood pressure, and temperature)
BCVA (ETDRS)
Slit lamp biomicroscopy and external eye exam
IOP measurement by applanation (Goldmann) tonometry
Dilated Fundus Exam
SD-OCT
Ocular comfort score (to be assessed by subjects) (pre-injection)
NOTE: All examinations need to be performed on both eyes.

Injection Procedure

At the conclusion of all the assessments on Visit 2, Day 1 as noted above, the Investigator will confirm that the subject continues to be eligible for the study and did not experience any protocol defined exclusion criteria.

Subjects can have only one eye treated with OTX-TKI. If both eyes are eligible the eye with the worse BCVA will be selected as the study eye. If both eyes are eligible and both eyes have the same BCVA then the Investigator will determine which eye will be selected as the study eye.

The contralateral eye, designated as the non-study eye (NSE), if needed, will be treated at the Investigator's discretion with a local therapy, e.g., either topically or intravitreally administered therapy, not systemic. This should be standard of care and in no case should another investigational drug be used for the contralateral eye. The contralateral eye must not be treated with OTX-TKI. The treatment of the NSE should remain consistent for the duration of the study.

OTX-TKI is for intravitreal use ONLY and should be administered only by a qualified ophthalmologist experienced in the injection procedure.

The study drug treatment will be administered by the Investigator according to the procedure described and detailed in the Study Reference Manual. For Cohort 3 subjects receiving 3 separate injections, at the discretion of the Investigator, administration of the OTX-TKI implants and anti-VEGF may be spaced out over 1-4 weeks.

Post-Injection Procedure

Subjects should be monitored for visual acuity after the injection of OTX-TKI. Within 30-60 minutes following injection of OTX-TKI:
- A Plasma sample for PK analysis will be drawn
- The subject should be monitored for elevated IOP. The subject should be monitored until the IOP is stable and <25 mmHg. The Investigator should be prepared to provide therapy in the event of persistent elevated IOP.
- The Investigator should visualize the optic nerve head at this time to verify perfusion during the immediate post-injection period.
- Prior to discharge from the visit the Investigator and study staff are responsible to ensure that:
  - Vision has stabilized and that the IOP is stable and <25 mmHg
  - Adverse events post-injection have been recorded in the CRF
  - The Investigator has recorded the ease of injection procedure (i.e., 'utilization'); the Investigator will grade the level of ease of injection of the intravitreal implant as "easy" (1), "moderate" (2) or "difficult" (3)
- Subjects are instructed to refrain from rubbing their eyes and to contact the Investigator in the event that they experience excessive pain, eye redness, photophobia, excessive discomfort, or loss of vision that lasts more than a few hours.
- Subjects are instructed that a member of the study staff will reach them by telephone on the next day following the injection of OTX-TKI to assess whether they have experienced an Adverse Event. The subject should also be informed that they may be asked to return to the clinic sooner that the Day 3 (Visit 3).

Post-Administration Follow Up Safety Call (Day 2)

A qualified member of the study staff will telephone each subject on the day following the injection procedure to assess whether the subject has experienced an Adverse Event. If there is suspicion of an Adverse Event, the subject may be asked to return to the clinic sooner than the Day 3 (Visit 3) study visit.

Follow-Up Visit 3 (Day 3+1 Day)

Visit 3 will take place on Day 3 (+1 Day) after the injection of OTX-TKI. At this visit the Investigator and study staff will perform the following procedures and assessments:
- Adverse events
- Concomitant medications
- Ocular comfort score (to be assessed by subjects)
- BCVA (ETDRS)
- Slit lamp biomicroscopy and external eye exam
- IOP measurement by applanation (Goldmann) tonometry
- Dilated Fundus Exam (including documentation of presence or absence of the OTX-TKI implant)
- SD-OCT
- Plasma sample for PK analysis NOTE: For subjects in Cohort 3 who receive three separate OTX-TKI injections (600 μg group) that may be spaced out over 1-4 weeks at Investigator's discretion, the Day 3 (Visit 3) sample for pharmacokinetic analysis may be obtained at the same study visit during which the third and final implant is injected (within 30-60 minutes following injection of the third and final OTX-TKI implant a plasma sample for PK analysis will be drawn).

NOTE: All examinations need to be performed on both eyes.

Follow-Up Visit 4 (Day 7±2 Days)

Visit 4 will take place on Day 7 (±2 days) after the injection of OTX-TKI. At this visit the Investigator and study staff will perform the following procedures and assessments:
- Adverse events
- Concomitant medications
- Ocular comfort score (to be assessed by subjects)
- BCVA (ETDRS)
- Slit lamp biomicroscopy and external eye exam
- IOP measurement by applanation (Goldmann) tonometry
- Dilated Fundus Exam (including documentation of presence or absence of the OTX-TKI implant)
- SD-OCT NOTE: All examinations need to be performed on both eyes.

Follow-Up Visit 5 (Day 14±2 Days)

Visit 5 will take place on Day 14+2 days following the injection of OTX-TKI. At this visit the Investigator and study staff will perform the following procedures and assessments:
- Adverse events
- Concomitant medications
- Vital signs (blood pressure only)
- Ocular comfort score (to be assessed by subjects)
- BCVA (ETDRS)
- Slit lamp biomicroscopy and external eye exam
- IOP measurement by applanation (Goldmann) tonometry Dilated Fundus Exam (including documentation of presence or absence of the OTX-TKI implant)
SD-OCT
NOTE: All examinations need to be performed on both eyes.

Follow-Up Assessments: Visit 6 (Month 1±2 Days), Visit 7 (Month 2±3 Days), Visit 9 (Month 4.5±3 Days) and Visit 11 (Month 7.5±3 Days)

At these visits the Investigator and study staff will perform the following procedures and assessments:
Adverse events
Concomitant medications
Ocular comfort score (to be assessed by subjects)
BCVA (ETDRS)
Slit lamp biomicroscopy and external eye exam
IOP measurement by applanation (Goldmann) tonometry
Dilated Fundus Exam (including documentation of presence or absence of the OTX-TKI implant)
SD-OCT
NOTE: All examinations need to be performed on both eyes. Pregnancy test should be performed on all females of childbearing potential if they have missed two consecutive menstrual periods.

Follow-Up Visit 8 (Month 3±3 Days) and Visit 10 (Month 6±3 Days)

Visit 8 will take place 3 months +3 days and Visit 10 will take place 6 months ±3 days following the injection of OTX-TKI. At this visit the Investigator and study staff will perform the following procedures and assessments:
Adverse events
Concomitant medications
Ocular comfort score (to be assessed by subjects)
Vital signs (blood pressure only)
BCVA (ETDRS)
Slit lamp biomicroscopy and external eye exam
IOP measurement by applanation (Goldmann) tonometry
Dilated fundus exam including fundus imaging and documentation of presence or absence of the OTX-TKI implant
SD-OCT
OCT-A
Plasma sample for PK analysis (At Visit 8 only)
Safety Laboratory testing
Additionally, at Visit 10 (Month 6) only:
Fluorescein angiography
Urine pregnancy test: if female of childbearing potential, subject must utilize two forms of adequate contraception from screening through the end of the study following injection of the implant, and have a negative urine pregnancy test
NOTE: All examinations need to be performed on both eyes. At Visit 8 (Month 3) a pregnancy test should be performed on all females of childbearing potential if they have missed two consecutive menstrual periods.

Final Follow-Up Visit 12 (Month 9±3 Days)

This is the final follow-up visit, excluding any unscheduled visits that may be required to follow an AE that has not resolved or stabilized. This visit will take place 9 months (±3 days) after injection of OTX-TKI. At this visit the Investigator should confirm that the OTX-TKI implant is no longer visible on examination. If the implant is still visible, the subject should be followed approximately monthly until the implant is no longer visible. At the Investigator's discretion, subjects who still have evidence of biological activity at month 9 should be followed monthly until the CNV leakage has returned to baseline levels or until the Investigator believes the subject is clinically stable.
All of the following procedures and assessments will be performed:
Adverse event assessment
Concomitant medications
Ocular comfort score (to be assessed by subjects)
Vital signs (blood pressure only)
Electrocardiogram (Appendix G)
BCVA (ETDRS)
Slit lamp biomicroscopy and external eye exam
IOP measurement by applanation (Goldmann) tonometry
Dilated fundus exam including fundus imaging and documentation of presence or absence of the OTX-TKI implant
SD-OCT
OCT-A
Fluorescein angiography
Safety Laboratory testing Urine pregnancy test: if female of childbearing potential, subject must utilize two forms of adequate contraception from screening through the end of the study following injection of the implant, and have a negative urine pregnancy test
NOTE: All examinations need to be performed on both eyes.

Unscheduled Visit

An unscheduled visit may occur at any time that the Investigator decides it is necessary to see the subject outside of the study visit windows. At the discretion of the Investigator, for Cohort 3 subjects receiving 3 separate injections, unscheduled visits may be used to space out administration of the OTX-TKI implants and anti-VEGF over 1-4 weeks. As many of these visits as necessary may be scheduled. Any unscheduled visits will be recorded on the "unscheduled" visit CRF with the reason for the visit.
The examinations and assessments are at the Investigator's discretion based on the reason for the visit. All examinations and assessments, including those listed below, may be performed at Unscheduled Visits:
Adverse event assessment
Concomitant medications
Ocular comfort score (to be assessed by subjects)
BCVA (ETDRS)
Slit lamp biomicroscopy and external eye exam
IOP measurement by applanation (Goldmann) tonometry
Dilated Fundus Exam (including documentation of presence or absence of the OTX-TKI implant)

Adverse Events

Throughout the course of the study, all efforts will be made to remain alert to possible AEs or untoward findings. If an AE occurs, the first concern will be the safety and welfare of the subject. Appropriate medical intervention should be undertaken. Any AEs observed by the Investigator or study staff or reported by the subject, whether or not ascribed to the study treatment, will be recorded on the subject's Adverse Event CRF.
Documentation regarding the AE should be made as to the nature, date of onset, end date, severity, relationship to the study drug, action(s) taken, seriousness, and outcome of any sign or symptom observed by the physician or reported by the subject.

Definition of an Adverse Event

An AE is any untoward medical occurrence in a patient or clinical investigation subject administered a pharmaceutical product and which does not necessarily have a causal relationship with the treatment.

An AE can therefore be any unfavorable and unintended sign (including an abnormal laboratory finding), symptom or disease temporally associated with the use of a medicinal (investigational) product, whether or not related to the medicinal (investigational) product.

Definition of a Serious Adverse Event (SAE)

An SAE is any untoward medical occurrence that at any dose:
  Results in death
  Is life-threatening
    The term "life-threatening" refers to an event in which the subject was at risk of death at the time of the event; it does not refer to an event which hypothetically might have caused death if it were more severe
  Requires in-patient hospitalization or prolongation of existing hospitalization
  Results in persistent or significant disability/incapacity
  Is a congenital abnormality/birth defect
  Medical and scientific judgment should be exercised in deciding whether other situations should be considered SAEs, such as important medical events that might not be immediately life-threatening or result in death or hospitalization but might jeopardize the subject or might require intervention to prevent one of the other outcomes listed above.

Examples of such events are intensive treatment in an emergency room or at home for allergic bronchospasm, blood dyscrasias, neoplasms or convulsion that do not result in hospitalization.

An AE that is assessed as 'severe' should not be confused with an SAE. The term "severe" is often used to describe the intensity (i.e., severity) of a specific event (as in mild, moderate, or severe myocardial infarction); the event itself, however, may be of relatively minor medical significance (such as a severe headache). This is not the same as "serious", which is based on the outcome or action criteria usually associated with events that pose a threat to life or functioning. Seriousness (not severity) and causality serve as a guide for defining regulatory reporting obligations.

Severity

Severity of an AE is defined as a qualitative assessment of the degree of intensity of the AE as determined by the Investigator or reported to the Investigator by the subject. The assessment of severity is made irrespective of relationship to the study drug or seriousness of the event and should be evaluated according to the following scale:
  Mild Event is noticeable to the subject, but is easily tolerated and does not interfere with the subject's daily activities
  Moderate Event is bothersome, possibly requiring additional therapy, and may interfere with the subject's daily activities
  Severe Event is intolerable, necessitates additional therapy or alteration of therapy, and interferes with the subject's daily activities For AEs that change in intensity, the start and stop date of each intensity should be recorded.

Relationship to Intravitreal Implant, Procedure, or Study Drug

For each (S)AE, the Investigator must determine whether the event is related to the study drug, the injection procedure or the intravitreal implant. In order to do so, the Investigator must determine whether, in his/her medical judgment, there is a reasonable possibility that the event may have been caused by the study drug, the injection procedure or the intravitreal implant.

The following is a guideline to be used by the Investigator as a guide when assessing the causal relationship of an (S)AE. The attribution of causality to the injection procedure, the intravitreal implant or the study drug will be identified in the CRF.
  No RELATIONSHIP SUSPECTED This category applies to those (S)AEs which, after careful consideration, are clearly and incontrovertibly due to extraneous causes (disease, environment, etc.); there is no reasonable probability that the (S)AE may have been caused by the study drug, the injection procedure, or the intravitreal implant
  RELATIONSHIP SUSPECTED The following criteria should be applied in considering inclusion of an (S)AE in this category:
    1) It bears a reasonable temporal relationship to the injection procedure or the presence of the intravitreal implant or the study drug
    2) It could not be reasonably explained by the known characteristics of the subject's clinical state, environmental or toxic factors or other factors (e.g., disease under study, concurrent disease(s) and concomitant medications) and modes of therapy administered to the subject
    3) It disappears or decreases on removal of the intravitreal implant
    4) It follows a known pattern of response to the injection procedure or the intravitreal implant or the study drug
  Where the causal relationship of the AE to the injection procedure or the intravitreal implant has not been determined, or is unknown, the AE will be treated as if a relationship is suspected for the purposes of regulatory reporting.

A suspected AE is any event for which there is a reasonable possibility that the study drug caused the AE. "Reasonable possibility" means there is evidence to suggest a causal relationship between the study drug and the AE. Types of evidence that would suggest a causal relationship between the study drug and the AE include: a single occurrence of an event that is uncommon and known to be strongly associated with drug exposure; one or more occurrences of an event that is not commonly associated with drug exposure, but is otherwise uncommon in the population exposed to the drug (e.g., tendon rupture); an aggregate analysis of specific events observed in a clinical trial (such as known consequences of the underlying disease or condition under investigation or other events that commonly occur in the study population independent of drug therapy)

that indicates those events occur more frequently in the drug treatment group than in a concurrent or historical control group.

Expectedness

The expectedness of an (S)AE should be determined based upon existing safety information about the study drug using these guidelines:

UNEXPECTED: An AE or that is not listed in the study protocol, IB, or prescribing information for the registered formulation of axitinib (INLYTA®) or is not listed at the specificity or severity that has been observed EXPECTED: An AE that is listed in the study protocol, IB, or prescribing information for axitinib at the specificity and severity that has been observed AEs that are mentioned in the IB as occurring with a class of drugs or as anticipated from the pharmacological properties of the drug but are not specifically mentioned as occurring with the particular drug under investigation are to be considered as expected.

The Investigator should initially classify the expectedness of an AE, but the final classification is subject to the Medical Monitor's determination.

Clarifications

Hospitalization

Hospitalization for the elective treatment of a pre-existing condition (i.e., a condition present prior to the subject's signature of the Informed Consent) that did not worsen during the study is not considered an SAE. Complications that occur during hospitalization are AEs. If a complication prolongs hospitalization, or meets any of the other SAE criteria, the complication is an SAE.

Pre-Existing Conditions

Pre-existing conditions (i.e., conditions present or detected at the start of the study) which worsen during the study, exacerbation of a pre-existing illness or an increase in frequency or intensity of a pre-existing episodic event or condition are (S)AEs. Anticipated day-to-day fluctuations of pre-existing condition(s) that do not worsen with respect to baseline are not (S)AEs.

Worsening or progression of wet AMD is considered to be a "lack of efficacy" or "failure of expected pharmacological action" per protocol and is already recorded as part of the efficacy assessment and therefore does not need to be recorded as an (S)AE. However, the signs and symptoms and/or clinical sequelae resulting from the lack of efficacy may be reported as an (S)AE if considered by the Investigator to fulfill the definition of an (S)AE.

Medical or Surgical Procedures

Medical or surgical procedures (e.g., colonoscopy) are not (S)AEs; however, the condition that leads to the procedure may be considered an (S)AE.

In the case of elective medical or surgical procedures, or pre-study planned medical or surgical procedures for pre-existing conditions (i.e., a condition present prior to the subject's signature of the Informed Consent) that did not worsen during the study the condition that leads to the procedure does not need to be reported as an (S)AE.

Death

Death is not an SAE; the condition that leads to the death is an SAE.

Abnormal Laboratory Values

In the absence of a diagnosis, abnormal laboratory values that are judged by the Investigator to be clinically significant must be recorded as an (S)AE. Clinical significant abnormal laboratory findings that are present at baseline and significantly worsen following the start of the study will also be reported as an (S)AE.

Procedures for Reporting Adverse Events

All AEs that are "Suspected" and "Unexpected" are to be reported to Ocular Therapeutix and the IRB as required by the IRB/IEC, local regulations and the governing Health Authorities.

All AEs observed during the course of this study from the time the subject signs the Informed Consent, regardless of severity or relationship to the study drug or intravitreal implant will be recorded on the appropriate CRF(s). To the extent possible, the event to be recorded and reported is the event diagnosis as opposed to the event symptoms.

Any Serious Adverse Event or any severe, sight-threatening AE, whether ascribed to the study treatment or not, will be communicated within 24 hours, by telephone, to Ocular Therapeutix or its designee. The Investigator must obtain and maintain in his/her files all pertinent medical records, information, and medical judgments from colleagues who assisted in the treatment and follow-up of the subject; provide Ocular Therapeutix or its designee with a complete case history, which includes a statement as to whether the event was or was not suspected to be related to the use of the study drug; and inform the IRB/IEC of the AE within the IRB/IEC guidelines for reporting SAEs. A written report detailing the event, signed by the Investigator, shall be submitted to the Sponsor or its designee within 5 working days. All subjects who experience an SAE must be followed until resolution or stabilization of the event and the outcome is reported in the CRF.

Type and Duration of the Follow-up of Adverse Events

AEs will be followed until:
Resolution of the event, i.e., return to the baseline value or status or to 'normal'
  AEs may be determined to have resolved completely or resolved with sequelae
The Investigator determines, for events that do not end (e.g. metastasis), the condition to be chronic; the event can be determined to be resolved or resolved with sequelae
The event has stabilized, i.e., no worsening expected by the Investigator. All AEs will be documented in the CRFs.

For subjects that reach the final scheduled visit (i.e. Visit 12 [Month 9]), an unscheduled visit may be conducted thereafter to follow-up on any AEs that the Investigator has not deemed to be resolved or stabilized.

Dose Escalation Criteria and Stopping Criteria

Due to limited human experience with the OTX-TKI implant, the first subject in Cohort 1 will receive the OTX-TKI implant in the study eye before any additional subjects are treated Once the first subject Cohort 1 has been evaluated for 2 weeks, and if the MM supports continuation, an additional 5 subjects will be treated in Cohort 1.

Subjects will be treated in Cohort 2 only after:
1. All subjects in Cohort 1 have received the OTX-TKI implant and have been followed for at least 2 weeks
2. Confirmation that no more than 1 out of the 6 subjects has experienced a DLT
3. The DSMC completes a safety review of all available clinical data and recommends dose escalation.

If one DLT is identified in Cohorts 1,2, or 3a, enrollment will continue until the cohort has been fully enrolled. If a second DLT is seen in Cohorts 1 or 2, then enrollment will stop. If a second DLT is seen in Cohort 3a, enrollment in that cohort will stop and the previous lower dose will be declared the MTD.

All subjects dosed prior to the decision to stop study enrollment are to continue to be followed per the protocol. The decision to stop further enrollment in a particular cohort will be made by the MM based on recommendations from the DSMC.

The specific DLT's which may warrant stopping further enrollment include (but are not limited to):
Ocular inflammation of 4+ or ocular inflammation of 2-3+ that does not decrease to ≤1+ within 30 days of onset
BCVA decrease of >15 letters on multiple consecutive visits compared to pre-treatment due to study drug
Increase in IOP of >10 mmHg or an IOP of >30 mmHg that does not return to pre-injection levels within 7 days of treatment

Statistical Methods

Statistical and Analytical Plans

This study is not designed to show statistical significance, therefore, there will be no statistical analyses completed. There will be a general Statistical Plan that will briefly summarize how the data will be presented, i.e., descriptive statistics, etc.

Determination of Sample Size

For this Phase I study, no formal sample size calculations have been performed. The study will enroll up to 6 subjects in the first cohort and the accumulated data will be reviewed by the DSMC before continuing enrollment in the second cohort. After the second cohort of up to 8 subjects has been enrolled, the DSMC and MM will review the accumulated data and provide a recommendation for dose escalation and continuation to Cohort 3, which will enroll up to 12 subjects.

Analysis Datasets

The safety population will consist of all subjects receiving the OTX-TKI implant. All safety and efficacy analyses will be performed on the safety population.

Demographics and Baseline Data

Subject disposition will be presented, including the number of subjects screened, enrolled and treated. The number of subjects who completed the study and reasons for discontinuation will be summarized. Data will be presented by cohort group and overall.

Demographic and baseline characteristics (including disease and medical history) will be summarized. Data will be presented by cohort group and overall.

Safety Analyses

Safety will be assessed by ocular and systemic adverse events, ocular comfort score assessment and other ocular-related outcomes.

Adverse events will be coded using Medical Dictionary for Regulatory Activities (MedDRA) by system organ class and preferred term. Separate summaries will be made for adverse events that are related to the study drug, the injection procedure and the OTX-TKI implant. In addition, serious adverse events will be summarized.

Summaries of other safety related outcomes will be provided. All safety data will be presented by cohort group and overall.

Efficacy Analyses

Efficacy will be assessed by mean change in CSFT from baseline, mean change in BCVA from baseline, percent of subjects with clinically significant change in leakage, percent of subjects with a decrease in CSFT of 50 μm, percentage of subjects with SRF, IRF and both SRF and IRF and percent of subjects who needed rescue therapy. Data will be presented by treatment group and overall.

Pharmacokinetic Data

Systemic OTX-TKI exposure as measured in blood samples will be summarized at each time point. Plasma concentrations and pharmacokinetic parameters will be summarized by treatment group and overall. Measured concentrations and pharmacokinetic parameters will be presented in data listings.

Abbreviations

List of abbreviations used for describing the study details:

| Abbreviation | Meaning |
| --- | --- |
| AE | Adverse Event |
| AMD/ARMD | Age-related Macular Degeneration |
| API | Active Pharmaceutical Ingredient |
| BCVA | Best Correct Visual Acuity |
| BRB | Blood Retinal Barrier |
| CNV | Choroidal Neovascularization |
| CNVM | Central Neovascular Membrane |
| COVID-19 | Coronavirus Disease 2019 |
| CRC | Central Reading Center |
| CRF | Case Report Form |
| CSFT | Central Subfield Thickness |
| DLT | Dose Limiting Toxicity |
| DME | Diabetic Macular Edema |
| DR | Diabetic Retinopathy |
| DSMC | Data Safety Monitoring Committee |
| ECG | Electrocardiography |
| ERG | Electroretinography |
| ETDRS | Early Treatment Diabetic Retinopathy Study |
| FA | Fluorescein Angiography |
| FDA | Food and Drug Administration |
| GCP | Good Clinical Practice |
| IB | Investigator's Brochure |
| ICH | International Conference on Harmonization |
| IEC | Independent Ethics Committee |
| IOP | Intraocular Pressure |
| IRB | Institutional Review Board |
| IRF | Intraretinal Fluid |

| Abbreviation | Meaning |
|---|---|
| IVT | Intravitreal (Intravitreous) |
| MM | Medical Monitor |
| MTD | Maximum Tolerated Dose |
| NSE | Non-study eye |
| NVAMD | Neovascular Age-Related Macular Degeneration |
| OCT - (A) | Ocular Coherence Tomography (angiography) |
| OHT | Ocular Hypertension |
| OTX-TKI | Ocular Therapeutix Axitinib Implant for Intravitreal Use |
| PEG | Polyethylene glycol |
| PLA | Polylactide |
| PVD | Posterior Vitreous Detachment |
| RCC | Renal Cell Carcinoma |
| RPE | Retinal Pigment Epithelium |
| SAE | Serious Adverse Event |
| SD-OCT | Spectral Domain Optical Coherence Tomography |
| SE | Study eye |
| SFNV | Subfoveal Neovascularization |
| SRF | Subretinal Fluid |
| TGA | Therapeutic Goods Association |
| TKI | Tyrosine Kinase Inhibitor |
| VEGF | Vascular Endothelial Growth Factor |

APPENDICES TO THE STUDY PROTOCOL

APPENDIX A

TIME AND EVENT SCHEDULE

| Visit Type<br>Visit Number | Screening/Baseline Visit<br>Day −14 to Day 0<br>Visit 1 | Injection Day[b]<br>Day 1<br>Visit 2 | Follow-up Telephone Call<br>Day 2<br>N/A | Follow-up Day<br>Day 3 + 1 day<br>Visit 3 | Follow-UP Day<br>Day 7 ± 2 days<br>Visit 4 | Follow-up Day<br>Day 14 ± 2 days<br>Visit 5 | Follow-up Month<br>Month 1 ± 2 days<br>Visit 6 | Follow-up Month<br>Month 2 ± 3 days<br>Visit 7 | Follow-up Month<br>Month 3 ± 3 days<br>Visit 8 |
|---|---|---|---|---|---|---|---|---|---|
| Informed Consent | X | | | | | | | | |
| Demographic Information | X | | | | | | | | |
| Medical and Ophthalmic History including treatment and procedures | X | | | | | | | | |
| Inclusion and Exclusion Criteria | X | X | | | | | | | |
| Prior and Concomitant Medication | X | X | | X | X | X | X | X | X |
| Adverse events | X | X | | X | X | X | X | X | X |
| Ocular Comfort Score (to be assessed by subjects) | | X[e] | | X | X | X | X | X | X |
| Vital signs[c] | X | X | | | | X | | | X |
| ECG | X | | | | | | | | |
| BCVA (ETDRS) | X | X | | X | X | X | X | X | X |
| Slit lamp biomicroscopy and external eye exam | X | X | | X | X | X | X | X | X |
| IOP Measurement by Goldmann | X | X | | X | X | X | X | X | X |
| Dilated Fundus Exam (including presence or absence of OTX-TKI) | X | X | | X | X | X | X | X | X |
| Fundus Imaging | X | | | | | | | | X |
| SD-OCT | X | X | | X | X | X | X | X | X |
| OCT-A | X | | | | | | | | X |
| Fluorescein angiography | X | | | | | | | | |
| Injection of OTX-TKI implant | | X | | | | | | | |
| Post-administration follow-up safety call | | | X | | | | | | |
| Urine Pregnancy test[f] | X | | | | | | | | |
| Plasma sample for PK | X | X[g] | | X[h] | | | | | X |
| Safety Laboratory analysis[d] | X | | | | | | | | X |

| Visit Type<br>Visit Number | Follow-up Month<br>4.5 ± 3 days<br>Visit 9 | Follow-up Month<br>6 ± 3 days<br>Visit 10 | Follow-up Month<br>7.5 ± 3 days<br>Visit 11 | Final Follow-up Month<br>9 ± 3 days<br>Visit 12 | Unscheduled Visit[a] |
|---|---|---|---|---|---|
| Informed Consent | | | | | |
| Demographic Information | | | | | |
| Medical and Ophthalmic History including treatment and procedures | | | | | |
| Inclusion and Exclusion Criteria | | | | | |
| Prior and Concomitant Medication | X | X | X | X | X |

APPENDIX A-continued

TIME AND EVENT SCHEDULE

| | | | | | |
|---|---|---|---|---|---|
| Adverse events | X | X | X | X | X |
| Ocular Comfort Score (to be assessed by subjects) | X | X | X | X | X |
| Vital signs[c] | | X | | X | X |
| ECG | | | | X | X |
| BCVA (ETDRS) Manifest Refraction | X | X | X | X | X |
| Slit lamp biomicroscopy and external eye exam | X | X | X | X | X |
| IOP Measurement by Goldmann | X | X | X | X | X |
| Dilated Fundus Exam (including presence or absence of OTX-TKI) | X | X | X | X | X |
| Fundus Imaging | | X | | X | X |
| SD-OCT | X | X | X | X | X |
| OCT-A | | X | | X | X |
| Fluorescein angiography | | X | | X | X |
| Injection of OTX-TKI implant | | | | | |
| Post-administration follow-Up safety call | | | | | |
| Urine Pregnancy test[f] | | X | | X | X |
| Plasma sample for PK | | | | | |
| Safety Laboratory analysis[d] | | X | | X | X |

[a]For any Unscheduled Visit the Investigator should determine which assessments need to be performed based on the reason for the unscheduled visit; not all assessments need be performed (see section 8.12 for list of required assessments).
[b]Subjects will be monitored 30-60 minutes post injection (see section 8.5 for details regarding post-injection monitoring); for Cohort 3, injections of the OTX-TKI implants and anti-VEGF may be spaced out over 1-4 weeks at the Investigator's discretion.
[c]Vital signs will encompass assessment of blood pressure, pulse rate and temperature at visits 1 and 2 only. At all other visits only the blood pressure measurement will be performed.
[d]Safety laboratory assessments comprise: CBC, Chem-7, LFTs and TFT.
[e]Ocular Comfort Score to be assessed by subjects' pre-injection of OTX-TKI on Visit 2 (Day 1).
[f]Pregnancy test will be performed on all females of childbearing potential at the Screening/Baseline Visit (Days −14 to 0), Visit 10, Visit 12 and at any time that the subject has missed 2 consecutive menstrual periods.
[g]Plasma sample for PK to be performed 30-60 minutes post-injection of OTX-TKI on Visit 2 (Day 1).
[h]For subjects in Cohort 3 who receive three separate OTX-TKI injections (600 μg group) that may be spaced out over 1-4 weeks at Investigator's discretion, the Day 3 (Visit 3) sample for pharmacokinetic analysis may be obtained at the same study visit during which the third and final implant is injected (within 30-60 minutes following injection of the third and final OTX-TKI implant a plasma sample for PK analysis will be drawn).

APPENDIX B: OCULAR COMFORT SCORE (TO BE ASSESSED BY SUBJECTS)

Subjects will be asked to grade their comfort level by asking them the following question: "On a scale of 0 to 10, 0 being very comfortable and 10 being very uncomfortable, how comfortable does your eye feel at this time?"

The examiner will record the number selected by the subject in whole numbers on the appropriate CRF.

APPENDIX C: RECOMMENDED PROCEDURES FOR BEST CORRECTED VISUAL ACUITY (BCVA)

Visual Acuity should be evaluated at the beginning of each study visit prior to performing other tests such as Goldmann tonometry and gonioscopy and prior to pupil dilation. Every effort should be made to have the same BCVA assessor throughout the study period. Visual acuity testing should be done starting with most recent correction.

BCVA should be measured using a backlit ETDRS chart such as Precision Vision's or equivalent. It is recommended that the site use a backlit, wall-mounted or caster stand ETDRS distance eye chart with a luminance of 85cd/m$^2$ set at 4 meters from the subject. A trial lens frame, or phoropter, set at 12.0 mm vertex distance should be used to obtain manifest refraction measurements. If possible, final refinement of sphere should be done at 4 meters with a trial lens set.

Eye Charts

All distance visual acuity measurement should be made using an Illuminator Box (or equivalent) set at 4 meters from the subject. Any subject unable to read at least 20 or more letters on the ETDRS chart at 4 meters should be tested at 1 meter according to the instructions provided for 1 meter testing. The fluorescent tubes in the light box should be checked periodically for proper functioning.

A maximum effort should be made to identify each letter on the chart. When the subject says he or she cannot read a letter, he or she should be encouraged to guess. If the subject identifies a letter as one of two letters, he or she should be asked to choose one letter and, if necessary, to guess. When it becomes evident that no further meaningful readings can be made, despite encouragement to read or guess, the examiner should stop the test for that eye. However, all letters on the last line should be attempted as letter difficulties vary and the last may be the only one read correctly. The number of letters missed or read incorrectly should be noted.

Log MAR Visual Acuity Calculations

The last line in which a letter is read correctly will be taken as the base log MAR reading. To this value will be added the number "N×0.02" where 'N' represents the total number of letters missed up to and included in the last line read. This total sum represents the log MAR visual acuity for that eye.

For Example: Subject correctly reads 4 of 5 letters on the 0.2 line, and 2 of 5 letters on the 0.1 line.

| | |
|---|---|
| Base logMAR | =0.1 |
| N (total number of letters incorrect on line 0.2 as well as 0.1) | =4 |

| | |
|---|---|
| N × T (T = 0.02) | =0.08 |
| Base logMAR + (N × T) | =0.1 + 0.08 |
| logMAR VA | =0.18 |

BCVA examination should begin with the right eye (OD). The procedure should be repeated for the left eye (OS).

1-Meter Testing

The subject must sit for the 1-meter test. The avoidance of any head movement forward or backward is particularly important during this test.

APPENDIX D: SLIT LAMP BIOMICROSCOPY EXAMINATION

The slit beam observations should be assessed in a dark room using the highest lamp voltage, an aperture of 0.3 mm, an illumination angle of 30 degrees and a magnification of 16×.

The clinician will use a slit lamp to assess the following as normal, abnormal clinically significant or abnormal not clinically significant:
  External adnexa—Presence or absence of lid erythema, edema or other abnormalities, evaluation of lashes for scurf or other abnormalities
  Conjunctiva—presence or absence of edema, erythema or other abnormalities
  Iris—presence or absence of stromal or other abnormalities
  Cornea—clarity, presence or absence of superficial punctate keratopathy or other abnormalities asses with fluorescein stain
  Anterior Chamber—adequacy of formation depth, cell score and flare count
  Lens—presence or absence of cataract, and severity of opacity, presence or absence of pseudophakia
  Explanation/comments should be provided on the CRF for any abnormal observations. If a corneal edema is observed, a notation on whether it is general or local should be added.

Anterior Chamber Cells and Flare

Assessment of anterior chamber cells should be performed as follows:
  Low ambient lighting
  1×1 mm slit beam
  Highest slit lamp voltage
  Illumination angle of 45 degrees
  High magnification The anterior chamber will be examined for the presence of signs of ocular inflammation. Anterior chamber cell count and flare will be graded using the SUN* Working Group grading scheme: Although an anterior chamber cell grade of "0" is reported as "<1 cell" in the SUN Working Group grading scheme, it will be characterized as 0 cells in the field for this study.

The anterior chamber cell count will be assessed as the actual number of cells counted within the slit beam of 1.0 mm height and 1.0 mm width described above, if fewer than 16 cells are seen. Only white blood cells will be counted. (Red blood cells and pigment cells are not to be counted). The number of cells counted and the corresponding grade per the below scale will both be recorded in the CRF.

| Anterior Chamber Cells | |
|---|---|
| Grade | Number of Cells in Field |
| 0 | 0 (rare cells, i.e., one cell in a minority of fields) |
| 0.5+ | 1-5 (trace) |
| 1+ | 6-15 (cells) |
| 2+ | 16-25 (cells) |
| 3+ | 26-50 (cells) |
| 4+ | >50 (cells) |

| Flare | |
|---|---|
| Grade | Description |
| 0 | None |
| 1+ | Faint |
| 2+ | Moderate iris and lens details clear |
| 3+ | Marked iris and lens details hazy |
| 4+ | Intense fibrin or plastic aqueous |

*Standardization of the Uveitis Nomenclature (SUN)[1]
If hypopyon is present, this should be noted in the source documents and eCRF.
[1] Jabs D A, Nussenblatt R B, Rosenbaum J T. Standardization of Uveitis Nomenclature (SUN) Working Group. Standardization of uveitis nomenclature for reporting clinical data. Results of the First International Workshop. Am J Ophthalmol. 2005 September; 140(3): 509-16.

APPENDIX E: IOP MEASUREMENT

Goldmann tonometry as the international gold standard for tonometry is quite accurate and reproducible if proper technique is used. When performing Goldmann tonometry the following procedures should be followed:
  1. Pre-tonometry procedures: Set tonometer in the correct position and make sure the prism is in the horizontal position on the slit lamp. Set the tension at 1 mmHg. Use Cobalt filter with slit beam open maximally with the angle between the illumination and the microscope at approximately 60 degrees.
  2. Instill one drop of a topical anesthetic and a moistened fluorescein strip may be lightly touched against the tarsal conjunctiva of the lower lid of each eye, taking care not to flood the ocular surface with fluorescein dye. Alternatively, a drop of topical anesthetic-fluorescein (e.g., Fluress) solution may be instilled into the lower conjunctival fornix of each eye, taking care not to flood the ocular surface with fluorescein dye. Ask subject to blink a few times just prior to tonometry.
  3. Place subject in adjustable chair so chin can fit comfortably on the slit lamp chin rest and the forehead can be snug against the forehead bar.
  4. Apply tonometer to the subject's eye while subject looks straight ahead and increase the force of applanation until the observer sees the inner portion of the two half fluorescein circles are touching. Record pressure on the CRF.

APPENDIX F: DILATED FUNDUS EXAM

Assessments should be conducted using indirect ophthalmoscopy. Each of the following will be evaluated and documented as normal, abnormal clinically significant or abnormal not clinically significant:
  Vitreous: When examining the vitreous, the Investigator should also document the presence or absence of the OTX-TKI implant at the macula, peripheral retina, choroid, and optic nerve.

The cup to disc (C/D) ratio will also be measured. Explanation/comment should be provided on the CRF for any abnormal pathology.

| The following scale will be used to define the extent of vitreous haze[2]: | |
|---|---|
| Absent | Clear view of optic disc, retinal vessels and nerve fiber layer |
| Trace | Slight blurring of optic disc margin of and of normal striations and reflex of nerve fiber layer cannot be visualize |
| 1+ | Mild blurring of optic disc margin and slight loss of retinal vessel definition |
| 2+ | Moderate blurring of optic disc margin and loss of retinal vessel definition |
| 3+ | Optic nerve head and large vessels visible but borders quite (very) blurry |
| 4+ | Optic nerve head obscured |

[2]Nussenblatt R B, Palestine A G, Chan C C, Roberge F. Standardization of vitreal inflammatory activity in intermediate and posterior uveitis. Ophthalmology 92: 467-471, 1985.

APPENDIX G: ELECTROCARDIOGRAM (ECG)

12-lead ECG

A 12-lead ECG will be performed during the Screening Phase. An ECG will be performed after the subject has been supine for approximately 3 minutes. Sites are to use their own, local ECG machines for the study and the ECG readings will be interpreted by the Investigator (or delegated qualified designee) by clinically correlating with the subject's condition.

The Investigator's interpretation will be recorded in the ECG eCRF as: normal; abnormal, not clinically significant; or abnormal, clinically significant. Results must be within normal limits or not clinically significant in order to allow a subject to continue in the study.

Example 6 3 Initial Results of the Study

Initial studies were performed in human subjects as follows: Subjects with neovascular age-related macular degeneration (nAMD), both treatment-naïve and those with a history of anti-VEGF therapy) were enrolled for administration of inventive hydrogel in a single study eye. Two groups completed enrollment and are under evaluation: 200 µg axitinib in a 7.5% PEG hydrogel (formed from 2 parts 4a20K PEG-SAZ to 1 parts 8a20K PEG amine) where the 7.5% represents the PEG weight divided by the fluid weight x 100 (1 implant; n=6) and 400 µg axitinib (2 implants; n=7). Spectral-domain optical coherence tomography (SD-OCT) imaging was used to assess retinal fluid and central subfield thickness (CSFT) was performed at Baseline. Injection visits occurred at days 3, 7, and 14, and at months 1, 2, 3, 4.5, 6, 7.5, 9, and approximately monthly until implant(s) were no longer visible. The inventive implants were visualized at every visit. Safety evaluations included: adverse event collection, vital signs, best-corrected visual acuity (BCVA), slit lamp biomicroscopy, tonometry, indirect and direct ophthalmoscopy and safety labs.

In the 400 µg group, an average reduction in central subfield thickness (CSFT) of 89.8±22.5 µm (mean± SEM) was observed by 2 months and was generally maintained through the 3 month timepoint (follow-up ongoing). For several subjects with a history of anti-VEGF therapy, the durability of anti-VEGF treatment was extended to >9 months in the 200 µg group and >3 months in the 400 µg group (follow-up ongoing). Best-corrected visual acuity (BCVA) was maintained with no serious ocular adverse events reported. The most common adverse events observed in the study eye include tiny pigmented keratic precipitates (3/13), subretinal hemorrhage (2/13) and subconjunctival hemorrhage (3/13) and pain (2/13) following implant injection. Implant(s) exhibited little movement in the vitreous and were no longer visible after 9-10.5 months in the 200 µg group.

The inventive implants were generally well-tolerated with a favorable safety profile. Minimal movement and consistent resorption of implant(s) has been observed up to 10.5 months.

Detailed results of the continuation of these initial studies with 200 µg (1 implant) and 400 µg(2 implants) axitinib doses and additional studies with a 600 µg (3 implants) axitinib dose as well as a 400 µg(2 implants) axitinib dose concurrently administered with an anti-VEGF agent are reported in detail in Example 6.4.

Example 6.4: Comprehensive Results of the Study

Evaluation of Doses of 200 and 400 µg Axitinib

As explained in the study protocol reproduced above, participants of cohort 1 (n=6) received one implant comprising an axitinib dose of 200 µg in one eye per patient and participants of cohort 2 (n=7) received two implants each comprising an axitinib dose of 200 µg in one eye per patient resulting in 400 µg dose in total per eye. Implants were administered intravitreally using a 27G needle. Even in the hydrated state the implants did not result in visual impact due to their compact size and shape. Patients of cohort 2 received the two implants on the same day, with the exception of subject #2 who received the implants 1 week apart. For formulation details and dimensions of the 200 µg implant used in this study see Table 21.1 (Implant #1). Overview charts presenting summary data regarding central subfield thickness (CSFT) and best corrected visual acuity (BCVA) of all subjects enrolled and analyzed so far in cohorts 1 and 2 are provided in FIGS. 17 and 18, respectively. In addition, in order to exemplary illustrate the course of CSFT and BCVA in subjects of cohorts 1 and 2, certain specific subjects are discussed herein in more detail, and images showing the CSFT and BCVA in these subjects at exemplary visits are provided in the Figures. These exemplary subjects are discussed to illustrate CSFT and BCVA measurement and development in subjects/patients who participated in the study, but are singular subjects. For the mean change of CSFT and BCVA over all subject of cohorts 1 and 2, it is referred to FIGS. 17 and 18. For FIGS. 17 and 18, six patients were followed in cohort 1 until month 9. Seven patients were followed in cohort 2 until month 12, five until month 14 and two until month 16.

31% (4 of 13) patients in cohorts 1 and 2 were female, 69% (9 of 13) were male with a median age of 75.2 years (standard deviation, SD: 4.5), wherein the youngest patient was 67 and the oldest patient 83 years. Participants of both cohorts were either previously treated with anti-VEGF therapeutic (such as ranibizumab or aflibercept) or naïve. An overview of the subjects from cohort 1 and 2 is further given in Table 22. The baseline CSFT for the 6 treated subjects in cohort 1 is 680±159 µm (mean+SE), and the baseline BCVA (Snellen equivalent) is 0.73 +0.26 (mean+SE). The baseline CSFT for the 7 treated subjects in cohort 2 is 450±29 µm (mean+SE), and the baseline BCVA (Snellen equivalent) is 0.47 +0.17 (mean+SE).

TABLE 22

Overview of subjects from the two cohorts (cohort 1 and 2). Age, Sex (male M, female F), together with prior treatment and study eye are presented. For the study eye (oculus dexter, (OD) or oculus sinister (OS)), pre-treatment BCVA is given as logMAR (logarithm of the minimal angle resolution) and Snellen equivalent. A conversion chart from EDTS letter score to LogMAR value and Snellen equivalent can be found in Beck et al., Am J Ophthalmol 2003, 135:194-205. In addition, CSFT pre-treatment is presented. All pre-treatment results are from day 1 of the study, except for cohort 1, subjects 3, 4, and 5 for which data was taken from the screening visit.

| Subject No. | Age | Sex | Prior Treatment | Study Eye | Pre-Treatment logMAR BCVA | Pre-Treatment Snellen BCVA | Pre-Treatment CSFT (μm) |
|---|---|---|---|---|---|---|---|
| Cohort 1 (200 μg) | | | | | | | |
| #1 | 74 | M | Naïve | OS | 1.14 @ 1 m | 20/276 | 1252 |
| #2 | 71 | M | Anti-VEGF | OD | 0 | 20/20 | 350 |
| #3 | 79 | M | Anti-VEGF | OD | 0.30 | 20/40 | 309 |
| #4 | 73 | F | Anti-VEGF | OS | 1.52 @ 1 m | 20/662 | 742 |
| #5 | 80 | M | Anti-VEGF | OS | 0.36 | 20/46 | 408 |
| #6 | 78 | M | Naïve | OD | 1.04 @ 1 m | 20/219 | 1030 |
| Cohort 2 (400 μg) | | | | | | | |
| #1 | 72 | M | Anti-VEGF | OD | −0.04 | 20/18 | 473 |
| #2 | 75 | F | Naïve | OS | 1.40 @ 1 m | 20/502 | 513 |
| #3 | 67 | M | Anti-VEGF | OS | 0.36 | 20/46 | 561 |
| #4 | 80 | M | Anti-VEGF | OS | 0.28 | 20/38 | 448 |
| #5 | 71 | M | Naïve | OD | 0.42 | 20/53 | 430 |
| #6 | 83 | F | Anti-VEGF | OS | 0.30 | 20/40 | 388 |
| #7 | 75 | F | Anti-VEGF | OD | 0.54 | 20/69 | 335 |

Participants were evaluated for changes in central subfield thickness (CSFT) and retinal fluid by spectral domain optical coherence tomography (SD-OCT), for best corrected visual acuity (BCVA), and for clinically-significant leakage using fluorescein angiography (FA) and/or OCT prior to treatment (baseline values—day 1), on days 3, 7, and 14, and months 1, 2, 3, 4.5, 6, 7.5, 9, 10.5, 11, 12, 13.5, 14, and/or 15.5 and approximately monthly for the subjects still in the study until the implants were no longer visible. In addition, slit lamp biomicroscopy, tonometry (for measurement of IOP), and indirect and direct ophthalmoscopy were performed on the study visits. Patients were monitored for adverse events on all study visits.

Biodegradation

Implants exhibited little movement in the vitreous. Generally, implants were no longer visible after 9-12 months in both cohorts. FIG. 15 exemplarily shows IR images for subject #1 of cohort 2.

Visual Quality and Central Subfield Thickness

Figure 16:
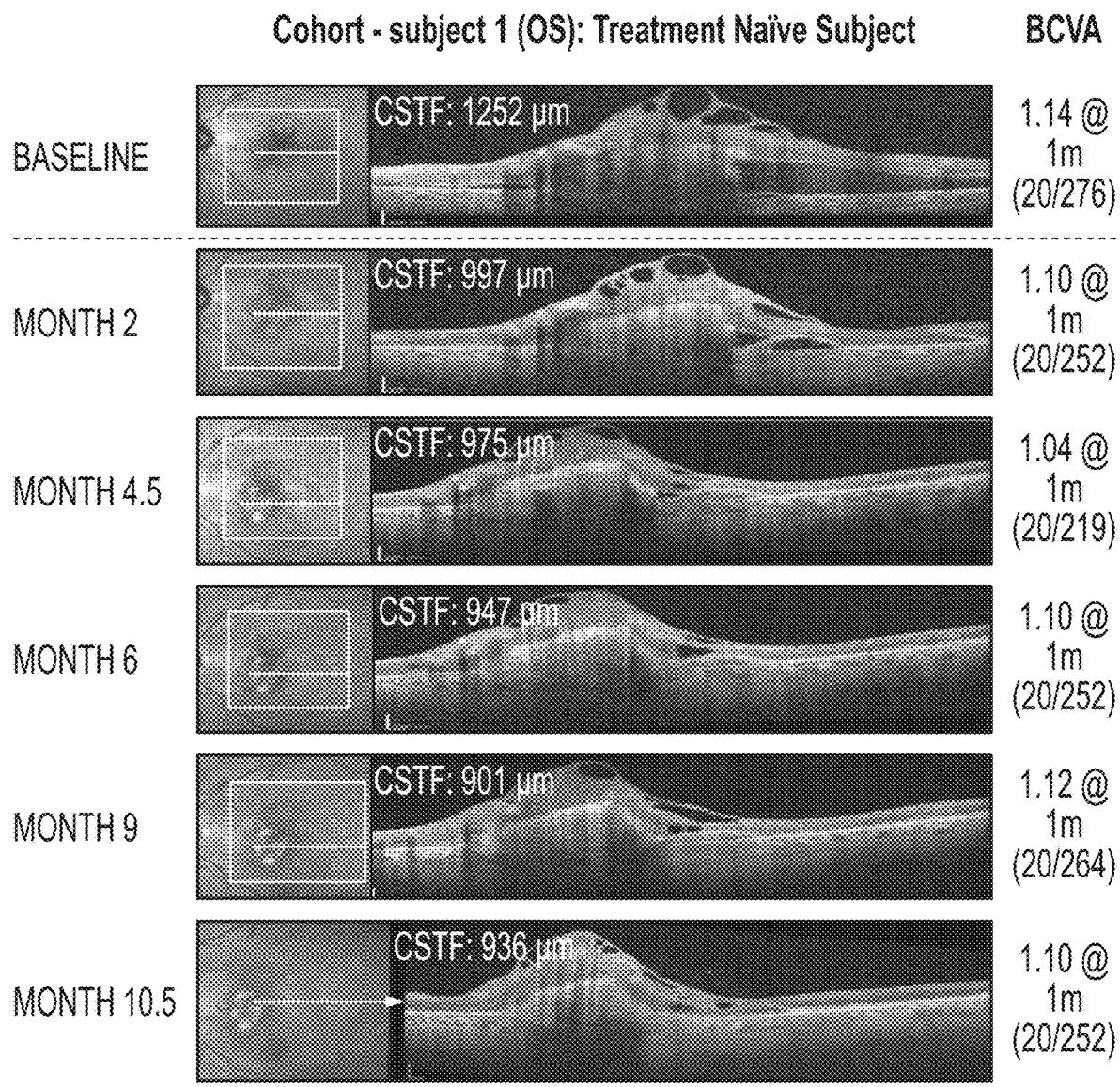
FIG. 16 One embodiment of spectral domain optical coherence tomography (SD-OCT) images from the study eye of subject #1 of cohort 1 (1 implant, 200 µg axitinib in total per eye). For this treatment naïve subject a significant reduction in central subfield thickness (CSFT) was observed while best corrected visual acuity (BCVA) was not impaired over 10.5 months.
Figure 17:
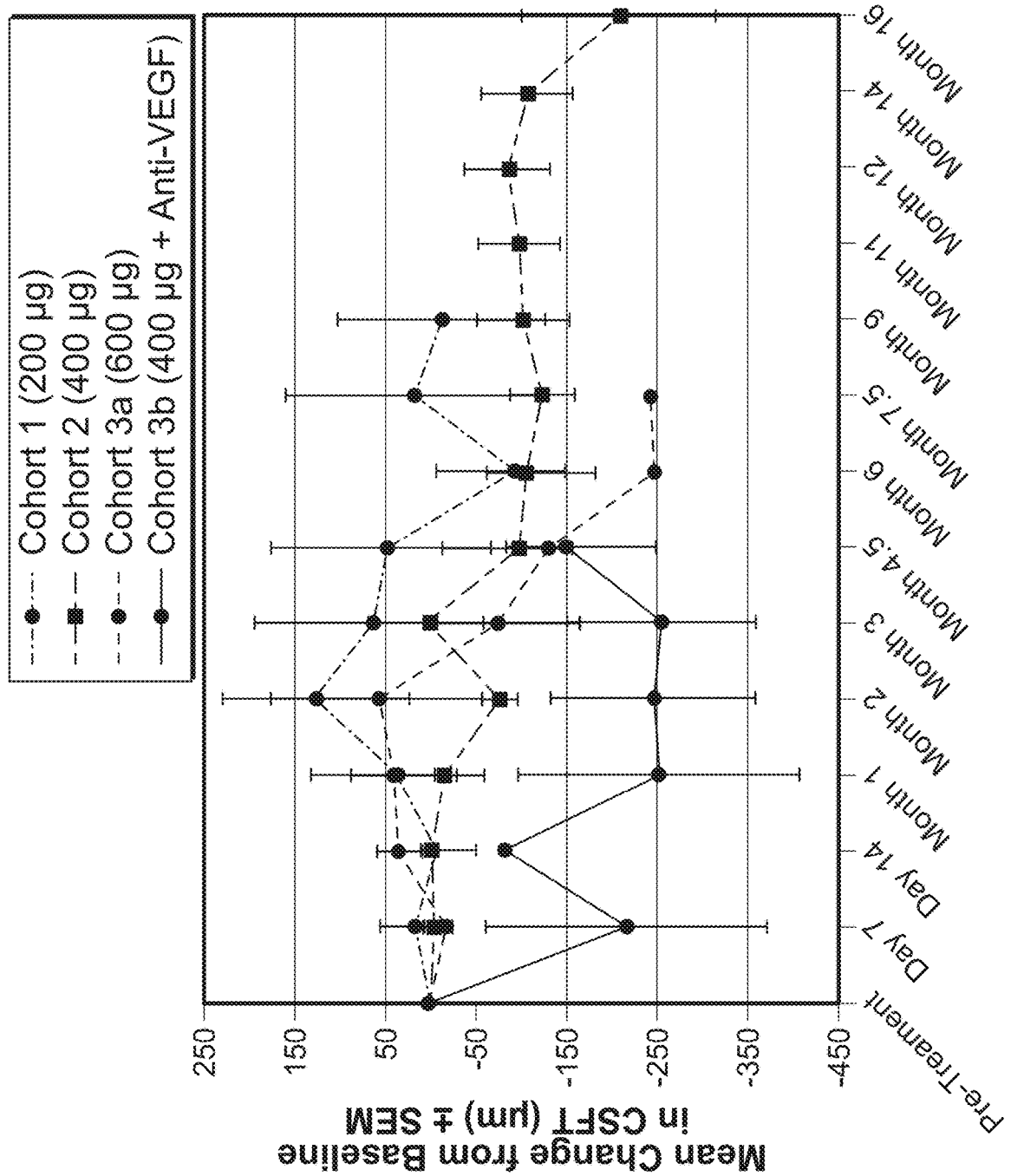
FIG. 17 One embodiment of central subfield thickness (CSFT) in the study eyes of patients suffering from neovascular age-related macular degeneration (wet AMD) treated with axitinib implants (one implant, total dose of 200 µg: cohort 1; two implants, total dose of 400 µg: cohort 2; three implants, total dose of 600 µg: cohort 3a; two implants, total dose of 400 µg and concurrent initial anti-VEGF: cohort 3b). Presented in this chart are mean changes in CSFT with standard error of the mean (SEM) compared to the baseline value. For this chart: Six patients were followed in cohort 1 until month 9. Seven patients were followed in cohort 2 until month 12, five until month 14 and two until month 16. Six patients were followed in cohort 3a until day 14, five until month 2, two until month 4.5, and one until months 6 and 7.5. Two patients were followed in cohort 3b until month 3, and one until month 4.5. Follow-up is ongoing.

In general, no substantial increase in the mean CSFT was observed for the subjects of cohort 1 over the 9-month study duration (FIG. 17). In some subjects of cohort 1, a reduction of CSFT was observed with the 200 μg dose. Subject #1 from cohort 1 (naïve) showed a significant reduction in CSFT in the study eye from 1252 μm (baseline value at day 1) to 936 μm (after 10.5 months), while visual acuity (referring to the clarity of vision) was not impaired in the study eye (FIG. 16). No rescue therapy was needed throughout the study duration of subject #1 (10.5 months). Mean visual acuity (BCVA) was not significantly impaired in the patients of cohort 1 (FIG. 18), meaning that BCVA was still within 15 ETDRS letters from baseline (determined prior to administration of the implant).

Figure 18:
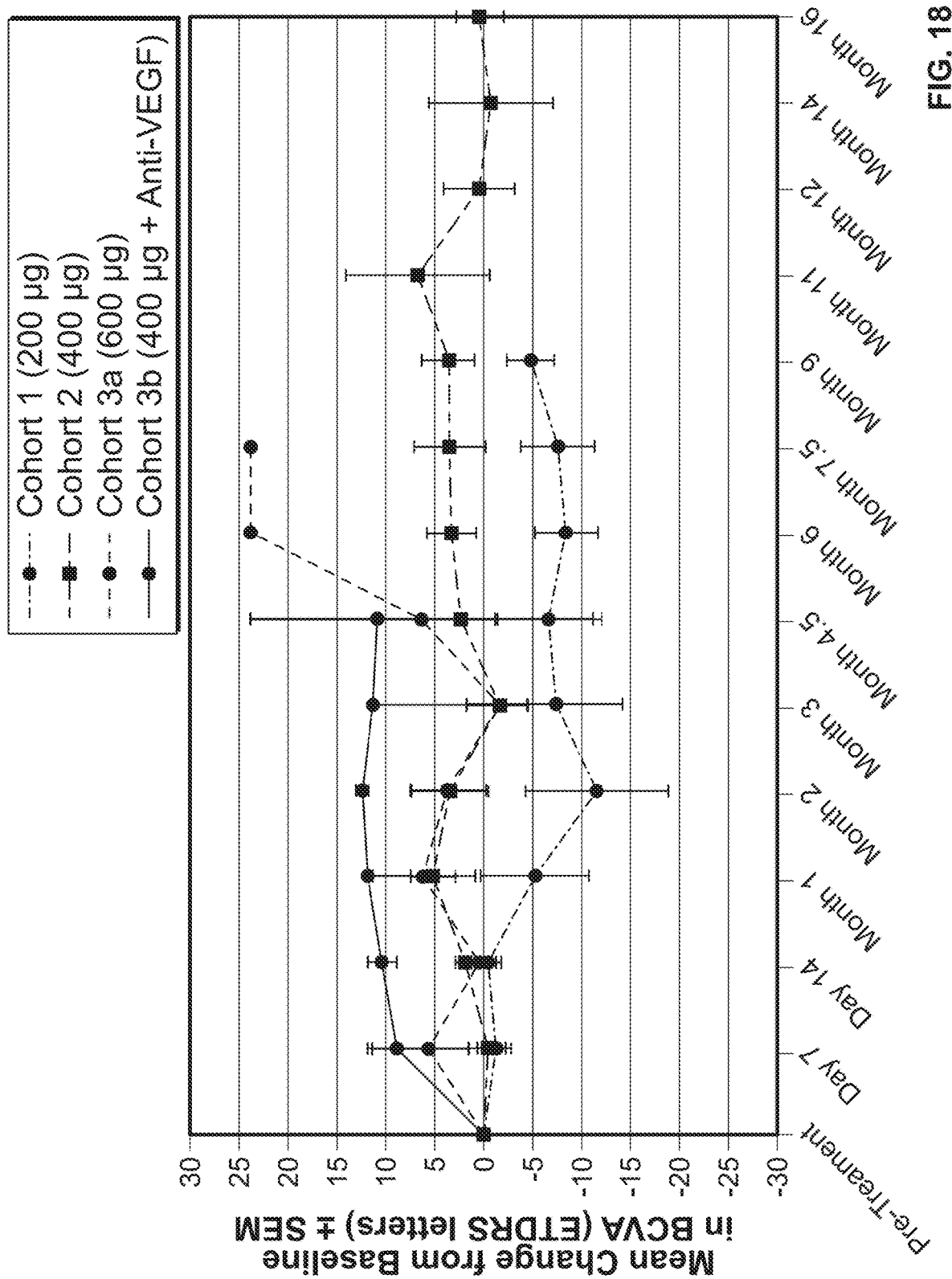
FIG. 18 One embodiment of best corrected visual acuity (BCVA) in the study eyes of patients suffering from neovascular age-related macular degeneration (wet AMD) treated with axitinib implants (one implant, total dose of 200 µg: cohort 1; two implants, total dose of 400 µg: cohort 2; three implants, total dose of 600 µg: cohort 3a; two implants, total dose of 400 µg and concurrent initial anti-VEGF: cohort 3b). Presented in this chart are mean changes in BCVA with standard error of the mean (SEM) compared to the baseline value in Early Treatment Diabetic Retinopathy Study (ETDRS) Letter Score (a representative value for letters that can be read correctly at a certain distance). For this chart (as for FIG. 17 above): Six patients were followed in cohort 1 until month 9. Seven patients were followed in cohort 2 until month 12, five until month 14 and two until month 16. Six patients were followed in cohort 3a until day 14, five until month 2, two until month 4.5, and one until months 6 and 7.5. Two patients were followed in cohort 3b until month 3, and one until month 4.5. Follow-up is ongoing.

The mean central subfield thickness (CSFT) was reduced for the subjects from cohort 2 over 14 months (FIG. 17). Moreover, mean visual acuity (BCVA) was not significantly impaired in the patients of cohort 2 (FIG. 18).

Figure 19A:
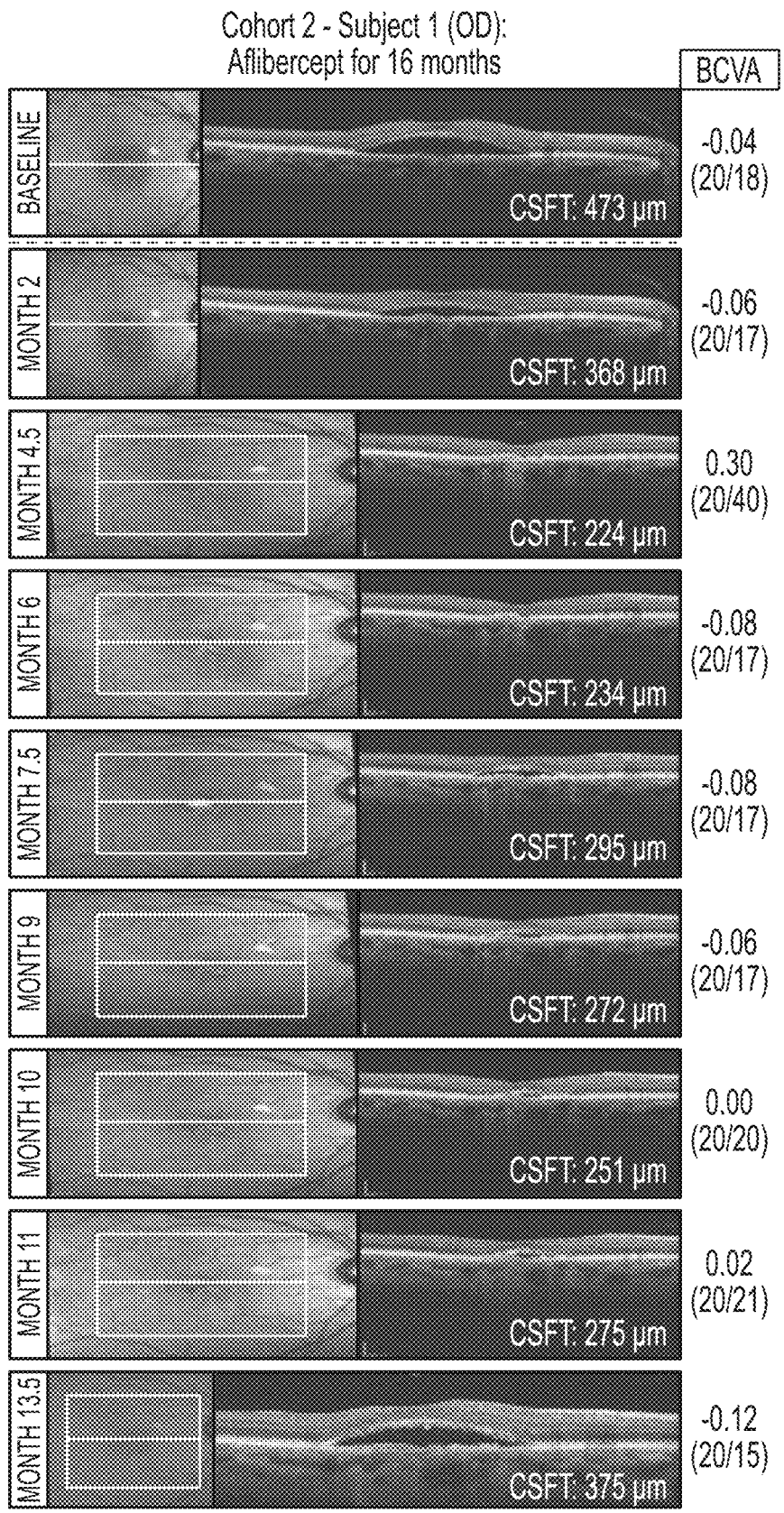
FIGS. 19A and 19B One embodiment of spectral domain optical coherence tomography (SD-OCT) images from the study eye of subject #1 of cohort 2 (2 implants, 400 µg axitinib in total per eye) with aflibercept treatment history of 16 months prior to injection of the implants in the right eye (OD). Sub-retinal fluid was clearly visible at baseline (pre-treatment). Importantly, the sub-retinal fluid was gone after 2-3 months after implants injection and this stage was essentially maintained over 15.5 months (15.5 months shown in FIG. 19B, the earlier visits in FIG. 19A). Best corrected visual acuity (BCVA) was not impaired.
Figure 19B:
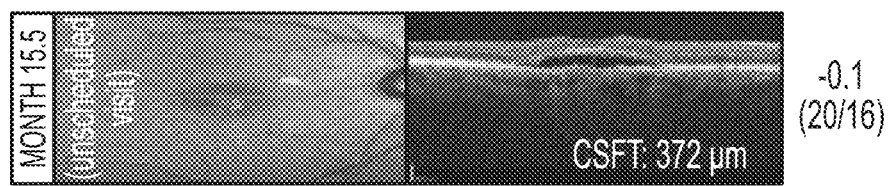
Figure 20:
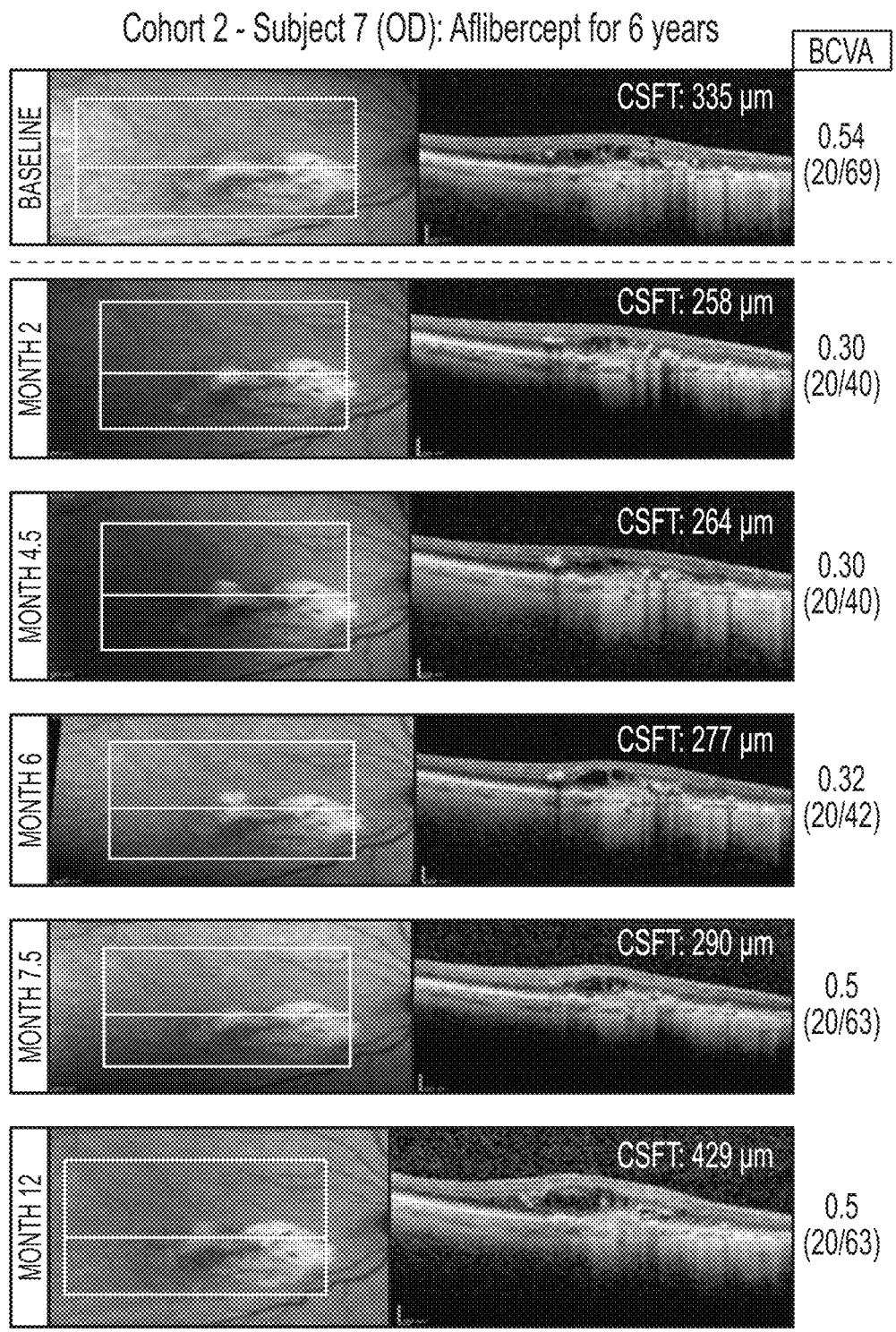
FIG. 20 One embodiment of spectral domain optical coherence tomography (SD-OCT) images from subject #7 of cohort 2 (2 implants, 400 μg axitinib in total per eye). Subject #7 who had received aflibercept for 6 years prior to study start showed significant reduction in CSFT and no impairment of BCVA for 9 months after implant injection.

FIGS. 19A and B, and FIG. 20 exemplarily show images from SD-OCT evaluation of two subjects from cohort 2. Subject #1 from cohort 2 had been treated with aflibercept for over a year (16 months) prior to injection of the axitinib implants in the right eye (oculus dexter, OD). Subretinal fluid was clearly visible at baseline (pre-treatment). Importantly, the sub-retinal fluid was gone after 2-3 months after implant injection and this stage was essentially maintained over the complete study duration of 15.5 months without rescue therapy (FIGS. 19A and B). Up to month 12.5 two implants were visible, thereafter one implant was visible. Subject #7 from cohort 2 had been treated with aflibercept for 6 years prior to implant administration. CSFT was efficiently reduced from 335 μm baseline through month 9 (e.g. CSFT of 271 μm at month 9) without rescue therapy (FIG. 20). At month 10 the CSFT started to increase again. Two implants were present until month 12. Follow-up is ongoing.

In summary, the clinical data demonstrate efficacy and implant persistence in the eye for up to about or even beyond 14 months in certain subjects. These observations have not been expected. In the in vitro real-time release experiments the complete axitinib dose was released after around 8 months (cf. FIG. 14A).

Plasma Concentration

Plasma concentrations of axitinib were below the lower limit of quantification (LLOQ<0.1 ng/mL) at all samples time-points in all subjects, indicating that administration of the implant(s) did not lead to systemic drug exposure. This further validates the overall safety of the axitinib implants of the present application.

Tolerability and Adverse Events

In general, the treatment has been safe and well-tolerated. Injection courses were uncomplicated for most of the subjects. FA and OCT revealed no clinically significant leakage for any of the subjects throughout the study duration. IOPs were normal independent of the dose for all subjects over the study duration. Inflammation was not observed for any of the subjects. No subjects needed ocular steroids.

All reported adverse events were mild to moderate, no severe adverse events or severe ocular adverse events were reported (Table 23).

TABLE 23

Adverse events reported for the cohorts 1 and 2.

| Number of subjects with: | Cohort 1: 200 µg axitinib (n = 6) | Cohort 2: 400 µg axitinib (n = 7) | Total n = 13 |
| --- | --- | --- | --- |
| Adverse Events (AEs) | 14 | 22 | 36 |
| Suspected relationship to study product | 1 | 2 | 3 |
| Suspected relationship to injection procedure | 1 | 3 | 4 |
| Ocular AEs | 12 | 15 | 27 |
| Ocular AEs in Study Eye | 7 | 13 | 20 |
| Serious Ocular AEs | 0 | 0 | 0 |
| By severity | | | |
| Mild | 12 | 17 | 29 |
| Moderate | 2 | 5 | 7 |
| Severe | 0 | 0 | 0 |

Adverse events observed in the study eye included tiny pigmented keratic precipitates (3/13), subconjunctival hemorrhage following injection (3/13) and pain following injection (2/13). Importantly, only 3 adverse events with suspected relationship to the study product were reported. For example, one patient had opacities around the implant, one patient hat vitreous floaters, three patients had tiny pigmented keratic precipitates (no treatment required), and one had foreign material (fiber and reflective particles). Further specific adverse events are listed in the following Table 2).

TABLE 24

Specific adverse events reported for the study eye for the cohorts 1 and 2.

| Number of subjects with: | Cohort 1: 200 µg axitinib (n = 6) | Cohort 2: 400 µg axitinib (n = 7) | Total n = 13 |
| --- | --- | --- | --- |
| Tiny Pigmented KPs | 3 | 0 | 3 |
| Opacities around OTX Implant | 1 | 0 | 1 |
| Discomfort/Difficulty opening eyes on waking | 1 | 0 | 1 |
| Dry eyes | 1 | 0 | 1 |
| Increased Geographic Atrophy | 0 | 1 | 1 |
| Pain | 0 | 2 | 2 |
| Vitreous Floaters | 0 | 1 | 1 |
| Corneal Scratch | 0 | 1 | 1 |
| Blepharitis | 0 | 1 | 1 |
| Subconjunctival Haemmorhage | 1 | 2 | 3 |
| TKI implant obstruction vision | 0 | 1 | 1 |
| Foreign material noted in vitreous | 0 | 1 | 1 |
| Worsen cataracts | 0 | 1 | 1 |
| Subconjunctival haemoatoma | 0 | 0 | 0 |
| Trace anterior chamber cells | 0 | 0 | 0 |
| Red eye | 0 | 1 | 1 |
| Watery eye | 0 | 1 | 1 |
| Eye discomfort | 0 | 0 | 0 |
| Foreign body sensation | 0 | 0 | 0 |
| Small hair in vision | 0 | 0 | 0 |

In summary, the axitinib implants of the present invention were safe and well-tolerated. The implants showed efficient reduction or showed essentially maintenance of CSFT versus the baseline determined prior to administration of the implant.

Evaluation of 600 µg Axitinib Dose and 400 µg Axitinib Dose with Anti-VEGF Co-Administration To further explore efficacy of the implants in humans, further clinical studies are ongoing with one cohort (cohort 3a) of subjects suffering from wet AMD (planned: n=6) receiving three of the 200 µg implants (Table 21.1, Implant #1) as separate injections resulting in a total axitinib dose of 600 µg per eye, as well as with another cohort (cohort 3b) of subjects suffering from wet AMD (planned: n=6) receiving two of the 200 µg implants (Table 21.1, Implant #1) as separate injections resulting in a total axitinib dose of 400 µg per eye and in addition receiving a single anti-VEGF injection (Avastin or EYLEA®), which is administered during the same session as the placement of the implants. One eye per patient is treated.

For cohort 3a, all 6 subjects have started treatment and are currently being treated, for cohort 3b, 2 subjects from the planned number of 6 subjects have started treatment and are currently being treated. Two out of the 8 currently treated subjects are female, 6 are male. The baseline CSFT for the 8 currently treated subjects in cohort 3 is 518±53 µm (mean±SE), and the baseline BCVA (Snellen equivalent) is 0.88±0.12 (mean±SE). In general, implants exhibited limited movement in the vitreous. An overview of the subjects enrolled to date in cohorts 3a and 3b is provided in Table 25. Overview charts presenting summary data regarding central subfield thickness (CSFT) and best corrected visual acuity (BCVA) of all subjects enrolled and analyzed so far in cohorts 3a and 3b are provided in FIGS. 17 and 18, respectively. In addition, in order to exemplary illustrate the course of CSFT and BCVA in subjects of cohorts 3a and 3b, certain specific subjects are discussed herein in more detail, and images showing the CSFT and BCVA in these subjects at exemplary visits are provided in the Figures. These exemplary subjects are discussed to illustrate CSFT and BCVA measurement and development in subjects/patients who participated in the study, but are singular subjects. For the mean change of CSFT and BCVA over a//subject of cohorts 3a and 3b, it is referred to FIGS. 17 and 18. For the charts in these FIGS. 17 and 18: Six patients were followed in cohort 3a until day 14, five until month 2, two until month 4.5, and one until months 6 and 7.5. Two patients were followed in cohort 3b until month 3, and one until month 4.5. Follow-up is ongoing.

TABLE 25

Overview of subjects from the two cohorts (cohort 3a and 3b). Age, Sex (male M, female F), together with prior treatment and study eye are presented. For the study eye (oculus dexter, (OD) or oculus sinister (OS)), pre-treatment BCVA is given as logMAR (logarithm of the minimal angle resolution) and Snellen equivalent. A conversion chart from EDTS letter score to LogMAR value and Snellen equivalent can be found in Beck et al., Am J Ophthalmol 2003, 135:194-205. In addition, CSFT pre-treatment is presented. All pre-treatment results are from day 1 of the study.

| | | | | | Study Eye | | |
|---|---|---|---|---|---|---|---|
| Subject No. | Age | Sex | Prior Treatment | Study Eye | Pre-Treatment log MAR BCVA | Pre-Treatment Snellen BCVA | Pre-Treatment CSFT (μm) |
| Cohort 3a (600 μg) | | | | | | | |
| #1 | 79 | M | Naïve | OS | 0.58 | 20/76 | 484 |
| #2 | 84 | M | Naïve | OD | 0.70 | 20/100 | 551 |
| #3 | 72 | M | Naïve | OD | 0.32 | 20/42 | 481 |
| #4 | 70 | M | Anti-VEGF | OS | 1.04 | 20/219 | 825 |
| #5 | 78 | F | Naïve | OS | 1.1 @ 1 m | 20/252 | 320 |
| #6 | 84 | M | Naïve | OD | 1.1 | 20/252 | 466 |
| Cohort 3b (400 μg + anti-VEGF) | | | | | | | |
| #1 | 71 | M | Naïve | OD | 0.88 @ 1 m | 20/152 | 423 |
| #2 | 80 | F | Anti-VEGF | OS | 1.34 @ 1 m | 20/438 | 559 |

Visual Quality and Central Subfield Thickness

Figure 21:
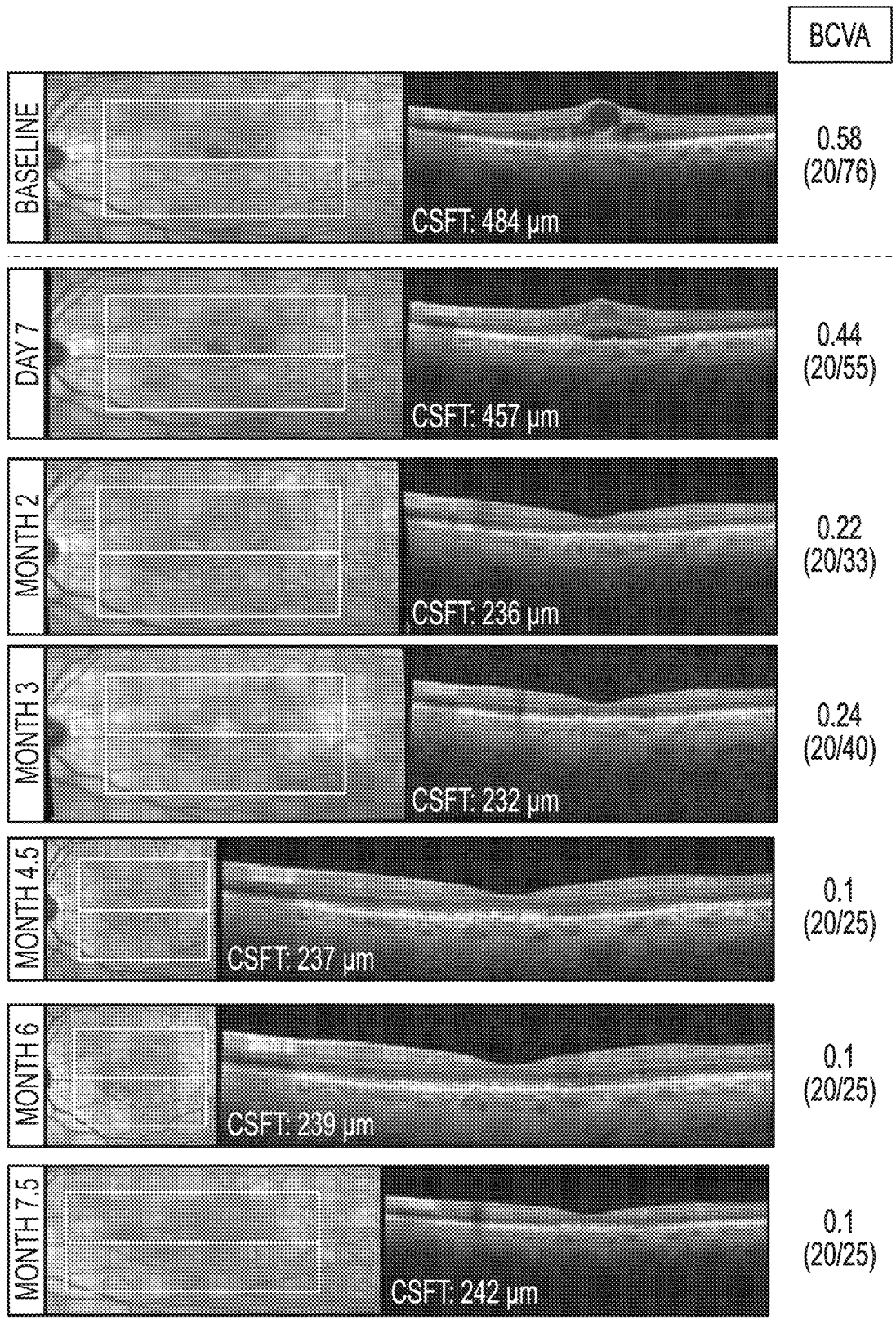
FIG. 21 One embodiment of spectral domain optical coherence tomography (SD-OCT) images from subject #1 of cohort 3a (3 implants, 600 μg axitinib in total per eye). A significant reduction in CSFT was observed at 2 months and maintained for 7.5 months in subject #1 from cohort 3a who was naïve for AMD treatment. BCVA was not impaired.

The first patient of cohort 3a (3×200 μg implant) is a 79 year-old male, who is naïve for AMD treatment. The injection course was uncomplicated. The implants were placed over one week (on days 1 (baseline) and 7) in the left eye (OS). Notably, CSFT was efficiently reduced over the first 7.5 months while BCVA remained unaffected (FIG. 21). The second patient of cohort 3a (3×200 μg implant; not shown in the Figures) is an 84 year-old male, who is naïve for treatment. The injection course was uncomplicated. The three implants were placed all in one day (day 1, baseline). CSFT was essentially stabilized for 4.5 months, i.e., did not clinically significantly increase. Follow-up is ongoing.

Generally, mean CSFT was greatly reduced at 6 months after insertion of the implants in patients of cohort 3a (FIG. 17). Mean BCVA increased markedly for cohort 3a after 3 months (FIG. 18).

Figure 22:
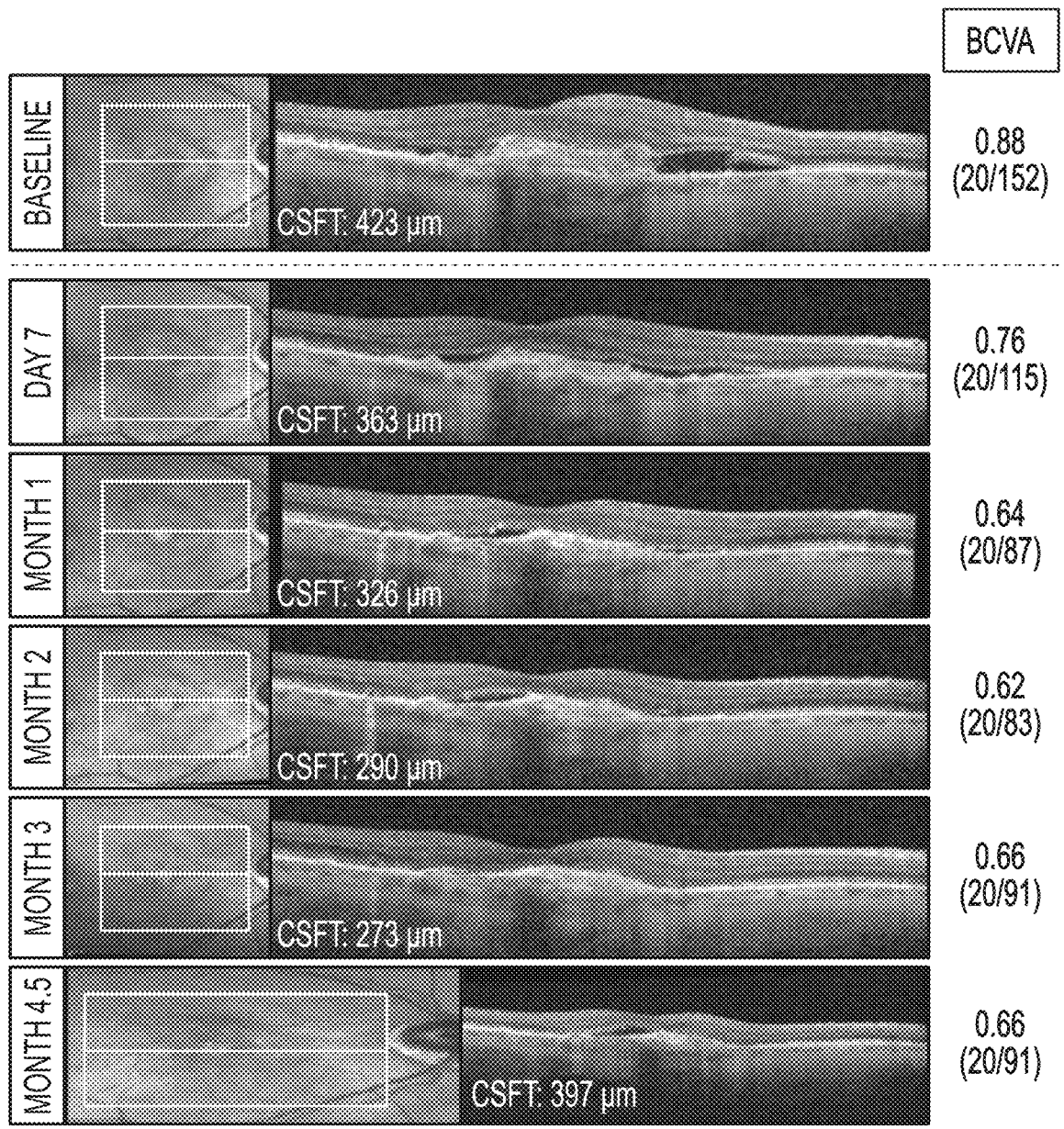
FIG. 22 One embodiment of spectral domain optical coherence tomography (SD-OCT) images from subject #1 from cohort 3b (2 implants, 400 μg axitinib in total per eye including co-administration of an anti-VEGF agent), who was anti-VEGF treatment naïve. CSFT was rapidly reduced within 7 days and further reduced and maintained low until month 3.
Figure 23:
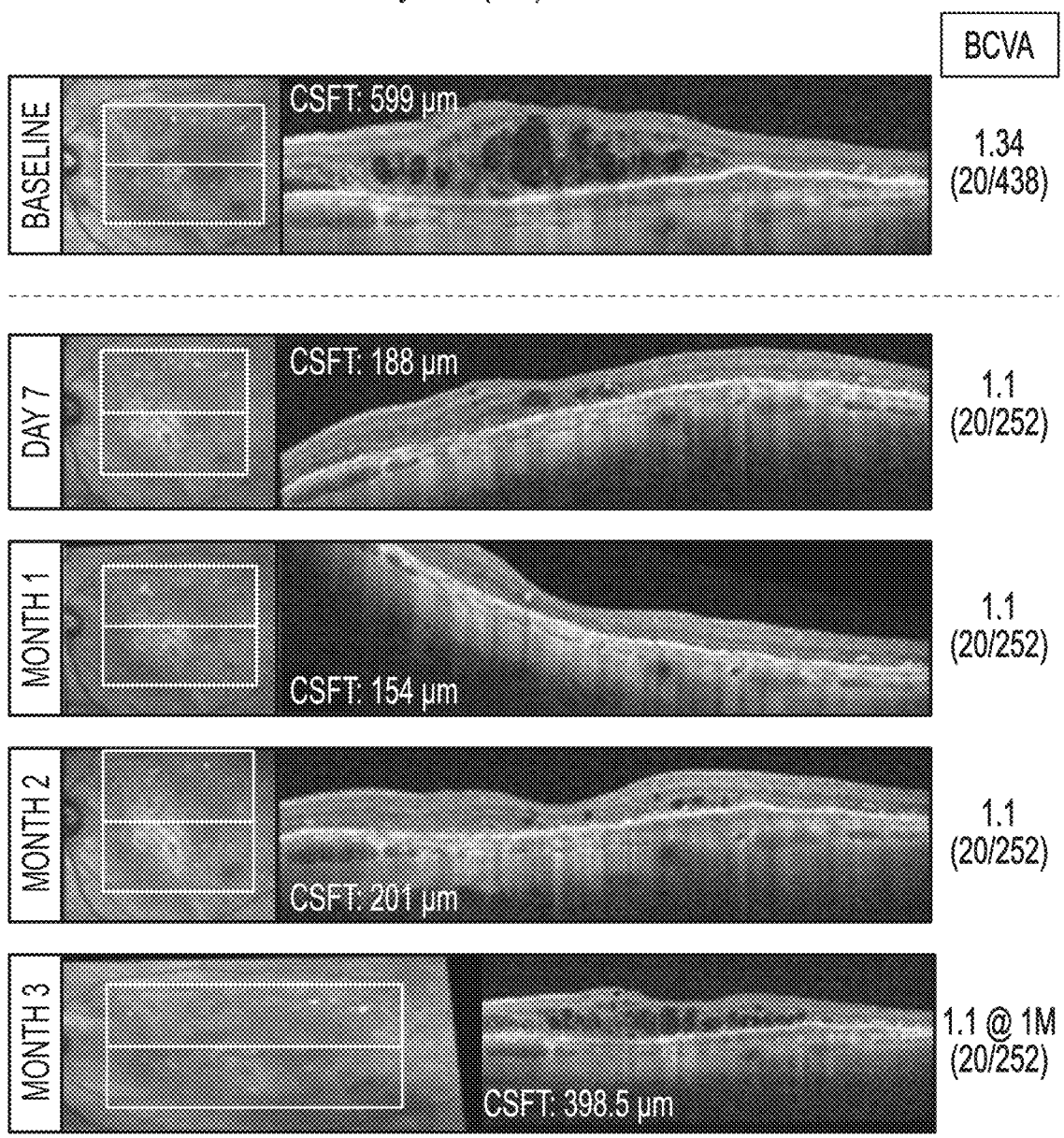
FIG. 23 One embodiment of spectral domain optical coherence tomography (SD-OCT) images from subject #2 from cohort 3b (2 implants, 400 μg axitinib in total per eye including initial co-administration of an anti-VEGF agent), who had received anti-VEGF treatment for 7 months prior to implant injection. CSFT was rapidly reduced within 7 days. The low CSFT value was maintained until month 2.

The first patient of cohort 3b (2×200 μg implant and anti-VEGF) is a 71 year old male, who is naïve for AMD treatment. The injection course was uncomplicated. The implants and the anti-VEGF injection were all placed on day 1 (baseline) in the right eye (OD). Already after 7 days a clear reduction in CSFT was visible while BCVA was not affected. The CSFT was further reduced and then essentially maintained over a 3 month treatment period, and started to increase at month 4.5 (FIG. 22). The second patient of cohort 3b had received anti-VEGF therapy for 7 months prior to insertion of the implants. Even after a short treatment period of only 7 days the CSFT was reduced by ⅔ (599 μm at baseline and 188 μm at day 7), while BCVA was not affected (FIG. 23). A low CSFT value was maintained through month 2, but started to increase at month 3. The subject received rescue therapy at month 4.5. Follow-up is ongoing.

Mean CSFT was efficiently reduced during the first 3 months after insertion of the implants in patients of cohort 3b (FIG. 17). Mean BCVA slightly increased (FIG. 18).

Tolerability and Adverse Events

In general, also the implants in cohort 3a and 3b have been safe and well-tolerated. Injection courses were uncomplicated for most of the subjects. IOPs were normal independent of the dose for all subjects over the study duration. Inflammation was not observed for any of the subjects. No subjects needed ocular steroids.

All reported adverse events were mild, no moderate or severe (ocular) adverse events were reported (Table 26.1). Importantly, only one adverse event with suspected relationship to study product was reported so far (see Table 26.1). Specific adverse events are reported in Table 26.2. Follow-up is ongoing for cohorts 3a and 3b.

TABLE 26.1

Adverse events reported for cohorts 3a and 3b (follow-up ongoing).

| Number of subjects with: | Cohort 3a: 600 μg axitinib (n = 6) | Cohort 3b: 400 μg axitinib + Anti-VEGF (n = 2) | Total n = 8 |
|---|---|---|---|
| Adverse Events (AEs) | 14 | 3 | 17 |
| Suspected relationship to study product | 1 | 0 | 1 |
| Susptected relationship to injection procedure | 9 | 2 | 11 |
| Ocular AEs | 12 | 2 | 14 |
| Ocular AEs in Study Eye | 10 | 2 | 12 |
| Serious Ocular AEs | 0 | 0 | 0 |
| By severity | | | |
| Mild | 14 | 3 | 17 |
| Moderate | 0 | 0 | 0 |
| Severe | 0 | 0 | 0 |

TABLE 26.2

Specific adverse events reported for the study eye for cohorts 3a and 3b so far (follow-up ongoing).

| Number of subjects with: | Cohort 3a: 600 μg axitinib (n = 6) | Cohort 3b: 400 μg axitinib + anti-VEGF (n = 2) | Total n = 8 |
|---|---|---|---|
| Tiny Pigmented KPs | 0 | 0 | 0 |
| Opacities around OTX Implant | 0 | 0 | 0 |
| Discomfort/Difficulty opening eyes on waking | 0 | 0 | 0 |
| Dry eyes | 0 | 0 | 0 |
| Increased Geographic Atrophy | 0 | 0 | 0 |
| Pain | 2 | 1 | 3 |
| Vitreous Floaters | 0 | 0 | 0 |
| Corneal Scratch | 0 | 0 | 0 |
| Blepharitis | 0 | 0 | 0 |
| Subconjunctival Haemmorhage | 3 | 1 | 4 |
| OTX Implant obstruction vision | 0 | 0 | 0 |
| Foreign material note in vitreous | 0 | 0 | 0 |
| Worsen Cataracts | 0 | 0 | 0 |
| Subjconjunctival Haemoatoma | 1 | 0 | 1 |
| Trace anterior chamber cells | 1 | 0 | 1 |
| Red eye | 0 | 0 | 0 |
| Watery eye | 0 | 0 | 0 |
| Eye discomfort | 1 | 0 | 1 |
| Foreign body sensation | 1 | 0 | 1 |
| Small hair in vision | 1 | 0 | 1 |

Alternatively, instead of three implants providing a total dose of 600 μg, one implant comprising a dose of 600 μg axitinib may be injected. Of note, injection of a 600 μg bolus dose in rabbits (cf. Example 3.6) did not result in significant tissue changes and inflammatory responses were normal. Formulation and dimension of 600 μg implants suitable for use in clinical studies are presented in Table 21.2.

Rescue Medication

If needed, according to the study protocol reproduced above any subject in any of cohorts 1, 2, 3a and 3b has received rescue therapy (an anti-VEGF agent, specifically an intravitreal injection of 2 mg aflibercept) at the investigator's discretion. The following criteria were used to identify subjects who would likely require rescue therapy:

loss of ≥15 letters from best previous BCVA due to AMD, with current BCVA not better than baseline; or loss of ≥10 letters on 2 consecutive visits from best previous BCVA due to AMD, with current BCVA score not better than baseline; or evidence of worsening disease activity manifest by greater than 75 microns CSFT from previous best value.

Not more than 50% of the subjects from cohorts 1, 2, 3a, and 3b required rescue medication as defined herein in the form of an anti-VEGF treatment within the first 6 months after start of treatment (implant injection) so far (Table 27). For instance, in cohort 2 71.4% of the subjects did not receive rescue medication at 3 months after implant insertion, and 6 months after implant insertion 57.1% of subjects did not receive rescue medication. Even after a long treatment period of 11 or 13.5 months in cohort 2, rescue medication was not needed for 28.6% or for 20% of the subjects, respectively (especially in cohorts 3a and 3b the studies are still ongoing). This low percentage of subjects needing rescue medication demonstrates that the therapeutic effect of a reduction of fluid achieved by the implants of the invention is maintained, and the patients are stabilized at the reduced fluid state for an extended period of time, such as for at least 3 months, at least 6 months, at least 9 months or at least 12 months. Specifically, the data of cohorts 1 and 2 (200 μg and 400 μg axitinib, respectively) in Table 27 show that the level of fluid in patients that had been achieved by the administration of the implants could be maintained in the period from 6 to 9 months without any need for rescue medication, while vision (expressed by means of the BCVA) was not significantly impaired (see FIG. 18).

TABLE 27

Percentage of subjects from all cohorts who did not require rescue therapy.

| Cohorts | At 3 months % (n/N) | At 6 months % (n/N) | At 7.5 months % (n/N) | At 9 months % (n/N) | At 11 months % (n/N) | At 13.5 months % (n/N) | At 15.5 months % (n/N) |
|---|---|---|---|---|---|---|---|
| Cohort 1 (200 μg) | 66.7 (4/6) | 50 (3/6) | 50 (3/6) | 50 (3/6) | NA | NA | NA |
| Cohort 2 (400 μg)* | 71.4 (5/7) | 57.1 (4/7) | 42.9 (3/7) | 42.9 (3/7) | 28.6 (2/7) | 20 (1/5)* | 20 (1/5)* |
| Cohort 3a (600 μg)* | 100 (3/3)* | 100 (1/1)* | 100 (1/1)* | TBD | TBD | TBD | TBD |
| Cohort 3b (400 μg + anti-VEGF)* | 100 (2/2)* | TBD | TBD | TBD | TBD | TBD | TBD |

*follow-up is ongoing.
TBD = to be determined.
Note:
in cohort 3a, one subject received rescue medication at month 1, however this is not yet reflected in Table 27 as of the total of six subjects in cohort 3a only three already reached 3 months, and none of these three had received rescue medication (the subject having received rescue mediaction at month 1 has not yet reached month 3).

The doses of axitinib in implants applied in humans (200-600 μg) are markedly lower compared to the approved INLYTA® dose (2×5 mg/day). Even if an entire 600 μg axitinib dose would be delivered systemically at one time, this would nevertheless allow a more than 15-fold safety margin of this full dose compared to the daily INLYTA® dose, further underlining the safety of the implants.

The above results demonstrate that the implants of the present invention administered to patients diagnosed with neovascular AMD were able to stabilize retinal fluid in these patients (i.e., to either reduce, maintain or at least not significantly increase retinal fluid) as evidenced by the CSFT, while not impairing the patients' vision as evidenced by the BCVA, for a treatment period of about 6 to about 9 months or even longer, and that the implants were well tolerated.

Example 6.5: Proposed Human Clinical Trial with a 600 µg Axitinib Implant

The proposed study is a prospective, multi-center, double-masked, randomized, parallel-group study to evaluate the efficacy and safety of OTX-TKI (600 µg axitinib implant) for intravitreal use in subjects with previously treated neovascular age-related macular degeneration (nAMD). The study objective is to evaluate the efficacy and safety of OTX-TKI (0.6 mg axitinib implant) for intravitreal use in previously treated patients with neovascular age-related macular degeneration (AMD).

The primary efficacy endpoint will be:
Mean change in BCVA from baseline to 7 months
The secondary efficacy endpoints will be:
Mean change in BCVA from baseline over time at all study visits
Mean change in central subfield thickness (CSFT) from baseline over time measured by SD-OCT at 7 months and all study visits and percent of subjects with no increase in CSFT 50 µm at all study visits compared to baseline through Month 12
Proportion of subjects with absence of retinal fluid (CSFT 300 µm on SD-OCT) at all study visits through Month 12, proportion of subjects with no clinically significant increase in leakage from baseline determined by FA at 7 months and all study visits, proportion of patients with absence of fluid by fluid type (subretinal fluid (SRF) or Intraretinal fluid (IRF); CSFT 300 µm on SD-OCT) at all study visits
Proportion of subjects receiving rescue therapy, mean time to rescue therapy, and mean number of rescue therapy injections through Month 4, 7, and 12.
Safety endpoint will be:
Incidence of treatment emergent adverse events (AEs)
Vital signs changes over time
Ocular Comfort Score changes over time
Clinically relevant vision loss defined as a 6-line loss in vision compared to baseline over time
Clinically significant change in ocular examination compared to baseline assessments (e.g., slit lamp biomicroscopy, fundus exam, and IOP) over time.

Figure 28:
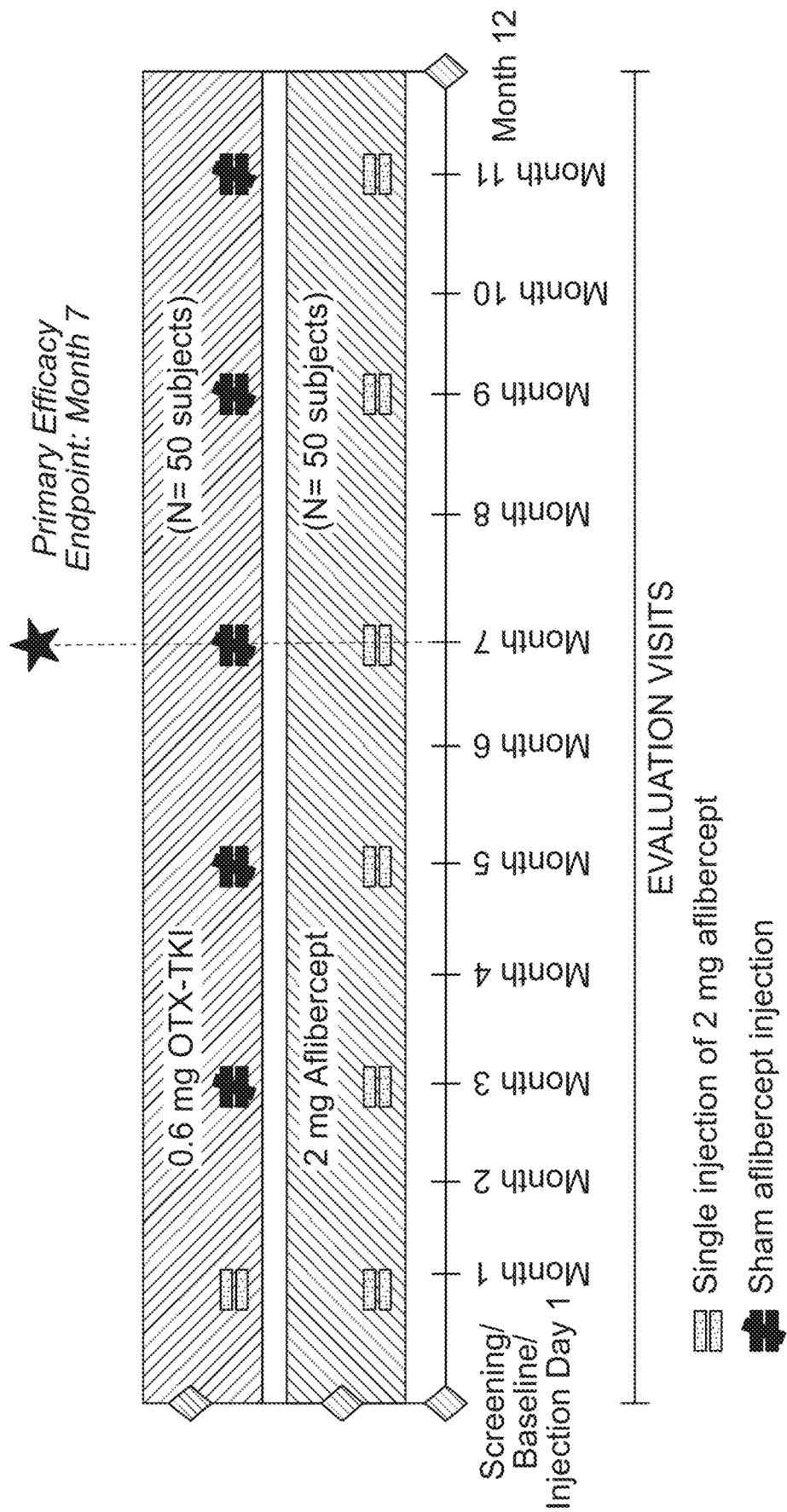
FIG. 28 Proposed phase 2 study design with an implant containing 600 μg axitinib according to one embodiment of the invention.

Approximately 100 subjects of age 50 will be enrolled and treated with 0.6 mg OTX-TKI (intravitreal implant) or 2 mg aflibercept (intravitreal injection). Following confirmation of eligibility at Visit 1 (Screening/Baseline), the subjects will be randomized 1:1 to one of two groups. Subjects randomized to OTX-TKI will receive a single injection of 0.6 mg OTX-TKI (0.6 mg axitinib), and subjects randomized to aflibercept will receive a sham (i.e., vehicle only) injection. At Visit 2 (Month 1) subjects randomized to OTX-TKI will receive a single injection of 2 mg aflibercept and subjects randomized to aflibercept will receive a single injection of 2 mg aflibercept (i.e., all subjects will receive an injection of 2 mg aflibercept at Visit 2/Month 1). Subsequently, subjects randomized to the aflibercept group will receive a single injection of 2 mg aflibercept every two months and subjects randomized to the OTX-TKI group will receive a sham injection every two months. The planned study design is shown in FIG. 28.

The study population will be subjects with a diagnosis of previously treated subfoveal neovascularization (SFNV) secondary to neovascular AMD with leakage involving the fovea who received their most recent anti-VEGF injection within the prior 1-4 weeks.

Example 7: Inflammation Study with Various TKIs

TKI sample preparation: Hydrogels containing several TKIs were prepared for tolerability testing in rabbit eyes: sunitinib axitinib, nintedanib and regorefanib. First, a diluent solution of 80% Provisc (Alcon, Inc.) and 20% of a 0.5 mg/mL sodium borate solution (pH 6.8) was prepared. Next, mixtures containing 9.6% API, 77.8% diluent, 8.4% 4a20kPEG SAZ and 4.2% 8a20kPEG NH2 were prepared. Prior to gelation, which occurred between 3.5 to 8 minutes after mixing, 10 µL was injected intravitreally in New Zealand white rabbit eyes using a Hamilton syringe.

Study Design: Briefly, on Day 0 rabbits were injected in the left and right eye with test articles as listed below in the study design table. Animals were euthanized at 2 weeks. Eyes were harvested, and fixed in Davidson's solution for histopathologic analysis.

TABLE 28

List of TKIs used in the inflammation study.

| Group | Treatment (OU) | Endpoint |
|---|---|---|
| 1 | Sunitinib | Histopathology |
| 2 | Nintedanib | Histopathology |
| 3 | Regorefanib | Histopathology |
| 4 | Axitinib | Histopathology |
| 5 | Sham | Histopathology |

Tissues examined: A total of 10 left and right eyes from 5 rabbits were submitted to Mass Histology and trimmed by a board-certified veterinary pathologist.

Conclusion: Under the conditions of the study intravitreal injection of rabbit eyes with formulations of hydrogel depots with tyrosine kinase inhibitors at 14 days post-injection resulted in the continued presence of the hydrogel in the vitreous chamber of at least one eye from each group except Group 1 and Group 3 where no hydrogel material was noted in either eye.

Inflammation was never present around any of the injected material observed in any of the eyes from Groups 2, 4, and 5. Minimal inflammation composed primarily of macrophages in the vitreous chamber and/or attached to the retina was observed in occasional samples from Groups 1 and 3. Again, no injected material was observed in either eye from Group 1 or Group 3.

Minimal inflammation and fibrosis were observed in a few slide samples from Groups 3 and 4. These were typically small linear areas of fibrosis with a few macrophages admixed. They are interpreted as sequela to needle injection.

One or a few small areas of retinal disruption or retinal folds were observed in at least 1 eye from Groups 1, 3, 4 and 5. These could be retinal invaginations due to needle injection. A very small retinal detachment measuring 100 microns in length is present in one eye at the location of the small retinal disruption (Group 3). No other retinal detachments were noted in any eye from any group.

A focus of mild histiocytic and multi-nucleated inflammation was observed around a small displaced focus of lens fibers in the vitreous chamber of one eye from Group 3. This is considered lens-induced granulomatous endophthalmitis, and may be due to a slight nick of the lens by the needle at injection. No other such lesions were observed in any eye from any group.

Example 8: Additional Examples

In certain embodiments, the present invention also relates to implants as disclosed herein that contain a high amount of TKI such as axitinib, such as a dose of axitinib of more than about 1200 µg, or more than about 1800 µg. Certain exemplary prophetic implants containing such a high dose of axitinib are disclosed in the following Table 29.

What is claimed is:

1. A method of manufacturing a sustained release biodegradable ocular implant comprising forming a hydrogel comprising tyrosine kinase inhibitor particles dispersed within the hydrogel, shaping the hydrogel, and drying the hydrogel, wherein the implant in its dry state has a length of about 6 mm to about 17 mm and a diameter of 0.1 mm to 0.5 mm; and has a total implant weight of about 0.2 mg to about 1.5 mg, wherein the ocular implant is not created in situ.

2. The method of claim 1, wherein the shaping comprises forming the hydrogel into a hydrogel strand.

3. The method of claim 2, further comprising stretching the hydrogel strand.

4. The method of claim 3, wherein the stretching is in a longitudinal direction.

5. The method of claim 4, wherein the stretch factor is from above 1 to about 4.

6. The method of claim 2, further comprising cutting the strand into segments.

7. The method of claim 1, wherein the tyrosine kinase inhibitor is axitinib.

8. The method of claim 6, wherein the tyrosine kinase inhibitor is axitinib and each segment comprises an amount of axitinib from about 150 µg to about 1200 µg.

9. The method of claim 1, wherein the hydrogel comprises a polymer network.

10. The method of claim 9, wherein the polymer network is formed by mixing and reacting an electrophilic group-containing multi-arm PEG precursor with a nucleophilic group-containing multi-arm PEG precursor or another nucleophilic group-containing crosslinking agent in a buff-

TABLE 29

Prophetic implants containing a high dose of axitinib (i.e., above 1200 µg)

| | Implant type | Implant #1 | Implant #2 | Implant #3 | Implant #4 |
|---|---|---|---|---|---|
| Formulation (% dry basis w/w) | Axitinib | 68.6% | 68.6% | 68.6% | 68.6% |
| | Dose | 1580 ug | 2360 ug | 6010 ug | 8990 ug |
| | PEG Hydrogel | 26.0% | 26.0% | 26.0% | 26.0% |
| | 4a20K PEG-SAZ | 17.4% | 17.4% | 17.4% | 17.4% |
| | 8a20K PEG-NH2 | 8.7% | 8.7% | 8.7% | 8.7% |
| | Sodium phosphate | 5.4% | 5.4% | 5.4% | 5.4% |
| Formulation (% wet basis w/w) | Axitinib | 16.5% | 16.5% | 16.5% | 16.5% |
| | PEG Hydrogel | 6.3% | 6.3% | 6.3% | 6.3% |
| | 4a20K PEG-SAZ | 4.2% | 4.2% | 4.2% | 4.2% |
| | 8a20K PEG-NH2 | 2.1% | 2.1% | 2.1% | 2.1% |
| | Sodium phosphate | 1.3% | 1.3% | 1.3% | 1.3% |
| | WFI | 75.9% | 75.9% | 75.9% | 75.9% |
| | Axitinib per final dry length | 145.0 ug/mm | 145.0 ug/mm | 551.4 ug/mm | 551.4 ug/mm |
| | Approximate Implant Mass (dose ug/API %) | 2303 | 3440 | 8761 | 13105 |
| Configuration | Stretching Method (Stretch Factor) | Wet (2.1) | Wet (2.1) | Wet (2.1) | Wet (2.1) |
| | Needle Size | 22G ETW (0.522 mm ID) | 22G ETW (0.522 mm ID) | 17G ETW (1.24 mm ID) | 17G ETW (1.24 mm ID) |
| | Injector/Syringe | Implant Injector | Implant Injector | Implant Injector | Implant Injector |
| | Packaging | Foil Pouches | Foil Pouches | Foil Pouches | Foil Pouches |
| | Sterilization Type | Gamma | Gamma | Gamma | Gamma |
| | Site Storage | Refrigerated | Refrigerated | Refrigerated | Refrigerated |
| Dimensions | Dried | | | | |
| | Diameter | 0.49 mm | 0.49 mm | 0.97 mm | 0.97 mm |
| | Length | 10.9 mm | 16.3 mm | 10.9 mm | 16.3 mm |
| | Volume | 2.1 mm³ | 3.1 mm³ | 8.0 mm³ | 12.0 mm³ |
| | Implant Mass | 2.3 mg | 3.4 mg | 8.8 mg | 13.1 mg |
| | Hydrated | | | | |
| | Diameter | 1.0 mm | 1.0 mm | 2.0 mm | 2.0 mm |
| | Length | 10.0 mm | 15.0 mm | 10.0 mm | 15.0 mm | ered solution in the presence of the tyrosine kinase inhibitor and allowing the mixture to gel to form the hydrogel.

* * * * *